United States Patent
Szyperski et al.

(10) Patent No.: US 7,920,972 B2
(45) Date of Patent: Apr. 5, 2011

(54) G-MATRIX FOURIER TRANSFORMATION (GFT) NUCLEAR MAGNETIC RESONANCE (NMR) EXPERIMENTS FOR RESONANCE ASSIGNMENT AND STRUCTURE DETERMINATION OF ORGANIC MOLECULES

(75) Inventors: Thomas A. Szyperski, Amherst, NY (US); Hanudatta S. Atreya, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 875 days.

(21) Appl. No.: 11/253,262

(22) Filed: Oct. 18, 2005

(65) Prior Publication Data

US 2006/0111846 A1 May 25, 2006

Related U.S. Application Data

(60) Provisional application No. 60/701,429, filed on Jul. 21, 2005, provisional application No. 60/620,070, filed on Oct. 18, 2004.

(51) Int. Cl.
- G06F 19/00 (2006.01)
- G01N 33/48 (2006.01)
- G01N 31/00 (2006.01)
- C12Q 1/00 (2006.01)

(52) U.S. Cl. .......... 702/27; 702/19; 702/22; 435/4

(58) Field of Classification Search .......... None
See application file for complete search history.

(56) References Cited

U.S. PATENT DOCUMENTS

| | | | |
|---|---|---|---|
| 4,480,228 A | 10/1984 | Bottomley | |
| 4,506,223 A | 3/1985 | Bottomley et al. | |
| 4,509,015 A | 4/1985 | Ordidge et al. | |
| 4,682,106 A | 7/1987 | Vatis et al. | |
| 4,703,270 A | 10/1987 | Hall et al. | |
| 5,081,417 A | 1/1992 | Bovee et al. | |
| 5,657,758 A | 8/1997 | Posse et al. | |
| 5,709,208 A | 1/1998 | Posse et al. | |
| 5,879,299 A | 3/1999 | Posse et al. | |
| 6,831,459 B2 | 12/2004 | Szyperski et al. | |
| 7,141,432 B2 | 11/2006 | Szyperski | |
| 7,365,539 B2 | 4/2008 | Szyperski et al. | |
| 7,396,685 B2 | 7/2008 | Szyperski et al. | |
| 7,408,346 B2 | 8/2008 | Szyperski et al. | |
| 2004/0095140 A1 | 5/2004 | Szyperski et al. | |
| 2009/0009166 A1 | 1/2009 | Szyperski et al. | |

(Continued)

FOREIGN PATENT DOCUMENTS

WO 0203081 A2 1/2002

(Continued)

OTHER PUBLICATIONS

Wagner G. Prospects for NMR of large proteins. Journal of Biomolecular NMR. vol. 3, 1993, pp. 375-385.*

(Continued)

*Primary Examiner* — Russell S Negin
(74) *Attorney, Agent, or Firm* — Nixon Peabody LLP

(57) ABSTRACT

The present invention discloses a suite of $G^2FT$ and GFT NMR experiments that can be used for complete resonance assignments of proteins and for obtaining structural (conformational and orientational) constraints for determining high resolution three-dimensional structures of biomolecules.

8 Claims, 50 Drawing Sheets
(6 of 50 Drawing Sheet(s) Filed in Color)

U.S. PATENT DOCUMENTS

2009/0033326 A1    2/2009    Szyperski et al.

FOREIGN PATENT DOCUMENTS

| WO | 2004007016 A2 | 1/2004 |
|---|---|---|
| WO | 2004011909 A2 | 2/2004 |
| WO | 2007002464 A2 | 1/2007 |
| WO | 2009018276 A1 | 2/2009 |

OTHER PUBLICATIONS

Parker et al. Signal-to-noise efficiency in magnetic resonance imaging. Medical Physics, 1990, vol. 17, pp. 250-257.*

Atreya et al., "Resonance Assignment of Proteins with High Shift Degeneracy Based on 5D Spectral Information Encoded in $G^2FT$ NMR Experiments," *J. Am. Chem. Soc.* 127:4554-4555 (2005).

Atreya & Szyperski, "G-Matrix Fourier Transform NMR Spectroscopy for Complete Protein Resonance Assignment," *Proc. Natl. Acad. Sci. USA* 101(26):9642-9647 (2004).

Brutscher et al., "Determination of an Initial Set of NOE-Derived Distance Constraints for the Structure Determination of $^{15}N/^{13}C$-Labeled Proteins," *J. Magn. Reson. Ser. B* 109:238-242 (1995).

Ding & Gronenborn, "Novel 2D Triple-Resonance NMR Experiments for Sequential Resonance Assignments of Proteins," *J. Magn. Reson.* 156:262-268 (2002).

Eletsky et al., "Probing Structure and Functional Dynamics of (Large) Proteins with Aromatic Rings: L-GFT-TROSY (4,3) HCCH NMR Spectroscopy," *J. Am. Chem. Soc.* 127(42):14578-14579 (2005).

Kim & Szyperski, "GFT NMR, a New Approach to Rapidly Obtain Precise High-Dimensional NMR Spectral Information," *J. Am. Chem. Soc.* 125:1385-1393 (2003).

Koźmiński & Zhukov, "Multiple Quadrature Detection in Reduced Dimensionality Experiments," *J. Biomol. NMR* 26:157-166 (2003).

Kupče & Freeman, "Projection-Reconstruction Technique for Speeding Up Multidimensional NMR Spectroscopy," *J. Am. Chem. Soc.* 126:6429-6440 (2004).

Liu et al., "NMR Data Collection and Analysis Protocol for High-Throughput Protein Structure Determination," *Proc. Natl. Acad. Sci. USA* 102(30):10487-10492 (2005).

Löhr & Rüterjans, "A New Triple-Resonance Experiment for the Sequential Assignment of Backbone Resonances in Proteins," *J. Biomol. NMR* 6:189-197 (1995).

Shen et al., "G-Matrix Fourier Transform NOESY-Based Protocol for High-Quality Protein Structure Determination," *J. Am. Chem. Soc.* 127:9085-9099 (2005).

Szyperski et al., "Reduced Dimensionality in Triple-Resonance NMR Experiments," *J. Am. Chem. Soc.* 115:9307-9308 (1993).

Szyperski et al., "Reduced-Dimensionality NMR Spectroscopy for High-Throughput Protein Resonance Assignment," *Proc. Natl. Acad. Sci. USA* 99:8009-8014 (2002).

Szyperski et al., "Useful Information from Axial Peak Magnetization in Projected NMR Experiments," *J. Am. Chem. Soc.* 118:8146-8147 (1996).

Venters et al., "(4,2)D Projection-Reconstruction Experiments for Protein Backbone Assignment: Application to Human Carbonic Anhydrase II and Calbindin $D_{28K}$," *J. Am. Chem. Soc.* 127:8785-8795 (2005).

Xia et al., "(3,2)D GFT-NMR Experiments for Fast Data Collection from Proteins," *J. Biomol. NMR* 29:467-476 (2004).

\* cited by examiner (a) NOE chemical shift doublets (b) NOE central peaks and NOEs detected on aromatic protons Backbone resonance assignments a (4,3)D HNNC$^{\alpha\beta}$C$^\alpha$ / C$^{\alpha\beta}$C$^\alpha$(CO)NHN (10.0 hrs)

b (5,2)D HACACONHN (1.5 hr); Phe 33

Side chain spin system identification c (4,3)D HCCH (4.0 hrs)
(Aliphatic; Ile 85)

d (4,3)D HCCH (1.4 hrs)
(Aromatic; Tyr 89)

SEQUENCE LISTING

<160> NUMBER OF SEQ ID NOS: 1

<210> SEQ ID NO 1
<211> LENGTH: 22
<212> TYPE: PRT
<213> ORGANISM: Escherichia coli

<400> SEQUENCE: 1

Met Gly Thr Ser His His His His His His Ser Ser Gly Arg Glu Asn
1               5                   10                  15

Leu Tyr Phe Gln Gly His
            20

G-MATRIX FOURIER TRANSFORMATION (GFT) NUCLEAR MAGNETIC RESONANCE (NMR) EXPERIMENTS FOR RESONANCE ASSIGNMENT AND STRUCTURE DETERMINATION OF ORGANIC MOLECULES

This application claims the benefit of U.S. Provisional Patent Application Ser. No. 60/620,070, filed Oct. 18, 2004, and U.S. Provisional Patent Application Ser. No. 60/701,429, filed Jul. 21, 2005, which are hereby incorporated by reference in their entirety.

This invention arose out of research sponsored by the National Institutes of Health (Grant No. P50 GM62413-01) and the National Science Foundation (Grant Nos. MCB 00075773 and 0416899). The U.S. Government may have certain rights in this invention.

FIELD OF THE INVENTION

The present invention relates to methods of conducting G-matrix Fourier transformation (GFT) nuclear magnetic resonance (NMR) experiments for resonance assignment and structure determination of organic molecules.

BACKGROUND OF THE INVENTION

Multidimensional nuclear magnetic resonance (NMR) spectroscopy is pivotal for pursuing NMR-based structural biology (Cavanagh et al., *Protein NMR Spectroscopy* Academic Press: San Diego (1996); Wüthrich, *NMR of proteins and Nucleic Acids* Wiley: New York (1986)). In many instances, it is desirable to obtain multidimensional spectral information as rapidly as possible. First, the costs related to spectrometer usage are reduced and the throughput of samples per NMR spectrometer can be increased. Second, the requirement for longevity of NMR samples is alleviated. Third, a higher time resolution can be achieved to study dynamic processes by multidimensional spectra. The first two objectives are at the heart of NMR-based structural genomics, which aims at establishing NMR spectroscopy as a powerful tool for exploring protein "fold space" and yielding at least one experimental structure for each family of protein sequence homologues (Montelione et al., *Nat. Struc. Biol.* 7:982-984 (2000)).

Fast acquisition of multidimensional spectra, however, is limited by the need to sample (several) indirect dimensions. This restriction can be coined the "NMR sampling problem"; above a threshold at which the measurement time is long enough to ensure a workable signal-to-noise ratio (S/N), the sampling of indirect dimensions determines the requirement for instrument time. In this "sampling-limited" data collection regime (Szyperski et al., *Proc. Natl. Acad. Sci. USA* 99:8009-8014 (2002)), valuable instrument time is invested to meet the sampling demand rather than to achieve sufficient "signal averaging." Hence, techniques to speed up NMR data collection focus on avoiding this regime, that is, they are devised to push data collection into the "sensitivity-limited" regime in order to properly adjust NMR measurement time to sensitivity requirements. In view of the well-known fact that NMR measurement times tend to increase with molecular weight, rapid sampling approaches for accurate adjustment of measurement times on the one hand and methodology developed to study large systems on the other (e.g., transverse relaxation optimized spectroscopy (TROSY; Pervushin et al., *Proc. Natl. Acad. Sci. USA* 94:12366-12371 (1997)) or protein deuteration (Gardner et al., *Ann. Rev. Biophys. Biomol. Struct.* 27:357-406 (1998)) are complementary.

The implementation of rapid data collection protocols avoiding sampling limitations requires that the number of acquired free induction decays (FIDs), i.e., the number of data points sampled in the indirect dimensions, is reduced. Notably, phase-sensitive acquisition of an ND Fourier transformation (FT) NMR experiment requires sampling of N–1 indirect dimensions with $n_1 \times n_2 \times \ldots \times n_{N-1}$ complex points, representing $2^{N-1} \times (n_1 \times n_2 \times \ldots \times n_{N-1})$ FIDs. There is a steep increase of the minimal measurement time, $T_m$, with dimensionality; acquiring 16 complex points in each indirect dimension (with one scan per FID each second) yields $T_m(3D)=0.5$ hours, $T_m(4D)=9.1$ hours, $T_m(5D)=12$ days, and $T_m(6D)=1.1$ years.

When reducing the number of acquired FIDs, the key challenge is to preserve the multidimensional spectral information that can be obtained by conventional linear sampling with appropriately long maximal evolution times in all indirect dimensions. Moreover, trimming the number of sampled data points may in turn require processing techniques that complement, or replace, widely used Fourier transformation of time domain data.

G-Matrix Fourier Transformation (GFT) NMR Spectroscopy

G-matrix Fourier Transformation (GFT) NMR spectroscopy (Kim et al., *J. Am. Chem. Soc.* 125:1385-1393 (2003)) represents a generalization of reduced dimensionality (RD) NMR spectroscopy and aims at providing high-dimensional spectral information with both accuracy and speed. GFT NMR spectroscopy results from "modules" derived for RD NMR and combines multiple phase-sensitive RD NMR, multiple "bottom-up" central peak detection, and (time domain) editing of the components of the chemical shift multiplets. This resulting data acquisition scheme requires additional processing of time domain data, the so called "G-matrix" transformation. Hence, the acronym "GFT" indicates a combined G-matrix and Fourier transformation.

The phase-sensitive joint sampling of several indirect dimensions of a high-dimensional NMR experiment requires that the spectral width, $SW_{GFT}$, in the resulting combined "GFT-dimension" is set to $SW_{GFT} = \Sigma \kappa_j SW_j$, where $SW_j$ and $\kappa_j$ represent, respectively, the jth spectral width and the factor to scale the sampling increments of the jth dimension, which enable adjustment for maximal evolution times (Kim et al., *J. Am. Chem. Soc.* 125:1385-1393 (2003)). As a result, the "sampling demand" increases only linearly when dimensions are added for joint sampling, that is, the minimal measurement time of a GFT NMR experiment scales with the sum of the number of complex points required to sample the individual dimensions. In sharp contrast, the minimal measurement time of a conventional multidimensional NMR scales with the product of the number of complex points. Hence, employment of GFT NMR makes it possible to reduce measurement times by about an order of magnitude for each dimension that is being added to the joint sampling scheme.

As described in Szyperski et al., *J. Biomol. NMR* 3:127-132 (1993), Szyperski et al., *J. Am. Chem. Soc.* 115:9307 (1993), Szyperski et al., *J. Magn. Reson.* B105:188-191 (1994), and Szyperski et al., *J. Magn. Reson.* B108:197-203 (1995), RD NMR yields doublets ("peak pairs") that arise from the joint sampling of two chemical shift evolution periods. In GFT NMR, the joint sampling of several shift evolution periods generates more complicated multiplet structures, which were named "chemical shift multiplets" (Kim et al., *J. Am. Chem. Soc.* 125:1385-1393 (2003)). If all projected shifts are measured in a cosine-modulated fashion, the components of the chemical shift multiplet are all inphase. Depending on which and how many shifts are measured in a sine-modulated manner, various components become antiphase. Recording of all combinations of cosine and sine modulations then allows the components of the shift multiplet to be edited into subspectra. In particular, G-matrix transformation enables this editing to be performed in the time domain. This is advantageous when linear prediction of time domain data is applied, because the S/N for each multiplet component is increased while a single component remains after editing for each subspectrum.

The GFT NMR formalism embodies a generally applicable NMR data acquisition scheme (Kim et al., *J. Am. Chem. Soc.* 125:1385-1393 (2003)). If m=K+1 chemical shift evolution periods of an ND experiment are jointly sampled in a single indirect GFT dimension, $2^m-1$ different (N-K)D spectra represent the GFT NMR experiment containing the information of the parent ND experiment. Hence, such a set of $2^m-1$ subspectra is named an (N,N-K)D GFT NMR experiment. For example, a (5,2)D HACACONHN GFT NMR experiment can be recorded for a 8.6 kDa protein with four scans per real increment in 138 minutes, i.e., the minimal measurement time with a single scan per increment amounts to 33 minutes. In contrast, a conventional 5D HACACONHN NMR sampled with $10(t_1/^1H^\alpha) \times 11(t_2/^{13}C^\alpha) \times 22(t_3/^{13}C') \times 13(t_4/^{15}N) \times 512$ $(t_5/^1HN)$ complex data points would have required 5.8 days of spectrometer time with a single scan per real data point. Thus, a 250-fold reduction in minimal measurement time could be achieved with GFT NMR. Moreover, the processed (5,2)D HACACONHN frequency domain data have a total size of 16 MByte, while a hypothetical 5D spectrum with the same digital resolution would represent a file of 618 GByte. Hence, employment of GFT NMR allows accurate adaptation of measurement times without sacrificing digital resolution.

Chemical shifts are multiply encoded in the shift multiplets registered in GFT NMR experiments. This corresponds to performing statistically independent multiple measurements, so that the chemical shifts can be obtained with high precision (Kim et al., *J. Am. Chem. Soc.* 125:1385-1393 (2003); Kim et al., *J. Biomol. NMR* 28:117-130 (2004)). Moreover, the well-defined peak pattern of the shift multiplets allows implementation of robust algorithms for peak picking (Moseley et al., *J. Magn. Reson.* 170:263-277 (2004)). Both features make GFT NMR highly amenable to automated analysis. Although GFT NMR has been shown to aid in high-throughput protein resonance assignments by enabling both fast and precise acquisition of high dimensional spectral information, spectral overlap can still hamper resonance assignments in large proteins.

NMR of Aromatic Rings in Protein

Aromatic amino acids in proteins have long attracted the attention of structural biologists due to their important role for the hydrophobic core. From structural studies using NMR spectroscopy, it is known that (i) aromatic rings in the molecular core provide a large number of crucial $^1H$—$^1H$ nuclear Overhauser effects (NOEs) required for obtaining a high-quality structure (Wüthrich, *NMR of Proteins and Nucleic Acids* Wiley: New York (1986); Smith et al., *J. Biomol. NMR* 8:360-368 (1996); Aghazadeh et al., *Nature Struct. Biol.* 5:1098-1107 (1998); Clore et al., *J. Am. Chem. Soc.* 121:6513-6514 (1999); Medek et al., *J. Biomol. NMR* 18:229-238 (2000); Shen et al., *J. Am. Chem. Soc.* 127:9085-9099 (2005)) and that (ii) aromatic rings flip about the $\chi^2$-angle (Wagner, *Quat. Rev. Biophys.* 16:1-57 (1983)). The flipping of the rings in the close-packed interior of a protein requires large movements of the surrounding atoms and, thus, provides invaluable information on larger-amplitude motional modes and protein dynamics (Skalicky et al., *J. Am. Chem. Soc.* 123:388-397 (2001)). Hence, sequence specific NMR assignment of aromatic resonances in proteins is of central importance for NMR-based structural studies.

Prior to the advent of multidimensional NMR spectroscopy, assignments of aromatic rings relied on combined use of one-dimensional (1D) spin decoupling experiments (Wagner et al., *J. Magn. Reson.* 20:565-569 (1975)), selective chemical modification (Snyder et al., *Biochemistry* 14:3765-3777 (1975)), or comparison of spectra of homologous proteins (Wagner et al., *Eur. J. Biochem.* 89:367-377 (1978)). Subsequently, the introduction of 2D [$^1H$, $^1H$]-NOESY and COSY facilitated resonance assignments in unlabeled proteins. An important addition was 2D [$^{13}C$, $^1H$] COSY and 2D [$^{13}C$, $^1H$] relayed COSY (Brühwiler et al., *J. Magn. Reson.* 69:546-551 (1986); Wagner et al., *Biochemistry* 25:5839-5843 (1986)), which provided higher resolution for the $^1H$ lines of aromatic rings (Wagner et al., *J. Mol. Biol.* 196 :227-231 (1987)) and which were typically acquired at natural $^{13}C$ abundance. However, these techniques were limited to small proteins (molecular weight <10 kDa). For proteins containing a large numbers of aromatic residues, spectral overlap in 2D renders complete assignment of the aromatic resonances difficult or impossible.

With the advent of $^{13}C/^{15}N$ isotope labeling of proteins, numerous additional multidimensional NMR experiments for the assignment of aromatic rings have been proposed (Kay et al., *J. Magn. Reson.* B101:333-337 (1993); Yamazaki et al., *J. Am. Chem. Soc.* 115:11054-11055 (1993); Grzesiek et al., *J. Am. Chem. Soc.* 117:6527-6531 (1995); Zerbe et al., *J. Biomol. NMR* 7:99-106 (1996); Carlomagno et al., *J. Biomol. NMR* 8:161-170 (1996); Löhr et al., *J. Magn. Reson.* B112: 259-268 (1996); Whitehead et al., *J. Biomol. NMR* 9:313-316 (1997); Prompers et al., *J. Magn. Reson.* 130:68-75 (1998); Löhr et al., *J. Biomol. NMR* 22:153-164 (2002)). The most commonly used approach is to first obtain spin system assignments within the aromatic rings using one-bond scalar couplings, followed by use of 3D/4D heteronuclear resolved [$^1H$, $^1H$]-NOESY for linking the aromatic resonances to those of the aliphatic side-chain moieties (Cavanagh et al., *Protein NMR Spectroscopy: Principles and Practice* Academic Press: San Diego (1996)). Alternatively, scalar couplings can be used to connect aliphatic and aromatic spins via $^{13}C^\gamma$ spins (Yamazaki et al., *J. Am. Chem. Soc.* 115:11054-11055 (1993); Löhr et al., *J. Magn. Reson.* B112:259-268 (1996); Prompers et al., *J. Magn. Reson.* 130:68-75 (1998)). In parallel, novel isotope labeling strategies have been developed for aromatic rings which alleviate the loss of sensitivity due to broad $^1H$ lines and passive $^{13}C$-$^{13}C$ couplings. These include the reverse labeling scheme (Vuister et al., *J. Am. Chem. Soc.* 116:9206-9210 (1994)), atom-type specific labeling (Wang et al., *J. Am. Chem. Soc.* 121:1611-1612 (1999)), biosynthetically directed fractional $^{13}C$-labeling (Szyperski et al., *J. Biomol. NMR* 2:323-334 (1992); Jacob et al., *J. Biomol. NMR* 24:231-235 (2002)), and selective protonation of aromatic rings in an otherwise fully deuterated protein (Rajesh et al., *J. Biomol. NMR* 27:81-86 (2003)).

For large proteins, HCCH spectroscopy, first introduced for aliphatic side-chain assignments (Kay et al., *J. Am. Chem. Soc.* 112:888-889 (1990)), has emerged as an efficient means to accomplish aromatic spin system identification. Experiments in this class include 3D (H)CCH and 3D H(C)CH (Cavanagh et al., *Protein NMR Spectroscopy: Principles and Practice* Academic Press: San Diego (1996)). Their combination with TROSY (Pervushin et al., *Proc. Natl. Acad. Sci. USA* 94:12366-12371 (1997)) has been shown to yield higher sensitivity (Pervushin et al., *J. Am. Chem. Soc.* 120:6394-6400 (1998); Meissner et al., *J. Magn. Reson.* 139:447-450 (1999)), thereby extending the molecular weight limit of proteins accessible to these experiments (i.e., for proteins in the "sensitivity-limited" regime (Szyperski et al., *Proc. Natl. Acad. Sci. USA* 99:8009-8014 (2002)). However, HCCH-type experiments suffer from the comparably low dispersion of aromatic $^{13}C/^1H$ shifts, making it advantageous to use 4D HCCH (note that good spectral resolution is also important for exploring aromatic ring flipping since accurate linewidths need to be measured (Skalicky et al., *J. Am. Chem. Soc.* 123:388-397 (2001)). The 4D experiments would, however, lead to increased minimal measurement times which may lead to sampling-limited data acquisition (Szyperski et al., *Proc. Natl. Acad. Sci. USA* 99:8009-8014 (2002)). Thus, an implementation that provides 4D information while being suited for both sensitivity and sampling limited data collection has not been available.

Nuclear Overhauser Effect Spectroscopy (NOESY)

Efficient NMR-based protein structure determination (Wüthrich, *NMR of Proteins and Nucleic Acids* Wiley: New York (1986)) relies on measurement of nuclear Overhauser effects (NOEs), which yield $^1H$-$^1H$ upper distance limit constraints. The assignment of NOEs quite generally depends on having (nearly) complete resonance assignments (Wüthrich, *NMR of Proteins and Nucleic Acids* Wiley: New York (1986); Cavanagh et al., *Protein NMR Spectroscopy* Academic Press: San Diego (1996)). However, due to the degeneracy of chemical shifts, the NOE assignment remains a non-trivial task even when complete resonance assignments are available. Nowadays, two approaches are routinely used to solve this "NOE assignment problem". First, proteins are $^{15}N/^{13}C$ double labeled (Kainosho, *Nature Struc. Biol.* 4:858-861 (1997); Acton, *Methods Enzymol.* 394:210-243 (2005)) so that NOEs can be measured in 3D $^{15}N$- or $^{13}C$-resolved [$^1H$, $^1H$]-NOE spectroscopy (NOESY) (Cavanagh et al., *Protein NMR Spectroscopy* Academic Press: San Diego (1996)). Dispersing NOE signals in a third dimension, which encodes a $^{13}C$ or a $^{15}N$ shift, typically allows one to assign for medium-sized proteins ~15-25% of the NOEs directly based on chemical shift data (compared to only a few percent in 2D [$^1H$, $^1H$]-NOESY (Wüthrich, *NMR of Proteins and Nucleic Acids* Wiley: New York (1986); Cavanagh et al., *Protein NMR Spectroscopy*, Academic Press: San Diego (1996)). Second, an initial structure is calculated which is used in conjunction with the chemical shifts to assign additional NOEs. Several such cycles of structure calculation and NOE assignment are usually performed iteratively until a refined structure is obtained.

Importantly, inaccuracies in the initial fold arising from incorrectly assigned NOEs may result in the mis-assignment of additional NOEs. Hence, proper convergence of the NMR structure determination depends on obtaining an appropriately accurate initial structure, i.e., it is advantageous if the bundle of conformers representing the initial solution structure covers a conformational subspace which overlaps with that of the refined ensemble of conformers. This requirement constitutes a key challenge for reliable automated NOE assignment (Güntert, *Prog. NMR Spectroscopy* 43:105-125 (2003); Baran et al., *Chem. Reviews* 104:3451-3455 (2004); Huang et al., *Methods Enzymol.* 394:111-141 (2005)) and, thus, also for the development of a robust and scalable platform for high-throughput structure determination in structural genomics (Montelione et al., *Nature Struc. Biol.* 7:982-984 (2000); Yee et al., *Proc. Natl. Acad. Sci. USA* 99:1825-1830 (2002)). Several programs have been established to automatically obtain accurate initial folds (Güntert, *Prog. NMR Spectroscopy* 43:105-125 (2003); Baran et al., *Chem. Reviews* 104:3451-3455 (2004); Huang et al., *Methods Enzymol.* 394:111-141 (2005)). Among those are AutoStructure (Moseley et al., *Methods Enzymol.* 339:91-108 (2001); Huang et al., *J. Mol. Biol.* 327:521-536 (2003); Huang et al., *J. Am. Chem. Soc.* 127:1665-1674 (2005)) and CYANA (Güntert et al., *J. Mol. Biol.* 273:283-298 (1997); Herrmann et al., *J. Mol. Biol.* 319:209-227 (2002); Güntert, *Methods Mol. Biol.* 278:347-372 (2004)), both of which are widely used. Conceptually, AutoStructure mimics the approach an expert usually takes when solving a structure manually. The initial fold is generated based on (i) intraresidue, sequential, and medium-range NOEs considering NOE patterns of secondary structure, and (ii) unique long-range packing constraints. In contrast, CYANA relies on NOE network-anchoring and combination of (ambiguous) upper distance limit constraints. This led Montelione et al. to classify the AutoStructure and CYANA approaches as being "bottom-up" and "top-down", respectively (Baran et al., *Chem. Reviews* 104:3451-3455 (2004)). Since the two programs use distinctly different algorithms, their coupled operation aiming at a consensus NOE assignment promises to further increase the reliability of initial structure calculations.

In the early 1990s, before the more sophisticated computational techniques (Güntert, *Prog. NMR Spectroscopy* 43:105-125 (2003); Baran et al., *Chem. Reviews* 104:3451-3455 (2004); Huang et al., *Methods Enzymol.* 394:111-141 (2005)) mentioned above were established, researchers devised 4D heteronuclear resolved [$^1H$, $^1H$]-NOESY and explored its impact for NMR structure determination of proteins (Kay et al., *Science* 249:411-414 (1990); Clore et al., *Biochemistry* 30:12-18 (1991); Fairbrother et al., *Biochemistry* 31:4413-4425 (1992); Grzesiek et al., *Biochemistry* 31:8180-8190 (1992); Archer et al., *Biochemistry* 32:6680-6687 (1993); Vuister et al., *J. Magn. Reson.* B101:210-213 (1993)). Such 4D NOESY represents a straightforward and robust approach to tackle the "initial fold problem"; dispersing signals in a fourth dimension enables one to assign the majority of NOEs directly based on chemical shift data. This may yield a highly accurate initial structure so that fast and reliable convergence of the structure determination can be accomplished. However, 4D NOESY suffers from two major drawbacks, which gave a competitive edge to computational methods in recent years. First, an additional heteronuclear polarization transfer needs to be inserted in the radiofrequency (r.f.) pulse scheme. This leads to additional losses arising from transverse relaxation and tends to limit the use of 4D NOESY to small and medium-sized proteins. Second, conventional sampling of three indirect dimensions leads to long (minimal) measurement times. Typically, several days to a week are required to collect a single data set, even when accepting comparably short maximal evolution times (which limits the spectral resolution). This drawback is further exacerbated if a (minimal) radiofrequency (r.f.) phase cycle is employed for artefact suppression (Cavanagh et al., *Protein NMR Spectroscopy* Academic Press: San Diego (1996)).

The first drawback of 4D NOESY, i.e., its low sensitivity, has been significantly alleviated by the commercial introduction of cryogenic NMR probes (Styles et al., *Magn. Reson.* 60:397-404 (1994)), which routinely deliver about three-fold higher sensitivity compared to conventional probes (Monleon et al., *J. Struc. Func. Genomics* 2:93-101 (2002)). Among the various options (Atreya et al., *Methods Enzymol.* 394:78-108 (2005)) to reduce the long minimal measurement times of heteronuclear NOESY, simultaneous ("time-shared") acquisition of $^{15}N$- and $^{13}C$-resolved NOESY (Farmer et al., *J. Biomol. NMR* 4:673-687 (1994); Pascal et al., *J. Magn. Reson.* 103:197-201 (1994); Jerala et al., *J. Magn. Reson.* B108:294-298 (1995); Uhrin et al., *J. Biomol. NMR* 18:253-259 (2000); Xia et al., *J. Biomol. NMR* 27:193-203 (2003)), extensive signal aliasing (Morshauser et al., *J. Magn. Reson.* 139:232-239 (1999)), and the employment of the RD approach (Szyperski et al., *J. Am. Chem. Soc.* 115:9307-9308 (1993); Szyperski et al., *J. Magn. Reson.* B105:188-191 (1994); Brutscher et al., *J. Magn. Reson.* B105:77-82 (1994); Szyperski et al., *J. Magn. Reson.* B108:197-203 (1995); Szyperski et al., *J. Am. Chem. Soc.* 118:8146-8147 (1996); Szyperski et al., *J. Biomol. NMR* 11:387-405 (1998); Szyperski et al., *Proc. Natl. Acad. Sci. USA* 99:8009-8014 (2002)) have been proposed (Brutscher et al., *J. Magn. Reson.* B109: 397404 (1995); Kupce et al., *J. Magn. Reson.* 172:330-333 (2004)). (Notably, rapid sampling techniques based on shortening of the relaxation delay between scans, such as longitudinal relaxation optimization (Pervushin et al., *J. Am. Chem. Soc.* 124:12898-12902 (2002); Atreya et al., *Proc. Natl. Acad. Sci. USA* 101:9642-9647 (2004)), are not well-suited for NOESY; it is desirable to keep $^1$H steady state magnetization close to its thermal equilibrium value in order to avoid an extensive modulation of NOE by $T_1(^1H)$ relaxation.)

Residual Dipolar Couplings

Residual dipolar couplings (RDC) are valuable NMR parameters yielding "orientational" constraints (Prestegard, *Nat. Struct. Biol.* 5:517-522 (1998)) to study biological macromolecules in solution; RDCs are used for (i) refining and validating NMR solution structures of single domain proteins (Tolman et al., *Proc. Natl. Acad. Sci. USA* 92:9279-9283 (1995); Tjandra et al., *Science* 278:1111-1114 (1997); Tolman, *Curr. Opin. Struc. Biol.* 11:532-539 (2001); Bax, *Protein Sci.* 12:1-16 (2003); Lipsitz et al., *Ann. Rev. Biophys. Biomol. Struct.* 33:387-413 (2004); Prestegard et al., *Chem. Rev.* 104:3519-3540 (2004)), (ii) determining the relative orientation of domains in multi-domain proteins and proteins in macromolecular complexes (Dosset et al., *J. Biomol. NMR* 20:223-231 (2001); Jain et al., *J. Mol. Biol.* 343:1379-1389 (2004)), (iii) determining the tertiary fold of a protein when only sparse nuclear Overhauser enhancement (NOE) derived distance constraint networks (Wüthrich, *NMR of Proteins and Nucleic Acids* Wiley: New York, N.Y. (1986)) can be obtained (Delaglio et al., *J. Am. Chem. Soc.* 122:2142-2143 (2000); Fowler et al., *J. Mol. Biol.* 304:447-460 (2000); Mueller et al. *J. Mol. Biol.* 300:197-212 (2000); Andrec et al., *J. Biomol. NMR* 21:335-347 (2001); Hus et al., *J. Am. Chem. Soc.* 123: 1541-1542 (2001); Rohl et al., *J. Am. Chem. Soc.* 124:2723-2729 (2002); Giesen et al., *J. Biomol. NMR* 25:63-71 (2003)), (iv) supporting the resonance assignment of proteins (Tian et al., *J. Am. Chem. Soc.* 123:11791-11796 (2001); Zweckstetter et al., *J. Am. Chem. Soc.* 123:9490-9491 (2001); Jung et al., *J. Biomol. NMR* 30:25-35 (2004)), and (v) elucidating protein dynamics (Tolman et al., *Nat. Struct. Biol.* 4:292-297 (1997); Tolman et al., *J. Am. Chem. Soc.* 123:1416-1424 (2001); Meiler et al., *J. Am. Chem. Soc.* 125:8072-8073 (2003)). Since RDC-derived structural constraints can be obtained rapidly, they are also attractive for structural genomics (Montelione et al., *Nat. Struc. Biol.* 7:982-984 (2000)). A dense set of orientational constraints can be obtained if different types of RDCs are considered [for example, $^{13}C^\alpha$—$^1H^\alpha$ ($^1D_{CH}$), $^{15}N$—$^1H^N$ ($^1D_{NH}$), or $^{15}N$—$^{13}C'$ ($^1D_{NC'}$) couplings]. The tightness of the constraints used for structure calculations depends on (i) the absence of systematic errors that may arise from varying conditions present during NMR data acquisition for the different types of couplings, (ii) the proper identification and assessment of internal motional modes which partially average RDCs (Tolman et al., *J. Am. Chem. Soc.* 123:1416-1424 (2001); Peti et al., *J. Am. Chem. Soc.* 124: 5822-5833 (2002), and (iii) evidently the precision of the RDC measurement per se (Tolman et al., *Proc. Natl. Acad. Sci. USA* 92:9279-9283 (1995); Tjandra et al., *Science* 278: 1111-1114 (1997); Tolman et al., *J. Am. Chem. Soc.* 123: 1416-1424 (2001); Bax, *Protein Sci.* 12:1-16 (2003); Lipsitz et al., *Ann. Rev. Biophys. Biomol. Struct.* 33:387-413 (2004); Prestegard et al., *Chem. Rev.* 104:3519-3540 (2004)).

To minimize systematic errors, it is desirable to measure multiple RDCs simultaneously in a single experiment (Wang et al., *J. Am. Chem. Soc.* 120:7385-7386 (1998); de Alba et al., *J. Biomol. NMR* 19:63-67 (2001); Bersch et al., *J. Biomol. NMR* 27:57-67 (2003); Ding et al., *J. Am. Chem. Soc.* 125: 11504-11505 (2003); Permi, *J. Biomol. NMR* 27:341-349 (2003); Wienk et al., *J. Biomol. NMR* 25:133-145 (2003); Hoshino et al., *J. Magn. Reson.* 171:270-276 (2004); Vijayan et al., *J. Magn. Reson.* 174:245-253 (2005)); this ensures that all couplings are obtained with the same spectrometer set-up and radiofrequency (r.f.) pulse duty cycle. In addition, it would be advantageous to mutually correlate all RDCs and chemical shifts belonging to a given covalent moiety, thereby breaking chemical shift degeneracy. Frequency labeling in a second indirect dimension to disperse signals is then not required, and large sets of unambiguously grouped RDCs can be obtained from two-dimensional (2D) plans exhibiting very high resolution in the indirect dimension. Notably, the shorter minimal measurement times of 2D versus 3D NMR approaches are advantageous when data need to be collected for slowly precipitating aligned protein samples; the different types of couplings, if measured separately, may turn out to be inconsistent with a single alignment tensor (Tolman et al., *Proc. Natl. Acad. Sci. USA* 92:9279-9283 (1995); Tjandra et al., *Science* 278:1111-1114 (1997); Tolman, *Curr. Opin. Struc. Biol.* 11:532-539 (2001); Bax, *Protein Sci.* 12:1-16 (2003); Lipsitz et al., *Ann. Rev. Biophys. Biomol. Struct.* 33:387-413 (2004); Prestegard et al., *Chem. Rev.* 104:3519-3540 (2004)).

Simultaneous measurement of RDCs has been implemented using spin state separation/selection (IPAP (Ottiger et al., *J. Magn. Reson.* 131:373-378 (1998)), $S^3E/S^3CT$ (Meissner et al., *J. Magn. Reson.* 128:92-97 (1997); Sørensen et al., *J. Biomol. NMR* 10:181-186 (1997)), α/β selection (Andersson et al., *J. Biomol. NMR* 12:435-441 (1998)) in the indirect dimension in conjunction with E.COSY-type (Andersson et al., *J. Biomol. NMR* 12:435-441 (1998); Montelione et al., *J. Am. Chem. Soc.* 111:5474-5475 (1989)) techniques, while TROSY (Pervushin et al., *Proc. Natl. Acad. Sci. USA* 94:12366-12371 (1997)) can be used to increase the precision of the measurements (Permi, *J. Biomol. NMR* 27:341-349 (2003); Wienk et al., *J. Biomol. NMR* 25:133-145 (2003); Hoshino et al., *J. Magn. Reson.* 171:270-276 (2004)). These experiments suffer, however, from several drawbacks, which are exacerbated if multiple RDCs shall be measured simultaneously: (i) The creation of anti-phase magnetization for spin state separation requires an additional delay (Andersson et al., *J. Biomol. NMR* 12:435-441 (1998); Ottiger et al., *J. Magn. Reson.* 131:373-378 (1998)) and results in reduced sensitivity due to transverse relaxation; (ii) In-phase and anti-phase magnetization components relax differentially so that spectral artifacts arise from spin state selection/separation (Ottiger et al., *J. Magn. Reson.* 131:373-378 (1998)); (iii) When multiple RDCs evolve simultaneously in a non-constant time (Cavanagh et al., *Protein NMR Spectroscopy* Academic Press: San Diego, Calif. (1996)) fashion, the resulting signals are broadened since transverse relaxation rates add up (Kontaxis et al., *J. Magn. Reson.* 143:184-196 (2004)). This limits the precision of simultaneous RDC measurements significantly.

The present invention is directed to overcoming the above-noted deficiencies in the art.

SUMMARY OF THE INVENTION

The present invention relates to a method of conducting a (5,3) dimensional (D) [HN{N,CO}{$C^{\alpha\beta}C^{\alpha}$}] G-matrix Fourier transformation (GFT) nuclear magnetic resonance (NMR) experiment. (This experiment is also referred to as a "G²FT (5,3) [HN{N,CO}{$C^{\alpha\beta}C^{\alpha}$}]NMR experiment" throughout this patent application.) The method involves providing a sample, where the sample is a protein molecule having two consecutive amino acid residues, i−1 and i, and the chemical shift values for the following nuclei are measured: (1) α- and β-carbons of amino acid residues i and i−1, $^{13}C^{\alpha/\beta}{}_{i/i-1}$; (2) a polypeptide backbone amide nitrogen of amino acid residue i, $^{15}N_i$; (3) a polypeptide backbone carbonyl carbon of amino acid residue i−1, $^{13}C'_{i-1}$; and (4) a polypeptide backbone amide proton of amino acid residue i, $^1H^N{}_i$. Next, radiofrequency pulses for a 5D FT NMR experiment are applied to the sample. Then, a first set of 2 indirect chemical shift evolution periods of the 5D FT NMR experiment, $^{13}C^{\alpha/\beta}{}_{i/i-1}$ and $^{13}C^{\alpha}{}_{i/i-1}$, is selected. Next, the first set of 2 indirect chemical shift evolution periods is jointly sampled in a first indirect time domain dimension, $t_1(^{13}C^{\alpha/\beta}{}_{i/i-1}, ^{13}C^{\alpha}{}_{i/i-1})$. Then, a second set of 2 indirect chemical shift evolution periods of the 5D FT NMR experiment, $^{15}N_i$ and $^{13}C'_{i-1}$, is selected. Next, the second set of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^{13}C^{\alpha/\beta}, ^{13}C^{\alpha})$, giving rise to 2 chemical shift doublet components in a second frequency domain dimension, $\omega_2(^{15}N, ^{13}C')$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components.

Another aspect of the present invention relates to a method of conducting a (5,3) dimensional (D) [HN{NCO}{$C^{\alpha\alpha}C^{\alpha}$}] G-matrix Fourier transformation (GFT) nuclear magnetic resonance (NMR) experiment. (This experiment is also referred to as a "G²FT (5,3) [HN{NCO}{$C^{\alpha\beta}C^{\alpha}$}]NMR experiment" throughout this patent application.) The method involves providing a sample, where the sample is a protein molecule having two consecutive amino acid residues, i−1 and i, and the chemical shift values for the following nuclei are measured: (1) α- and β-carbons of amino acid residue i−1, $^{13}C^{\alpha/\beta}{}_{i-1}$; (2) a polypeptide backbone amide nitrogen of amino acid residue i, $^{15}N_i$; (3) a polypeptide backbone carbonyl carbon of amino acid residue i−1, $^{13}C'_{i-1}$; and (4) a polypeptide backbone amide proton of amino acid residue i, $^1H^N{}_i$. Next, radio frequency pulses for a 5D FT NMR experiment are applied to the sample. Then, a first set of 2 indirect chemical shift evolution periods of the 5D FT NMR experiment, $^{13}C^{\alpha/\beta}{}_{i-1}$ and $^{13}C^{\alpha}{}_{i-1}$, is selected. Next, the first set of 2 indirect chemical shift evolution periods is jointly sampled in a first indirect time domain dimension, $t_1(^{13}C^{\alpha/\beta}{}_{i-1}, ^{13}C^{\alpha}{}_{i-1})$. Then, a second set of 2 indirect chemical shift evolution periods of the 5D FT NMR experiment, $^{15}N_i$ and $^{13}C'_{i-1}$, is selected. Next, the second set of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^{13}C^{\alpha/\beta}, ^{13}C^{\alpha})$, giving rise to 2 chemical shift doublet components in a second frequency domain dimension, $\omega_2(^{15}N, ^{13}C')$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components.

Another aspect of the present invention relates to a method of conducting a (5,3) dimensional (D) [HN{$NC^{\alpha}$}{$C^{\alpha\beta}C^{\alpha}$}] G-matrix Fourier transformation (GFT) nuclear magnetic resonance (NMR) experiment. (This experiment is also referred to as a "G²FT (5,3) [HN{$NC^{\alpha}$}{$C^{\alpha\beta}C^{\alpha}$}] NMR experiment" throughout this patent application.) The method involves providing a sample, where the sample is a protein molecule having two consecutive amino acid residues, i−1 and i, and the chemical shift values for the following nuclei are measured: (1) α- and β-carbons of amino acid residue i and i−1, $^{13}C^{\alpha/\beta}{}_{i/i-1}$; (2) a polypeptide backbone amide nitrogen of amino acid residue i, $^{15}N_i$; and (3) a polypeptide backbone amide proton of amino acid residue i, $^1H^N{}_i$. Next, radiofrequency pulses for a 5D FT NMR experiment are applied to the sample. Then, a first set of 2 indirect chemical shift evolution periods of the 5D FT NMR experiment, $^{13}C^{\alpha/\beta}{}_{i/i-1}$ and $^{13}C^{\alpha}{}_{i/i-1}$, is selected. Next, the first set of 2 indirect chemical shift evolution periods is jointly sampled in a first indirect time domain dimension, $t_1(^{13}C^{\alpha/\beta}{}_{i/i-1}, ^{13}C^{\alpha}{}_{i/i-1})$. Then, a second set of 2 indirect chemical shift evolution periods of the 5D FT NMR experiment, $^{15}N_i$ and $^{13}C^{\alpha}{}_{i/i-1}$, is selected. Next, the second set of 2 indirect chemical shift evolution periods is jointly sampled in a second indirect time domain dimension, $t_2(^{15}N_i, ^{13}C^{\alpha}{}_{i/i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^{13}C^{\alpha/\beta}, ^{13}C^{\alpha})$, giving rise to 2 chemical shift doublet components in a second frequency domain dimension, $\omega_2(^{15}N, ^{13}C^{\alpha})$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components.

Another aspect of the present invention relates to a method of conducting a (5,3) dimensional (D) [HN{$N(CO)C^{\alpha}$}{$C^{\alpha\beta}C^{\alpha}$}] G-matrix Fourier transformation (GFT) nuclear magnetic resonance (NMR) experiment. (This experiment is also referred to as a "G²FT (5,3) [HN{$N(CO)C^{\alpha}$}{$C^{\alpha\beta}C^{\alpha}$})]NMR experiment" throughout this patent application.) The method involves providing a sample, where the sample is a protein molecule having two consecutive amino acid residues, i−1 and i, and the chemical shift values for the following nuclei are measured: (1) α- and β-carbons of amino acid residue i−1, $^{13}C^{\alpha/\beta}{}_{i-1}$; (2) a polypeptide backbone amide nitrogen of amino acid residue i, $^{15}N_i$; and (3) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^{13}C^{\alpha/\beta}_{i-1}$ and $^{13}C^{\alpha}_{i-1}$, is selected. Next, the first set of 2 indirect chemical shift evolution periods is jointly sampled in a first indirect time domain dimension, $t_1(^{13}C^{\alpha/\beta}_{i-1}, ^{13}C^{\alpha}_{i-1})$. Then, a second set of 2 indirect chemical shift evolution periods of the 5D FT NMR experiment, $^{15}N_i$ and $^{13}C^{\alpha}_{i-1}$, is selected. Next, the second set of 2 indirect chemical shift evolution periods is jointly sampled in a second indirect time domain dimension, $t_2(^{15}N_i, ^{13}C^{\alpha}_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^{13}C^{\alpha/\beta}, ^{13}C^{\alpha})$, giving rise to 2 chemical shift doublet components in a second frequency domain dimension, $\omega_2(^{15}N, ^{13}C^{\alpha})$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components.

Another aspect of the present invention relates to a method of conducting a (5,3) dimensional (D) [HN{N,CO}{C$^\alpha$H$^\alpha$}] G-matrix Fourier transformation (GFT) nuclear magnetic resonance (NMR) experiment. (This experiment is also referred to as a "G$^2$FT (5,3) [HN{N,CO}{C$^\alpha$H$^\alpha$}]NMR experiment" throughout this patent application.) The method involves providing a sample, where the sample is a protein molecule having two consecutive amino acid residues, i−1 and i, and the chemical shift values for the following nuclei are measured: (1) (α-carbon of amino acid residues i and i−1, $^{13}C^{\alpha}_{i/i-1}$; (2) α-proton of amino acid residues i and i−1, $^1H^{\alpha}_{i/i-1}$; (3) a polypeptide backbone amide nitrogen of amino acid residue i, $^{15}N_i$; (4) a polypeptide backbone carbonyl carbon of amino acid residue i−1, $^{13}C'_{i-1}$; and (5) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^1H^{\alpha}_{i/i-1}$ and $^{13}C^{\alpha}_{i/i-1}$, is selected. Next, the first set of 2 indirect chemical shift evolution periods is jointly sampled in a first indirect time domain dimension, $t_1(^1H^{\alpha}_{i/i-1}, ^{13}C^{\alpha}_{i/i-1})$. Then, a second set of 2 indirect chemical shift evolution periods of the 5D FT NMR experiment, $^{15}N_i$ and $^{13}C'_{i-1}$, is selected. Next, the second set of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^1H^{\alpha}, ^{13}C^{\alpha})$, giving rise to 2 chemical shift doublet components in a second frequency domain dimension, $\omega_2(^{15}N, ^{13}C')$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components.

Another aspect of the present invention relates to a method of conducting a (5,3) dimensional (D) [{H$^\alpha$C$^\alpha$}{CON}HN] G-matrix Fourier transformation (GFT) nuclear magnetic resonance (NMR) experiment. (This experiment is also referred to as a "G$^2$FT (5,3) [{H$^\alpha$C$^\alpha$}{CON}HN]NMR experiment" throughout this patent application.) The method involves providing a sample, where the sample is a protein molecule having two consecutive amino acid residues, i−1 and i, and the chemical shift values for the following nuclei are measured: (1) α-carbon of amino acid residue i−1, $^{13}C^{\alpha}_{i-1}$; (2) α-proton of amino acid residue i−1, $^1H^{\alpha}_{i-1}$; (3) a polypeptide backbone amide nitrogen of amino acid residue i, $^{15}N_i$; (4) a polypeptide backbone carbonyl carbon of amino acid residue i−1, $^{13}C'_{i-1}$; and (5) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^1H^{\alpha}_{i-1}$ and $^{13}C^{\alpha}_{i-1}$, is selected. Next, the first set of 2 indirect chemical shift evolution periods is jointly sampled in a first indirect time domain dimension, $t_1(^1H^{\alpha}_{i-1}, ^{13}C^{\alpha}_{i-1})$. Then, a second set of 2 indirect chemical shift evolution periods of the 5D FT NMR experiment, $^{15}N_i$ and $^{13}C'_{i-1}$, is selected. Next, the second set of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^1H^{\alpha}, ^{13}C^{\alpha})$, giving rise to 2 chemical shift doublet components in a second frequency domain dimension, $\omega_2(^{15}N, ^{13}C')$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components.

Another aspect of the present invention relates to a method of conducting a (6,3) dimensional (D) [{H$^{\alpha\beta}$C$^{\alpha\beta}$C$^\alpha$}{CON}HN] G-matrix Fourier transformation (GFT) nuclear magnetic resonance (NMR) experiment. (This experiment is also referred to as a "G$^2$FT (6,3) [{H$^{\alpha\beta}$C$^{\alpha\beta}$C$^\alpha$}{CON}HN]NMR experiment" throughout this patent application.) The method involves providing a sample, where the sample is a protein molecule having two consecutive amino acid residues, i−1 and i, and the chemical shift values for the following nuclei are measured: (1) α- and β-carbons of amino acid residue i−1, $^{13}C^{\alpha/\beta}_{i-1}$; (2) α- and β-protons of amino acid residue i−1, $^1H^{\alpha/\beta}_{i-1}$; (3) a polypeptide backbone carbonyl carbon of amino acid residue i−1, $^{13}C'_{i-1}$; (4) a polypeptide backbone amide nitrogen of amino acid residue i, $^{15}N_i$; and (5) a polypeptide backbone amide proton of amino acid residue i, $^1H^N_i$. Next, radiofrequency pulses for a 6D FT NMR experiment are applied to the sample. Then, a first group of 3 indirect chemical shift evolution periods of the 6D FT NMR experiment, $^1H^{\alpha/\beta}_{i-1}$, $^{13}C^{\alpha/\beta}_{i-1}$, and $^{13}C^{\alpha}_{i-1}$, is selected. Next, the first group of 3 indirect chemical shift evolution periods is jointly sampled in a first indirect time domain dimension, $t_1(^1H^{\alpha/\beta}_{i-1}, ^{13}C^{\alpha/\beta}_{i-1}, ^{13}C^{\alpha}_{i-1})$. Then, a second group of 2 indirect chemical shift evolution periods of the 6D FT NMR experiment, $^{15}N_i$ and $^{13}C'_{i-1}$, is selected. Next, the second group of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 8 components resulting from each of 4 chemical shift doublet components in a first frequency domain dimension, $\omega_1(^{13}C^{\alpha/\beta}, ^{13}C^{\alpha})$, giving rise to 2 chemical shift doublet components in a second frequency domain dimension, $\omega_2(^{15}N, ^{13}C')$, thereby enabling phase-sensitive sampling of all jointly sampled 5 indirect chemical shift evolution periods. Finally, the 3D basic NMR spectra are transformed into 3D phase-sensitively edited basic NMR spectra, where the 8 chemical shift multiplet components of the 3D basic NMR spectra are edited to yield 3D phase-sensitively edited basic NMR spectra having individual chemical shift multiplet components.

Yet another aspect of the present invention relates to a method of conducting a (5,3) dimensional (D) [HC(C)C—CH] G-matrix Fourier transformation (GFT) nuclear magnetic resonance (NMR) experiment. The method involves providing a sample, where the sample is a protein molecule and the chemical shift values for the following nuclei are measured: (1) a proton, $^1H$; (2) a carbon coupled to $^1H$, $^{13}C$; (3) a carbon coupled, via another carbon, to $^{13}C$, $^{13}C^{coupled}$; and (4) a proton coupled to $^{13}C^{coupled}$, $^1H^{coupled}$, where the chemical shift of $^{13}C^{coupled}$ provides signal dispersion in an indirect dimension. Next, radiofrequency pulses for a 5D FT NMR experiment are applied to the sample. Then, 3 indirect chemical shift evolution periods of the 5D FT NMR experiment, $^1H$, $^{13}C$, and $^{13}C^{coupled}$, are selected. Next, the 3 indirect chemical shift evolution periods are jointly sampled in an indirect time domain dimension, $t_1(^1H, ^{13}C, ^{13}C^{coupled})$. Then, NMR signals detected in a direct dimension are independently cosine and sine modulated to generate 3D basic NMR spectra containing frequency domain signals with 4 chemical shift multiplet components, thereby enabling phase-sensitive sampling of all jointly sampled 3 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components.

The present invention also relates to a method of conducting a longitudinal aromatic proton relaxation optimized (4,3) dimensional (D) [HCCH] G-matrix Fourier transformation (GFT) nuclear magnetic resonance (NMR) experiment. The method involves providing a sample, where the sample is a protein molecule and the chemical shift values for the following nuclei are measured: (1) an aromatic proton, $^1H$; (2) an aromatic carbon coupled to $^1H$, $^{13}C$; (3) a carbon coupled to $^{13}C$, $^{13}C^{coupled}$; and (4) a proton coupled to $^{13}C^{coupled}$, $^1H^{coupled}$. Next, radiofrequency pulses for a 4D FT NMR experiment are applied to the sample, under conditions effective to allow longitudinal relaxation optimization of the aromatic protons. Then, 2 indirect chemical shift evolution periods of the 4D FT NMR experiment, $^1H$ and $^{13}C$, are selected. Next, the 2 indirect chemical shift evolution periods are jointly sampled in an indirect time domain dimension, $t_1(^1H, ^{13}C)$. Then, NMR signals detected in a direct dimension are independently cosine and sine modulated to generate 3D basic NMR spectra containing frequency domain signals with 2 chemical shift doublet components, thereby enabling phase-sensitive sampling of the jointly sampled 2 indirect chemical shift evolution periods. Finally, the 3D basic NMR spectra are transformed into 3D phase-sensitively edited basic NMR spectra, where the 2 chemical shift doublet components of the 3D basic NMR spectra are edited to yield 3D phase-sensitively edited basic NMR spectra having individual chemical shift doublet components.

Another aspect of the present invention relates to a method of conducting a longitudinal aromatic proton relaxation optimized (4,3) dimensional (D) [HCCH] G-matrix Fourier transformation (GFT) nuclear magnetic resonance (NMR) experiment. The method involves providing a sample, where the sample is a protein molecule and the chemical shift values for the following nuclei are measured: (1) an aromatic proton, $^1H$; (2) an aromatic carbon coupled to $^1H$, $^{13}C$; (3) a carbon coupled to $^{13}C$, $^{13}C^{coupled}$; and (4) a proton coupled to $^{13}C^{coupled}$, $^1H^{coupled}$. Next, radiofrequency pulses for a 4D FT NMR experiment are applied to the sample under conditions effective to allow longitudinal relaxation optimization of the aromatic protons. Then, 2 indirect chemical shift evolution periods of the 4D FT NMR experiment, $^{13}C$ and $^{13}C^{coupled}$, are selected. Next, the 2 indirect chemical shift evolution periods are jointly sampled in an indirect time domain dimension, $t_1(^{13}C, ^{13}C^{coupled})$. Then, NMR signals detected in a direct dimension are independently cosine and sine modulated to generate 3D basic NMR spectra containing frequency domain signals with 2 chemical shift doublet components, thereby enabling phase-sensitive sampling of the jointly sampled 2 indirect chemical shift evolution periods. Finally, the 3D basic NMR spectra are transformed into 3D phase-sensitively edited basic NMR spectra, where the 2 chemical shift doublet components of the 3D basic NMR spectra are edited to yield 3D phase-sensitively edited basic NMR spectra having individual chemical shift doublet components.

Another aspect of the present invention relates to a method of conducting a longitudinal aromatic proton relaxation optimized (4,3) dimensional (D) [HCCH] G-matrix Fourier transformation (GFT) nuclear magnetic resonance (NMR) experiment. The method involves providing a sample, where the sample is a protein molecule and the chemical shift values for the following nuclei are measured: (1) an aromatic proton, $^1H$; (2) an aromatic carbon coupled to $^1H$, $^{13}C$; (3) a carbon coupled to $^{13}C$, $^{13}C^{coupled}$; and (4) a proton coupled to $^{13}C^{coupled}$, $^1H^{coupled}$. Next, radiofrequency pulses for a 4D FT NMR experiment are applied to the sample under conditions effective to allow longitudinal relaxation optimization of the aromatic protons. Then, 2 indirect chemical shift evolution periods of the 4D FT NMR experiment, $^1H$ and $^{13}C^{coupled}$, are selected. Next, the 2 indirect chemical shift evolution periods are jointly sampled in an indirect time domain dimension, $t_1(^1H, ^{13}C^{coupled})$. Then, NMR signals detected in a direct dimension are independently cosine and sine modulated to generate 3D basic NMR spectra containing frequency domain signals with 2 chemical shift doublet components, thereby enabling phase-sensitive sampling of the jointly sampled 2 indirect chemical shift evolution periods. Finally, the 3D basic NMR spectra are transformed into 3D phase-sensitively edited basic NMR spectra, where the 2 chemical shift doublet components of the 3D basic NMR spectra are edited to yield 3D phase-sensitively edited basic NMR spectra having individual chemical shift doublet components.

In addition, the present invention relates to a method of conducting a (3,2) dimensional (D) <[$^1H^XX$]-nuclear Overhauser enhancement spectroscopy (NOESY)-[$^1H$]> G-matrix Fourier transformation (GFT) nuclear magnetic resonance (NMR) experiment. The method involves providing a sample, where the sample is a protein molecule and the chemical shift values for the following nuclei are measured: (1) a proton, $^1H$; (2) X, where X is an aliphatic carbon, $^{13}C^{ali}$, an aromatic carbon, $^{13}C^{aro}$, or a nitrogen, $^{15}N$; and (3) a proton bound to X, $^1H^X$. Next, radiofrequency pulses for a first 3D NOESY FT NMR experiment are applied to the sample. Then, a first set of 2 indirect chemical shift evolution periods of the 3D NOESY FT NMR experiment, $^1H^X$ and X, is jointly sampled in an indirect time domain dimension, $t_1(^1H^X,X)$. Next, NMR signals detected in a direct dimension are independently cosine and sine modulated to generate 2D basic NMR spectra containing frequency domain signals with 2 chemical shift doublet components, thereby enabling phase-sensitive sampling of the jointly sampled first set of 2 indirect chemical shift evolution periods. Finally, the 2D basic NMR spectra are transformed into 2D phase-sensitively edited basic NMR spectra, where the 2 chemical shift doublet components of the 2D basic NMR spectra are edited to yield 2D phase-sensitively edited basic NMR spectra having individual chemical shift doublet components.

Another aspect of the present invention relates to a method of conducting a (4,3) dimensional (D) <[$^1H^X$X]-nuclear Overhauser enhancement spectroscopy $(\overline{NOESY})$-[$Y^1H^Y$]> G-matrix Fourier transformation (GFT) nuclear magnetic resonance (NMR) experiment. The method involves providing a sample, where the sample is a protein molecule and the chemical shift values for the following nuclei are measured: (1) X, where X is an aliphatic carbon, $^{13}C^{ali}$, an aromatic carbon, $^{13}C^{aro}$, or a nitrogen, $^{15}N$; (2) a proton bound to X, $^1H^X$; (3) Y, where Y is an aliphatic carbon, $^{13}C^{ali}$, an aromatic carbon, $^{13}C^{aro}$, or a nitrogen, $^{15}N$; and (4) a proton bound to Y, $^1H^Y$. Next, radiofrequency pulses for a first 4D NOESY FT NMR experiment are applied to the sample. Then, a first set of 2 indirect chemical shift evolution periods of the 4D NOESY FT NMR experiment, $^1H^X$ and X, is selected. Next, the first set of 2 indirect chemical shift evolution periods is jointly sampled in an indirect time domain dimension, $t_1(^1H^X,X)$. Then, NMR signals detected in a direct dimension are independently cosine and sine modulated to generate 3D basic NMR spectra containing frequency domain signals with 2 chemical shift doublet components, thereby enabling phase-sensitive sampling of the jointly sampled 2 indirect chemical shift evolution periods. Finally, the 3D basic NMR spectra are transformed into 3D phase-sensitively edited basic NMR spectra, where the 2 chemical shift doublet components of the 3D basic NMR spectra are edited to yield 3D phase-sensitively edited basic NMR spectra having individual chemical shift doublet components.

Another aspect of the present invention relates to a method of conducting a (4,2) dimensional (D) <[$^1H^X$X]-nuclear Overhauser enhancement spectroscopy $(\overline{NOESY})$-[$Y^1H^Y$]> G-matrix Fourier transformation (GFT) nuclear magnetic resonance (NMR) experiment. The method involves providing a sample, where the sample is a protein molecule and the chemical shift values for the following nuclei are measured: (1) X, where X is an aliphatic carbon, $^{13}C^{ali}$, an aromatic carbon, $^{13}C^{aro}$, or a nitrogen, $^{15}N$; (2) a proton bound to X, $^1H^X$; (3) Y, where Y is an aliphatic carbon, $^{13}C^{ali}$, an aromatic carbon, $^{13}C^{aro}$, or a nitrogen, $^{15}N$; and (4) a proton bound to Y, $^1H^Y$. Next, radiofrequency pulses for a first 4D NOESY FT NMR experiment are applied to the sample. Then, a first group of 3 indirect chemical shift evolution periods of the 4D NOESY FT NMR experiment, $^1H^X$, X, and Y, is selected. Next, the first group of 3 indirect chemical shift evolution periods is jointly sampled in an indirect time domain dimension, $t_1(^1H^X,X,Y)$. Then, NMR signals detected in a direct dimension are independently cosine and sine modulated to generate 2D basic NMR spectra containing frequency domain signals with 4 chemical shift multiplet components, thereby enabling phase-sensitive sampling of all jointly sampled 3 indirect chemical shift evolution periods. Finally, the 2D basic NMR spectra are transformed into 2D phase-sensitively edited basic NMR spectra, where the 4 chemical shift multiplet components of the 2D basic NMR spectra are edited to yield 2D phase-sensitively edited basic NMR spectra having individual chemical shift multiplet components.

The present invention also relates to a method of conducting a (6,2) dimensional (D) [($H^\alpha$—$C^\alpha$—CO)—N—HN] G-matrix Fourier transformation (GFT) nuclear magnetic resonance (NMR) experiment. The method involves providing a sample, where the sample is a protein molecule having two consecutive amino acid residues, i–1 and i, and the chemical shift values for the following nuclei: (1) a polypeptide backbone amide nitrogen of amino acid residue i, $^{15}N_i$; and (2) a polypeptide backbone amide proton of amino acid residue i, $^1H^N_i$, are measured in combination with four spin-spin couplings between (1) an α-proton of amino acid residue i–1, $^1H^\alpha_{i-1}$, and an α-carbon of amino acid residue i–1, $^{13}C^\alpha_{i-1}$; (2) an α-carbon of amino acid residue i–1, $^{13}C^\alpha_{i-1}$, and a polypeptide backbone carbonyl carbon of amino acid residue i–1, $^{13}C'_{i-1}$; (3) a polypeptide backbone carbonyl carbon of amino acid residue i–1, $^{13}C'_{i-1}$, and a polypeptide backbone amide nitrogen of amino acid residue i, $^{15}N_i$; (4) a polypeptide backbone amide nitrogen of amino acid residue i, $^{15}N_i$, and a polypeptide backbone amide proton of amino acid residue i, $^1H^N_i$. Next, radiofrequency pulses for a 6D FT NMR experiment are applied to the sample. Then, an indirect chemical shift evolution period of the 6D FT NMR experiment, $^{15}N_i$, is selected. Next, the indirect chemical shift evolution period is jointly sampled with the four indirect spin-spin coupling evolution periods resulting from sampling the four spin-spin couplings. Then, NMR signals detected in a direct dimension resulting from time evolution of the indirect chemical shift and the four spin-spin couplings are independently cosine and sine modulated to generate 2D basic NMR spectra containing frequency domain signals with 16 multiplet components, thereby enabling phase-sensitive sampling of the indirect chemical shift evolution period and the indirect spin-spin coupling evolution periods. Finally, the 2D basic NMR spectra are transformed into 2D phase-sensitively edited basic NMR spectra, where the 16 multiplet components of the 2D basic NMR spectra are edited to yield 2D phase-sensitively edited basic NMR spectra having individual multiplet components.

Previously described GFT NMR experiments comprised phase sensitive joint sampling of several chemical shifts along a single indirect dimension (also called as the "GFT dimension") of a multidimensional NMR experiment, thereby providing high spectral dispersion. However, in large proteins, spectral overlap can still hamper resonance assignments. The present invention alleviates this problem by additionally employing another indirect dimension as a second GFT dimension, resulting in significant gains in spectral resolution. The phase sensitive joint sampling of two independent sets of spins along two indirect dimensions requires the sequential application of two appropriate G-matrix transformations along each of the GFT dimensions independently; hence, these are called $G^2$FT NMR experiments. The present application discloses a suite of novel (5,3)D and (6,3)D $G^2$FT triple resonance NMR experiments encoding highly resolved 5D and 6D spectral information for sequential resonance assignment of proteins exhibiting high chemical shift degeneracy. Efficient resonance assignment is achieved by separate joint sampling of (i) chemical shifts which solely serve to provide increased resolution and (ii) shifts which also provide sequential connectivities. In the (5,3)D $G^2$FT experiments, for example, two G-matrix transformations are employed. Peaks are resolved along a first GFT dimension at both $\Omega(^{15}N)+\Omega(^{13}C')$ and $\Omega(^{15}N)-\Omega(^{13}C')$, or at $\Omega(^{15}N)+\Omega(^{13}C^\alpha)$ and $\Omega(^{15}N)-\Omega(^{13}C^\alpha)$, in order to break backbone $^{15}N$, $^1H^N$ chemical shift degeneracy. Sequential connectivities are established along a second GFT dimension by measuring intraresidue and sequential correlations at 2 $\Omega(^{13}C^\alpha)$, $\Omega(^{13}C^\alpha+^{13}C^\beta)$ and $\Omega(^{13}C^\alpha-^{13}C^\beta)$, or at $\Omega(^{13}C^\alpha+^{1}H^\alpha)$ and $\Omega(^{13}C^\alpha-^{1}H^\alpha)$, in order to resolve $^{13}C^{\alpha/\beta}$, $^{1}H^\alpha$ chemical shift degeneracy. The present invention demonstrates that longitudinal proton relaxation optimization of out-and-back implementations suitable for deuterated proteins, and non-linear data sampling combined with maximum entropy reconstruction further accelerate G²FT NMR data acquisition speed. As a result, the spectral information can be obtained within hours, so that (5,3)D G²FT experiments are viable options for high-throughput structure determination in structural genomics. Applications are also presented for 17 kDa α-helical protein YqbG and 13.5 kDa protein rps24e, targets of the Northeast Structural Genomics consortium, as well as for 9 kDa protein Z-domain. The high resolving power of the G²FT NMR experiments makes them attractive choices to study α-helical globular/membrane or (partially) unfolded proteins, thus promising to pave the way for NMR-based structural genomics of membrane proteins.

In addition, NMR assignment of aromatic rings in proteins is a prerequisite for obtaining high-quality solution structures of proteins and for studying the dynamics and folding of their molecular cores. The present application discloses sensitive PFG-PEP L-GFT-(TROSY) (4,3)D HCCH NMR (as well as other L-GFT (4,3) NMR experiments) for identification of aromatic spin systems based on 4D spectral information which can be rapidly obtained with high digital resolution. The GFT experiment relies on newly introduced longitudinal relaxation (L-)optimization for aromatic protons and is optimally suited for both sensitivity and sampling limited data collection, making it particularly attractive for NMR-based structural genomics. L-GFT (4,3)D HCCH offers ~25% higher intrinsic sensitivity at optimal relaxation delay between scans for medium-sized proteins when compared with the non-L congener. L-GFT (4,3)D HCCH also allows one to collect the 4D spectral information about four times faster (due to the ability to acquire data with four times shorter relaxation delays between scans), while the same intrinsic sensitivity (sensitivity per unit time) is observed as for the non-L congener at optimal relaxation delays between scans. Applications are also presented for 21 kDa and 13 kDa proteins, HR41 and MaR11, targets of the Northeast Structural Genomics Consortium for which data collection is, respectively, sensitivity and sampling limited. Complete assignment of aromatic rings enabled high-quality NMR structure determination, and nearly complete analysis of aromatic proton linewidths allowed one to assess the flipping of most rings in HR41. Specifically, the ring of Tyr 90 flips very slowly on the seconds time scale, thereby proving the absence of fast larger amplitude motional modes which could allow the ring to flip. This indicates remarkable rigidity of the substructure in which the ring is embedded. Tyr 90 is conserved among ubiquitin-conjugating enzymes E2 to which HR41 belongs, and is located in spatial proximity to the interface between E2 and ubiquitin-protein ligase E3. Hence, the conformational rigidity and/or the slow motional mode probed by the ring might be of functional importance.

In addition, the present application discloses a protocol for high-quality structure determination based on GFT NMR and NOESY. Five through-bond chemical shift correlation experiments providing 4D and 5D spectral information at high digital resolution are performed for resonance assignment. These are combined with a newly implemented (4,3)D GFT NOESY experiment which encodes information of 4D $^{15}N/^{15}N$-, $^{13}C^{aliphatic}/^{15}N$-, and $^{13}C^{aliphatic}/^{13}C^{aliphatic}$-resolved [$^{1}H$, $^{1}H$]-NOESY in two subspectra, each containing one component of chemical shift doublets arising from 4D→3D projection at $\omega_1$:$\Omega(^{1}H)\pm\Omega(X)$ [X=$^{15}N$, $^{13}C^{aliphatic}$]. The peaks located at the centers of the doublets are obtained from simultaneous 3D $^{15}N/^{13}C^{aliphatic}/^{13}C^{aromatic}$-resolved [$^{1}H$, $^{1}H$]-NOESY, where NOEs detected on aromatic protons are also obtained. The protocol was applied for determining a high-quality structure of the 14 kDa Northeast Structural Genomics consortium target protein, YqfB (PDB ID 1TE7). Through-bond correlation and NOESY spectra were acquired, respectively, in 16.9 hours and 39 hours (30 hours for shift doublets, 9 hours for central peaks) on a 600 MHz spectrometer equipped with a cryogenic probe. The rapidly collected highly resolved 4D NOESY information allows one to assign the majority of NOEs directly from chemical shifts, which yields accurate initial structures "within" ~2 Å to the final structure. Information theoretical "QUEEN" analysis of initial distance limit constraint networks revealed that, in contrast to structure-based protocols, such NOE assignment is not biased toward identifying additional constraints that tend to be redundant with respect to the available constraint network. The protocol enables rapid NMR data collection for robust high-quality structure determination of proteins up to ~20-25 kDa in high-throughput.

Lastly, in recent years, residual dipolar couplings (RDC) in biomolecular systems have emerged as a subject of widespread interest in NMR based structural biology and genomics. In all the applications, the importance of the number and different types of RDCs that are measured and their accuracy/precision has been recognized. An additional aspect that is being increasingly considered vital is the simultaneous measurement of different types of RDCs. The present application discloses a novel scheme for simultaneous and precise measurement of multiple RDCs in a protein within a single experiment, which is based on the principle of GFT NMR spectroscopy. Analogues to phase sensitive joint sampling of chemical shifts, multiple scalar/dipolar couplings are jointly detected in a single dimension. Four mutually correlated one-bond couplings, namely, $^{13}C^\alpha$—$^{1}H^\alpha$, $^{13}C^\alpha$—$^{13}C'$, $^{15}N$—$^{13}C'$ and $^{15}N$—$^{1}H^N$ are simultaneously measured in conjunction with $^{15}N$ and $^{1}H^N$ chemical shifts. This experiment is named "J-GFT (6,2)D [(H$^\alpha$—C$^\alpha$—CO)—N—HN]". The existing delays in the pulse scheme are utilized for joint sampling of couplings in a constant-time fashion, thereby avoiding loss of resolution and sensitivity. Accuracy and high precision of the RDCs obtained were experimentally verified for Z-domain at two different field strengths. Such mutually correlated sets of RDCs are invaluable as an aid to resonance assignments, studying protein dynamics or in protein structure refinement/validation.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

1. $\Omega_0$($^{13}C^\alpha_i$)+$\Omega_1$($^{13}C^\alpha_i$)
2. $\Omega_0$($^{13}C^\alpha_{i-1}$)+$\Omega_1$($^{13}C^\alpha_{i-1}$)
3. $\Omega_0$($^{13}C^\alpha_{i-1}$)+$\Omega_1$($^{13}C^\beta_{i-1}$)
4. $\Omega_0$($^{13}C^\alpha_i$)+$\Omega_1$($^{13}C^\beta_i$)
5. $\Omega_0$($^{13}C^\alpha_i$)−$\Omega_1$($^{13}C^\alpha_i$)
6. $\Omega_0$($^{13}C^\alpha_{i-1}$)−$\Omega_1$($^{13}C^\alpha_{i-1}$)
7. $\Omega_0$($^{13}C^\alpha_{i-1}$)−$\Omega_1$($^{13}C^\beta_{i-1}$)
8. $\Omega_0$($^{13}C^\alpha_i$)−$\Omega_1$($^{13}C^\beta_i$)

Figure 3:
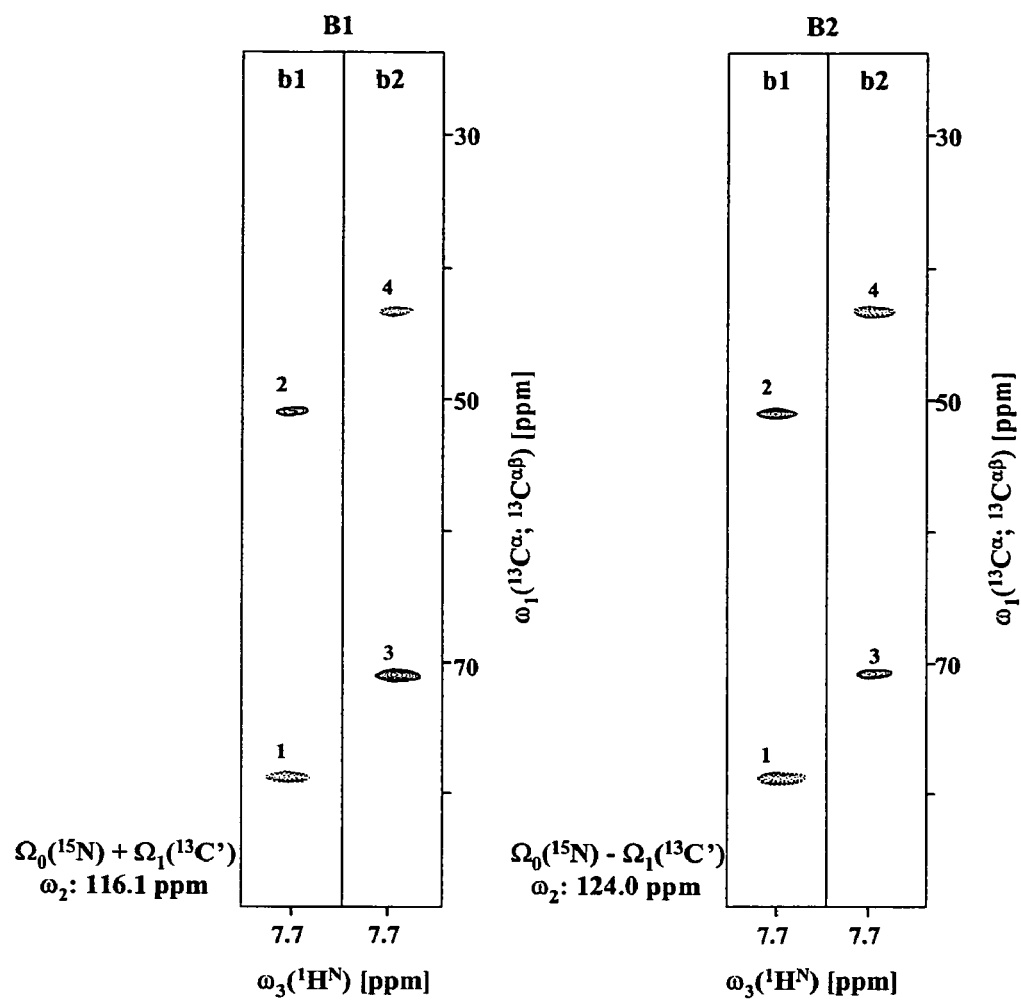

FIG. 3 shows composite plots of [$\omega_1$($^{13}C^\alpha$; $^{13}C^{\alpha\beta}$), $\omega_3$($^1H^N$)] strips taken from the basic spectra of G$^2$FT (5,3)D HN{NCO}{$C^{\alpha\beta}C^\alpha$}. The four basic spectra are grouped into two sets, B1 and B2, comprising peaks at $\Omega_0$($^{15}N_i$)+$\Omega_1$($^{13}C'_{i-1}$) and $\Omega_0$($^{15}N_i$)−$\Omega_1$($^{13}C'_{i-1}$) along $\omega_2$, respectively. B1 and B2 each contain two spectra (labeled as "b1" and "b2") comprising peaks at $\Omega_0$($^{13}C^\alpha_{i-1}$)±$\Omega_1$($^{13}C^{\alpha/\beta}_{i-1}$) along $\omega_1$. Positive and negative peaks are shown, respectively, with solid and dotted contour lines. As an example, strips are shown for the residue Ala 55 of the 8 kDa protein Z-domain. Peaks labeled 1-2 in "b1" and 3-4 in "b2" correspond to the following linear combination of chemical shifts along $\omega_1$:

1. $\Omega_0$($^{13}C^\alpha_{i-1}$)+$\Omega_1$($^{13}C^\alpha_{i-1}$)
2. $\Omega_0$($^{13}C^\alpha_{i-1}$)+$\Omega_1$($13C^\beta_{i-1}$)
3. $\Omega_0$($^{13}C^\alpha_{i-1}$)−$\Omega_1$($13C^\beta_{i-1}$)
4. $\Omega_0$($^{13}C^\alpha_{i-1}$)−$\Omega_1$($13C^\alpha_{i-1}$)

Figure 4:
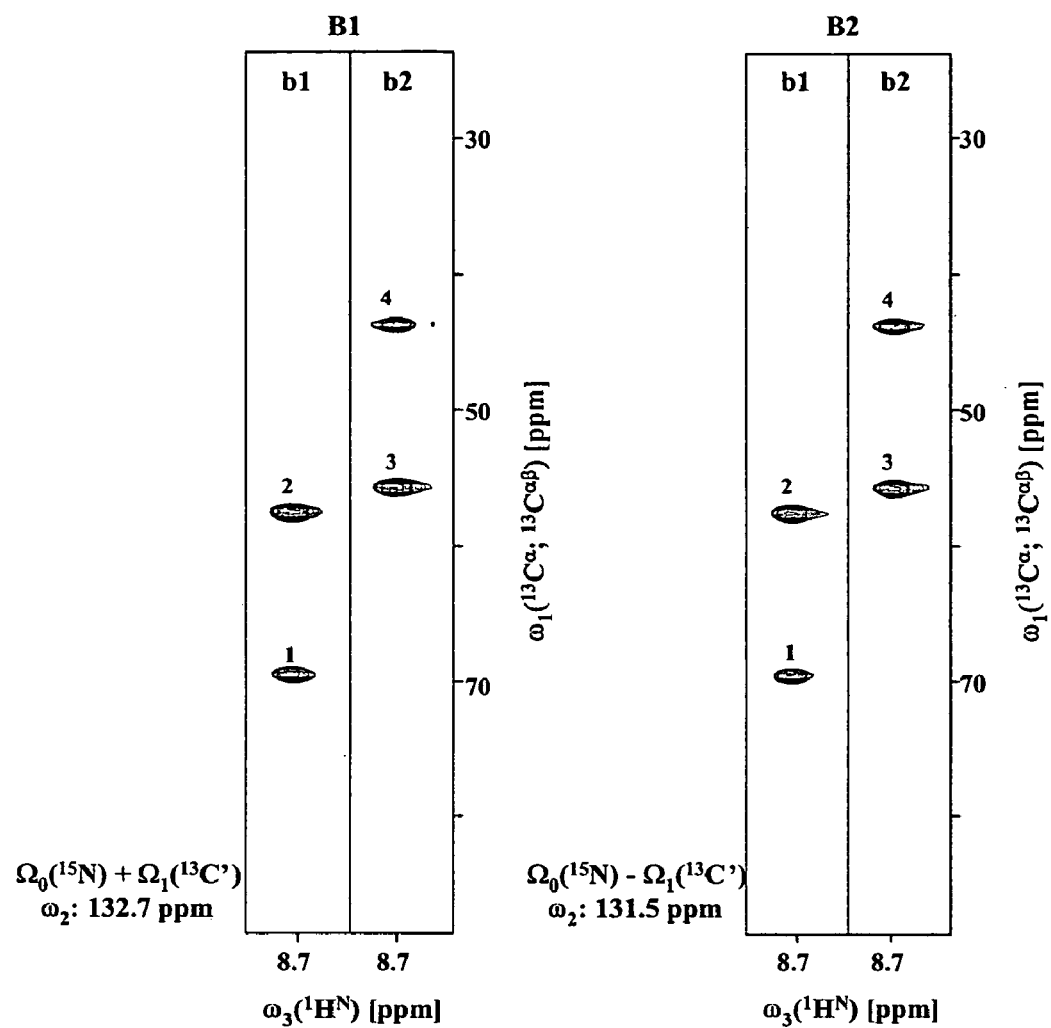

FIG. 4 shows composite plots of [$\omega_1$($^{13}C^\alpha$; $^{13}C^{\alpha\beta}$), $\omega_3$($^1H^N$)] strips taken from the basic spectra of G$^2$FT (5,3)D {$C^{\alpha\beta}C^\alpha$}{NCO}HN. The four basic spectra are grouped into two sets, B1 and B2, comprising peaks at $\Omega_0$($^{15}N_i$)+$\Omega_1$($^{13}C'_{i-1}$) and $\Omega_0$($^{15}N_i$)−$\Omega_1$($^{13}C'_{i-1}$) along $\omega_1$, respectively. B1 and B2 each contain two spectra (labeled as "b1" and "b2") comprising peaks at $\Omega_0$($^{13}C^\alpha_{i-1}$)±$\Omega_1$($^{13}C^{\alpha/\beta}_{i-1}$) along $\omega_1$. As an example, strips are shown for the residue Ala 46 of Ubiquitin. Peaks labeled 1-4 in "b1" and "b2" correspond to the following linear combination of chemical shifts along $\omega_1$:

1. $\Omega_0$($^{13}C^\alpha_{i-1}$)+$\Omega_1$($^{13}C^\alpha_{i-1}$)
2. $\Omega_0$($^{13}C^\alpha_{i-1}$)+$\Omega_1$($^{13}C^\beta_{i-1}$)
3. $\Omega_0$($^{13}C^\alpha_{i-1}$)−$\Omega_1$($^{13}C^\beta_{i-1}$)
4. $\Omega_0$($^{13}C^\alpha_{i-1}$)−$\Omega_1$($^{13}C^\alpha_{i-1}$)

Figure 5:
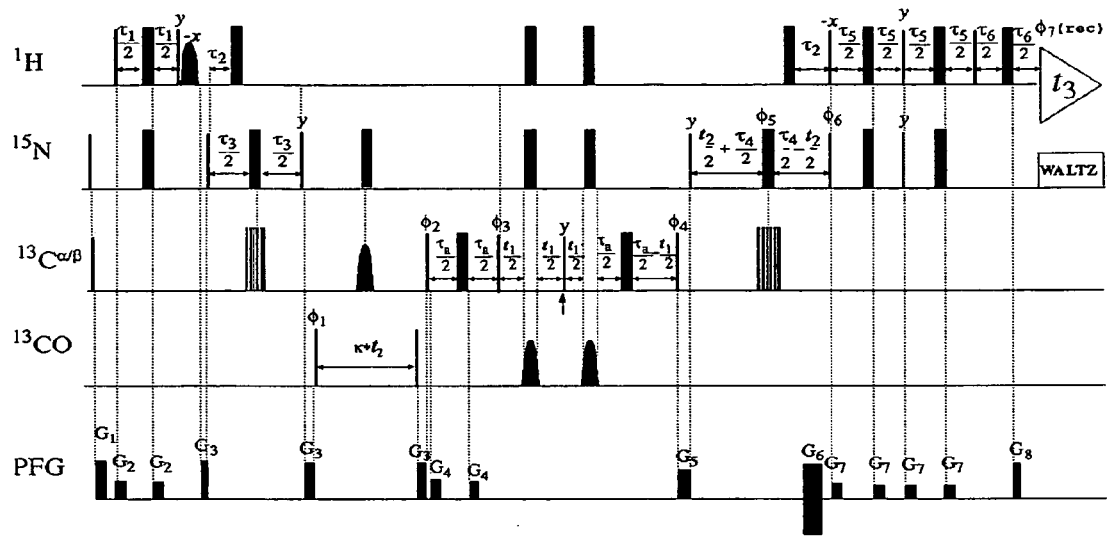

FIG. 5 depicts the r.f. pulse scheme of G$^2$FT L-(5,3)D HN{N,CO}{$C^{\alpha\beta}C^\alpha$}. Rectangular 90° and 180° pulses are indicated by thin and thick vertical bars, respectively, and phases are indicated above the pulses. Where no r.f. phase is marked, the pulse is applied along x. High-power 90° pulse lengths are: 5.7 μs for $^1H$, 15.0 μs for $^{13}C$ and 40 μs for $^{15}N$, and κ=0.25. The scaling (Kim et al., *J. Am. Chem. Soc.* 125:1385-1393 (2003); Szyperski et al., *J. Am. Chem. Soc.* 115:9307-9308 (1993), which are hereby incorporated by reference in their entireties) factor κ for $^{13}C'$ shift evolution was set to 0.25, because (i) polarization transfer in the sequential counterpart (i.e. (5,3)D HN{NCO}{$C^{\alpha\beta}C^\alpha$} (FIGS. 1 and 6)) limits $t_{max}$ ($^{13}C'$) to ~6 ms; (ii) a short $t_{max}$($^{13}C'$) limits T$_2$($^{13}C'$) losses in (5,3)D HN{N,CO}{$C^{\alpha\beta}C^\alpha$} with non-constant time (Cavanagh et al., *Protein NMR Spectroscopy* Academic Press: San Diego (1996), which is hereby incorporated by reference in its entirety) $^{13}C'$ shift evolution; (iii) $t_{max}$($^{15}N$) ~24 ms ensures high spectral resolution in $\omega_2$. Lengths of 90° and 180° pulse applied to $^{13}C^{\alpha\beta}$ are set to 48 μs and 43 μs, respectively (at a $^1H$ resonance frequency of 600 MHz), prior to and during the first $t_1$ delay [$t_1$($^{13}C^{\alpha\beta}$)], and to 54 μs and 48 μs, respectively, during the second $t_1$ delay [$t_1$($^{13}C^\alpha$)] in order to minimize perturbation of $^{13}C'$ spins. A 90° E-BURP2 pulse (Geen et al., *J. Magn. Reson.*, 93:93-142 (1991), which is hereby incorporated by reference in its entirety) after the 2$^{nd}$ 90° $^1H$ pulse (1.2 ms; 0-6 ppm excitation; carrier: 3 ppm) enables water flip-back (Cavanagh et al., *Protein NMR Spectroscopy* Academic Press: San Diego (1996), which is hereby incorporated by reference in its entirety) and L-optimization (Atreya et al., *Proc. Natl. Acad. Sci. USA* 101;9642-9647 (2004); Pervushin et al., *J. Am. Chem. Soc.* 124:12898-12902 (2002), which are hereby incorporated by reference in their entireties). SEDUCE (Cavanagh et al., *Protein NMR Spectroscopy* Academic Press: San Diego (1996), which is hereby incorporated by reference in its entirety) off-resonance 180° pulses of duration 200 μs and 103 μs, respectively, are used to decouple $^{13}C'$ during $t_1$($^{13}C^{\alpha\beta}$) and $t_1$($^{13}C^\alpha$). A six-pulse composite sequence (Shaka, *Chem. Phy. Lett.*, 120:201-205 (1985), which is hereby incorporated by reference in its entirety) is used to simultaneously invert/refocus $^{13}C^\alpha$/$^{13}C'$ magnetization during $^{13}C^\alpha$-$^{13}C'$ polarization transfers. The SEDUCE (Cavanagh et al., *Protein NMR Spectroscopy* Academic Press: San Diego (1996), which is hereby incorporated by reference in its entirety) sequence is used for decoupling of $^{13}C^\alpha$ during $t_2$($^{15}N$). WALTZ16 (Cavanagh et al., *Protein NMR Spectroscopy* Academic Press: San Diego (1996), which is hereby incorporated by reference in its entirety) is employed to decouple of $^{15}N$ (r.f.=1.70 kHz) during acquisition. The $^1H$ r.f. carrier is placed at the position of the solvent line at 4.77 ppm. The $^{15}N$ carrier position is set to 118.5 ppm. The $^{13}C$ carrier position is set initially to 56 ppm and switched to 175 ppm before the first 90° pulse in $^{13}CO$. It is switched to 43 ppm prior to and during $t_1$($^{13}C^{\alpha\beta}$) and back to 56 ppm during $t_1$($^{13}C^\alpha$) (indicated by an arrow). The duration and strengths of the pulsed rectangular z-field gradients (PFGs) are: G$_1$(1.0 ms, 24 G/cm); G$_2$(0.5 ms, 8 G/cm); G$_3$(1.0 ms, 20 G/cm); G$_4$(0.5 ms, 4 G/cm); G$_5$(1.0 ms, 15 G/cm); G$_6$(1.25 ms, 30 G/cm); G$_7$(0.5 ms, 8 G/cm); G$_8$(0.125 ms, 29.5 G/cm). Delays: $\tau_1$=5.5 ms; $\tau_2$=5.4; $\tau_3$=$\tau_4$=28; $\tau_5$=4.6; $\tau_6$=1.0; $\tau_a$=7.0. Phase cycling: $\phi_1$=x,−x; $\phi_2$=x; $\phi_3$=y; $\phi_4$=2(x),2(−x); $\phi_5$=4(x), 4(−x); $\phi_6$=x; $\phi_7$(receiver)=x,2(−x),x. A sensitivity enhancement scheme (Kay et al., *J. Am Chem. Soc.* 114:10663-10665 (1992), which is hereby incorporated by reference in its entirety) is employed, i.e., the sign of G6 is inverted in concert with a 180° shift of $\phi_6$. Quadrature detection in $t_1$($^{13}C^\alpha$) is accomplished by altering the phases $\phi_4$ according to States-TPPI (Cavanagh et al., *Protein NMR Spectroscopy* Academic Press: San Diego (1996), which is hereby incorporated by reference in its entirety), whereas quadrature detection in $t_2$($^{15}N$) is achieved by use of the sensitivity enhancement scheme. GFT NMR phase-cycle: $\phi_1$=x,y; $\phi_2$=2x,2y; $\phi_3$=2y, 2x, yielding, in conjunction with quadrature detection, 16 data sets which are linearly combined employing a G-matrix transformation with the G-matrix of Equation 10 (see Detailed Description of the Invention section).

Figure 6:
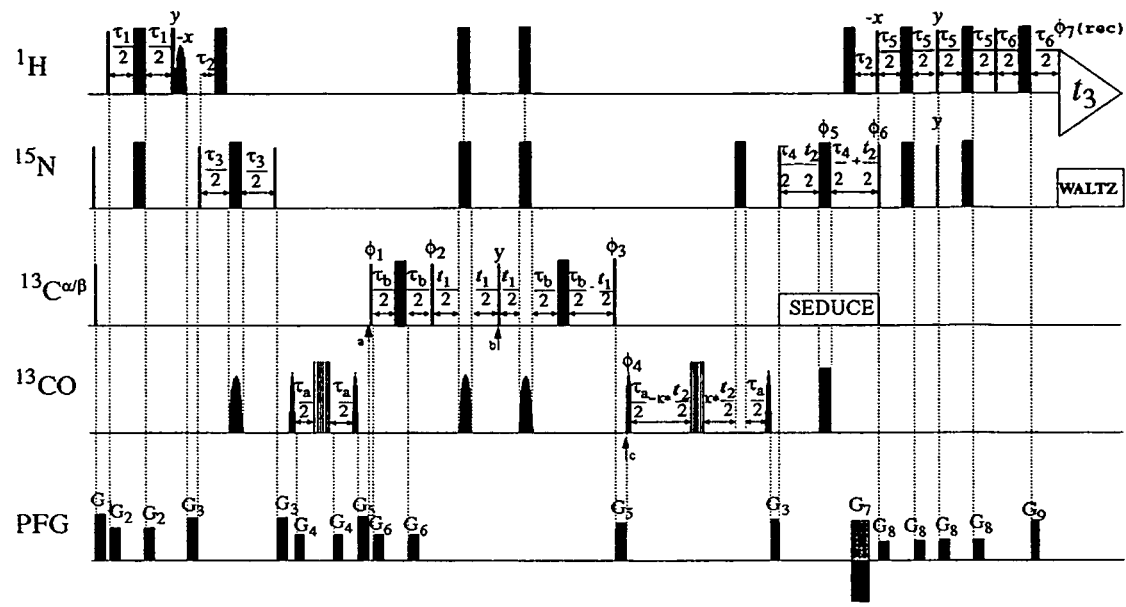

FIG. 6 depicts the r.f. pulse scheme of G$^2$FT L-(5,3)D HN{NCO}{$C^{\alpha\beta}C^\alpha$}. Rectangular 90° and 180° pulses are indicated by thin and thick vertical bars, respectively, and phases are indicated above the pulses. Where no r.f. phase is marked, the pulse is applied along x. High-power 90° pulse lengths are: 5.7 μs for $^1H$, 15.0 μs for $^{13}C$ and 40 μs for $^{15}N$, and κ=0.25. Lengths of 90° and 180° pulse applied to $^{13}C^{\alpha\beta}$ are set to 48 μs and 43 μs, respectively (at a $^1H$ resonance frequency of 600 MHz), prior to and during the first $t_1$ delay $[t_1(^{13}C^{\alpha\beta})]$, and to 54 μs and 48 μs, respectively, during the second $t_1$ delay $[t_1(^{13}C^{\alpha})]$ in order to minimize perturbation of $^{13}C'$ spins. A 90° E-BURP2 pulse (Geen et al., *J. Magn. Reson.*, 93:93-142 (1991), which is hereby incorporated by reference in its entirety) after the $2^{nd}$ 90° $^1H$ pulse (1.2 ms; 0-6 ppm excitation; carrier: 3 ppm) enables water flip-back (Cavanagh et al., *Protein NMR Spectroscopy* Academic Press: San Diego (1996), which is hereby incorporated by reference in its entirety) and L-optimization (Atreya et al., *Proc. Natl. Acad. Sci. USA* 101:9642-9647 (2004); Pervushin et al., *J. Am. Chem. Soc.* 124:12898-12902 (2002), which are hereby incorporated by reference in their entirety). SEDUCE (Cavanagh et al., *Protein NMR Spectroscopy* Academic Press: San Diego (1996), which is hereby incorporated by reference in its entirety) off-resonance 180° pulses of duration 200 μs and 103 μs, respectively, are used to decouple $^{13}C'$ during $t_1(^{13}C^{\alpha\beta})$ and $t_1(^{13}C^{\alpha})$. The 90° and 180° pulse lengths for the sinc lobe pulse on-resonance at $^{13}C'$ is 88 μs and 81 μs, respectively. A six-pulse composite sequence (Shaka, *Chem. Phy. Lett.*, 120:201-205 (1985), which is hereby incorporated by reference in its entirety) is used to simultaneously invert/refocus $^{13}C^{\alpha}/^{13}C'$ magnetization during $^{13}C^{\alpha}$—$^{13}C'$ polarization transfers. The SEDUCE (Cavanagh et al., *Protein NMR Spectroscopy*, Academic Press: San Diego (1996), which is hereby incorporated by reference in its entirety) sequence is used for decoupling of $^{13}C^{\alpha}$ during $t_2(^{15}N)$. WALTZ16 (Cavanagh et al., *Protein NMR Spectroscopy*, Academic Press: San Diego (1996), which is hereby incorporated by reference in its entirety) is employed to decouple of $^{15}N$ (r.f.=1.70 kHz) during acquisition. The $^1H$ r.f. carrier is placed at the position of the solvent line at 4.77 ppm. The $^{15}N$ carrier position is set to 118.5 ppm. The $^{13}C$ carrier position is set initially to 175 ppm, and switched to 43 ppm prior to and during $t_1(^{13}C^{\alpha\beta})$ (indicated by an arrow at point a), to 56 ppm during $t_1(^{13}C^{\alpha})$ (at b) and back to 175 ppm (at c) during the reverse $^{13}C'$—$^{13}C^{\alpha}$ polarization transfer. The duration and strengths of the pulsed rectangular z-field gradients (PFGs) are: G1 (1.0 ms, 24 G/cm); G2 (0.5 ms, 8 G/cm); G3 (1.0 ms, 20 G/cm); G4 (0.5 ms, 8 G/cm); G5 (1.0 ms, 20 G/cm); G6 (0.5 ms, 8 G/cm); G7 (1.25 ms, 30 G/cm); G8 (0.5 ms, 4 G/cm); G9 (0.125 ms, 29.5 G/cm). The delays are: $\tau_1$=5.4 ms, $\tau_2$=5.4 ms, $\tau_3$=24 ms, $\tau_4$=24 ms, $\tau_5$=4.6 ms, $\tau_6$=1.0 ms, $\tau_a$=9.0 ms, $\tau_b$=7.0 ms. Phase cycling: $\phi_1$=x, -x; $\phi_2$=y; $\phi_3$=2(x),2(-x); $\phi_4$=x, $\phi_5$=2(x), 2(-x); $\phi_6$=x; $\phi_7$(receiver)=x, -x, -x, x. A sensitivity enhancement scheme (Kay et al., *J. Am. Chem. Soc.* 114:10663-10665 (1992), which is hereby incorporated by reference in its entirety) is employed, i.e., the sign of G7 is inverted in concert with a 180° shift of $\phi_6$. Quadrature detection in $t_1(^{13}C^{\alpha})$ is accomplished by altering the phases $\phi_3$ according to States-TPPI (Cavanagh et al., *Protein NMR Spectroscopy* Academic Press: San Diego (1996), which is hereby incorporated by reference in its entirety), whereas quadrature detection in $t_2(^{15}N)$ is achieved by use of the sensitivity enhancement scheme. GFT NMR phase-cycle: $\phi_1$=x, y; $\phi_2$=y, x; $\phi_4$=2x, 2y, yielding, in conjunction with quadrature detection, 16 data sets which are linearly combined employing a G-matrix transformation with the G-matrix of Equation 10 (see Detailed Description of the Invention section).

Figure 7:
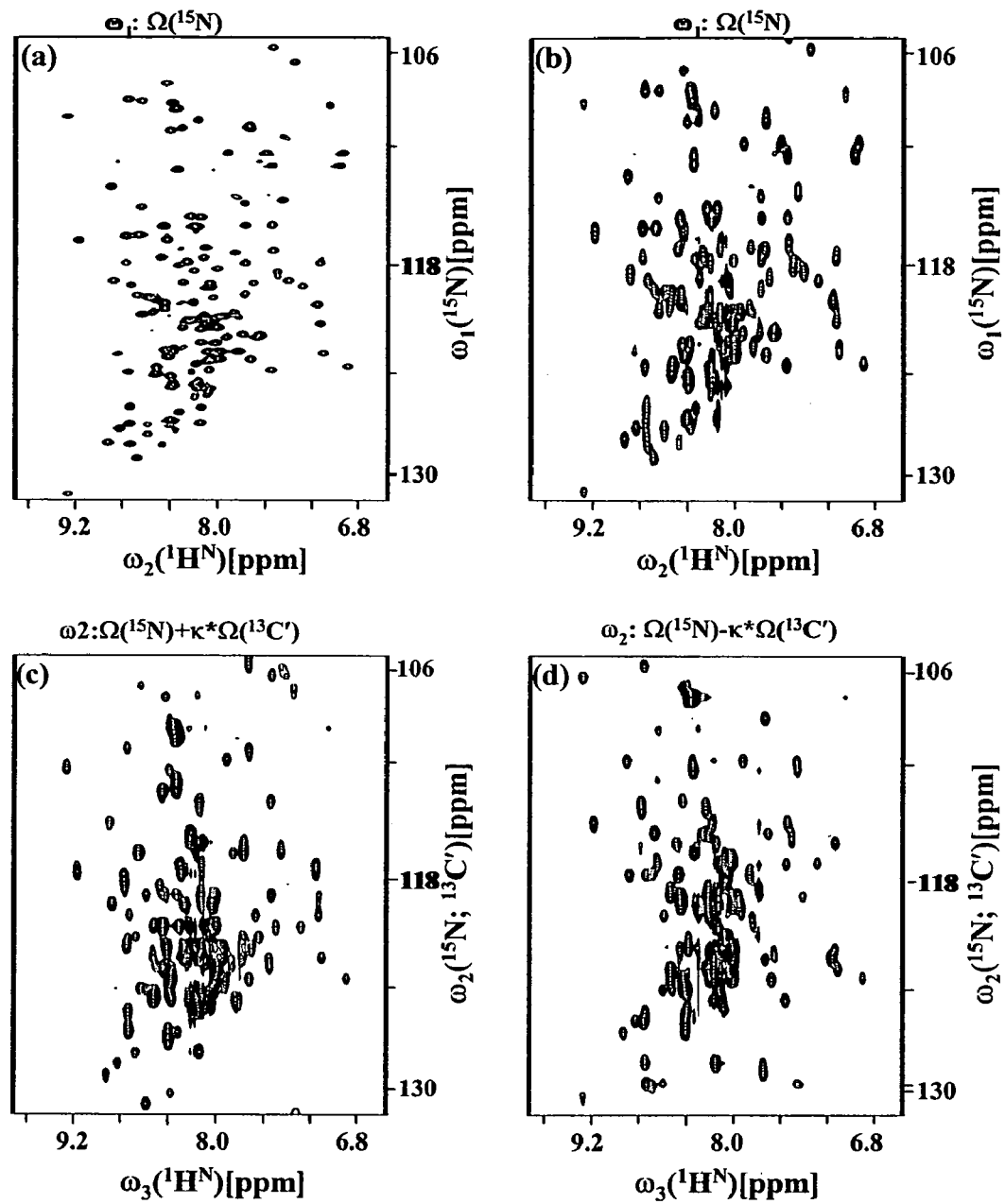

FIGS. 7(a)-(d) show contour plots of spectra recorded for 17 kDa protein yqbG on Varian INOVA 600 spectrometer equipped with a cryogenic probe. FIG. 7(a) shows a plot of 2D $[^{15}N$—$^1H^N]$ HSQC; FIG. 7(b) shows a plot of GFT (4,3)D HNNC$^{\alpha\beta}C^{\alpha}$ along $\omega_3(^1H^N)$]-projection of GFT (4,3)D HNNC$^{\alpha\beta}C^{\alpha}$ along $\omega_1(^{13}C^{\alpha}; ^{13}C^{\alpha\beta})$; FIG. 7(c) shows a plot of $[\omega_2(^{15}N; ^{13}C'),\omega_3(^1H^N)]$-projection of G$^2$FT L-(5,3)D HN{N,CO}C$^{\alpha\beta}C^{\alpha}$ along $\omega_1(^{13}C^{\alpha}; ^{13}C^{\alpha\beta})$ comprising peaks at $\omega_2:\overline{\Omega(^{15}N)}+\kappa^*\Omega$ ($^{13}C'$); and FIG. 7(d) shows a plot of $[\omega_2(^{15}N; ^{13}C'),\omega_3(^1H^N)]$-projection of G$^2$FT L-(5,3)D HN{N,CO}C$^{\alpha\beta}C^{\alpha}$ along $\omega_1(^{13}C^{\alpha}; ^{13}C^{\alpha\beta})$ comprising peaks at $\overline{\omega_1:\Omega(^{15}N)}-\overline{\kappa}*\Omega(^{13}C')$ ($\kappa$=0.25). 2D $[^{15}N$—$^1H^N]$ HSQC was acquired with $t_{2max}$($^{15}N$)=80 ms (Table 1), whereas $t_{2max}$($^{15}N$)=24.0 ms for the projections (Table 1). Spectral resolution of the projections was enhanced by linear prediction (Cavanagh et al., *Protein NMR Spectroscopy* Academic Press: San Diego (1996), which is hereby incorporated by reference in its entirety), extending the time domain data to $t_{2max}$($^{15}N$)=36.0 ms (and yielding 64 points along $\omega_2$ after zero-filling prior to FT).

Figure 8:
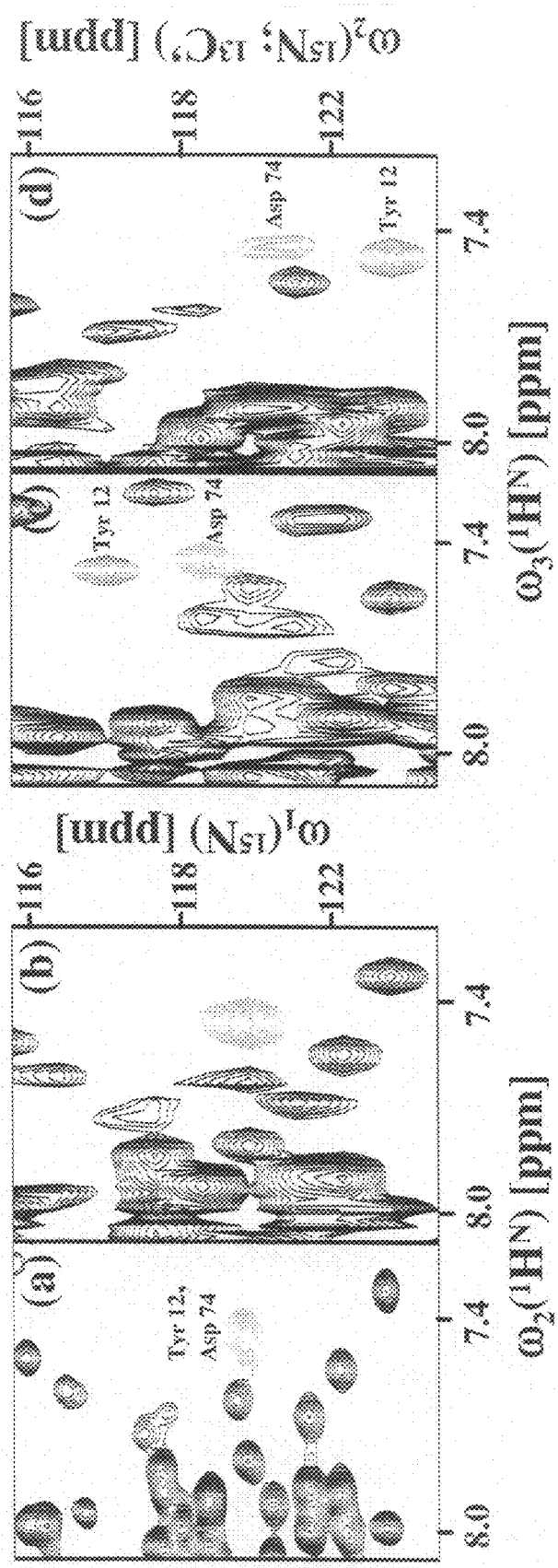

FIGS. 8(a)-(b) show plots of 2D $[^{15}N, ^1H]$-HSQC (Cavanagh et al., *Protein NMR Spectroscopy* Academic Press: San Diego (1996), which is hereby incorporated by reference in its entirety) (FIG. 8(a)) and $[\omega_1(^{15}N),\omega_3(^1H^N)]$ projection of $^{15}N$-resolved 3D spectra (FIG. 8(b)) recorded for protein yqbG (95% $H_2O$/5% $^2H_2O$; 20 mM MES, pH=6.5, 100 mM NaCl, 10 mM DTT, 5 mM $CaCl_2$, 0.02% $NaN_3$). FIGS. 8(c) and 8(d) show $[\omega_2(^{15}N; ^{13}C'),\omega_3(^1H^N)]$ planes from NCO-resolved experiments ($\kappa$=0.25) showing signals at $\overline{\Omega(^{15}N)}+\kappa\Omega(^{13}C')$ (left) and $\Omega(^{15}N)+\kappa\Omega(^{13}C')$ (right). The green signal in FIGS. 8(a) and 8(b) arises from Tyr 12 and Asp 74 having degenerate $^{15}N$ and $^1H^N$ shifts; peaks are resolved in FIGS. 8(c) and 8(d) due to non-degenerate $^{13}C'$ shifts and are shown as blue and red signals.

FIGS. 9(a)-(d) show contour plots of spectra recorded for 17 kDa protein yqbG on Varian INOVA 600 spectrometer equipped with a cryogenic probe. FIG. 9(a) shows a plot of 2D $[^{15}N$—$^1H^N]$ HSQC; FIG. 9(b) shows a plot of basic spectra of (3,2)D HNNCO (Szyperski et al., *J. Am. Chem. Soc.* 115:9307-9308 ($\overline{1993}$); Brutscher et al., *J. Magn. Reson.* B109:238-242 (1995), which are hereby incorporated by reference in their entirety) exhibiting peaks at $\omega_1:\Omega(^{15}N)\pm\kappa\Omega$ ($^{13}C'$) ($\kappa$=0.25); FIG. 9(c) shows a plot of $[\omega_1(^{13}C^{\alpha}; ^{13}C^{\alpha\beta}), \omega_3(^1H^N)]$-strips taken from GFT L-(5,3)D HNNC$^{\alpha\beta}C^{\alpha}$ (Atreya et al., *Proc. Natl. Acad. Sci. USA* 101:$\overline{9642\text{-}9647}$ (2004), which is hereby incorporated by reference in its entirety) (labeled as "a") and L-(5,3)D HNN(CO)C$^{\alpha\beta}C^{\alpha}$ (labeled as "b") showing a $^{15}N$-resolved "sequential $\overline{walk}$"; and FIG. 9(d) shows a plot of $[\omega_1(^{13}C^{\alpha}; ^{13}C^{\alpha\beta}),\omega_3(^1H^N)]$-strips taken from G$^2$FT L-(5,3)D HN{N,CO}C$^{\alpha\beta}C^{\alpha}$ (labeled as "a") and L-(5,3)D HN{NCO}{$\overline{C^{\alpha\beta}C^{\alpha}}$} (labeled as "b") showing $\Omega(^{15}N)\pm\kappa\Omega(^{13}C')$-$\overline{resolved}$ sequential walks. Strips were taken at $\omega_2:\Omega(^{15}N)$ and $\omega_2:\Omega(^{15}N)\pm\kappa\Omega(^{13}C')$ ($\kappa$=0.25) of residues Ile (one-letter code: I) 122 to Lys (K) 125 (chemical shifts indicated at bottom) and comprise peaks at $\omega_1:\Omega$ ($^{13}C^{\alpha})\pm\Omega(^{13}C^{\alpha})$ (red) and $\omega_1:\Omega(^{13}C^{\alpha})\pm\Omega(^{13}C^{\alpha\beta})$ (blue). The acquisition parameters are given in Table 1. Peaks labeled "1"-"9" are assigned to: Gly (G) 121 (3); Ile (I) 122 (1,2); Glu (E) 123 (4,5); Ala (A) 124 (6,7); Lys (K) 125 (8,9). Sequential connectivities are indicated by dashed lines. In FIGS. 9(a) and 9(c), peaks belonging to Ala 50 are overlapped with those of Lys 125 due to $^{15}N$, $^1H^N$ degeneracy (peaks are in green boxes). However, they are resolved in FIG. 9(b) due to their non-degenerate $^{13}C'$ shifts and hence do not appear in strips taken at $\omega_2(^{15}N; ^{13}C')$ of Lys 125 shown in FIG. 9(d).

Figure 10:
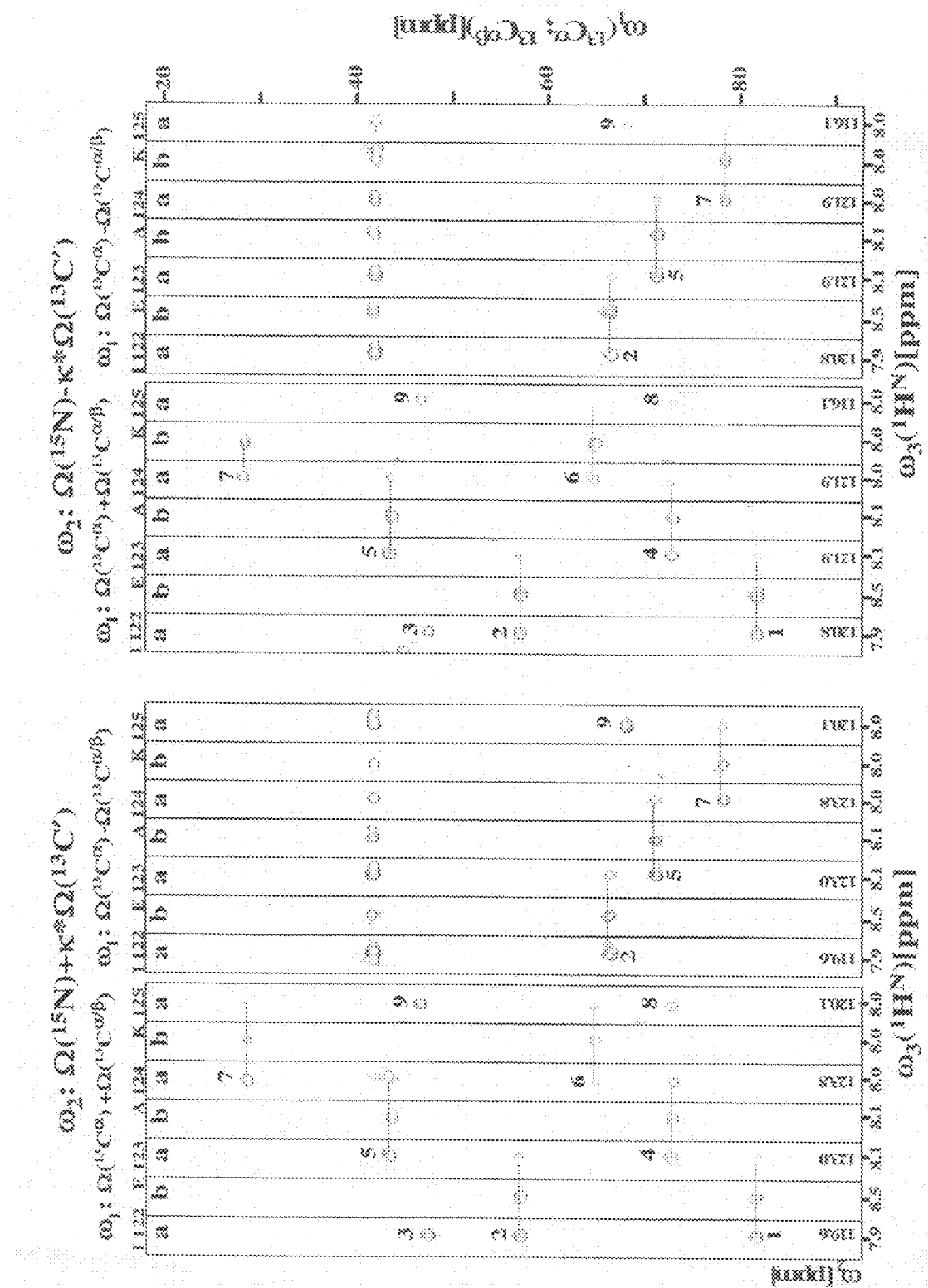

FIG. 10 shows the $[\omega_1(^{13}C^{\alpha}; ^{13}C^{\alpha\beta}),\omega_3(^1H^N)]$-strips taken from G$^2$FT (5,3)D HN{N,CO}{$C^{\alpha\alpha}C^{\alpha}$} ("a") and HN{NCO}{$C^{\alpha\beta}C^{\alpha}$} ("b") recorded for 1$\overline{7}$ kDa protein yqbG. Strips were taken at $\omega_2(^{15}N; ^{13}C')$ of residues Ile 122 to Lys 125 (chemical shifts indicated at bottom) and comprise peaks at $\Omega_0(^{13}C^{\alpha})\pm\Omega_1(^{13}C^{\alpha})$ (red) and $\Omega_0(^{13}C^{\alpha})\pm\Omega_1(^{13}C^{\beta})$ (blue). Peaks "1"-"9" are assigned to Gly (one letter code: G) 121 (3); Ile (I) 122 (1,2); Glu (E) 123 (4,5); Ala (A) 124 (6,7); Lys (K) 125 (8,9). Connectivities are indicated by dashed lines: six sequential "walks" are established.

Figure 11:
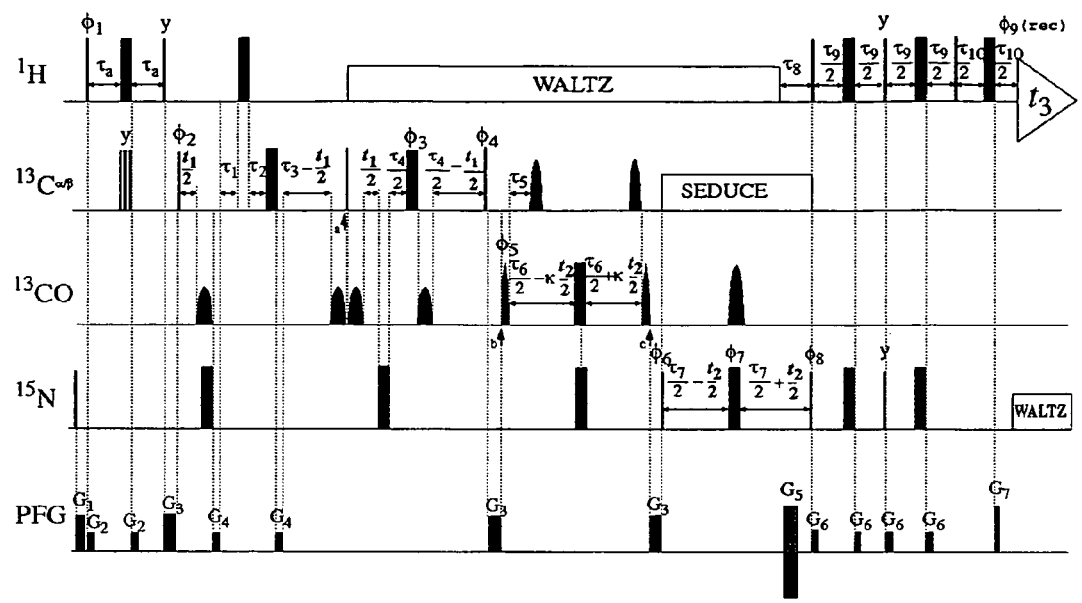

FIG. 11 depicts the r.f. pulse scheme of G²FT (5,3)D {C$^{\alpha\beta}$C$^{\alpha}$}{CON}HN. Rectangular 90° and 180° pulses are indicated by thin and thick vertical bars, respectively, and phases are indicated above the pulses. Where no r.f. phase is marked, the pulse is applied along x. High-power 90° pulse lengths are: 5.7 μs for $^1$H, 15.0 μs for $^{13}$C and 40 μs for $^{15}$N and κ=0.25. Pulses on $^{13}$C prior to t$_1$($^{13}$C) are applied at high power, and $^{13}$C—$^1$H coupling during the first INEPT (Cavanagh et al., *Protein NMR Spectroscopy* Academic Press: San Diego (1996), which is hereby incorporated by reference in its entirety) is achieved using a (90°$_x$-180°$_y$-90°$_x$) composite pulse. Subsequently, the 90° and 180° pulse lengths applied on $^{13}$C$^{\alpha\beta}$ (at a $^1$H resonance frequency of 600 MHz) are adjusted to 48 μs and 43 μs, respectively, during the first t$_1$ delay [t$_1$($^{13}$C$^{\alpha\beta}$)] and to 54 μs and 48 μs, respectively, during the second t$_1$ delay [t$_1$($^{13}$C$^{\alpha}$)] to minimize perturbation of $^{13}$C' spins. All pulses applied on $^{13}$C' are of SEDUCE (Cavanagh et al., *Protein NMR Spectroscopy* Academic Press: San Diego (1996), which is hereby incorporated by reference in its entirety) shape. Off-resonance 180° pulses with a length of 200 μs and 103 μs are used, respectively, to decouple $^{13}$C' during t$_1$($^{13}$C$^{\alpha\beta}$), t$_1$($^{13}$C$^{\alpha}$), and t$_2$($^{15}$N). The duration of 90° pulse applied on-resonance at $^{13}$C' is 200 μs. SEDUCE (Cavanagh et al., *Protein NMR Spectroscopy* Academic Press: San Diego (1996), which is hereby incorporated by reference in its entirety) off-resonance 180° pulses of duration 100 μs are used to decouple $^{13}$C$^{\alpha}$ during t$_2$($^{13}$C'). WALTZ16 (Cavanagh et al., *Protein NMR Spectroscopy* Academic Press: San Diego (1996), which is hereby incorporated by reference in its entirety) is employed to decouple $^1$H (r.f. field strength=6.0 kHz) during the heteronuclear magnetization transfers as well as to decouple $^{15}$N during acquisition (r.f.=1.7 kHz). The SEDUCE (Cavanagh et al., *Protein NMR Spectroscopy*, Academic Press: San Diego (1996), which is hereby incorporated by reference in its entirety) sequence is used for decoupling $^{13}$C$^{\alpha}$ during t$_2$($^{15}$N). The $^1$H r.f. carrier position is placed at 4.78 ppm and that of $^{15}$N at 118.5 ppm. The $^{13}$C carrier position is initially set to 43 ppm during t$_1$($^{13}$C$^{\alpha\beta}$). This is then switched to 56 ppm during t$_1$($^{13}$C$^{\alpha}$) (indicated by an arrow as point a), to 175 ppm during t$_2$($^{13}$C') (point b) and back to 56 ppm during t$_2$($^{15}$N) (at point c). The duration and strengths of the pulsed rectangular z-field gradients (PFGs) are: G1 (1 ms, 24 G/cm); G2 (0.5 ms, 8 G/cm); G3 (1.0 ms, 20 G/cm); G4 (0.5 ms, 8 G/cm); G5 (1.25 ms, 30 G/cm); G6 (0.5 ms, 8 G/cm); G7 (0.125 ms, 29.5 G/cm). The delays are: τ$_a$=1.7 ms, τ$_1$=350 μs, τ$_2$=2.8 ms, τ$_3$=2.65 ms, τ$_4$=7.2 ms, τ$_5$=4.4 ms, τ$_6$=24.6 ms, τ$_7$=24.6 ms, τ$_8$=5.5 ms, τ$_9$=4.6 ms, τ$_{10}$=1.0 ms. Phase cycling: φ$_1$=x; φ$_2$=x, x, -x,-x; φ$_3$=x, -x; φ$_4$=x; φ$_6$=x,-x; φ$_7$=x, x, -x, -x; φ$_8$=x; φ$_9$ (receiver)=x, -x, -x, x. A sensitivity enhancement scheme (Kay et al., *J. Am Chem. Soc.* 114:10663-10665 (1992), which is hereby incorporated by reference in its entirety) is employed, i.e., the sign of G5 is inverted in concert with a 180° shift of φ$_8$ Quadrature detection in t$_1$($^{13}$C$^{\alpha}$) is accomplished by altering the phases φ$_4$ according to States-TPPI (Cavanagh et al., *Protein NMR Spectroscopy* Academic Press: San Diego (1996), which is hereby incorporated by reference in its entirety), whereas that of t$_2$($^{15}$N) is achieved by use of the sensitivity enhancement scheme. GFT NMR phase-cycle: φ$_2$=x, y; φ$_5$=2x, 2y, yielding, in conjunction with quadrature detection, 16 data sets which are linearly combined employing a G-matrix transformation with the G-matrix of Equation 10 (see Detailed Description of the Invention section).

Figure 12:
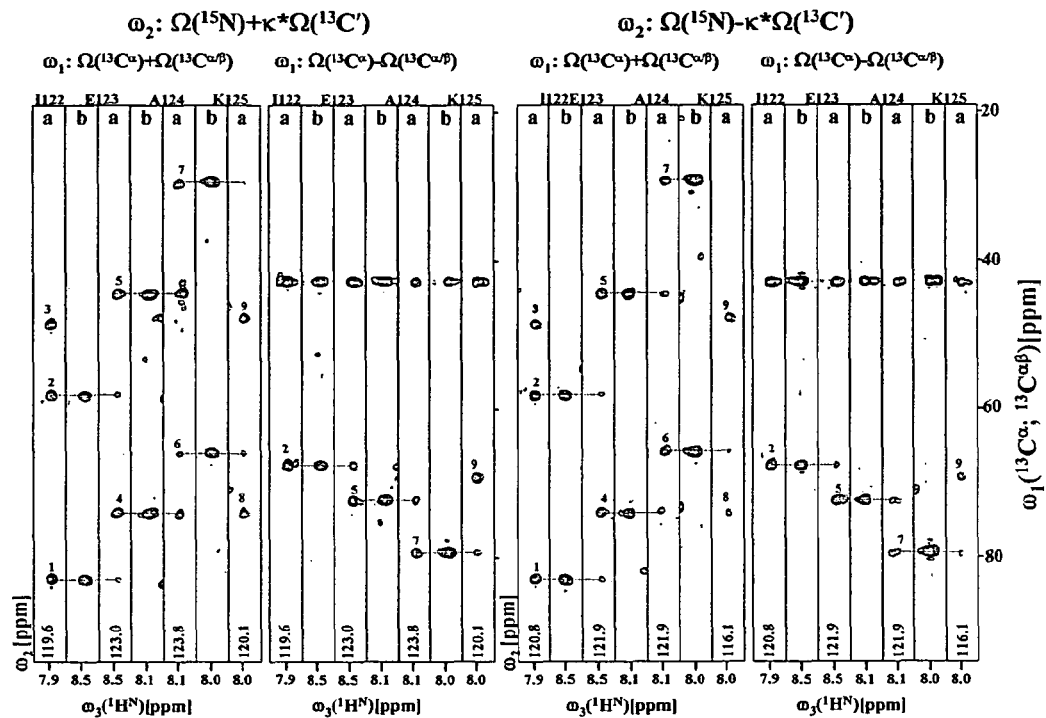

FIG. 12 shows the [ω$_1$($^{13}$C$^{\alpha}$; $^{13}$C$^{\alpha\beta}$),ω$_3$($^1$H$^N$)]-strips taken from G²FT L-(5,3)D HN{N,CO}{C$^{\alpha\beta}$C$^{\alpha}$} (labeled as "a") and (5,3)D {C$^{\alpha\beta}$C$^{\alpha}$}{CON}HN (labeled as "b") recorded for the 17 kDa protein yqbG on Varian INOVA 600 spectrometer equipped with cryogenic probe. Strips were taken at ω$_2$:Ω ($^{15}$N)±κΩ($^{13}$C') (κ=0.25) of residues Ile (one-letter code: I) 122 to Lys (K) 125 (chemical shifts are indicated at bottom) and comprise peaks at ω$_1$:Ω($^{13}$C$^{\alpha}$)±Ω($^{13}$C$^{\alpha}$) (peaks labeled "1", "3", "4", "6", and "8") and Ω$_1$:Ω($^{13}$C$^{\alpha}$)±Ω($^{13}$C$^{\beta}$) (peaks labeled "2", "5", "7", and "9"). Acquisition parameters are given in Table 1. Peaks are assigned to the following residues: Gly (G) 121 (3); Ile (I) 122 (1,2); Glu (E) 123 (4,5); Ala (A) 124 (6,7); Lys (K) 125 (8,9). Sequential connectivities are indicated by dashed lines, demonstrating that six "sequential walks" are established [see also FIG. 10, where (5,3)D HN{NCO}{C$^{\alpha\beta}$C$^{\alpha}$} instead of (5,3)D {C$^{\alpha\beta}$C$^{\alpha}$}{CON}HN is used].

Figure 13:
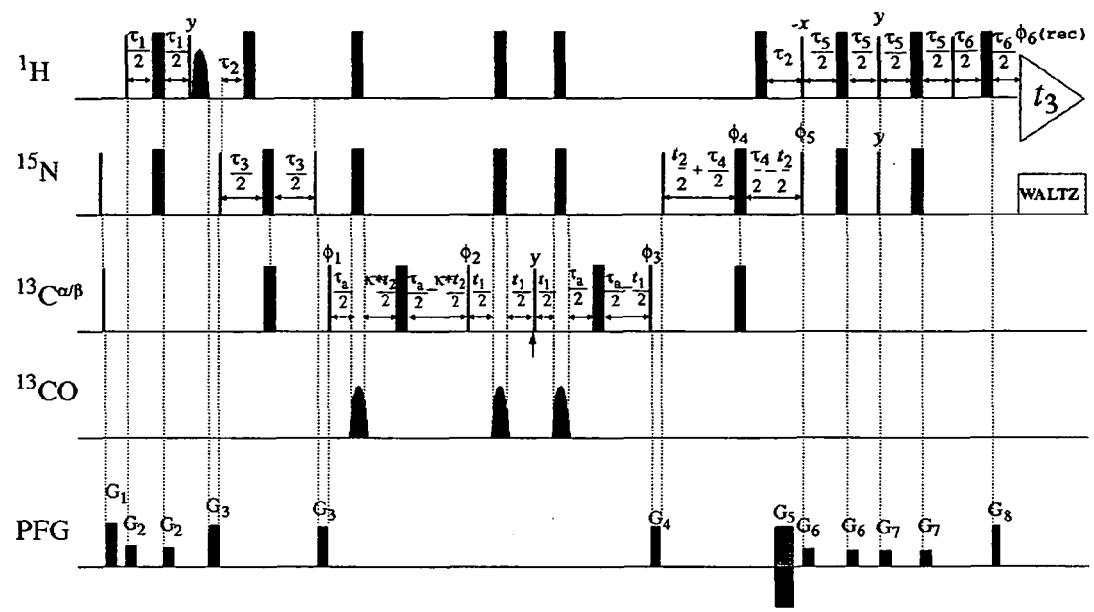

FIG. 13 depicts the r.f. pulse scheme of G²FT L-(5,3)D HN{NC$^{\alpha}$}{C$^{\alpha\beta}$C$^{\alpha}$}. Rectangular 90° and 180° pulses are indicated by thin and thick vertical bars, respectively, and phases are indicated above the pulses. Where no r.f. phase is marked, the pulse is applied along x. High-power 90° pulse lengths are: 5.7 μs for $^1$H, 15.0 μs for $^{13}$C and 40 μs for $^{15}$N, and κ=0.25. All 90° and 180° pulse lengths applied on $^{13}$C$^{\alpha\beta}$ are adjusted (at a $^1$H resonance frequency of 750 MHz) to 39 μs and 34 μs, respectively, prior to and during the first t$_1$ delay [t$_1$($^{13}$C$^{\alpha\beta}$)], and to 43 μs and 39 μs, respectively, during the second t, delay [t$_1$($^{13}$C$^{\alpha}$)] in order to minimize perturbation of $^{13}$C' spins. A 90° E-BURP2 pulse (Geen et al., *J. Magn. Reson.*, 93:93-142 (1991), which is hereby incorporated by reference in its entirety) after the 2$^{nd}$ 90° $^1$H pulse (1.2 ms; 0-6 ppm excitation; carrier: 3 ppm) enables water flip-back (Cavanagh et al., *Protein NMR Spectroscopy* Academic Press: San Diego (1996), which is hereby incorporated by reference in its entirety) and L-optimization (Atreya et al., *Proc. Natl. Acad. Sci. USA* 101:9642-9647 (2004); Pervushin et al., *J. Am. Chem. Soc.* 124:12898-12902 (2002), which are hereby incorporated by reference in their entirety). WALTZ16 (Cavanagh et al., *Protein NMR Spectroscopy*, Academic Press: San Diego (1996), which is hereby incorporated by reference in its entirety) is employed to decouple $^{15}$N (r.f.=1.70 kHz) during acquisition. The $^1$H and $^{15}$N r.f. carriers are placed at the position of the solvent line at 4.77 ppm, and at 118.5 ppm, respectively. The $^{13}$C carrier position is set to 43 ppm prior to and during t$_1$($^{13}$C$^{\alpha\beta}$) and switched to 56 ppm during t$_1$($^{13}$C$^{\alpha}$) (indicated by the arrow). The duration and strengths of the pulsed rectangular z-field gradients (PFGs) are: G1 (1.0 ms, 20 G/cm); G2 (0.5 ms, 6 G/cm); G3 (1.0 ms, 20 G/cm); G4 (1.0 ms, 20 G/cm); G5 (1.25 ms, 30 G/cm); G6 (0.5 ms, 4 G/cm); G7 (0.5 ms, 4 G/cm); G8 (0.125 ms, 29.5 G/cm). All PFG pulses are of rectangular shape. The delays are: τ$_1$=5.5 ms; τ$_2$=5.4 ms; τ$_3$=24 ms; τ$_4$=24 ms; τ$_5$=4.6 ms; τ$_6$=1.0 ms; τ$_a$=8.0 ms. Phase cycling: φ$_1$=x=x; φ$_2$=y,-y; φ$_3$=2(x),2(-x); = y; φ$_4$=x; φ$_5$=4(x), 4(-x); φ$_6$=x; φ$_7$(receiver)=x, -x, -x, x. A sensitivity enhancement scheme (Kay et al., *J. Am. Chem. Soc.* 114:10663-10665 (1992), which is hereby incorporated by reference in its entirety) is employed, i.e., the sign of G5 is inverted in concert with a 180° shift of 45. Quadrature detection in t$_1$($^{13}$C$^{\alpha}$) is accomplished by altering the phases φ$_3$ according to States-TPPI, whereas quadrature detection in t$_2$($^{15}$N) is achieved by use of the sensitivity enhancement scheme. GFT NMR phase-cycle: φ$_1$=2(x, y); φ$_2$=y, x, x, y, yielding, in conjunction with quadrature detection, 16 data sets which are linearly combined employing a G-matrix transformation with the G-matrix of Equation 10 (see Detailed Description of the Invention section).

Figure 9:
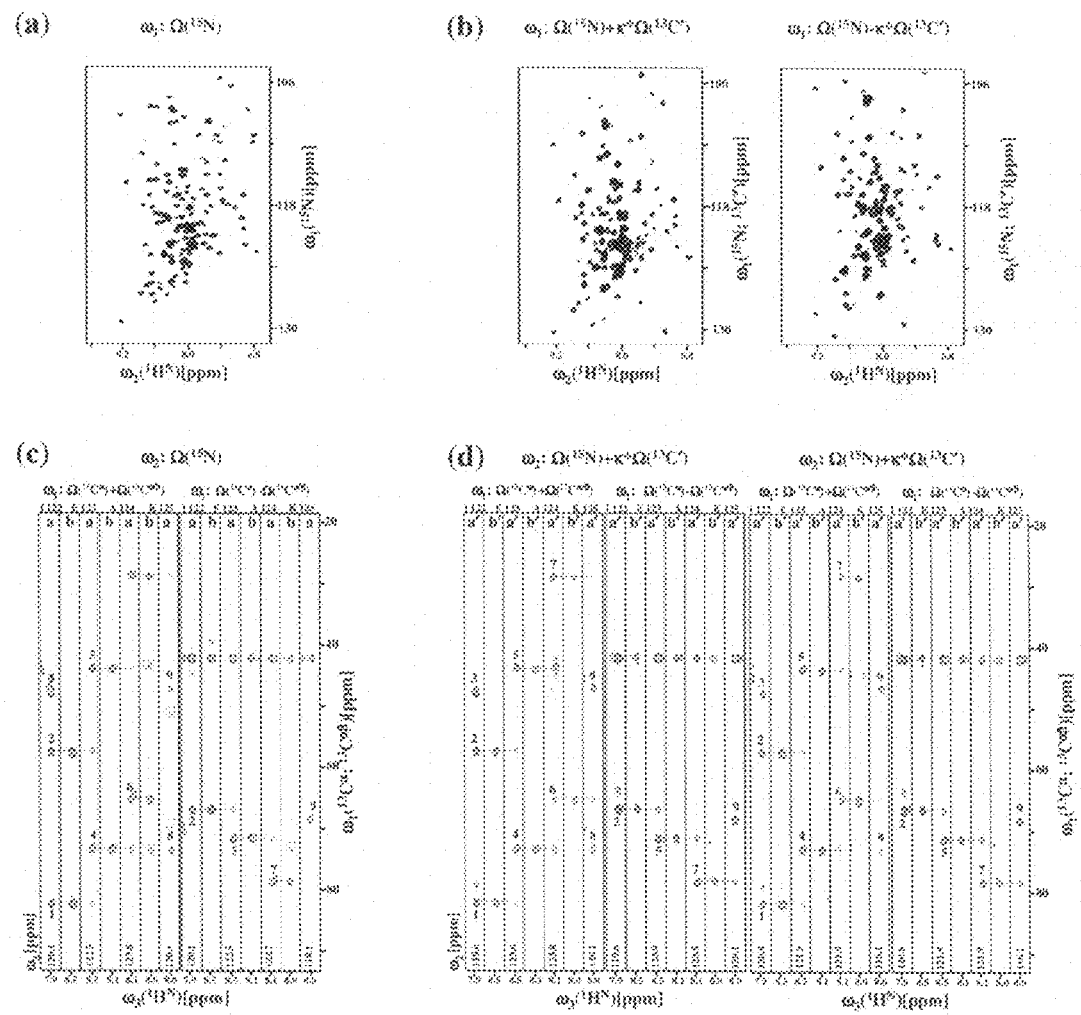
Figure 14:
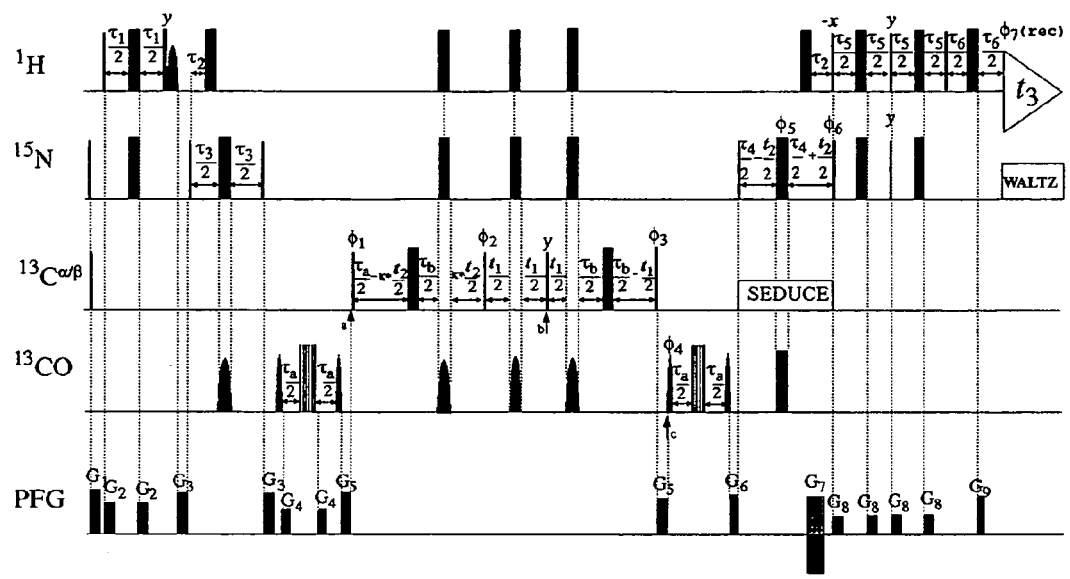

FIG. 14 depicts the r.f. pulse scheme of G²FT L-(5,3)D HN{N(CO)C$^{\alpha}$}{C$^{\alpha\beta}$C$^{\alpha}$}. Rectangular 90° and 180° pulses are indicated by thin and thick vertical bars, respectively, and phases are indicated above the pulses. Where no r.f. phase is marked, the pulse is applied along x. High-power 90° pulse lengths are: 5.7 μs for $^1H$, 15.0 μs for $^{13}C$ and 40 μs for $^{15}N$, and κ=0.25. 90° and 180° pulse lengths applied on $^{13}C^{\alpha\beta}$ are adjusted (at a $^1H$ resonance frequency of 750 MHz) to 39 μs and 34 μs, respectively, prior to and during the first $t_1$ delay $[t_1(^{13}C^\alpha)]$ and to 43 μs and 39 μs, respectively, during the second $t_1$ delay $[t_1(^{13}C^\alpha)]$ to minimize perturbation of $^{13}C'$ spins. A 90° E-BURP2 pulse (Geen et al., *J. Magn. Reson.*, 93:93-142 (1991), which is hereby incorporated by reference in its entirety) after the $2^{nd}$ 90° $^1H$ pulse (1.2 ms; 0-6 ppm excitation; carrier: 3 ppm) enables water flip-back (Cavanagh et al., *Protein NMR Spectroscopy* Academic Press: San Diego (1996), which is hereby incorporated by reference in its entirety) and L-optimization (Atreya et al., *Proc. Natl. Acad. Sci. USA* 101:9642-9647 (2004); Pervushin et al., *J. Am. Chem. Soc.* 124:12898-12902 (2002), which are hereby incorporated by reference in their entirety). SEDUCE (Cavanagh et al., *Protein NMR Spectroscopy* Academic Press: San Diego (1996), which is hereby incorporated by reference in its entirety) off-resonance 180° pulses of duration 200 μs and 103 μs, respectively, are used to decouple $^{13}C'$ during $t_1(^{13}C^{\alpha\beta})$ and $t_1(^{13}C^\alpha)$. The 90° and 180° pulse lengths for the sinc lobe pulse on-resonance at $^{13}C'$ is 88 μs and 81 μs, respectively. A six-pulse composite sequence is used to simultaneously invert/refocus $^{13}C^\alpha/^{13}C'$ magnetization during $^{13}C^\alpha$—$^{13}C'$ polarization transfers. (In the three sets of subspectra constituting (5,3)D HN{N,CO}{$C^{\alpha\beta}C^\alpha$}, (5,3)D HN{NCO}{$C^{\alpha\beta}C^\alpha$} and (4,3)D HN$\overline{NC^{\alpha\beta}C^\alpha}$, nine sequential walks are established (FIG. 9). Hence, combination of all three pairs of (5,3)D $G^2FT$ experiments described in the present application can provide a total of 24 independent sequential walks.) The SEDUCE (Cavanagh et al., *Protein NMR Spectroscopy* Academic Press: San Diego (1996), which is hereby incorporated by reference in its entirety) sequence is used for decoupling of $^{13}C^\alpha$ during $t_2(^{15}N)$. WALTZ16 (Cavanagh et al., *Protein NMR Spectroscopy* Academic Press: San Diego (1996), which is hereby incorporated by reference in its entirety) is employed to decouple of $^{15}N$ (r.f.=1.70 kHz) during acquisition. The $^1H$ r.f. carrier is placed at the position of the solvent line at 4.77 ppm after the first selective pulse on $^1H$. The $^{15}N$ carrier position is set to 118.5 ppm. The $^{13}C$ carrier position is set initially to 175 ppm, then switched to 43 ppm prior to $t_1(^{13}C^{\alpha\beta})$ (indicated by an arrow as point a), to 56 ppm during $t_1(^{13}C^\alpha)$ (at b) and back to 175 ppm (at c) during the reverse $^{13}C$ɔ—$^{13}C^\alpha$ polarization transfer. The duration and strengths of the pulsed rectangular z-field gradients (PFGs) are: G1 (1.0 ms, 24 G/cm); G2 (0.5 ms, 8 G/cm); G3 (1.0 ms, 20 G/cm); G4 (0.5 ms, 4 G/cm); G5 (1.0 ms, 20 G/cm); G6 (0.5 ms, 8 G/cm); G7 (1.25 ms, 30 G/cm); G8 (0.5 ms, 4 G/cm); G9 (0.125 ms, 29.5 G/cm). The delays are: $\tau_1$=5.4 ms, $\tau_2$=5.4 ms, $\tau_3$=24 ms, $\tau_4$=24 ms, $\tau_5$=4.6 ms, $\tau_6$=1.0 ms, $\tau_a$=8.0 ms, $\tau_b$=7.0 ms. Phase cycling: $\phi_1$=x, -x; $\phi_2$=y; $\phi_3$=2(x),2(-x); $\phi_4$=x, $\phi_5$=4(x), 4(-x); $\phi_6$=x; $\phi_7$(receiver)=x, -x, -x, x. A sensitivity enhancement scheme (Kay et al., *J. Am. Chem. Soc.* 114:10663-10665 (1992), which is hereby incorporated by reference in its entirety) is employed, i.e., the sign of G7 is inverted in concert with a 180° shift of $\phi_6$. Quadrature detection in $t_1(^{13}C^\alpha)$ is accomplished by altering the phases $\phi_3$ according to States-TPPI, whereas quadrature detection in $t_2(^{15}N)$ is achieved by use of the sensitivity enhancement scheme. GFT NMR phase-cycle: $\phi_1$=2(x, y); $\phi_2$=y, x, x, y, yielding, in conjunction with quadrature detection, 16 data sets which are linearly combined employing a G-matrix transformation with the G-matrix of Equation 10 (see Detailed Description of the Invention section).

Figure 15:
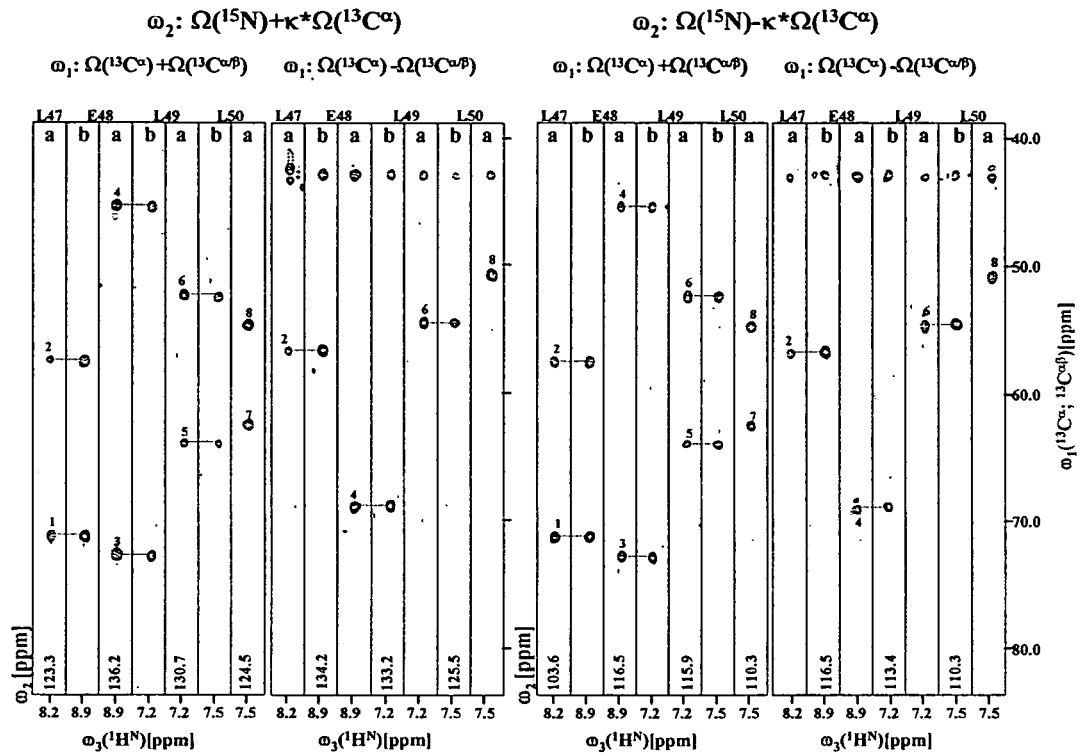

FIG. 15 shows the $[\omega_1(^{13}C^\alpha; ^{13}C^{\alpha\beta}),\omega_3(^1H^N)]$-strips taken from $G^2FT$ L-(5,3)D HN{$NC^\alpha$}{$C^\alpha C^{\alpha\beta}$}(labeled as "a") and L-(5,3)D HN{$\underline{N}(CO)\underline{C}^\alpha$}{$\overline{C^\alpha C^{\alpha\beta}}$}(labeled as "b") recorded for the 13.5 kDa protein rsp24e equipped with a $^1H${$^{13}C, ^1H$} triple resonance probe. Strips were taken at $\omega_2:\Omega(^{15}N)+\kappa\Omega$ ($^{13}C'$) (left) and $\omega_2:\Omega(^{15}N)-\kappa\Omega(^{13}C')$ (right) (κ=0.25) of residues Leu (one-letter code: L) 47 to Leu (L) 50 (chemical shifts are indicated at bottom) and comprise peaks at $\omega_1:\Omega(^{13}C^\alpha)\pm\Omega(^{13}C^\alpha)$ (peaks "1", "3", "4", "7") and $\Omega(^{13}C^\alpha)\pm(^{13}C^\beta)$ (peaks "2", "4", "6", "8"). The acquisition parameters are given in Table 1. The peaks are assigned to the following residues: Leu (L) 47 ("1", "2"), Glu (E) 48 ("3", "4"); Leu (L) 49 ("5", "6"); Leu (L) 50 ("7", "8"). Sequential connectivities are indicated by dashed lines, demonstrating that six "sequential walks" are established.

Figure 16:
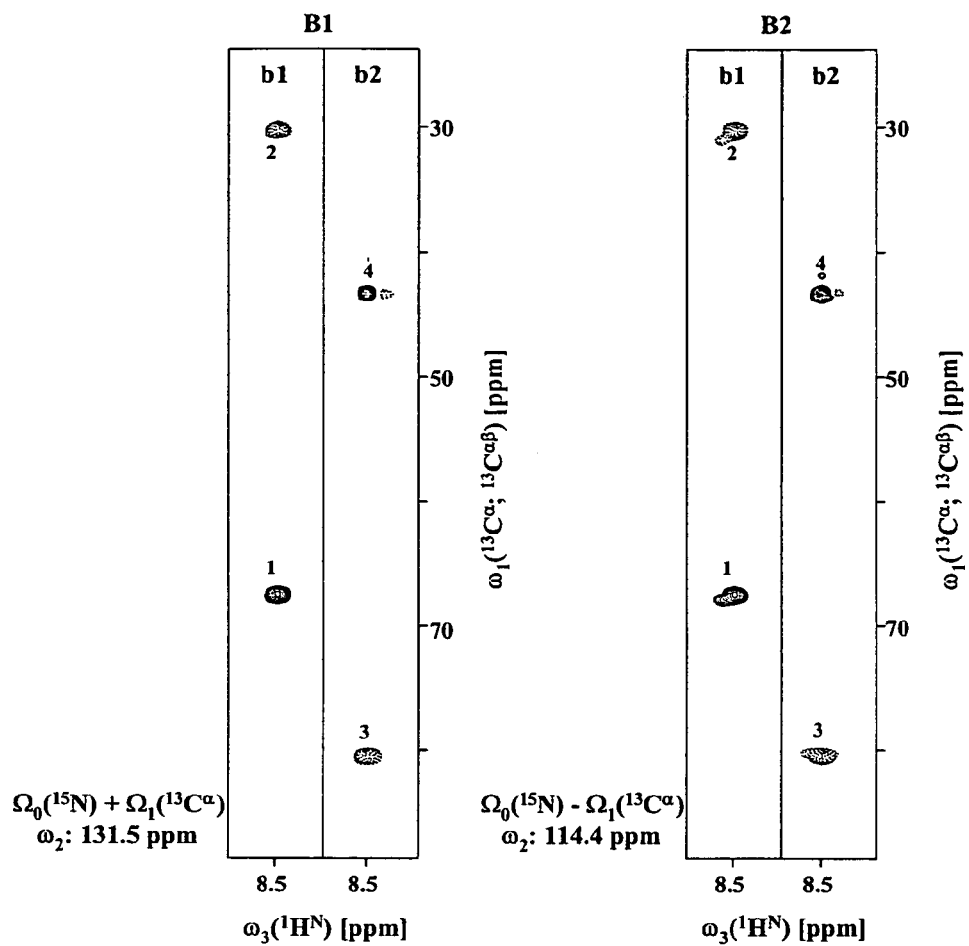
Figure 17:
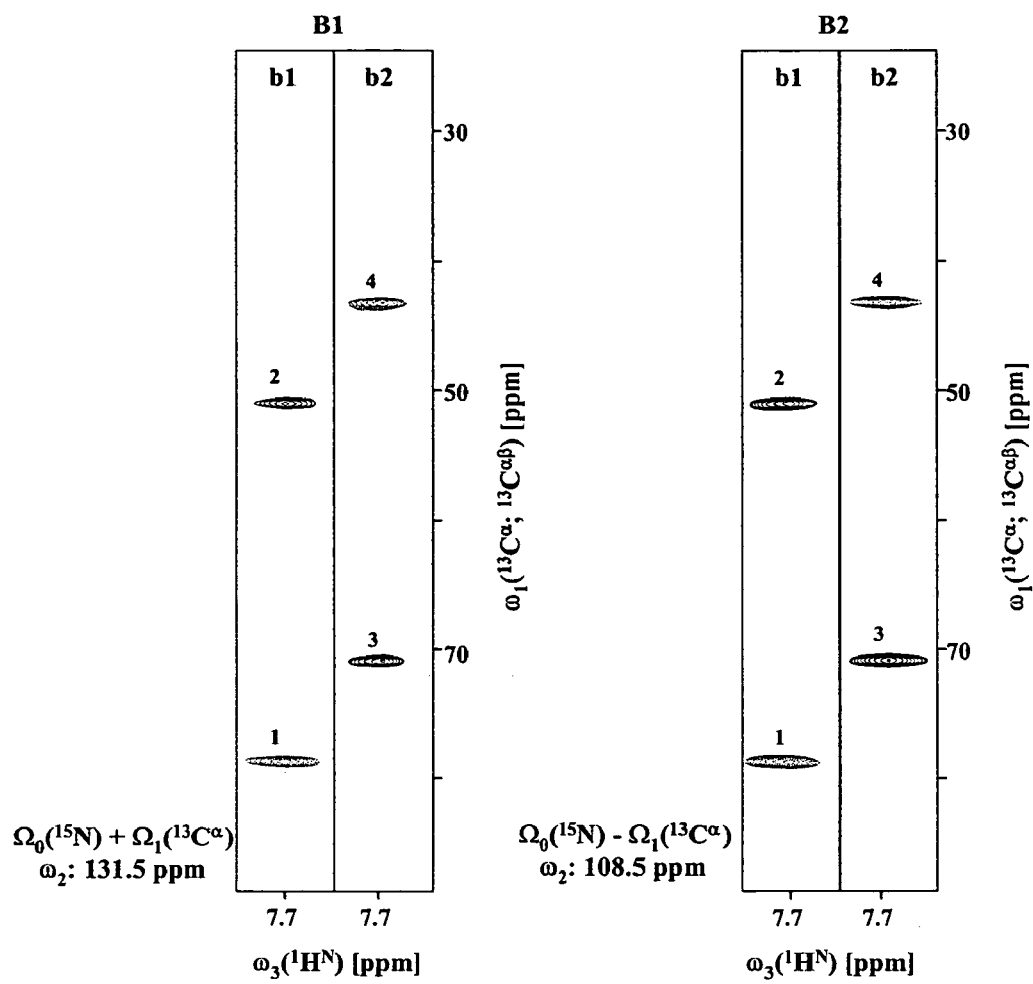
Figure 18:
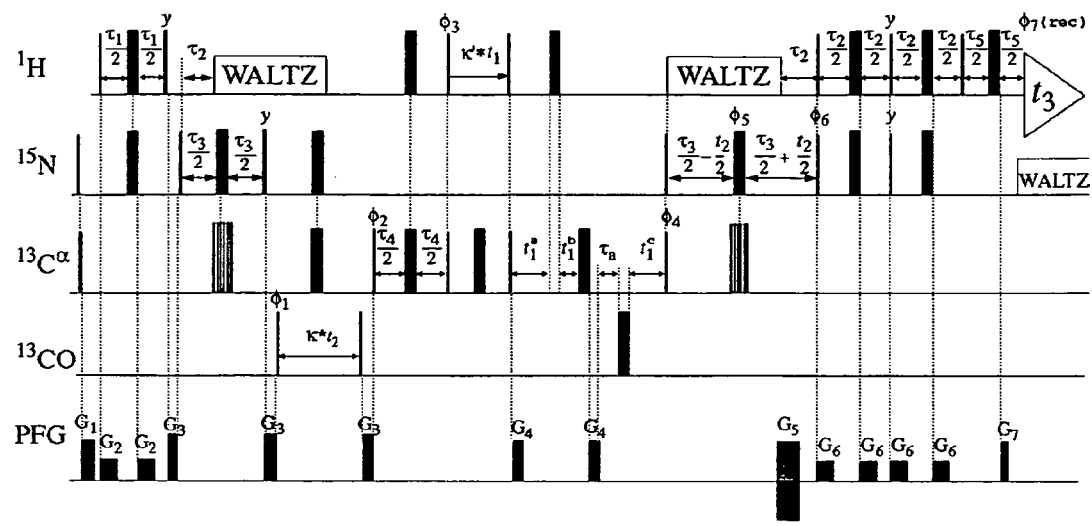

FIG. 16 shows composite plots of $[\omega_1(^{13}C^\alpha; ^{13}C^{\alpha\beta}), \omega_3(^1H^N)]$ strips taken from the basic spectra of $G^2FT$ (5,3)D HN{$NC^\alpha$}{$C^{\alpha\beta}C^\alpha$}. The four basic spectra are grouped into two sets, B1 and B2, comprising peaks at $\Omega_0(^{15}N_i)+\Omega_1(^{13}C^\alpha_i)$ and $\Omega_0(^{15}N_i)-\Omega_1(^{13}C^\alpha_i)$ along $\omega_2$, respectively. B1 and B2 each contain two spectra (labeled as "b1" and "b2") comprising peaks at $\Omega_0(^{13}C^\alpha_{i/i-1})\pm\Omega_1(^{13}C^{\alpha/\beta}_{i/i-1})$ along $\omega_1$. Positive and negative peaks are shown, respectively, with solid and dotted contour lines. As an example, strips are shown for the residue Ala 55 of the 7 kDa protein Z-domain. Peaks labeled 1-4 in "b1" and "b2" correspond to the following linear combination of chemical shifts along $\omega_1$:

1. $\Omega_0(^{13}C^\alpha_{i-1})+\Omega_1(^{13}C^\alpha_{i-1})$
2. $\Omega_0(^{13}C^\alpha_{i-1})+\Omega_1(^{13}C^\beta_{i-1})$
3. $\Omega_0(^{13}C^\alpha_{i-1})-\Omega_1(13C^\beta_{i-1})$
4. $\Omega_0(^{13}C^\alpha_{i-1})-\Omega_1(13C^\alpha_{i-1})$ FIG. 17 shows composite plots of $[\omega_1(^{13}C^\alpha; ^{13}C^{\alpha\beta}), \omega_3(^1H^N)]$ strips taken from the basic spectra of $G^2FT$ (5,3)D HN{$N(CO)\underline{C}^\alpha$}{$C^{\alpha\beta}C^\alpha$}. The four basic spectra are grouped into two sets, B1 and B2, comprising peaks at $\Omega_0(^{15}N_i)+\Omega_1(^{13}C^\alpha_{i-1})$ and $\Omega_0(^{15}N_i)-\Omega_1(^{13}C^\alpha_{i-1})$ along $\omega_2$, respectively. B1 and B2 each contain two spectra (labeled as "b1" and "b2") comprising peaks at $\Omega_0(^{13}C^\alpha_{i-1})\pm\Omega_1(^{13}C^{\alpha/\beta}_{i-1})$ along $\omega_1$. Positive and negative peaks are shown, respectively, with solid and dotted contour lines. As an example, strips are shown for the residue Lys 63 of the 7 kDa protein Z-domain. Peaks labeled 1-4 in "b1" and "b2" correspond to the following linear combination of chemical shifts along $\omega_1$:

1. $\Omega_0(^{13}C^\alpha_{i-1})+\Omega_1(^{13}C^{'\alpha}_{i-1})$
2. $\Omega_0(^{13}C^\alpha_{i-1})+\Omega_1(^{13}C^\beta_{i-1})$
3. $\Omega_0(^{13}C^\alpha_{i-1})-\Omega_1(^{13}C^\beta_{i-1})$
4. $\Omega_0(^{13}C^\alpha_{i-1})-\Omega_1(^{13}C^\alpha_{i-1})$ FIG. 18 depicts the r.f pulse scheme of $G^2FT$ (5,3)D HN{N,CO}{$C^\alpha H^\alpha$}. Rectangular 90° and 180° pulses are indicated by thin and thick vertical bars, respectively, and phases are indicated above the pulses. Where no r.f. phase is marked, the pulse is applied along x. High-power 90° pulse lengths are: 5.7 μs for $^1H$, 15.0 μs for $^{13}C$ and 40 μs for $^{15}N$ and κ=0.25. A six-pulse composite sequence (Shaka, *Chem. Phy. Lett.*, 120:201-205 (1985), which is hereby incorporated by reference in its entirety) is used to simultaneously transfer magnetization from $^{15}N(i)$ to $^{13}C^\alpha$ (i/i−1) and $^{13}C$ɔ (i−1), and back. The lengths of the 90° and 180° pulses applied on $^{13}C^\alpha$ are adjusted (at a $^1H$ resonance frequency of 600 MHz) to 51.6 μs and 46 μs, respectively, during $t_1(^{13}C^\alpha)$ to minimize perturbation of $^{13}C'$ spins. The width of the 90° pulses applied to $^{13}CO$ pulse is 52 μs and the corresponding off-resonance 180° pulse is applied with same power. A rectangular phase modulated off-resonance 180° pulse with a length of 46 μs is used to decouple $^{13}C^\alpha$ during $t_2(^{13}C$ɔ). WALTZ16 (Cavanagh et al., *Protein NMR Spectroscopy* Academic Press: San Diego (1996), which is hereby incorporated by reference in its entirety) (r.f. field strength=6.0 kHz) is employed to decouple $^1H$ during the heteronuclear magnetization transfers as well as to decouple $^{15}N$ during acquisition (r.f.=1.7 kHz). The scaling factor κ' for $^1$H chemical shift evolution during $t_1$ is set to 1.0. The $^1$H and $^{15}$N r.f. carriers are set to 4.78 ppm and 118.5 ppm, respectively. The $^{13}$C carrier position is initially set to 56 ppm, and switched to 175 ppm before the first 90° pulse on $^{13}$C', and back to 56 ppm after the second 90° pulse on $^{13}$C'. $^{13}$C$^\alpha$-frequency labeling is achieved in a semi constant-time fashion with (at 600 MHz): $t_1^a(0)$=1.7 ms, $t_1^b(0)$=1 μs, $t_1^c(0)$=1.701 ms, $\Delta t_1^a$=12.5 μs, $\Delta t_1^b$=6.6 μs, $\Delta t_1^c$=−5.9 μs. Hence, the fractional increase of the semi constant-time period with $t_1$ equals to $\lambda$=1+$\Delta t_1^c/\Delta t_1^a$=0.53. The duration and strengths of the pulsed rectangular z-field gradients (PFGs) are: G1 (1 ms, 20 G/cm); G2 (0.5 ms, 8 G/cm); G3 (1.0 ms, 20 G/cm); G4 (0.5 ms, 16 G/cm); G5 (1.25 ms, 30 G/cm); G6 (0.5 ms, 8 G/cm); G7 (0.125 ms, 29.5 G/cm). The delays are: $\tau_1$=5.4 ms, $\tau_2$=5.6 ms, $\tau_3$=28 ms, $\tau_4$=1.7 ms, $\tau_5$=1.0 ms, $\tau_a$=1.7 ms. Phase cycling: $\phi_1$=x, −x; $\phi_2$=x, x, −x,−x; $\phi_3$=x; $\phi_4$=y; $\phi_5$=4(x)4(−x); $\phi_6$=x; $\phi_7$(receiver)=x, −x, −x, x. A sensitivity enhancement scheme (Kay et al., *J. Am. Chem. Soc.* 114:10663-10665 (1992), which is hereby incorporated by reference in its entirety) is employed, i.e., the sign of G$_5$ is inverted in concert with a 180° shift of $\phi_6$. Quadrature detection in $t_1(^{13}C^\alpha)$ is accomplished by altering the phases $\phi_4$ according to States-TPPI, whereas quadrature detection in $t_2(^{15}N)$ is achieved by use of the sensitivity enhancement scheme. GFT NMR phase-cycle: $\phi_1$=x, y; $\phi_3$=2x, 2y, yielding in conjunction with quadrature detection 16 data sets which are linearly combined employing a G-matrix transformation with the G-matrix of Equation 10 (see Detailed Description of the Invention section).

Figure 19:
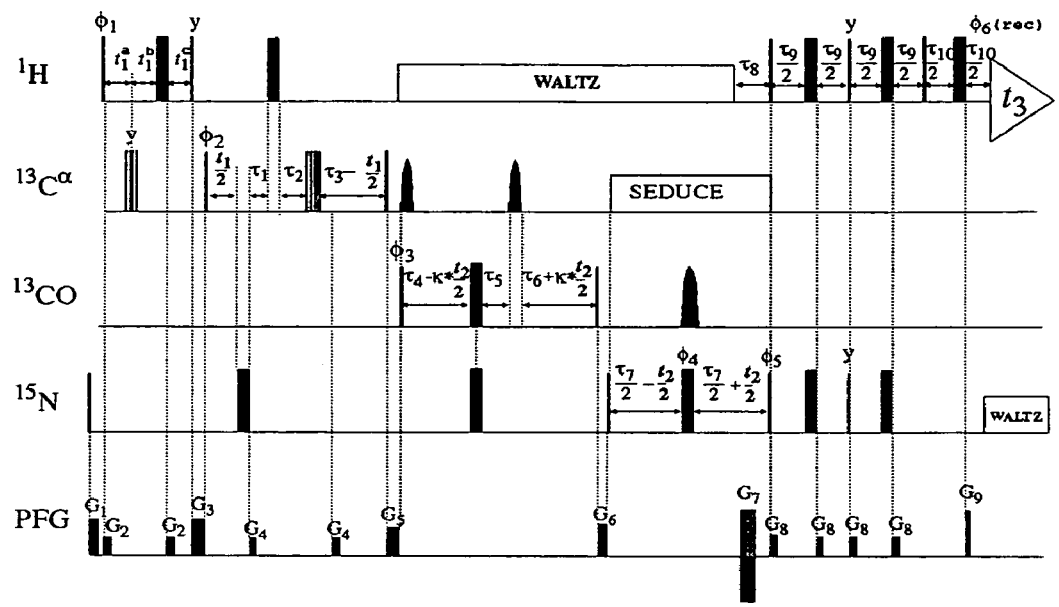

FIG. 19 depicts the r.f. pulse scheme of G$^2$FT (5,3)D {H$^\alpha$C$^\alpha$}{CON}HN. Rectangular 90° and 180° pulses are indicated by thin and thick vertical bars, respectively, and phases are indicated above the pulses. Where no r.f. phase is marked, the pulse is applied along x. The high power 90° pulse lengths were: 5.8 μs for $^1$H and 15.0 μs for $^{31}$C, and 38 μs for $^{15}$N, and κ=0.25. Pulses on $^{13}$C prior to $t_1(^{13}C)$ are applied at high power, and $^{13}$C decoupling during $t_1(^1H)$ is achieved using a (90°$_x$-180°$_y$-90°$_x$) composite pulse. Subsequently, the 90° and 180° pulse lengths of $^{13}$C$^\alpha$ are adjusted (at a $^1$H resonance frequency of 600 MHz) to 54 μs and 46 μs, respectively, to minimize perturbation of the $^{13}$C' spins. A six-pulse composite sequence (Shaka, *Chem. Phy. Lett.*, 120:201-205 (1985), which is hereby incorporated by reference in its entirety) is used to simultaneously invert/refocus $^{13}$C$^\alpha$/$^{13}$C' magnetization during $^{13}$C$^\alpha$—$^{13}$C' polarization transfer. The length of 90° pulses applied to $^{13}$C' is 52 μs and the corresponding 180° pulses are applied with same power. WALTZ16 (Cavanagh et al., *Protein NMR Spectroscopy* Academic Press: San Diego (1996), which is hereby incorporated by reference in its entirety) is employed to decouple $^1$H (r.f. field strength=6.0 kHz) during the heteronuclear magnetization transfers as well as to decouple $^{15}$N during acquisition (r.f.=1.7 kHz). The SEDUCE (Cavanagh et al., *Protein NMR Spectroscopy* Academic Press: San Diego (1996), which is hereby incorporated by reference in its entirety) sequence is used for decoupling of $^{13}$C$^\alpha$ during the $^{15}$N chemical shift evolution period. The $^1$H r.f. carrier is placed at the position of the solvent line at 4.78 ppm. The $^{13}$C$^\alpha$ carrier is set to 56 ppm except during $t_2(^{13}C')$, where it is set to 175 ppm. The $^{15}$N r.f. carrier is set to 120.9 ppm. The duration and strengths of the pulsed rectangular z-field gradients (PFGs) are: G1 (1 ms, 24 G/cm); G2 (0.1 ms, 8 G/cm); G3 (1 ms, 20 G/cm); G4 (0.5 ms, 8 G/cm); G5 (1.0 ms, 20 G/cm); G6 (1.0 ms, 20 G/cm); G7 (1.25 ms, 30 G/cm); G8 (0.5 ms, 8 G/cm); G9 (0.125 ms, 29.5 G/cm). The delays are: $\tau_1$=850 μs, $\tau_2$=3.6 ms, $\tau_3$=4.4 ms, $\tau_4$=12.5 ms, $\tau_5$=8 ms, $\tau_6$=4.5 ms, $\tau_7$=24 ms, $\tau_8$=5.5 ms, $\tau_9$=4.6 ms, $\tau_{10}$=1 ms. $^1$H-frequency labeling is achieved in a semi constant-time fashion with $t_1^a(0)$=1.7 ms, $t_1^b(0)$=1 μs, $t_1^c(0)$=1.701 ms, $\Delta t_1^a$=60 μs, $\Delta t_1^b$=35.4 μs, $\Delta t_1^c$=−24.6 μs. Hence, the fractional increase of the semi constant-time period with $t_1$ equals to $\lambda$=1+$\Delta t_1^c/\Delta t_1^a$=0.58. Phase cycling: $\phi_1$=x; $\phi_2$=x, −x; $\phi_3$=x; $\phi_4$=4(x), 4(−x); $\phi_5$=x; $\phi_6$(receiver)=x, −x, −x, x. A sensitivity enhancement scheme (Kay et al., *J. Am. Chem. Soc.* 114: 10663-10665 (1992), which is hereby incorporated by reference in its entirety) is employed, i.e., the sign of G7 is inverted in concert with a 180° shift of $\phi_5$. Quadrature detection in $t_1(^{13}C^\alpha)$ is accomplished by altering the phases $\phi_2$ according to States-TPPI, quadrature detection in $t_2(^{15}N)$ is achieved by use of the sensitivity enhancement scheme. GFT NMR phase-cycle: $\phi_1$=x, y; $\phi_3$=2x, 2y, yielding, in conjunction with quadrature detection, 16 data sets which are linearly combined employing a G-matrix transformation with the G-matrix of Equation 10 (see Detailed Description of the Invention section).

Figure 20:
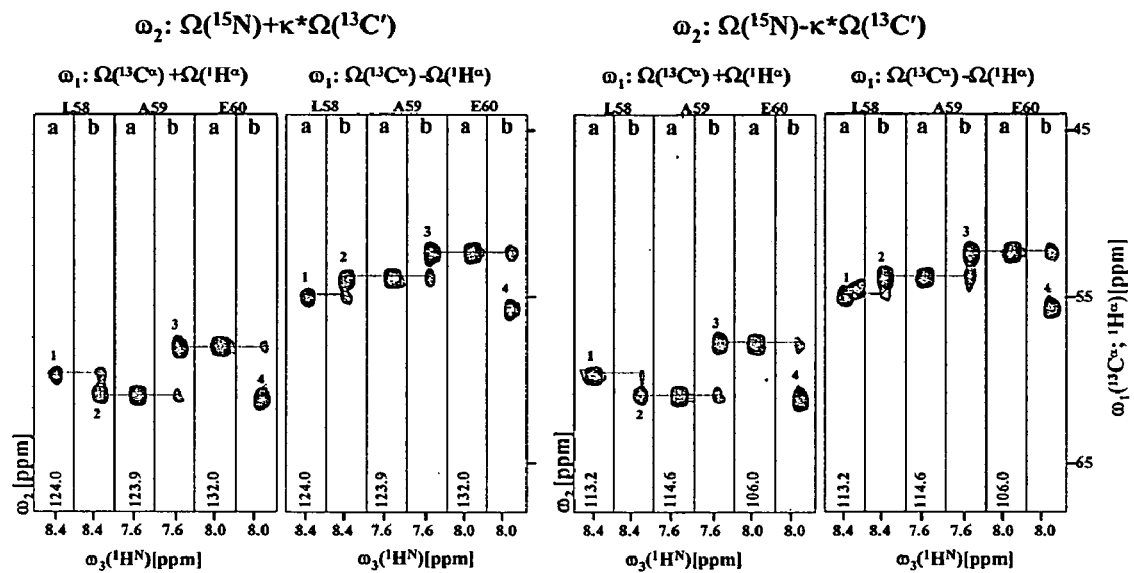

FIG. 20 shows the [$\omega_1(^{13}C^\alpha; ^1H^\alpha),\omega_3(^1H^N)$]-strips taken from G$^2$FT (5,3)D HN{N,CO}{C$^\alpha$H$^\alpha$}(labeled as "a") and (5,3)D {H$^\alpha$C$^\alpha$}{CON}HN (labeled as "b") recorded for the 8 kDa protein Z-domain (Montelione et al., *Nature Struct. Biol.* 7:982-984 (2002), which is hereby incorporated by reference in its entirety) on Varian INOVA 600 spectrometer equipped with a cryogenic probe. Strips were taken at $\omega_2:\Omega(^{15}N)\pm\kappa\Omega(^{13}C')$ (κ=0.25) of residues Leu (one-letter code: L) 58 to Glu (E) 60 (chemical shifts are indicated at bottom) and comprise peaks at $\omega_1:\Omega(^{13}C^\alpha)\pm\Omega(^1H^\alpha)$ (peaks labeled "1"-"4"). These peaks have been assigned to the following residues: Leu (L) 57 ("1"), Leu (L) 58 ("2"); Ala (A) 59 ("3"); Glu (E) 60 ("4"). Sequential connectivities are indicated by dashed lines, demonstrating that four sequential walks are established.

Figure 21:
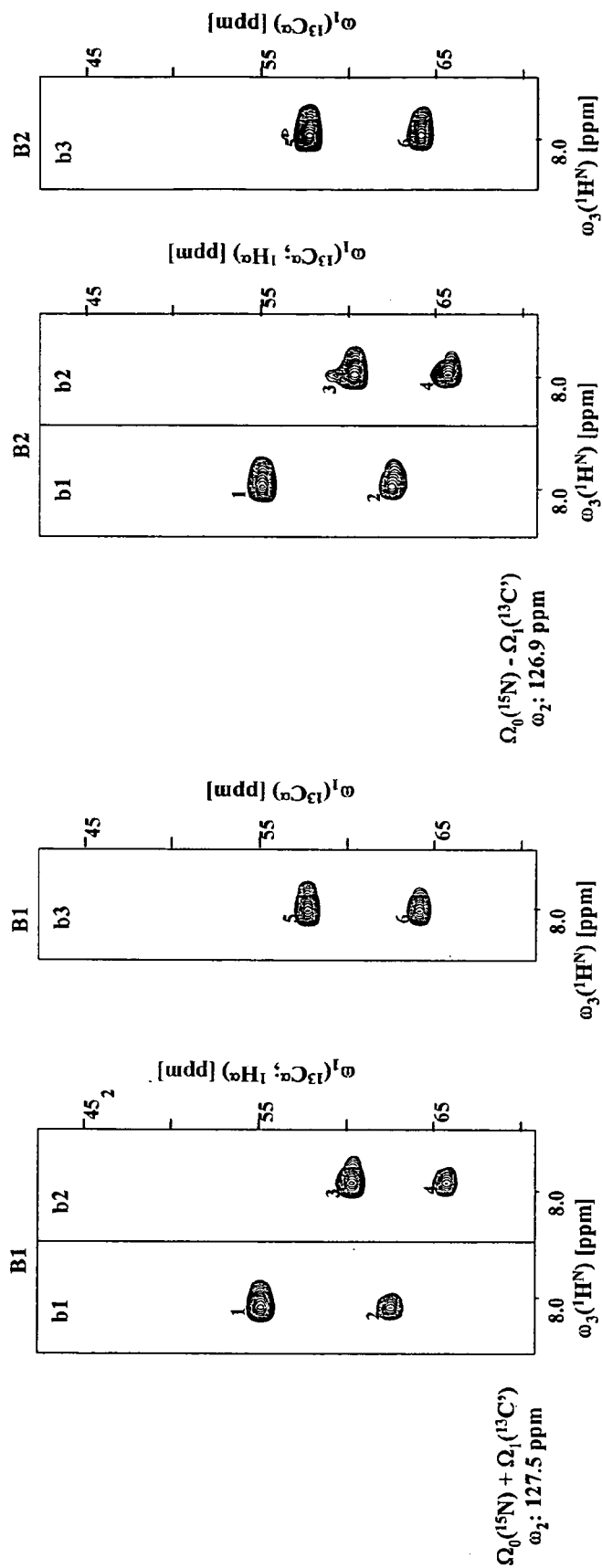
Figure 22:
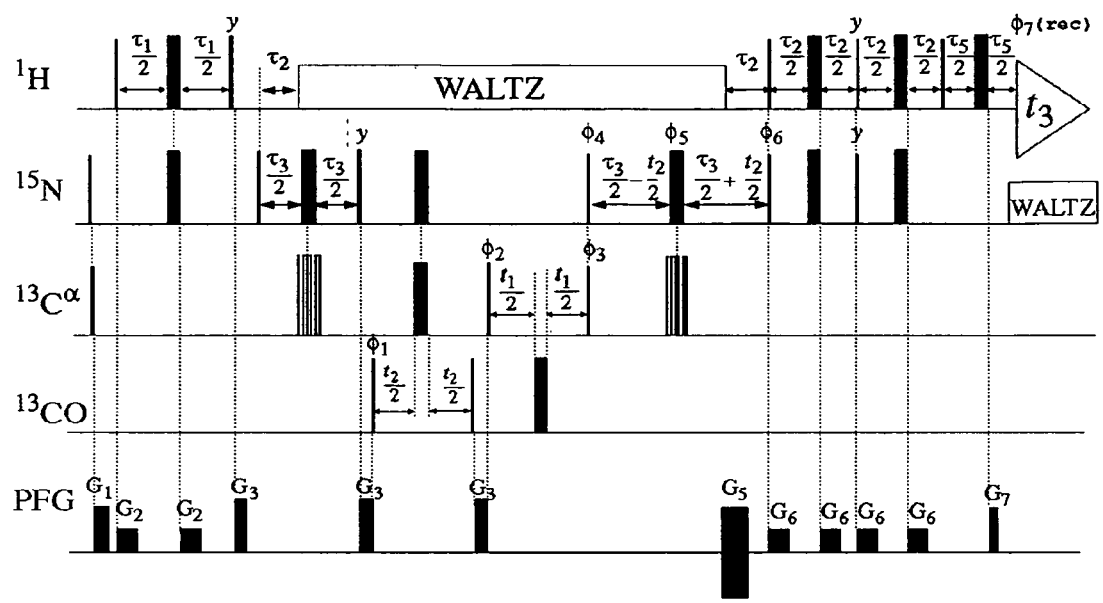

FIG. 21 shows composite plots of [$\omega_1(^{13}C^\alpha; ^1H^\alpha)$, $\omega_3(^1H^N)$] strips taken from the basic and central peak spectra of G$^2$FT (5,3)D HN{N,CO}{C$^\alpha$H$^\alpha$}. The four basic spectra are grouped into two sets, B1 and B2, comprising peaks at $\Omega_0(^{15}N_i)+\Omega_1(^{13}C'_{i-1})$ and $\Omega_0(^{15}N_i)-\Omega_1(^{13}C'_{i-1})$ along $\omega_2$, respectively. B1 and B2 each contain two spectra (labeled as "b1" and "b2") comprising peaks at $\Omega_0(^{13}C^\alpha_{i/i-1})\pm\Omega_1(^1H^\alpha_{i/i-1})$ along $\omega_1$. The first order central peak spectrum (labeled as "b3") comprising peaks at $\Omega_0(^{13}C^\alpha_{i/i-1})$ along $\omega_1$ is obtained by separately recording a G$^2$FT (4,3)D HN{N,CO}C$^\alpha$. As an example, strips are shown for the residue Ala 55 of Z-domain. Peaks labeled 1-6 in "b1", "b2", and "b3" correspond to the following linear combination of chemical shifts along $\omega_1$:

1. $\Omega_0(^{13}C^\alpha_i)+\Omega_2(^1H^\alpha_i)$
2. $\Omega_0(^{13}C^\alpha_{i-1})+\Omega_2(^1H^\alpha_{i-1})$
3. $\Omega_0(^{13}C^\alpha_i)-\Omega_2(^1H^\alpha_i)$
4. $\Omega_0(^{13}C^\alpha_{i-1})-\Omega_2(^1H^\alpha_{i-1})$
5. $\Omega_0(^{13}C^\alpha i)$
6. $\Omega_0(^{13}C^\alpha_{i-1})$ FIG. 22 depicts the r.f pulse scheme of G$^2$FT (4,3)D HN{N,CO}C$^\alpha$. Rectangular 90° and 180° pulses are indicated by thin and thick vertical bars, respectively, and phases are indicated above the pulses. Where no r.f. phase is marked, the pulse is applied along x. High-power 90° pulse lengths are: 5.7 μs for $^1$H, 15.0 μs for $^{13}$C and 40 μs for $^{15}$N. A six-pulse composite sequence (Shaka, *Chem. Phy. Lett.*, 120:201-205 (1985), which is hereby incorporated by reference in its entirety) is used to tranfer magnetization from $^{15}$N(i) to $^{13}$C$^\alpha$ (i/i−1) and $^{13}$C$^a$ (i−1) simultaneously and back. The 90° and 180° pulse lengths applied on $^{13}$C$^\alpha$ (at a $^1$H resonance frequency of 600 MHz) are adjusted to to 51.6 μs and 46 μs, respectively, during the $t_1$ delay period ($t_1(^{13}C^\alpha)$) to minimize perturbation of $^{13}$C' spins. The width of the 90° pulses applied to $^{13}$CO pulse is 52 μs and the corresponding off-resonance 180° pulse is applied with same power. A hard off-resonance 180° pulse with a length of 46 μs is used to decouple $^{13}$C$^\alpha$ during during $t_2(^{13}C^a)$. WALTZ16 is employed to decouple $^{15}N$ during acquisition (r.f.=1.78 kHz). The $^1H$ r.f. carrier position is placed at 4.78 ppm and that of $^{15}N$ at 118.5 ppm. The $^{13}C$ carrier position is initially set to 56 ppm. This is then switched to 175 ppm before the first 90° pulse on $^{13}C'$ and back to 56 ppm after the second 90° pulse on $^{13}C'$. The duration and strengths of the pulsed z-field gradients (PFGs) are: G1 (1 ms, 20 G/cm); G2 (500 µs, 8 G/cm); G3 (1.0 ms, 20 G/cm); G4 (500 µs, 16 G/cm); G5 (1.25 ms, 30 G/cm); G6 (500 µs, 8 G/cm); G7 (125 µs, 29.5 G/cm). All PFG pulses are of rectangular shape. The delays are: $\tau_1$=5.4 ms, $\tau_2$=5.6 ms, $\tau_3$=28 ms, $\tau_4$=1.7 ms, $\tau_5$=1.0 ms, $\tau_a$=1.7 ms. Phase cycling: $\phi_1$=x, -x; $\phi_2$=x, x, -x,-x; $\phi_3$=x; $\phi_4$=y; $\phi_5$=4(x)4(-x); $\phi_6$=x; $\phi_7$(receiver)=x, -x, -x, x. A sensitivity enhancement scheme (Kay et al., *J. Am. Chem. Soc.* 114:10663-10665 (1992), which is hereby incorporated by reference in its entirety) is employed, i.e., the sign of $G_5$ is inverted in concert with a 180° shift of $\phi_6$. Quadrature detection in $t_1(^{13}C^\alpha)$ is accomplished by altering the phases $\phi_2$ according to States-TPPI whereas that of $t_2(^{15}N)$ is achieved via gradient selection of coherences using G5. GFT-NMR super phase-cycle for recording the 2 basic spectra along $\omega_2$ is: $\phi_1$=x,y.

Figure 23:
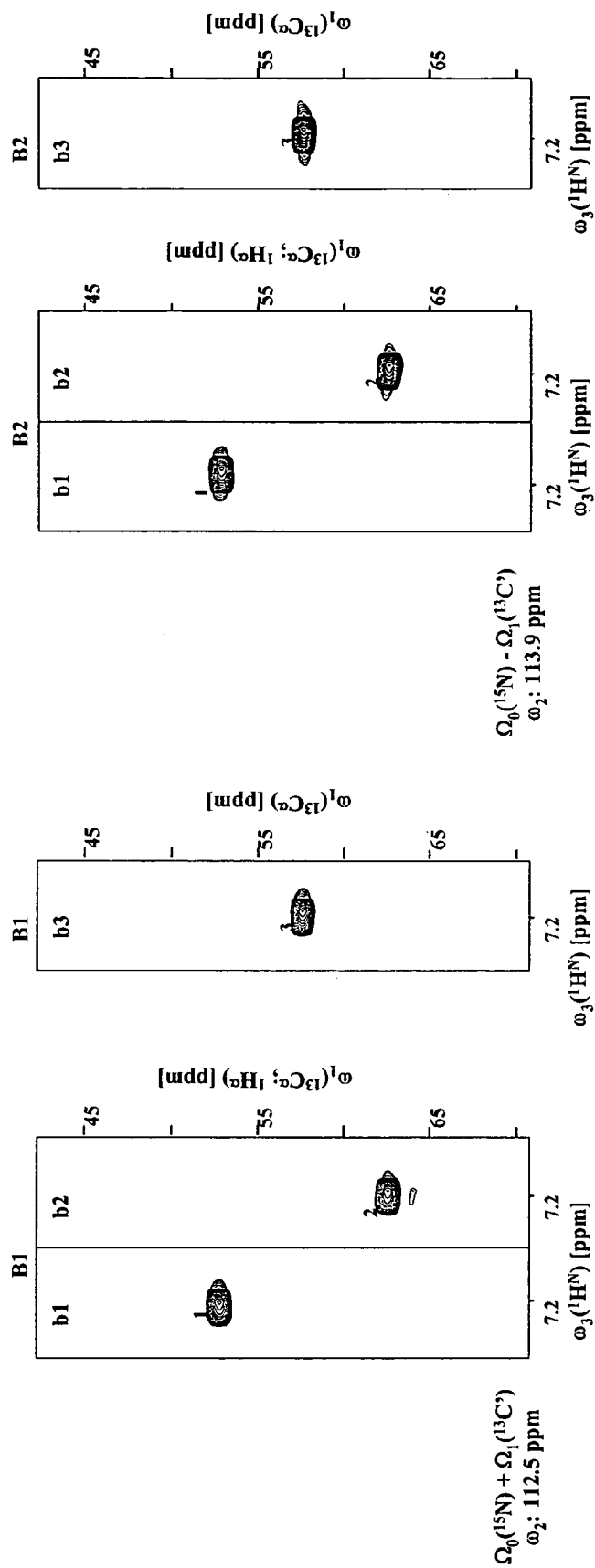
Figure 24:
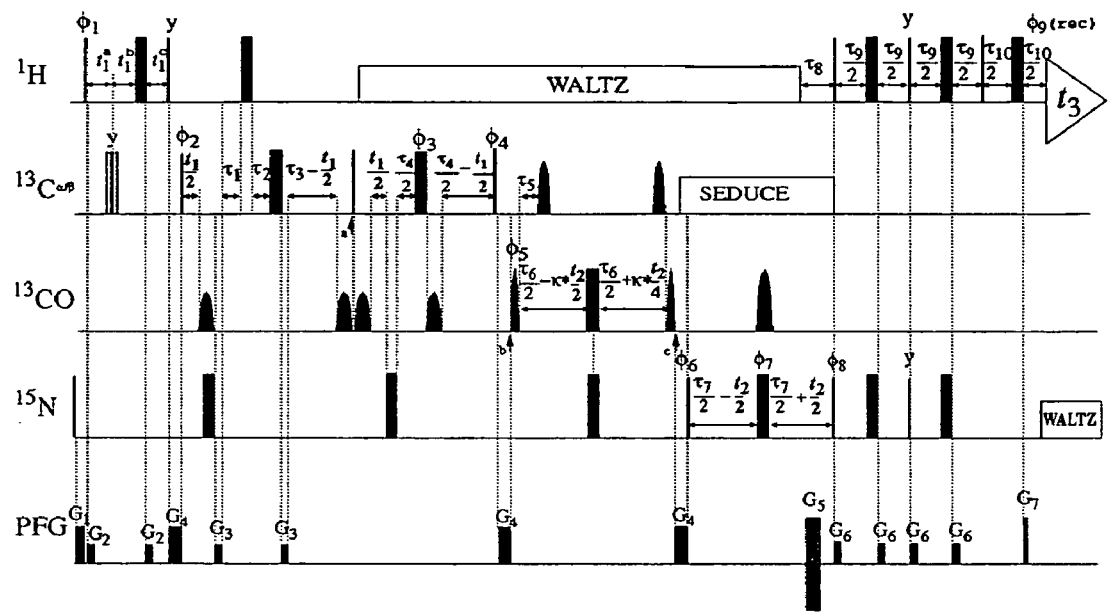

FIG. 23 shows composite plots of $[\omega_1(^{13}C^\alpha; {}^1H^\alpha), \omega_3(^1H^N)]$ strips taken from the basic and central peak spectra of $G^2FT$ (5,3)D {$H^\alpha C^\alpha$}{CON}HN. The four basic spectra are grouped into two sets, B1 and B2, comprising peaks at $\Omega_0(^{15}N_i)+\Omega_1(^{13}C'_{i-1})$ and $\Omega_0(^{15}N_i)-\Omega_1(^{13}C'_{i-1})$ along $\omega_2$, respectively. B1 and B2 each contain two spectra (labeled as "b1" and "b2") comprising peaks at $\Omega_0(^{13}C^\alpha_{i-1})\pm\Omega_1(^1H^\alpha_{i-1})$ along $\omega_1$. The first order central peak spectrum (labeled as "b3") comprising peaks at $\Omega_0(^{13}C^\alpha_{i-1})$ along $\omega_1$ is obtained by omitting the frequency labeling of $H^\alpha$. As an example, strips are shown for the residue His 31 of Z-domain. Peaks labeled 1-3 in "b1", "b2", and "b3" correspond to the following linear combination of chemical shifts along $\omega_1$:

1. $\Omega_0(^{13}C^\alpha_{i-1})+\Omega_1(^1H^\alpha_{i-1})$
2. $\Omega_0(^{13}C^\alpha_{i-1})-\Omega_1(^1H^\alpha_{i-1})$
3. $\Omega_0(^{13}C^\alpha_{i-1})$ FIG. 24 depicts the r.f. pulse scheme of $G^2FT$ (6,3)D {$H^{\alpha\beta}C^\alpha$}{CON}HN. Rectangular 90° and 180° pulses are indicated by thin and thick vertical bars, respectively, and phases are indicated above the pulses. Where no r.f. phase is marked, the pulse is applied along x. High-power 90° pulse lengths are: 5.7 µs for $^1H$, 15.0 µs for $^{13}C$ and 40 µs for $^{15}N$ and $\kappa$=0.25. Pulses on $^{13}C$ prior to $t_1(^{13}C)$ are applied at high power, and $^{13}C$ decoupling during $t_1(^1H)$ is achieved using a $(90°_x-180°_y-90°_x)$ composite pulse. Subsequently, the lengths of 90° and 180° pulses applied on $^{13}C^{\alpha\beta}$ are adjusted (at a $^1H$ resonance frequency of 750 MHz) to 39 µs and 34 µs, respectively, during $t_1(^{13}C^{\alpha\beta})$, and to 43 µs and 39 µs, respectively, during $t_1(^{13}C^\alpha)$ in order to minimize perturbation of $^{13}C'$ spins. All pulses applied on $^{13}C'$ are of SEDUCE (Cavanagh et al., *Protein NMR Spectroscopy* Academic Press: San Diego (1996), which is hereby incorporated by reference in its entirety) shape. Off-resonance 180° pulses with a length of 200 µs and 103 µs is used, respectively, to decouple $^{13}C'$ during $t_1(^{13}C^{\alpha\beta})$, $t_1(^{13}C^\alpha)$ and $t_2(^{15}N)$. The duration of 90° pulses applied on-resonance on $^{13}C'$ is 200 µs. WALTZ16 (Cavanagh et al., *Protein NMR Spectroscopy* Academic Press: San Diego (1996), which is hereby incorporated by reference in its entirety) is employed to decouple $^1H$ during the heteronuclear magnetization transfer and $^{15}N$ during acquisition (r.f.=1.78 kHz). The $^1H$ and $^{15}N$ r.f. carrier positions are placed at 4.78 ppm and 118.5 ppm, respectively. The $^{13}C$ carrier position is initially set to 43 ppm during $t_1(^{13}C^{\alpha\beta})$, and switched to 56 ppm during $t_1(^{13}C^\alpha)$ (indicated by an arrow as point a), to 175 ppm during $t_2(^{13}C')$ (at b) and back to 56 ppm during $t_2(^{15}N)$ (at c). $^1H$-frequency labeling (at a $^1H$ resonance frequency of 750 MHz) is achieved in a semi constant-time fashion with $t_1^a(0)$=1.7 ms, $t_1^b(0)$=1 µs, $t_1^c(0)$=1.701 ms, $\Delta t_1^a$=33.3 µs, $\Delta t_1^b$=17.0 µs, $\Delta t_1^c$=-16 µs. Hence, the fractional increase of the semi constant-time period with $t_1$ equals to $\lambda=1+\Delta t_1^c/\Delta t_1^a$=0.51. The duration and strengths of the pulsed rectangular z-field gradients (PFGs) are: G1 (1 ms, 24 G/cm); G2 (0.5 ms, 8 G/cm); G3 (0.5 ms, 8 G/cm); G4 (1.0 ms, 20 G/cm); G5 (1.25 ms, 30 G/cm); G6 (0.5 ms, 8 G/cm); G7 (0.125 ms, 29.5 G/cm). The delays are: $\tau_1$=350 µs, $\tau_2$=2.8 ms, $\tau_3$=3.15 ms, $\tau_4$=7.2 ms, $\tau_5$=4.4 ms, $\tau_6$=24.6 ms, $\tau_7$=24.6 ms, $\tau_8$=5.5 ms, $\tau_9$=4.6 ms, $\tau_{10}$=1.0 ms. Phase cycling: $\phi_1$=x; $\phi_2$=x, x, -x,-x; $\phi_3$=x, -x; $\phi_4$=x; $\phi_6$=x, -x; $\phi_7$=x, x, -x, -x; $\phi_8$=x; $\phi_9$(receiver)=x, -x, -x, x. A sensitivity enhancement scheme (Kay et al., *J. Am Chem. Soc.* 114: 10663-10665 (1992), which is hereby incorporated by reference in its entirety) is employed, i.e., the sign of $G_6$ is inverted in concert with a 180° shift of $\phi_8$. Quadrature detection in $t_1(^{13}C^\alpha)$ is accomplished by altering the phases $\phi_4$ according to States-TPPI, whereas quadrature detection of $t_2(^{15}N)$ is achieved by used of the sensitivity enhancement scheme. GFT NMR phase-cycle: $\phi_1$=x, y; $\phi_2$=2x, 2y; $\phi_5$=4(x), 4(y), yielding, in conjunction with quadrature detection, 32 data sets which are linearly combined employing a G-matrix transformation with the G-matrix of Equation 11 (see Detailed Description of the Invention section). For acquisition of central peaks along $\omega_1$ which are derived from $^{13}C$ steady state magnetization, a second data set with $\phi_1$=-x is collected. The sum and the difference of the two resulting data sets generate two subspectra containing the central peaks and peak pairs.

Figure 25:
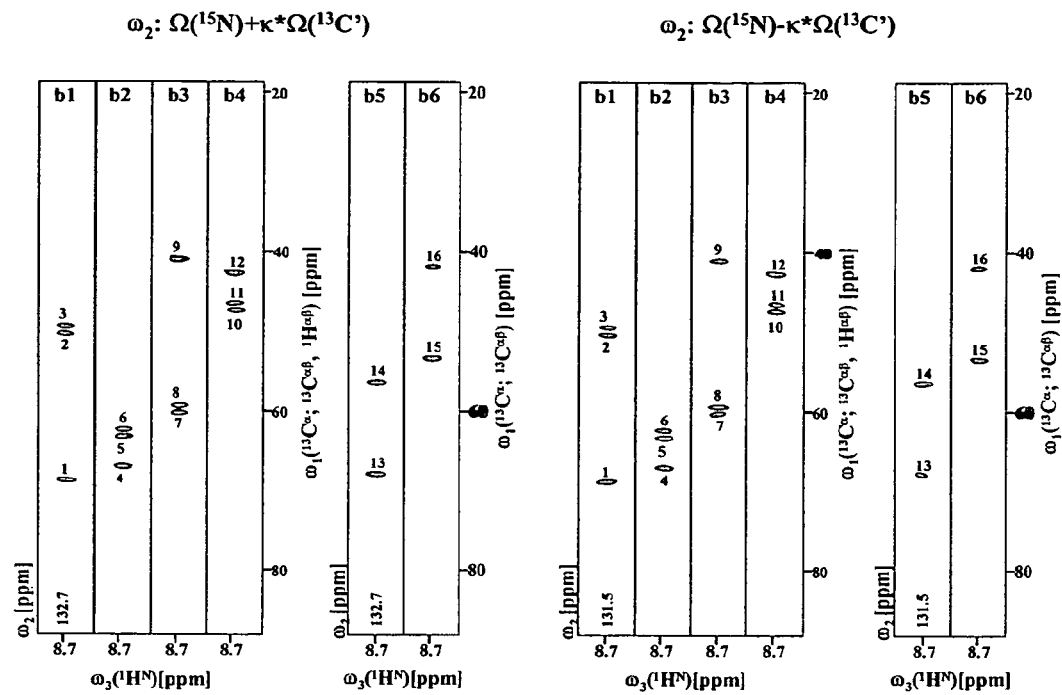

FIG. 25 illustrates peak patterns observed in $G^2FT$ (6,3)D {$H^{\alpha\beta}C^{\alpha\beta}C^\alpha$}{CON}HN recorded for the 8.6 kDa protein ubiquitin on Varian INOVA 750 spectrometer equipped with a $^1H\{^{13}C, {}^1H\}$ triple resonance probe. $[\omega_1(^{13}C^\alpha; C^{\alpha\beta}; {}^1H^{\alpha\beta}), \omega_3(^1H^N)]$ and $[\omega_1(^{13}C^\alpha;C^{\alpha\beta}),\omega_3(^1H^N)]$-strips were taken, respectively, from the basic spectra (labeled "b1"-"b4") comprising peaks at $\omega_1:\Omega(^{13}C^\alpha_{i-1})\pm\omega(^{13}C^{\alpha/\beta}_{i-1})\pm\Omega(^1H^{\alpha/\beta}_{i-1})$ and first order central peak spectra (labeled "b5" and "b6") comprising peaks at $\omega_1:\Omega(^{13}C^\alpha_{i-1})\pm\Omega(^{13}C^{\alpha/\beta}_{i-1})$ at $\omega_2:\Omega(^{15}N)+\kappa\Omega(^{13}C')$ (right) and $\omega_2:\Omega(^{15}N)-\kappa\Omega(^{13}C')$ (left) ($\kappa$=0.5) of residue Ala 46 (chemical shifts indicated at bottom). Acquisition parameters are given in Table 1. Peaks labeled 1-16 in "b1"-"b6" correspond to the following linear combination of chemical shifts of Phe 45 along $\omega_1$: $\Omega_0(^{13}C^\alpha)\pm\Omega_1(^{13}C^\alpha)\pm\Omega_2(^1H^\alpha)$ ("1", "4", "9", "12"); $\Omega_0(^{13}C^\alpha)\pm\Omega_1(^{13}C^\beta)\pm\Omega_2(^1H^{\beta2})$ ("2", "5", "8", "11"); $\Omega_0(^{13}C^\alpha)\pm\Omega_1(^{13}C^\beta)\pm\Omega_2(^1H^{\beta3})$ ("3", "6", "7", "10"); $\Omega_0(^{13}C^\alpha)\pm\Omega_1(^{13}C^\alpha)$ ("13", "16") and $\Omega_0(^{13}C^\alpha)\pm\Omega_1(^{13}C^\beta)$ ("14", "15"). The subspectra "b1"-"b6" encode the following linear combination of shifts:

b1: $\Omega_0(^{13}C^\alpha)+\Omega_1(^{13}C^\alpha)+\Omega_2(^1H^\alpha)$; $\Omega_0(^{13}C^\alpha)+\Omega_1(^{13}C^\beta)+\Omega_2(^1H^{\beta2/\beta3})$;
b2: $\Omega_0(^{13}C^\alpha)+\Omega_1(^{13}C^\alpha)-\Omega_2(^1H^\alpha)$; $\Omega_0(^{13}C^\alpha)+\Omega_1(^{13}C^\beta)-\Omega_2(^1H^{\beta2/\beta3})$;
b3: $\Omega_0(^{13}C^\alpha)-\Omega_1(^{13}C^\alpha)+\Omega_2(^1H^\alpha)$; $\Omega_0(^{13}C^\alpha)-\Omega_1(^{13}C^\beta)+\Omega_2(^1H^{\beta2/\beta3})$;
b4: $\Omega_0(^{13}C^\alpha)-\Omega_1(^{13}C^\alpha)-\Omega_2(^1H^\alpha)$; $\Omega_0(^{13}C^\alpha)-\Omega_1(^{13}C^\beta)-\Omega_2(^1H^{\beta2/\beta3})$;
b5: $\Omega_0(^{13}C^\alpha)+\Omega_1(^{13}C^\alpha)$; $\Omega_0(^{13}C^\alpha)-\Omega_1(^{13}C^\beta)$;
b6: $\Omega_0(^{13}C^\alpha)-\Omega_1(^{13}C^\alpha)$; $\Omega_0(^{13}C^\alpha)-\Omega_1(^{13}C^\beta)$.

Figure 26:
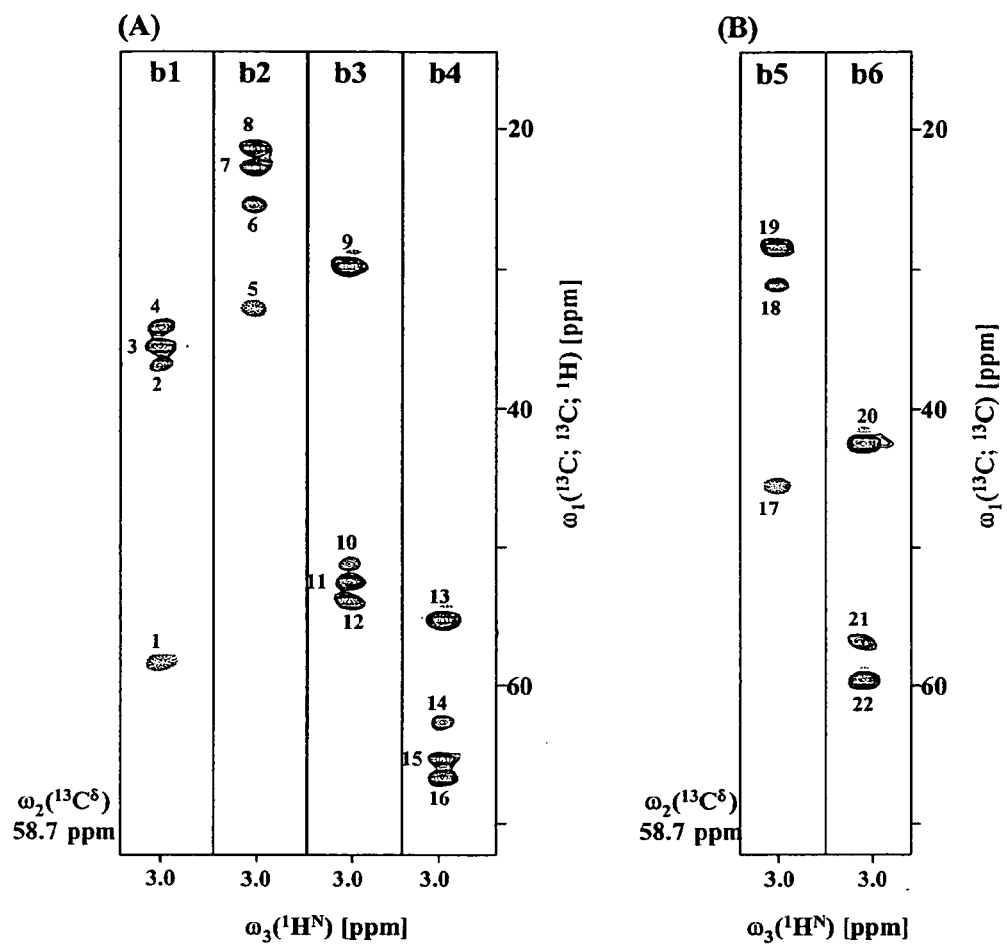

FIG. 26 shows composite plots of $[\omega_1(^{13}C; {}^{13}C, {}^1H), \omega_3(^1H)]$ strips taken from the basic spectra (labeled b1-b4) and first order central peak spectra (labeled b5 and b6) of (5,3)D HC(C)C—CH. As an example, strips corresponding to $\omega_2(^{13}C^\delta)$ and $\overline{\omega}_3(^1H^\delta)$ chemical shifts for residue Arg 88 of the 14 kDa protein PfR13 are shown. Peaks labeled 1-22 correspond to the following linear combination of chemical shifts along $\omega_1$:

| Corresponding peak type in 4D Relay-HC(C)CH (peaks 1-16) and 3D Relay (H)C(C)CH (peaks 17-22) | |
|---|---|
| 1. $\Omega_0(^{13}C^\delta) + \Omega_1(^{13}C^\delta) + \Omega_2(^1H^{\delta2/\delta3})$ | "Diagonal peak" |
| 2. $\Omega_0(^{13}C^\delta) + \Omega_1(^{13}C^\gamma) + \Omega_2(^1H^{\gamma2})$ | "Cross peak" |
| 3. $\Omega_0(^{13}C^\delta) + \Omega_1(^{13}C^\gamma) + \Omega_2(^1H^{\gamma3})$ | "Cross peak" |
| 4. $\Omega_0(^{13}C^\delta) + \Omega_1(^{13}C^\beta) + \Omega_2(^1H^{\beta2/\beta3})$ | "Relay peak" |
| 5. $\Omega_0(^{13}C^\delta) + \Omega_1(^{13}C^\delta) - \Omega_2(^1H^{\delta2/\delta3})$ | "Diagonal peak" |
| 6. $\Omega_0(^{13}C^\delta) + \Omega_1(^{13}C^\gamma) - \Omega_2(^1H^{\gamma2})$ | "Cross peak" |
| 7. $\Omega_0(^{13}C^\delta) + \Omega_1(^{13}C^\gamma) - \Omega_2(^1H^{\gamma3})$ | "Cross peak" |
| 8. $\Omega_0(^{13}C^\delta) + \Omega_1(^{13}C^\beta) - \Omega_2(^1H^{\beta2/\beta3})$ | "Relay peak" |
| 9. $\Omega_0(^{13}C^\delta) - \Omega_1(^{13}C^\delta) + \Omega_2(^1H^{\delta2/\delta3})$ | "Diagonal peak" |
| 10. $\Omega_0(^{13}C^\delta) - \Omega_1(^{13}C^\gamma) + \Omega_2(^1H^{\gamma2})$ | "Cross peak" |
| 11. $\Omega_0(^{13}C^\delta) - \Omega_1(^{13}C^\gamma) + \Omega_2(^1H^{\gamma3})$ | "Cross peak" |
| 12. $\Omega_0(^{13}C^\delta) - \Omega_1(^{13}C^\beta) + \Omega_2(^1H^{\beta2/\beta3})$ | "Relay peak" |
| 13. $\Omega_0(^{13}C^\delta) - \Omega_1(^{13}C^\delta) - \Omega_2(^1H^{\delta2/\delta3})$ | "Diagonal peak" |
| 14. $\Omega_0(^{13}C^\delta) - \Omega_1(^{13}C^\gamma) - \Omega_2(^1H^{\gamma2})$ | "Cross peak" |
| 15. $\Omega_0(^{13}C^\delta) - \Omega_1(^{13}C^\gamma) - \Omega_2(^1H^{\gamma3})$ | "Cross peak" |
| 16. $\Omega_0(^{13}C^\delta) - \Omega_1(^{13}C^\beta) - \Omega_2(^1H^{\beta2/\beta3})$ | "Relay peak" |
| 17. $\Omega_0(^{13}C^\delta) + \Omega_1(13C^\delta)$ | "Diagonal peak" |
| 18. $\Omega_0(^{13}C^\delta) + \Omega_1(13C^\gamma)$ | "Cross peak" |
| 19. $\Omega_0(^{13}C^\delta) + \Omega_1(13C^\beta)$ | "Relay peak" |
| 20. $\Omega_0(^{13}C^\delta) - \Omega_1(13C^\delta)$ | "Diagonal peak" |
| 21. $\Omega_0(^{13}C^\delta) - \Omega_1(13C^\gamma)$ | "Cross peak" |
| 22. $\Omega_0(^{13}C^\delta) - \Omega_1(13C^\beta)$ | "Relay peak" |

Figure 27:
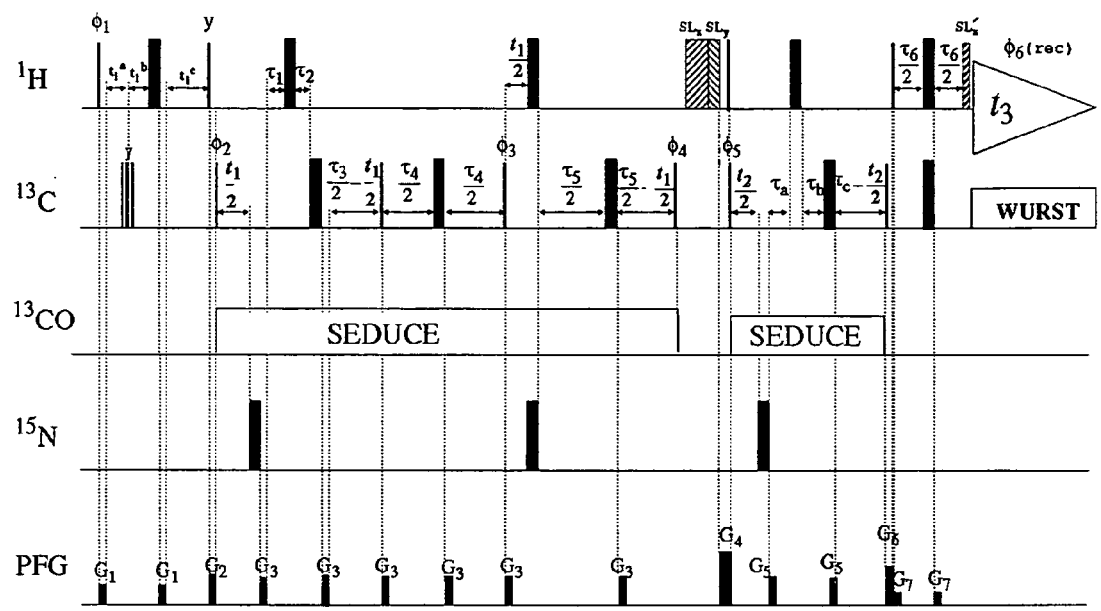

FIG. 27 depicts the r.f. pulse scheme of GFT (5,3)D HC(C)C—CH. Rectangular 90° and 180° pulses are indicated by thin and thick vertical bars, respectively, and phases are indicated above the pulses. Where no r.f. phase is marked, the pulse is applied along x. High-power 90° pulse lengths are: 5.5 is for $^1$H, 15.0 µs for $^{13}$C and 38 µs for $^{15}$N. $^{13}$C decoupling during $t_1(^1H)$ is achieved using a $(90°_x\text{-}180°_y\text{-}90°_x)$ composite pulse. The SEDUCE sequence is used for decoupling of $^{13}$C' during $t_1(^{13}C)$ and $t_2(^{13}C)$ (r.f field strength=1 kHz). WURST is used for decoupling of $^{13}$C during acquisition. The duration of $^1$H spin-lock purge pulses for suppression of the water line are: $SL_x$: 4.9 ms; $SL_y$: 2.6 ms; $SL_x'$: 1.6 ms. The $^1$H carrier position is placed at 0 ppm before the first 90° $^1$H pulse and then switched to 4.77 ppm after the second 90° $^1$H pulse. The $^{13}$C and $^{15}$N r.f. carrier positions are set to 43 ppm (for aliphatic spin system assignments) and 118.5 ppm, respectively. $^1$H-frequency labeling at a $^1$H resonance frequency of 600 MHz is achieved in a semi constant-time fashion with $t_1{}^a(0)=1.7$ ms, $t_1{}^b(0)=1$ µs, $t_1{}^c(0)=1.701$ ms, $\Delta t_1{}^a=33.3$ µs, $\Delta t_1{}^b \times 19.3$ µs, $\Delta t_1{}^c=-14$ µs. Hence, the fractional increase of the semi constant-time period with $t_1$ equals to $\lambda=1+\Delta t_1{}^c/\Delta t_1{}^a=0.58$. The duration and strengths of the pulsed z-field gradients (PFGs) are: G1 (500 µs, 6 G/cm); G2 (500 µs, 12 G/cm); G3 (500 µs, 11 G/cm); G4 (2.0 ms, 22 G/cm); G5 (100 µs, 12 G/cm); G6 (2.0 ms, 15 G/cm); G7 (500 µs, 6 G/cm). All PFG pulses are of rectangular shape. The delays are: $\tau_1=350$ µs, $\tau_2=2.65$ ms, $\tau_3=\tau_5=7.0$ ms, $\tau_4=7.0$ ms, $\tau_a=850$ µs, $\tau_b=1.65$ ms and $\tau_c=2.5$ ms. Phase cycling: $\phi_1$=x; $\phi_1$=x, -x; $\phi_3$=x, -x; $\phi_4$=x; $\phi_5$=y; $\phi_6$(receiver)=x, -x. Quadrature detection in $t_1(^{13}C/^1H)$ and $t_2(^{13}C)$ is accomplished by altering the phases $\phi_4$ and $\phi_5$, respectively, according to States-TPPI. GFT NMR super phase-cycle for recording the 4 basic spectra: $\phi_1$=x,y; $\phi_2$=2(x),2(y). For acquisition of central peaks derived from $^{13}$C steady state magnetization, a second data set with $\phi_1$=-x is collected. The sum and the difference of the two resulting data sets generate two subspectra containing the central peaks and peak pairs.

FIGS. 28(a)-(b) depict the r.f. pulse schemes of PFG-PEP sensitivity-enhanced L-2D [$^{13}$C, $^1$H]-HSQC (FIG. 28(a)) and L-2D [$^{13}$C, $^1$H]-TROSY (FIG. 28(b)). 90° $^1$H pulses with "rising" and "falling" shapes represent, respectively, E-BURP2 and time-reversed E-BURP2 pulses (Geen et al., J. Magn. Reson. 93:93-141 (1991), which is hereby incorporated by reference in its entirety) of 1.1 ms duration. These pulses are applied 2.5 ppm upfield of the $^1$H carrier, which is placed on the water line, and serve to selectively flip $^1H^{aliphatic}/^1H_2O$ magnetization. Shaped 180° pulses on $^{13}$C represent REBURP pulses (Cavanagh et al., Protein NMR Spectroscopy: Principles and Practice Academic Press: San Diego (1996), which is hereby incorporated by reference in its entirety) of 610 µs duration. Carbon spins are decoupled during acquisition with GARP ($\gamma B_1/2\pi=2.5$ kHz) (Cavanagh et al., Protein NMR Spectroscopy: Principles and Practice Academic Press: San Diego (1996), which is hereby incorporated by reference in its entirety). For FIG. 28(a): $\lambda=1.3$ ms, T=8 ms, $\epsilon=0.3$ ms; $\phi_1=\{y\}$, $\phi_2=\{x,-x\}$, $\phi_3=\{x\}$, $\phi_{rec}=\{x,-x\}$; G$_1$: 4 G/cm, 0.5 ms; G$_2$: 20.6 G/cm, 1 ms; G$_C$: 24 G/cm, 1.6 ms; G$_H$: 24 G/cm, 0.4 ms. Quadrature detection in $t_1$ is achieved by recording a second scan with $\phi_3=\{-x\}$ and G$_C$ inverted. For FIG. 28(b): $\lambda=1.3$ ms, T'=T-$\lambda$=6.7 ms; $\phi_1=\{x,-x\}$, $\phi_2=\{-y\}$, $\phi_{rec}=\{x,-x\}$; G$_1$: 9 G/cm, 0.8 ms; G$_2$: 7 G/cm, 1 ms; G$_C$: 18.8 G/cm, 1 ms; G$_H$: 4.7 G/cm. Quadrature detection in $t_1$ is achieved by recording a second scan with $\phi_2=\{y\}$ and G$_C$ inverted.

Figure 29:
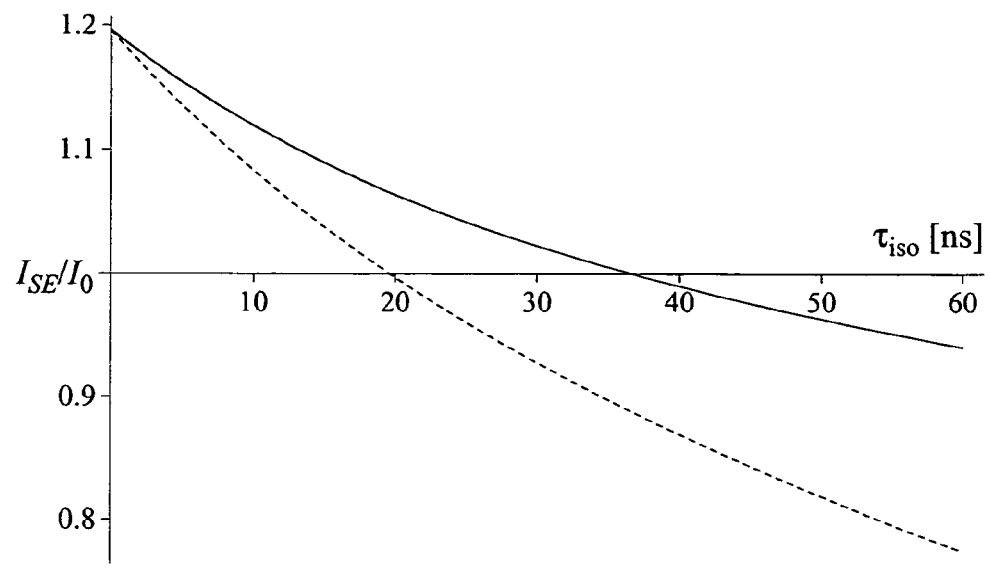

FIG. 29 illustrates the calculated relative sensitivity ($I_{SE}/I_0$) resulting from employment of PFG-PEP ($^1$H frequency: 750 MHz; gradient echo length $2\epsilon$: 200 µs). For comparison, the dashed line is obtained for $2\epsilon=600$ µs, indicating that careful optimization of this parameter is advantageous for large systems.

FIGS. 30(a)-(b) show $SN_t$ plotted versus $t_{rel}$ for three representative cross peaks. Filled (open) symbols and solid (dashed) lines correspond to spectra acquired with (without) L-optimization. FIG. 30(a) shows data from 2D [$^{13}$C, $^1$H]-HSQC spectra recorded at 20° C. FIG. 30(b) shows data from 2D [$^{13}$C, $^1$H]-TROSY spectra recorded at 4° C. with suppression of signals arising from $^{13}$C polarization.

Figure 31:
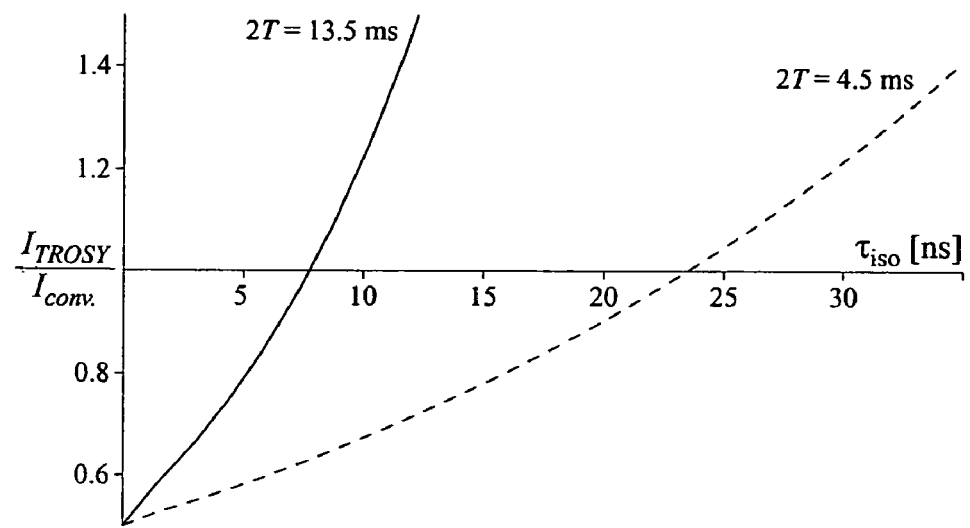

FIG. 31 illustrates the calculated relative sensitivity of TROSY over non-TROSY in $^1H^{aromatic}$—$^{13}C^{aromatic}$ correlation experiments with ct $^{13}C^{aromatic}$ frequency labeling at a $^1$H resonance frequency of 750 MHz. Solid and dashed lines correspond, respectively, to ct evolution periods of 13.5 ms and 4.5 ms. The latter is preferably used for implementing L-GFT (4,3)D HCCH (FIG. 32; see Example 8).

Figure 32:
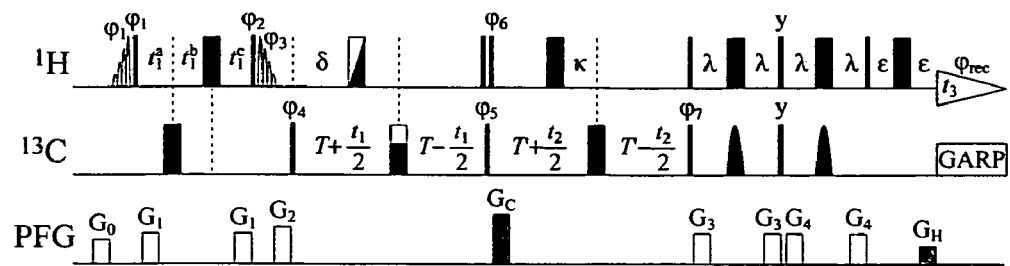

FIG. 32 depicts the r.f. pulse scheme of L-GFT-TROSY (4,3)D HCCH. 90° and 180° pulses are represented by thin and thick vertical bars. Selective 90° $^1$H pulses with "rising" and "falling" shapes are 1.1 ms (at 750 MHz) E-BURP2 and time-reversed E-BURP2 pulses (Geen et al., J. Magn. Reson. 93:93-141 (1991), which is hereby incorporated by reference in its entirety) applied at 2 ppm. Those "flip" $^1H^{aliphatic}/^1H_2O$ magnetization while $^1H^{aromatic}$ magnetization is along z. During reverse INEPT, "flip-back" pulses are not required since (i) hard $^1$H pulses yield a 720° rotation of $^1$H magnetization and (ii) selective 180° $^{13}C^{aromatic}$ REBURP pulses (Geen et al., J. Magn. Reson. 93:93-141 (1991), which is hereby incorporated by reference in its entirety) of 610 µs duration (at 750 MHz) decouple $^1H^{aliphatic}$ from $^{13}C^{aliphatic}$. Phases of $^1$H r.f. pulses are adjusted such that $^1H^{aliphatic}/^1H_2O$ magnetization is along +z at the beginning of $t_3$. Decoupling of $^{13}C^{aromatic}$ during $t_3$ is accomplished using GARP ($\gamma B_1/2\pi=2.5$ kHz) (Cavanagh et al., Protein NMR Spectroscopy: Principles and Practice Academic Press: San Diego (1996), which is hereby incorporated by reference in its entirety). Delays: $\lambda=1.3$ ms, $\kappa=1.5$ ms, T=T'=2.25 ms, $\delta$=T-$\kappa$+$t_1$/2, $\epsilon=0.3$ ms. $^1H^{(1)}$ shift evolution during $t_1$ is implemented in a semi ct manner with $t_{1,max}=2T$, $t_1{}^a(0)=\lambda$, $t_1{}^b(0)=1$ μs, $t_1{}^c(0)=\lambda+1$ μs, and $\Delta t_1{}^a=t_1/2$, $\Delta t_1{}^b=\Delta t_1{}^a+\Delta t_1{}^c$, $\Delta t_1{}^c=-\lambda t_1/2T$. Quadrature detection in $t_2$ ($^{13}C^{(2)}$) is achieved with sensitivity enhancement ($G_C$ is inverted with a 180° shift for $\phi_7$); in $t_1(^{13}C^{(1)}; {}^1H^{(1)})$, $\phi_4$ is altered according to States-TPPI (Cavanagh et al., *Protein NMR Spectroscopy: Principles and Practice* Academic Press: San Diego (1996), which is hereby incorporated by reference in its entirety). PFGs: $G_1$(0.5 ms, 11 G/cm), $G_2$(1, 13), $G_3$(0.5, 21), $G_4$(0.5, 11), $G_C$(1.2, 24), $G_H$ (0.3, −24). Phase cycling: $\phi_1=\{x\}$, $\phi_2=\{-y, y\}$, $\phi_3=\{8(-y), 8(y)\}$, $\phi_4=\{x, -y, -x, y\}$, $\phi_5=\{4(x), 4(-x)\}$, $\phi_6=\{8(x), 8(-x)\}$, $\phi_7=\{x\}$, $\phi_{rec}=\{2(x), 2(-x)\}$. An S³-filter (Meissner et al., *J. Magn. Reson.* 139:447-450 (1999), which is hereby incorporated by reference in its entirety) implements TROSY: the black-and-white 180° pulse on $^1H$ is applied only every odd step of the phase cycle. To decouple $^1J(^{13}C^\gamma - {}^{13}C^\beta)$ for enhancing signals at $\Omega(^{13}C^\gamma)$ in central peak subspectra (FIG. 33), the 180° pulse during $t_1(^{13}C^{(2)})$ is applied with (Cavanagh et al., *Protein NMR Spectroscopy: Principles and Practice* Academic Press: San Diego (1996), which is hereby incorporated by reference in its entirety) $\gamma B_1 = \Delta\omega/\sqrt{3}$ ($\Delta\omega$ is difference between $^{13}C^{aromatic}$ carrier and average $^{13}C^\beta$ shift). GFT NMR phase-cycle: $\phi_1=x,y,-x,-y$ to obtain basic subspectra from $^1H$ and central peak subspectra from $^{13}C$ polarization (Kim et al., *J. Am. Chem. Soc.* 125:1385-1393 (2003), which is hereby incorporated by reference in its entirety). For L-GFT (4,3)D HCCH: $\delta=\kappa$, the black-and-white 180° pulse during $t_1(^{13}C^{(2)})$ is at high power and a $^{13}C$ 90° pulse before PFG $G_0$ is added. Phase cycling: $\phi_2=\{y\}$, $\phi_3=\{4(y),4(-y)\}$, $\phi_4=\{x,-x\}$, $\phi_5=\{x, x, -x, -x\}$, $\phi_6=\{4(x), 4(-x)\}$, $\phi_7=\{x\}$, $\phi_{rec}=\{x,-x\}$. GFT NMR phase cycle: $\phi_1=x,y$ for basic subspectra; the central peak subspectrum is recorded by omitting $^1H^{(1)}$ shift evolution.

Figure 33:
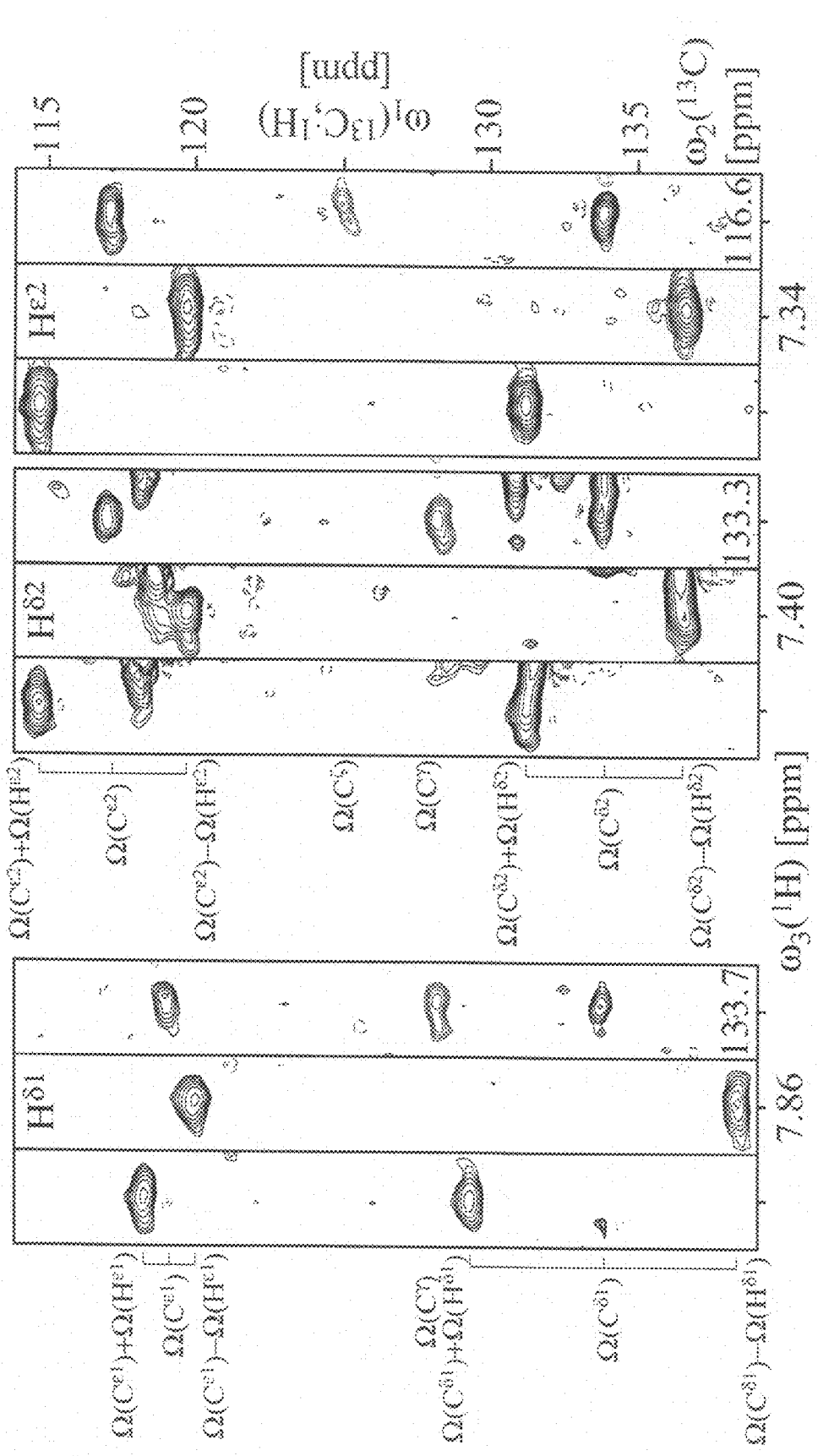

FIG. 33 shows $[\omega_1(^{13}C^{(1)}; {}^1H^{(1)},\omega_3(^1H^{(2)})]$-strips taken along the GFT dimension of L-GFT-TROSY (4,3)D HCCH recorded at 750 MHz for 21 kDa HR41 with $t_{rel}=1$ s. Peaks belong to the slowly flipping ring of Tyr 90. Central peaks arising from $^{13}C^{\gamma/\zeta}$ polarization are depicted in blue.

Figure 34:
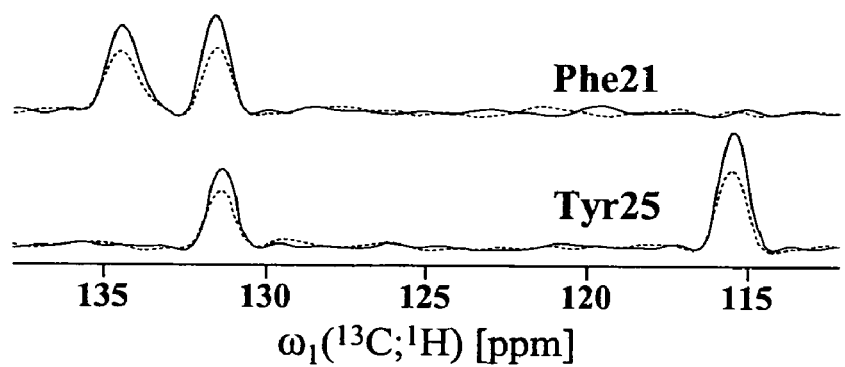

FIG. 34 depicts cross sections taken along the GFT dimension from L-GFT (4,3)D HCCH (solid traces) and GFT (4,3)D HCCH (dotted traces) acquired for 11 kDa protein MaR11 in 25 min each.

Figure 35:
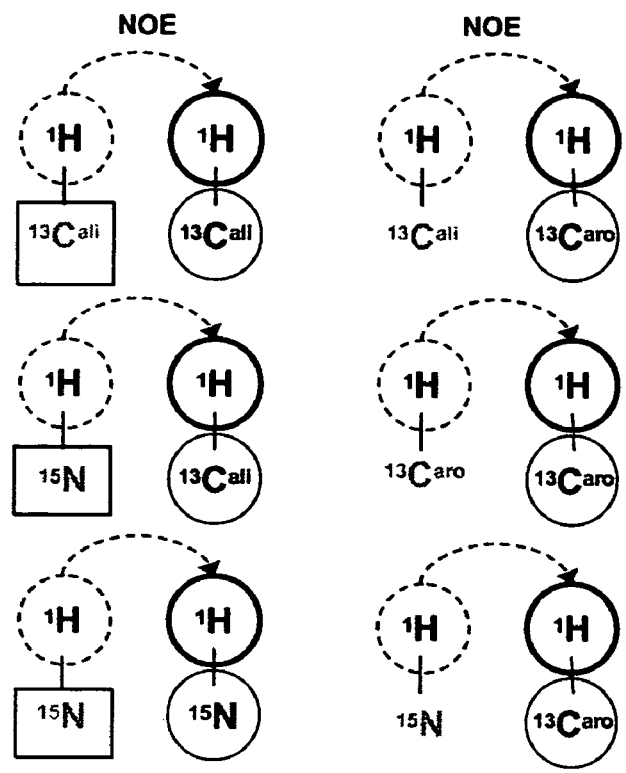

FIG. 35 indicates NOEs and chemical shifts which are measured in (4,3)D [HC$^{ali}$/HN]-NOESY-[CH$^{ali}$/NH], provided that central peaks are detected in 3D [H]-NOESY-[CH$^{ali}$/CH$^{aro}$/NH]. The proton from which the NOE originates and the proton on which the signal is detected are shown, respectively, in dashed and bold circles. For the heteronuclei (depicted in black) which are attached to the detected proton, the chemical shift is measured in both (4,3)D [HC$^{ali}$/HN]-NOESY-[CH$^{ali}$/NH] and 3D [H]-NOESY-[CH$^{ali}$/CH$^{aro}$/NH]. The heteronuclei attached to the "originating" proton are shown in grey. The boxes around $^{15}$N and $^{13}C^{aliphatic}$ indicate that these shifts are measured in shift doublet subspectra of (4,3)D [HC$^{ali}$/HN]-NOESY-[CH$^{ali}$/NH], thereby providing 4D NOESY information. For clarity, transposed NOEs are not indicated.

FIGS. 36(a)-(b) depict r.f. pulse schemes employed for acquisition of NOESY data. FIG. 36(a) shows detection of shift doublets in (4,3)D [HC$^{ali}$/HN]-NOESY-[CH$^{ali}$/NH], while FIG. 36(b) shows detection of shifts in 3D [H]-NOESY-[CH$^{ali}$/CH$^{aro}$/NH]. Both schemes are derived from simultaneous 3D $^{15}$N/$^{13}C^{aliphatic}$-resolved [$^1$H, $^1$H]-NOESY (Xia et al., *J. Biomol. NMR* 27:193-203 (2003), which is hereby incorporated by reference in its entirety). Rectangular 90° and 180° pulses are indicated by thin and thick vertical bars, respectively, and phases are indicated above the pulses. Where no r.f. phase is marked, the pulse is applied along x. High-power 90° pulse lengths are: 9.0 μs for $^1$H, 17.0 μs for $^{13}$C, and 40 μs for $^{15}$N. WURST (Cavanagh et al., *Protein NMR Spectroscopy* Academic Press: San Diego (1996), which is hereby incorporated by reference in its entirety) is used for decoupling of $^{13}$C during acquisition. WALTZ16 (Cavanagh et al., *Protein NMR Spectroscopy* Academic Press: San Diego (1996), which is hereby incorporated by reference in its entirety) is employed to decouple $^{15}$N (r.f.=1.70 kHz) during acquisition. $^{13}$C decoupling during indirect $^1$H chemical shift evolution is achieved using a (90°$_x$-180°$_y$-90°$_x$) composite pulse (Cavanagh et al., *Protein NMR Spectroscopy* Academic Press: San Diego (1996), which is hereby incorporated by reference in its entirety). SEDUCE (Cavanagh et al., *Protein NMR Spectroscopy*, Academic Press: San Diego (1996), which is hereby incorporated by reference in its entirety) is used for decoupling of $^{13}$C, during $t_1(^1$H$/^{13}$C$/^{15}$N) and $t_2(^{13}$C$/^{15}$N) (r.f. field strength=1 kHz). The duration of $^1$H spin-lock purge pulses applied immediately after acquisition to improve suppression of the water line (Xia et al., *J. Biomol. NMR* 27:193-203 (2003), which is hereby incorporated by reference in its entirety) are: SL$_x$, 4.9 ms; SL$_y$, 2.6 ms. The $^1$H r.f. and $^{15}$N carrier positions are set to 4.78 ppm and 118 ppm, respectively. For $t_2(^{13}$C$/^{15}$N), sampling starts at $1/(2\cdot SW(^{13}C/^{15}N))$ to ensure 180° first order phase correction (Cavanagh et al., *Protein NMR Spectroscopy* Academic Press: San Diego (1996), which is hereby incorporated by reference in its entirety). Parameters specific for the individual r.f. pulse schemes: For FIG. 36(a): the scaling factor was set to $\kappa=0.5$, and the $^{13}$C carrier position is set to 36 ppm. $^1$H-$^{13}$C INEPT rely on (90°$_x$-180°$_y$-90°$_x$) composite pulses (Cavanagh et al., *Protein NMR Spectroscopy* Academic Press: San Diego (1996), which is hereby incorporated by reference in its entirety), and the $^1$H-$^{13}$C INEPT delays are set to 3.9 ms (corresponding to a $^1J_{CHaliphatic} \sim 130$ Hz). $^1$H-frequency labeling (at a $^1$H resonance frequency of 600 MHz) is achieved in a semiconstant-time fashion (Cavanagh et al., *Protein NMR Spectroscopy* Academic Press: San Diego (1996), which is hereby incorporated by reference in its entirety) with $t_1{}^a(0)=1.9$ ms, $t_1{}^b(0)=1.0$ μs, $t_1{}^c(0)=2.5$ ms, $\Delta t_1{}^a=40$ μs, $\Delta t_1{}^b=35$ μs, $\Delta t_1{}^c=-15$ μs. Hence, the fractional increase of the semiconstant-time period with $t_1$ equals to $\lambda=\Delta t_1{}^c/\Delta t_1{}^a=0.63$. The duration and strengths of the rectangular pulsed z-field gradients (PFGs) are: $G_1$ (3 ms, 8 G/cm); $G_2$ (0.5 ms, 6 G/cm); $G_3$ (4 ms, 30 G/cm); $G_4$ (3 ms, −20 G/cm); $G_5$ (0.5 ms, 8 G/cm); $G_6$ (3.0 ms, 4 G/cm); $G_7$ (1.0 ms, 8 G/cm). The delays are: $\tau_1=2.0$ ms, $\tau_2=0.4$ ms, $\Sigma_3=2.4$ ms. The mixing time was set to $\tau_m=70$ ms. Phase cycling: $\phi_1=x$, $-x$; $\phi_2=x$; $\phi_3=2(x)$, $2(-x)$; $\phi_4$(receiver)=x, −x, −x, x. Quadrature detection in $t_1(^1$H$/^{13}$C$/^{15}$N) and $t_2(^{13}$C$/^{15}$N) is accomplished by altering the phases $\phi_2$ and $\phi_3$, respectively, according to States-TPPI (Cavanagh et al., *Protein NMR Spectroscopy* Academic Press: San Diego (1996), which is hereby incorporated by reference in its entirety). GFT NMR phase-cycle for recording the two basic spectra: $\phi_1=x, y$. For FIG. 36(b): simultaneous inversion of $^{13}C^{aliphatic}$ and $^{13}C^{aromatic}$ spins during $^1$H—$^{13}$C INEPT is achieved using adiabatic 180° $^{13}$C r.f. pulses of 1.0 ms duration (Cavanagh et al., *Protein NMR Spectroscopy* Academic Press: San Diego (1996), which is hereby incorporated by reference in its entirety), and the INEPT delay is tuned to a compromise value of ½ $^1J_{CH}$=3.4 ms (corresponding to $^1J_{CHaliphatic} < {}^1J_{CH}=150$ Hz$<{}^1J_{CHaromatic}$) to allow simultaneous detection of NOEs on aliphatic and aromatic protons. The $^{13}$C carrier position is initially set to 70 ppm and shifted to 36 ppm at the time point indicated by the first arrow and shifted back to 70 ppm at the time point indicated by the second arrow. Bloch simulations show that the loss of sensitivity for the aromatic signals that arise from off-resonance effects of the two rectangular 90° pulses applied at a $^{13}$C carrier position of 36 ppm is less than ~30% at 600 MHz $^1$H resonance frequency. [At higher field strengths, it is advantageous to minimize off-resonance effects by placing the $^{13}$C carrier between aliphatic and aromatic resonances (at ~70 ppm) and employing time proportional phase incrementation (Cavanagh et al., *Protein NMR Spectroscopy* Academic Press: San Diego (1996); Szyperski et al., *J. Magn. Reson.* B108:197-203 (1995), which are hereby incorporated by reference in their entirety) to shift the $^{13}$C carrier position to 36 ppm. At 900 MHz, for example, sensitivity losses at the edges of the $^{13}$C spectral range, i.e. for methyl groups and downfield aromatic resonances, are then limited to ~25%.]. The spectral widths along $\omega_2$ are: $\omega_2(^{15}N)$=1,680 Hz, $\omega_2(^{13}C^{aliphatic},$ $^{13}C^{aromatic})$=4,300 Hz. This ensures that NOEs detected on aromatic protons are aliased along $\omega_2(^{13}C^{aliphatic},$ $^{13}C^{aromatic})$ and, provided that a 180° first order phase correction is applied, have opposite sign than NOEs detected on amide protons to facilitate assignment. Moreover, mutual cancellation of these two types of NOEs is avoided. The duration and strengths of the rectangular pulsed z-field gradients (PFGs) are: G$_1$ (3 ms, 6 G/cm); G$_2$ (3 ms, 4 G/cm); G$_3$ (1 ms, 8 G/cm); G$_4$ (0.5 ms, 8 G/cm); G$_5$ (4 ms, 30 G/cm); G$_6$ (3 ms, -20 G/cm); G$_7$ (0.5 ms, 6 G/cm). The delays are: $\tau_1$=1.2 ms, $\tau_2$=0.2 ms, $\tau_3$=2.4 ms. The mixing time was set to $\tau_m$=70 ms. Phase cycling: $\phi_1$=2(x), 2(-x); $\phi_2$=x, -x; $\phi_3$=x; $\phi_4$ (receiver)=x, -x, -x, x. Quadrature detection in t$_1$($^1$H) and t$_2$($^{13}$C/$^{15}$N) is accomplished by altering the phases $\phi_1$ and $\phi_2$, respectively, according to States-TPPI (Cavanagh et al., *Protein NMR Spectroscopy* Academic Press: San Diego (1996), which is hereby incorporated by reference in its entirety).

FIGS. 37(a)-(d) illustrate resonance assignment based on GFT NMR experiments (Tables 10 and 11) exemplified for protein YqfB. Panel (a) shows [$\omega_1$($^{13}$C$^\alpha$; $^{13}$C$^{\alpha\beta}$),$\omega_3$($^1$H$^N$)]-strips taken from (4,3)D C$^{\alpha\beta}$C$^\alpha$(CO)NHN (labeled with "a1") and (4,3)D HNNC$^{\alpha\beta}$C$^\alpha$ (labeled with "a2"). The strips were taken at $\omega_2$($^{15}$N) (the $^{15}$N chemical shifts are indicated at the bottom of the strips) of residues 57 to 60 (referred to as residue i), and are centered along $\omega_3$($^1$H$^N$) about their backbone $^1$H$^N$ shifts. Along $\omega_1$($^{13}$C$^\alpha$; $^{13}$C$^{\alpha\beta}$), peaks are observed at $\Omega$($^{13}$C$^\alpha$)±$\Omega$($^{13}$C$^{\alpha/\beta}$) of residue i–1 in "a1" and of residue i in "a2" (in addition, peaks originating from residue i–1 are observed in "a2" if transfer via $^2$J$_{NC\alpha}$ is sufficiently effective). $\Omega$(X) (X=$^{13}$C$^\alpha$, $^{13}$C$^\beta$) denotes the offset relative to the carrier position [during t$_1$($^{13}$C$^{\alpha\beta}$), the $^{13}$C carrier frequency is placed at 43 ppm; during t$_1$($^{13}$C$^\alpha$), $^{13}$C$^\alpha$ is detected in quadrature and the carrier frequency is placed at 56 ppm; see FIGS. S7 and S9 of Atreya et al., *Proc. Natl. Acad. Sci. USA* 101:9642-9647 (2004), which is hereby incorporated by reference in its entirety]. The composite plot of strips on the left was taken from the GFT subspectrum comprising peaks at $\Omega$($^{13}$C$^\alpha$)+$\Omega$($^{13}$C$^\alpha$) (labeled as 1, 3, 5, 7) and $\Omega$($^{13}$C$^\alpha$)+$\Omega$($^{13}$C$^\beta$) (labeled as 2, 4, 6, 8), and the composite plot on the right was taken from the subspectrum comprising peaks at $\Omega$($^{13}$C$^\alpha$)–$\Omega$($^{13}$C$^\alpha$) (1, 3, 5, 7) and $\Omega$($^{13}$C$^\alpha$)–$\Omega$($^{13}$C$^\beta$) (2, 4, 6, 8) (the type of linear combination of chemical shifts is indicated above the composite plots). The combined use of (4,3)D C$^{\alpha\beta}$C$^\alpha$(CO)NHN/HNNC$^{\alpha\beta}$C$^\alpha$ yields three sequential "walks" along the polypeptide backbone which are indicated by dashed lines [note: peaks at $\Omega$($^{13}$C$^\alpha$)–$\Omega$($^{13}$C$^\alpha$) on the right are all located at the carrier position (43 ppm) and do not provide connectivities]. Peaks were sequentially assigned to the $^{13}$C$^{\alpha/\beta}$ shifts of Ala 57 (1, 2), Thr 58 (3, 4), Ser 59 (5, 6), and Thr 60 (7, 8) after $^{13}$C'$_{i-1}$, $^{15}$N$_i$, $^1$H$^N$-spin system identification was accomplished in the second- and third-order central peak spectra B13-B15 of (5,2)D HACACONHN (Kim et al., *J. Am. Chem. Soc.* 125:1385-1393 (2003), which is hereby incorporated by reference in its entirety), which represents (3,2)D HNNCO and thus encodes 3D HNNCO (Cavanagh et al., *Protein NMR Spectroscopy* Academic Press: San Diego (1996), which is hereby incorporated by reference in its entirety) spectral information. This is indicated in panel (b) which shows composite plots of strips taken from (5,2)D HACACONHN (Kim et al., *J. Am. Chem. Soc.* 125:1385-1393 (2003), which is hereby incorporated by reference in its entirety). This (5,2)D experiment is used to sequence specifically assign $^1$H$^\alpha$ and $^{13}$C' shifts after having obtained the sequence specific assignments of $^{13}$C$^{\alpha/\beta}$, $^{15}$N, and $^1$H$^N$ from (4,3)D C$^{\alpha\beta}$C$^\alpha$(CO)NHN/HNNC$^{\alpha\beta}$C$^\alpha$. The signals in panel (b) arise from magnetization transfer from $^1$H$^\alpha$ of His 32 to $^1$H$^N$ of Phe 33. The eight basic spectra (labeled B1-B8) encode the chemical shifts of $^1$H$\alpha_{i-1}$, $^{13}$C$^\alpha_{i-1}$, $^{13}$C'$_{i-1}$, and $^{15}$N$_i$ in a single GFT dimension ($\omega_1$). Due to the particular choice for quadrature detection of $^{15}$N and central peak detection (Kim et al., *J. Am. Chem. Soc.* 125:1385-1393 (2003), which is hereby incorporated by reference in its entirety), combination of chemical shifts are registered as $\Omega_0\pm\Omega_1\pm\Omega_2\pm\Omega_3$ with $\Omega_0$=$\Omega$($^{15}$N), $\Omega_1$=$\Omega$($^{13}$C'), $\Omega_2$=$\Omega$($^{13}$C$^\alpha$) and $\Omega_3$=$\Omega$($^1$H$^\alpha$). Note that the ppm-scale along $\Omega_1$ is defined by the type of nucleus detected in quadrature ($^{15}$N in this case). As a result, the jointly sampled chemical shifts of different types of nuclei ($^1$H and $^{13}$C in this case) are scaled up by the ratio of the gyromagnetic ratios (for example, the $^1$H chemical shifts in ppm are scaled up 10-times on the $^{15}$N ppm scale). Specifically, the linear combinations observed in sub-spectra B1-B8 are: B1 [$\Omega_0$+$\Omega_1$+$\Omega_2$+$\Omega_3$]; B2 [$\Omega_0$–$\Omega_1$+$\Omega_2$+$\Omega_3$]; B3 [$\Omega_0$+$\Omega_1$–$\Omega_2$+$\Omega_3$]; B4 [$\Omega_0$–$\Omega_1$–$\Omega_2$+$\Omega_3$]; B5 [$\Omega_0$+$\Omega_1$+$\Omega_2$–$\Omega_3$]; B6 [$\Omega_0$–$\Omega_1$+$\Omega_2$–$\Omega_3$]; B7 [$\Omega_0$+$\Omega_1$–$\Omega_2$–$\Omega_3$]; B8 [$\Omega_0$–$\Omega_1$–$\Omega_2$–$\Omega_3$]. To resolve potential shift degeneracies, first-order central peak spectra are acquired (B9-B12) comprising peaks at: B9 [$\Omega_0$+$\Omega_1$+$\Omega_2$]; B10 [$\Omega_0$–$\Omega_1$+$\Omega_2$]; B11 [$\Omega_0$+$\Omega_1$–$\Omega_2$]; B12 [$\Omega_0$–$\Omega_1$–$\Omega_2$], second-order central peaks (B13-B14) comprise peaks at B13 [$\Omega_0$+$\Omega_1$] and B14 [$\Omega_0$–$\Omega_1$], and third-order central peaks (B15) are signals of 2D [$^{15}$N, $^1$H]-HSQC at $\Omega_0$. Panel (c) shows assignment of aliphatic side chains exemplified for Ile 85. On the left, two composite plots show strips taken from the basic subspectra providing $\Omega$($^{13}$C)+$\Omega$($^1$H) (labeled B1) and $\Omega$($^{13}$C)–$\Omega$($^1$H) (labeled B2) along the GFT dimension $\omega_1$ (Table 10). On the right, a composite plot (labeled B3) shows strips taken from the central peak spectrum of (4,3)D HCCH providing $\Omega$($^{13}$C) along $\omega_1$ [that is, 3D (H)CCH information (Cavanagh et al., *Protein NMR Spectroscopy* Academic Press: San Diego (1996), which is hereby incorporated by reference in its entirety)]. For aliphatic spin system identification, sums and differences of shifts of covalently attached $^{13}$C and $^1$H nuclei (Table 10) are delineated in B1 and B2, while $^{13}$C shifts are matched in B3 (indicated by dashed lines). Sequence-specific assignments are inferred from $^1$H$^\alpha$ and $^{13}$C$^{\alpha\beta}$ shifts assigned in (4,3)D HNNC$^{\alpha\beta}$C$^\alpha$/C$^{\alpha\beta}$C$^\alpha$(CO)NHN (Atreya et al., *Proc. Natl. Acad. Sci. USA* 101:9642-9647 (2004), which is hereby incorporated by reference in its entirety) and (5,2)D HACACONHN (Kim et al., *J. Am. Chem. Soc.* 125:1385-1393 (2003), which is hereby incorporated by reference in its entirety) as described in the description for panels (a) and (b). The five [$\omega_1$($^{13}$C; $^1$H),$\omega_3$($^1$H)]-strips were taken along $\omega_2$($^{13}$C) at the shifts of $^{13}$C$^\alpha$, $^{13}$C$^\beta$, $^{13}$C$^{\gamma 1}$, $^{13}$C$^{\gamma 2}$, and $^{13}$C$^{\delta 1}$ of Ile 85 (indicated at the bottom of the strips of B3). The peaks encode along $\omega_1$ linear combinations of the following shifts: $^{13}$C$^\alpha$/$^1$H$^\alpha$ (labeled as 1), $^{13}$C$^\beta$/$^1$H$^\beta$ (2), $^{13}$C$^{\gamma 12,\gamma 13}$/$^1$H$^{\gamma 12,\gamma 13}$ (3), $^{13}$C$^{\gamma 2}$/$^1$H$^{\gamma 2}$ (4) and $^{13}$C$^{\delta 1}$/$^1$H$^{\delta 1}$ (5). Panel (d) depicts the identification of aromatic spin systems in (4,3)D HCCH demonstrated for Tyr 89. On the left, two composite plots show strips taken from basic subspectra providing $\Omega(^{13}C)+\Omega(^{1}H)$ (labeled B1) and $\Omega(^{13}C)-\Omega(^{1}H)$ (labeled B2). The composite plot shown on the right (labeled B3) shows strips taken from the central peak spectrum of (4,3)D HCCH providing $\Omega(^{13}C)$ along $\omega_1$. Aromatic spin system identification was accomplished in a manner similar to that described in the legend of panel (c) for aliphatic spin systems, and sequence-specific assignments were inferred from observation (Wüthrich, *NMR of proteins and Nucleic Acids* Wiley: New York (1986), which is hereby incorporated by reference in its entirety) of intraresidue NOEs. The two $[\omega_1(^{13}C;{}^{1}H),\omega_3(^{1}H)]$-strips from each of the three subspectrum were taken along $\omega_2(^{13}C)$ at the shifts of $^{13}C^\delta$ and $^{13}C^\epsilon$ of Tyr 89 (indicated at the bottom of the strips of B3). The peaks encode along (ok linear combinations of the following shifts: $^{13}C^\delta/^{1}H^\delta$ (labeled as 1) and $^{13}C^\epsilon/^{1}H^\epsilon$ (2) (since $\Omega(^{1}H^\delta)$=7.2 ppm and $\Omega(^{1}H^\epsilon)$=6.7 ppm, the separation of peaks labeled with 1 in B1 and B2 appears to be similar to the separation of peaks labeled with 2).

Figure 38:
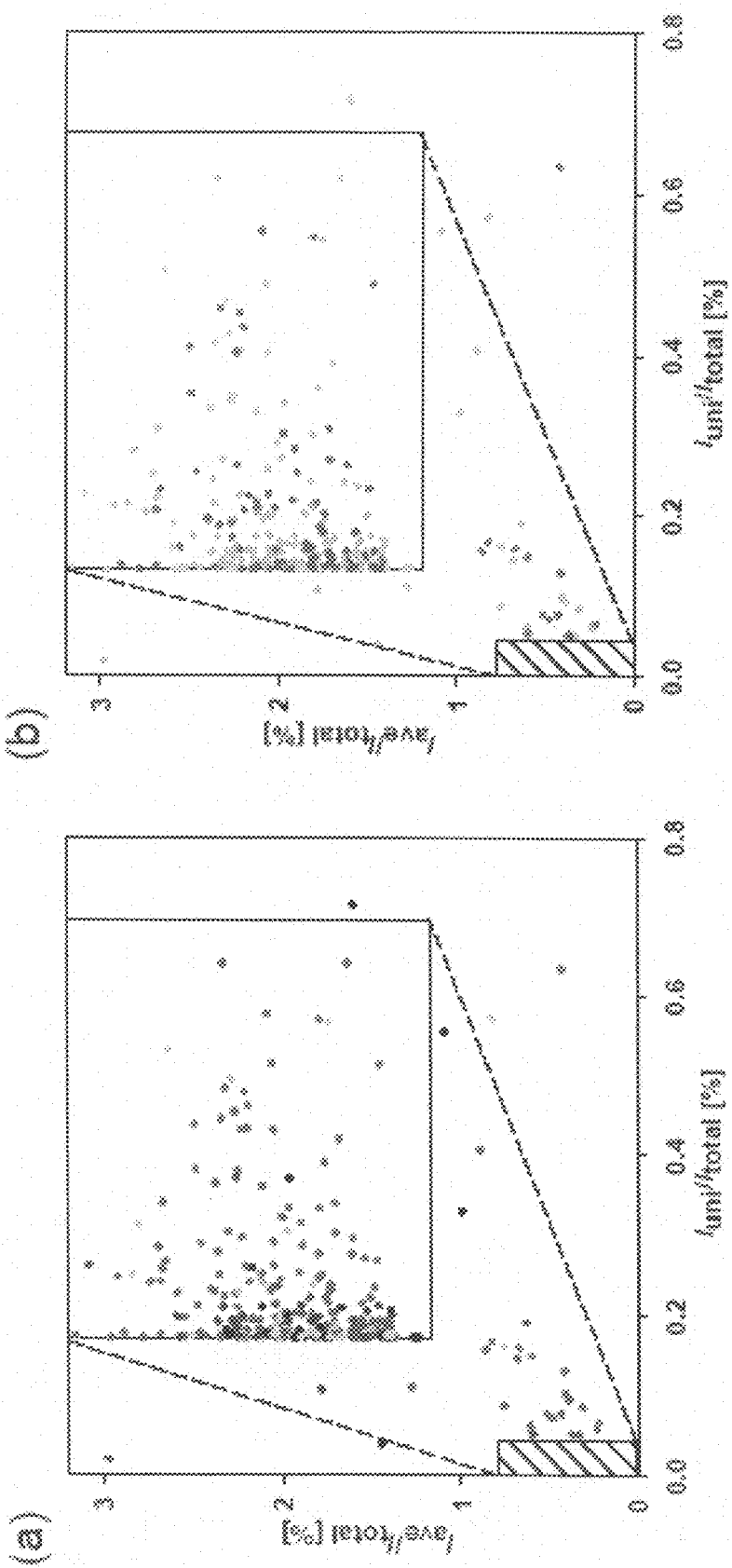

FIGS. 38(*a*)-(*b*) are $[I_{uni}, I_{ave}]$ plots calculated with the program QUEEN (Nabuurs et al., *J. Am. Chem. Soc.* 125: 12026-12034 (2003), which is hereby incorporated by reference in its entirety) of upper distance limit constraints derived from the 3D [H]-NOESY-[CH$^{ali}$/CH$^{aro}$/NH] peak list (see Examples 18, 21, and 24) used to calculate the reference YqfB structure (1TE7). In FIG. 38(*a*), constraints obtained in 3D [H]-NOESY-[CH$^{ali}$/CH$^{aro}$/NH] based on chemical shift data only are depicted as green circles, additional constraints assigned with reference to shift doublet data sets I and II of (4,3)D [HC$^{ali}$/HN]-NOESY-[CH$^{ali}$/NH] are shown as red and blue circles, respectively. Aromatic and other aliphatic constraints which could be assigned only with reference to an (initial) structure are displayed as black and grey circles, respectively. The distribution of the circles shows that chemical shift based NOE assignment is, as expected, not dependent on the information content of an NOE. In FIG. 38(*b*), additional constraints, which were identified by the program CYANA (Herrmann et al., *J. Mol. Biol.* 319:209-227 (2002), which is hereby incorporated by reference in its entirety) in the first cycle with a probability of >85%, are depicted as red circles while those assigned based on shifts are in green [as in FIG. 38(*a*)], and others are displayed in grey. Comparison with (a) reveals significant bias toward identification of constraints with lower information content. The average $I_{uni}/I_{total}$ and $I_{ave}/I_{total}$ are 0.071% and 0.679% for the red constraints (total: 72) in FIG. 38(*a*), which were identified with chemical shift doublet data set I. The corresponding values for the red constraints (total: 40) in FIG. 38(*b*), which were assigned with CYANA, are only 0.011% and 0.254%, respectively.

Figure 39:
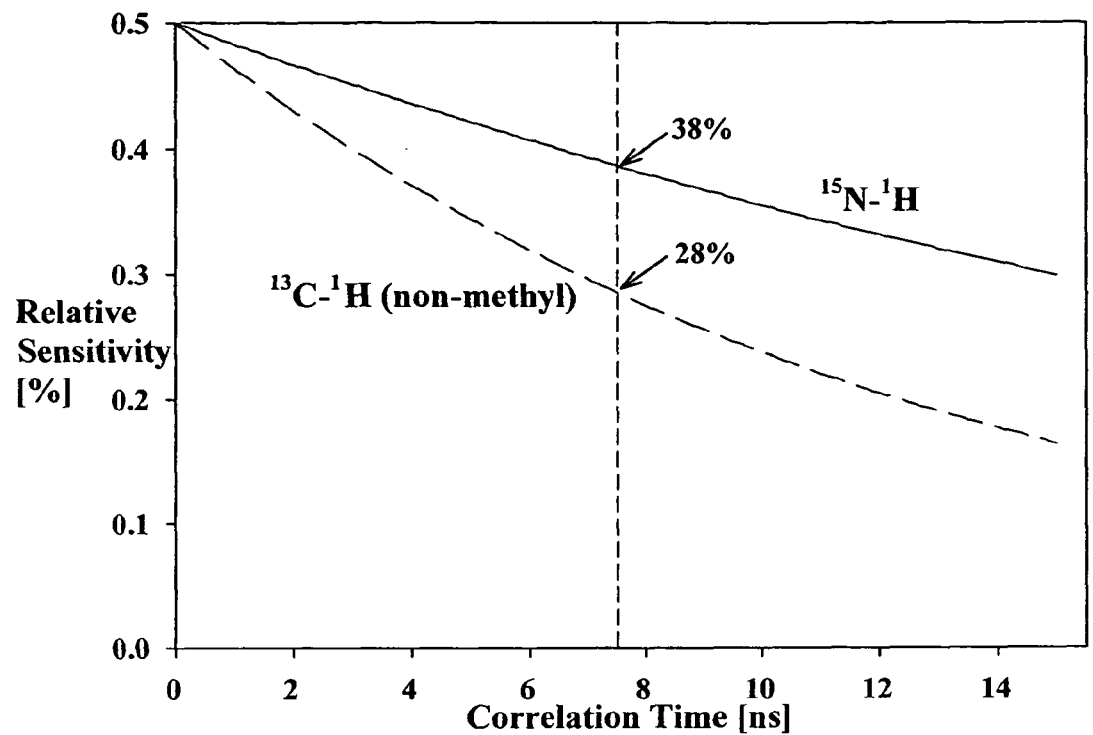

In FIG. 39, the sensitivity of each of the peaks forming a shift doublet registered in (4,3)D [HC$^{ali}$/HN]-NOESY-[CH$^{ali}$/NH] relative to the corresponding central peak [in %] is plotted as a function of the correlation time for the isotropic overall rotational tumbling of a rigid protein. Doublets encoding $\Omega(^{15}N)$ and $\Omega(^{13}C^{aliphatic})$ are represented by solid and dashed lines, respectively. Since doublets arise from an inphase splitting of central peaks, the relative sensitivity is a priori reduced to 50%. The curves reflect further $T_2$ spin relaxation losses that occur during the additional simultaneous [$^{15}N$, $^{1}H$]/[$^{13}C$, $^{1}H$]-HSQC module (FIG. 36(*a*)). The transverse relaxation rates of $^{1}HN$, $^{15}N$, $^{13}C^{aliphatic}$ and $^{1}H^{aliphatic}$ as a function of the protein correlation time, $\tau_r$, were taken from Wagner, *J. Biomol. NMR* 3:375-385 (1993), which is hereby incorporated by reference in its entirety. The relative sensitivity predicted for YqfB is given and $\tau_r$=7.7 is indicated by a vertical dotted line.

Figure 40:
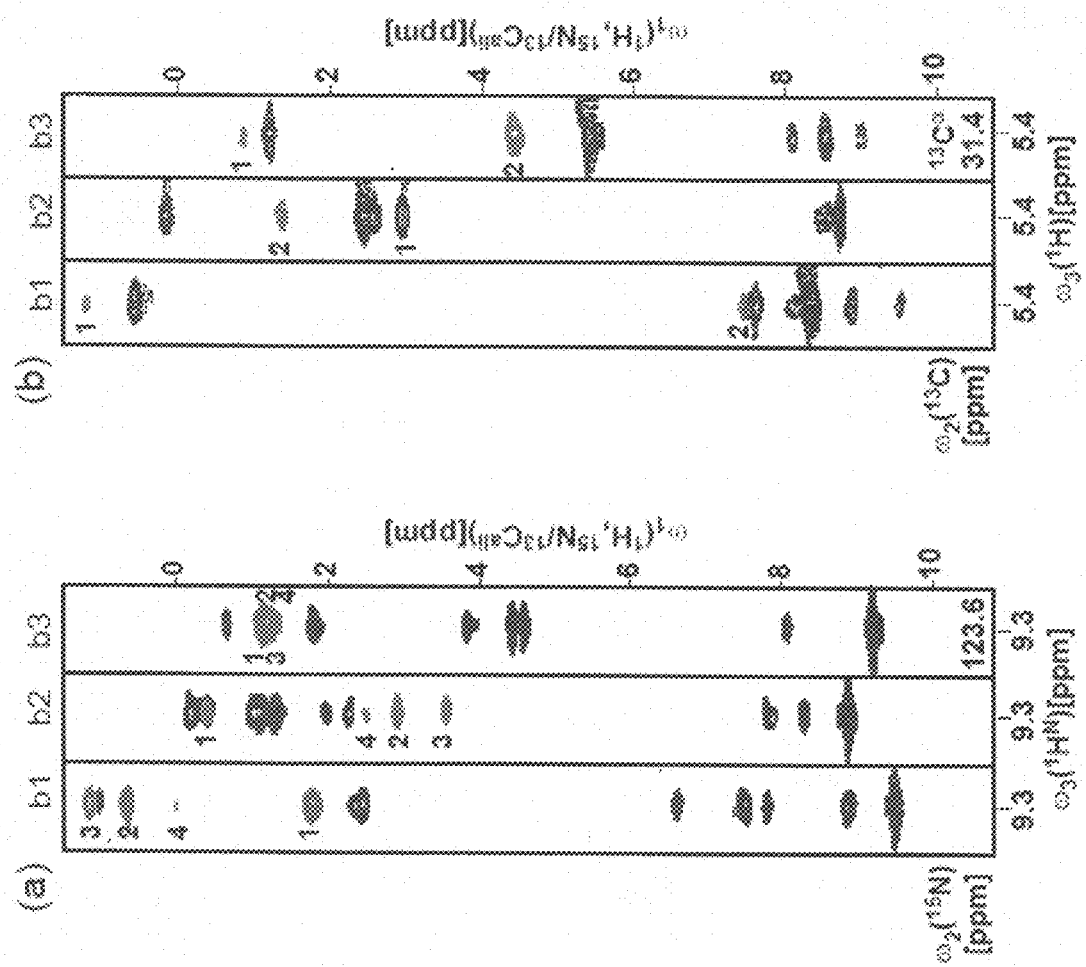

FIGS. 40(*a*)-(*b*) illustrate the chemical shift based NOE assignment in (4,3)D [HC$^{ali}$/HN]-NOESY-[CH$^{ali}$/NH] acquired with 3D [H]-NOESY-[CH$^{ali}$/CH$^{aro}$/NH] for central peak detection. Panel (a) shows the $^{15}N$-resolved part: [$\omega_1$, $\omega_3(^{1}H^N)$]-strips taken from the shift doublet sub-spectrum exhibiting peaks at $\Omega(^{1}H)+\Omega(X)$ along $\omega_1$ (X=$^{15}N$, $^{13}C$; shown on the left and indicated as b1), from the shift doublet subspectrum exhibiting peaks at $\Omega(^{1}H)-\Omega(X)$ along $\omega_1$ (X=$^{15}N$, $^{13}C$; indicated in the middle as b2) and the central peak subspectrum (3D [H]-NOESY-[CH$^{ali}$/CH$^{aro}$/NH]; indicated on the right as b3). Signals were detected on the backbone amide proton of Leu 78. Four peaks are shown in red which are overlapped in the central peak spectrum. These peaks are well resolved and can be unambiguously assigned directly from chemical shifts in the shift doublet subspectra (data set I recorded in 30 hours). Assignments: NOEs between H$^N$ of Leu 78 and (1) H$^{\beta 2}$ of Leu 78, (2) CH$_3^{\gamma 2}$ of Thr 77, (3) CH$_3^{\beta}$ of Ala 71, and (4) H$^\gamma$ of Leu 78. Panel (b) shows the $^{13}C$-resolved part: [$\omega_1$,$\omega_3(^{1}H^{aliphatic})$]-strips taken from the same subspectra. Signals were detected on $\alpha$-proton of residue Thr 58. Two long-range NOEs are shown in red which can be unambiguously assigned directly from chemical shifts in the shift doublet subspectra. Assignments: NOEs between H$^\alpha$ of Thr 58 and (1) CH$_2^\gamma$ of Ile 98, (2) H$^\alpha$ of Ile 98.

Figure 41:
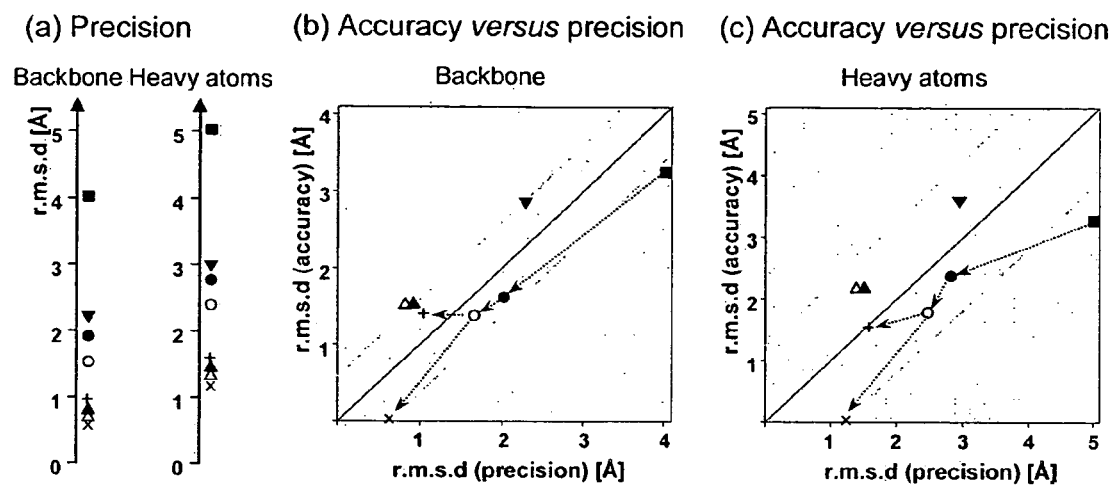

FIGS. 41(*a*)-(*c*) illustrate the precision (FIG. 41(*a*)) and accuracy (FIGS. 41(*b*)-(*c*)) of comparative YqfB structure calculations (r.m.s.d. values were taken from Table 13). In FIG. 41(*a*), r.m.s.d. values reflecting precision were calculated for the backbone heavy atoms N, C$^\alpha$ and C' (on the left) and all heavy atoms (on the right) of residues 4-101, and are displayed on vertical scales. In FIG. 41(*b*) (for backbone) and FIG. 41(*c*) (for heavy atoms), plots of r.m.s.d. values reflecting accuracy were calculated between mean coordinates of the 20 DYANA conformers of a given structure and the mean coordinates of the 20 conformers of the reference structure (1TE7), and are displayed versus the precision r.m.s.d. values provided in FIG. 41(*a*). The dashed line above the diagonal represents the equality r.m.s.d. (accuracy)=r.m.s.d.(precision)+r.m.s.d.(reference structure). Structures below this line can be considered to be 'accurate', since the allowed conformational subspaces overlap (see text). The dashed line below the diagonal represents the equality r.m.s.d.(accuracy) =r.m.s.d.(precision)−r.m.s.d.(reference structure). Structures below this line can be considered to be ideally suited for further refinement, since the allowed conformational space of the initial structure largely includes the allowed space of the reference structure. Codes (FIG. 42; Table 13): ×reference structure (1TE7); + reference structure calculated after omission of stereo-specific assignments; ■: initial structure calculated with NOEs assigned in 3D [H]-NOESY-[CH$^{ali}$/CH$^{aro}$/NH] based on chemical shift data only; ● and ○: initial structures calculated with additional NOEs assigned in 3D [H]-NOESY-[CH$^{ali}$/CH$^{aro}$/NH] with reference to shift doublet data sets I and II of (4,3)D [HC$^{ali}$/HN]-NOESY-[CH$^{ali}$/NH] (FIG. 40); ▼: intial structure calculated with the program CYANA (Güntert et al., *J. Mol. Biol.* 273:283-298 (1997); Herrmann et al., *J. Mol. Biol.* 319:209-227 (2002); Güntert, *Methods Mol. Biol.* 278:347-372 (2004), which are hereby incorporated by reference in their entirety) (1$^{st}$ cycle); ▲ and Δ: final structures calculated with the program CYANA when starting with constraint input used for ● and ○. The "refinement trajectory" (see Example 25) is indicated by dotted arrows; the bifurcation represents the availability or non-availability of stereospecific assignments (Table 12).

Figure 42:
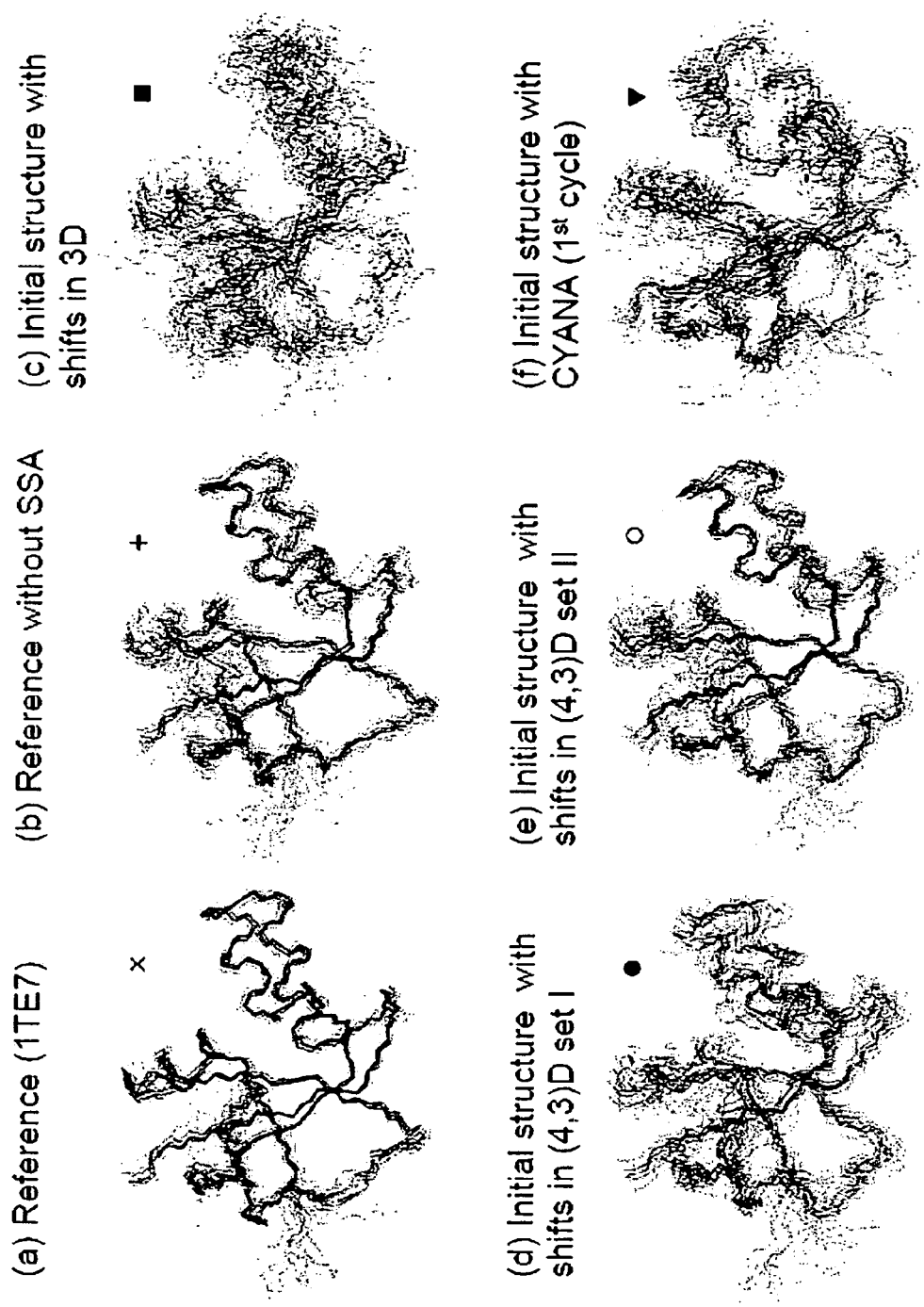

FIGS. 42(*a*)-(*f*) depict a survey of YqfB structures. FIG. 42(*a*) is the reference structure (PDB ID 1TE7; code in FIG.

42: x) FIG. 42(b) is the reference structure calculated after omission of stereospecific assignments (+). FIG. 42(c) is the initial structure calculated with NOEs assigned in 3D [H]-NOESY-[CH$^{ali}$/CH$^{aro}$/NH] based on chemical shift data only (■). FIG. 42(d) is the initial structure calculated with additional NOEs assigned in 3D [H]-NOESY-[CH$^{ali}$/CH$^{aro}$/NH] with reference to shift doublet data sets I of (4,3)D [HC$^{ali}$/HN]-NOESY-[CH$^{ali}$/NH] (●). FIG. 42(e) is the same as in FIG. 42(d) but with shift doublet data set II (○). FIG. 42(f) is the initial structure calculated with the program CYANA (1$^{st}$ cycle out of 7; Herrmann et al., *J. Mol. Biol.* 319:209-227 (2002), which is hereby incorporated by reference in its entirety) with TALOS dihedral angle constraints and intraresidue, sequential, and medium-range distance constraints as input (▼). The 20 DYANA conformers with the lowest residual target function value were chosen to represent the NMR solution structures. These conformers were superimposed for minimal r.m.s.d. of backbone heavy atoms N, C$^\alpha$, and C' of residues 4-101 and the heavy atoms of the best defined side-chains (Table 12). The figure was generated using the program Molmol (Koradi et al., *J. Mol. Graphics* 14:51-55 (1996), which is hereby incorporated by reference in its entirety).

Figure 43:
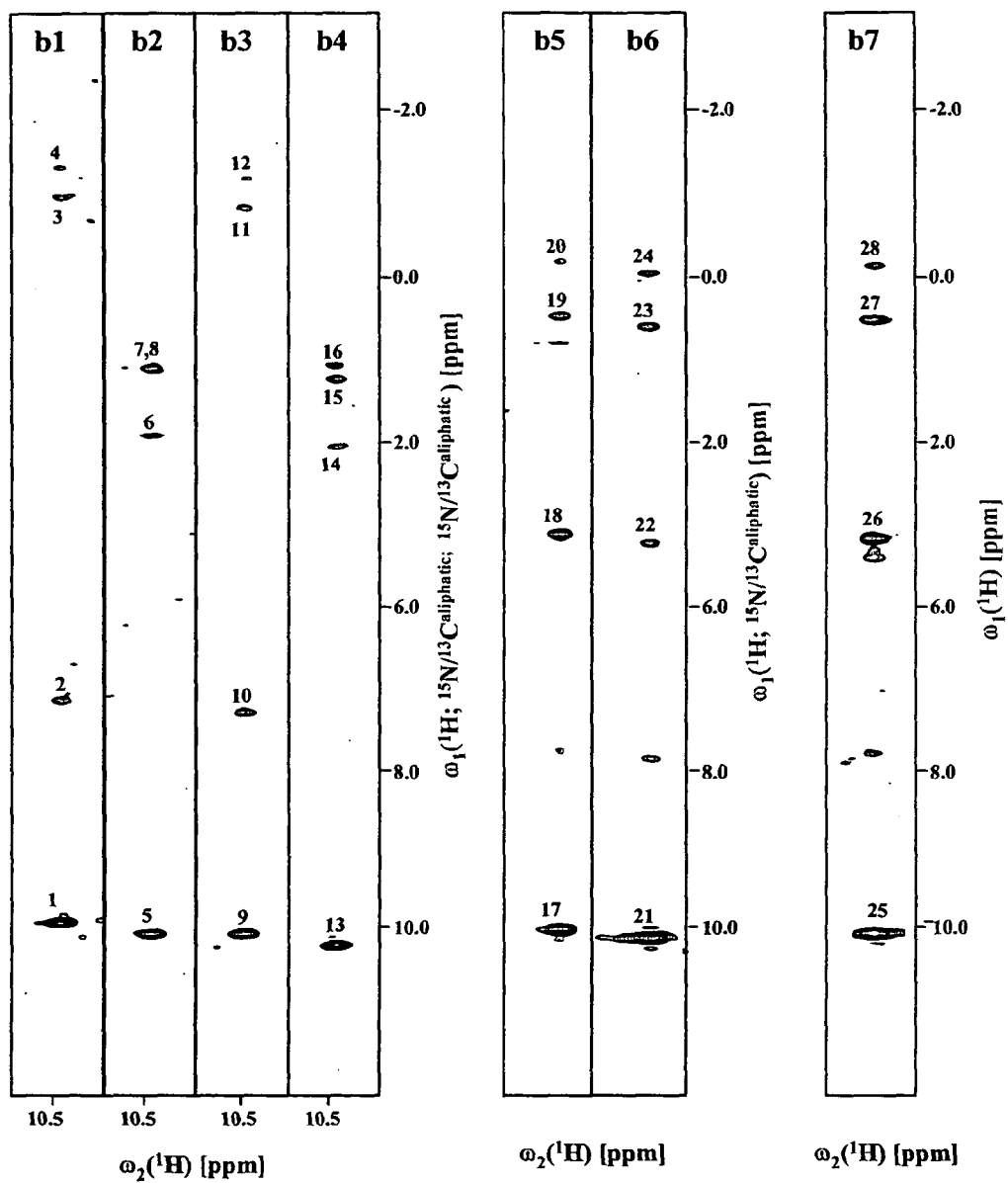
Figure 44:
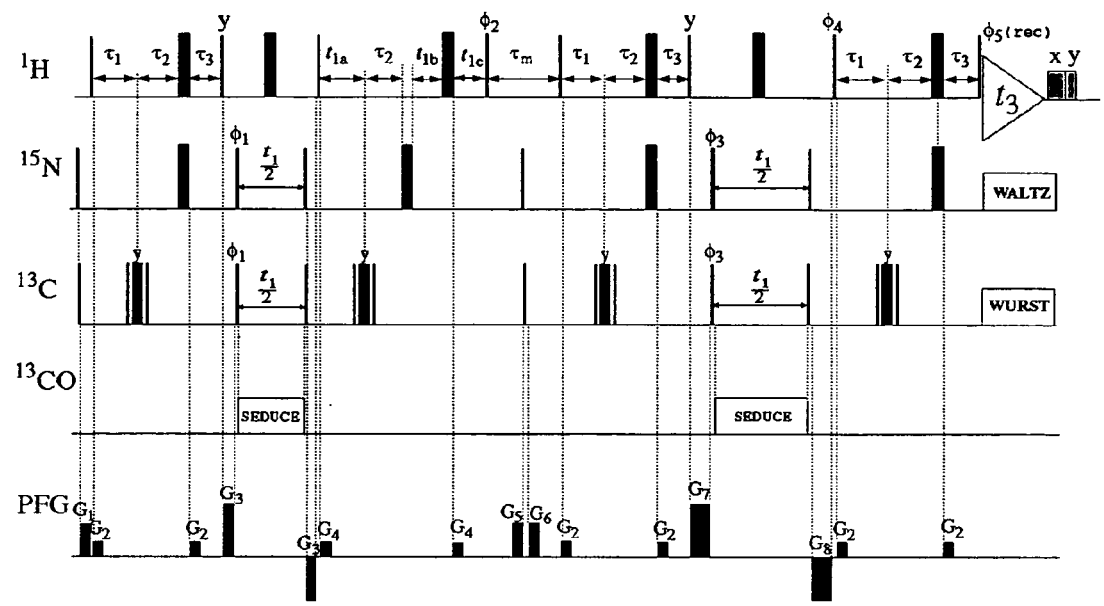

FIG. 43 shows composite plots of [ω$_1$($^1$H; $^{15}$N/$^{13}$C$^{aliph}$), ω$_2$($^1$H)] strips taken from the basic and first order central peak spectra of (4,2)D $^{15}$N/$^{13}$C$^{aliph}$ resolved [$^1$H, $^1$H] NOESY. The basic spectra (labeled "b1"-"b4"), the first order central peak spectra (labeled "b5"-"b6") and the second order central peak spectra (labeled "b7") are centered on the respective ω$_2$($^1$H) chemical shifts. Strips have been taken at ω$_1$($^1$H$^N$) chemical shift of residue Thr 67. The peaks labeled 1-28 correspond to the following linear combination of chemical shifts along ω$_1$ (i=Thr 67; i−1=Thr 67):

1. $\Omega_0(^1H^N_i)+\Omega_1(^{15}N_i)/2.0+\Omega_2(^{15}N_i)/2.0$
2. $\Omega_0(^1H^\alpha_{i-1})+\Omega_1(^{15}N_i)/2.0+\Omega_2(^{13}C^\alpha_{i-1})/2.0$
3. $\Omega_0(^1H^{\gamma2}_i)+\Omega_1(^{15}N_i)/2.0+\Omega_2(^{13}C^{\gamma2}_i)/2.0$
4. $\Omega_0((^1H^{\delta1}_{i-1})_3)+\Omega_1(^{15}N_i)/2.0+\Omega_2(^{13}C^{\delta1}_{i-1})/2.0$
5. $\Omega_0(^1H^N_i)+\Omega_1(^{15}N_i)/2.0-\Omega_2(^{15}N_i)/2.0$
6. $\Omega_0(^1H^\alpha_{i-1})+\Omega_1(^{15}N_i)/2.0-\Omega_2(^{13}C^\alpha_{i-1})/2.0$
7. $\Omega_0(^1H^{\gamma2}_i)+\Omega_1(^{15}N_i)/2.0-\Omega_2(^{13}C^{\gamma2}_i)/2.0$
8. $\Omega_0((^1H^{\delta1}_{i-1})_3)+\Omega_1(^{15}N_i)/2.0-\Omega_2(^{13}C^{\delta1}_{i-1})/2.0$
9. $\Omega_0(^1H^N_i)-\Omega_1(^{15}N_i)/2.0+\Omega_2(^{15}N_i)/2.0$
10. $\Omega_0(^1H^\alpha_{i-1})-\Omega_1(^{15}N_i)/2.0+\Omega_2(^{13}C^\alpha_{i-1})/2.0$
11. $\Omega_0(^1H^{\gamma2}_i)-\Omega_1(^{15}N_i)/2.0+\Omega_2(^{13}C^{\gamma2}_i)/2.0$
12. $\Omega_0((^1H^{\delta1}_{i-1})_3)-\Omega_1(^{15}N_i)/2.0+\Omega_2(^{13}C^{\delta1}_{i-1})/2.0$
13. $\Omega_0(^1H^N_i)-\Omega_1(^{15}N_i)/2.0-\Omega_2(^{15}N_i)/2.0$
14. $\Omega_0(^1H^\alpha_{i-1})-\Omega_1(^{15}N_i)/2.0-\Omega_2(^{13}C^\alpha_{i-1})/2.0$
15. $\Omega_0(^1H^{\gamma2}_i)-\Omega_1(^{15}N_i)/2.0-\Omega_2(^{13}C^{\gamma2}_i)/2.0$
16. $\Omega_0((^1H^{\delta1}_{i-1})_3)-\Omega_1(^{15}N_i)/2.0-\Omega_2(^{13}C^{\delta1}_{i-1})/2.0$
17. $\Omega_0(^1H^N_i)+\Omega_1(^{15}N_i)/2.0$
18. $\Omega_0(^1H^\alpha_{i-1})+\Omega_1(^{15}N_i)/2.0$
19. $\Omega_0(^1H^{\gamma2}_i)+\Omega_1(^{15}N_i)/2.0$
20. $\Omega_0((^1H^{\delta1}_{i-1})_3)+\Omega_1(^{15}N_i)/2.0$
21. $\Omega_0(^1H^N_i)-\Omega_1(^{15}N_i)/2.0$
22. $\Omega_0(^1H^\alpha_{i-1})-\Omega_1(^{15}N_i)/2.0$
23. $\Omega_0(^1H^{\gamma2}_i)-\Omega_1(^{15}N_i)/2.0$
24. $\Omega_0((^1H^{\delta1}_{i-1})_3)-\Omega_1(^{15}N_i)/2.0$
25. $\Omega_0(^1H^N_i)$
26. $\Omega_0(^1H^\alpha_{i-1})$
27. $\Omega_0(^1H^{\gamma2}_i)$
28. $\Omega_0((^1H^{\delta1}_{i-1})_3)$ FIG. 44 depicts the r.f. pulse scheme of (4,2)D $^{15}$N/$^{13}$C$^{aliphatic}$-resolved [$^1$H, $^1$H]-NOESY. Rectangular 90° and 180° pulses are indicated by thin and thick vertical bars, respectively, and phases are indicated above the pulses. Where no r.f. phase is marked, the pulse is applied along x. High-power 90° pulse lengths are: 9.0 μs for $^1$H, 17.0 μs for $^{13}$C and 40 μs for $^{15}$N. SEDUCE is used for decoupling of $^{13}$C' during t$_1$($^{13}$C/$^{15}$N) and t$_2$($^{13}$C/$^{15}$N) (r.f. field strength=1 kHz). WURST is used for decoupling of $^{13}$C during acquisition and $^{13}$C decoupling during t$_1$($^1$H) is achieved using a (90°$_x$-180°$_y$-90°$_x$) composite pulse. WALTZ16 is employed to decouple $^{15}$N (r.f.=1.70 kHz) during acquisition. The duration of $^1$H spin-lock purge pulses applied immediately after acquisition for suppression of the water line are: SL$_x$, 4.9 ms; SL$_y$: 2.6 ms. The $^1$H r.f. carrier position is placed at 4.78 ppm. The $^{15}$N and $^{13}$C carrier positions are set to 118.0 ppm and 36 ppm, respectively. $^1$H-frequency labeling (at a $^1$H resonance frequency of 600 MHz) is achieved in a semi constant-time fashion with t$_1^a$(0)=ms, t$_1^b$(0)=μs, t$_1^c$(0)=ms, Δt$_1^a$=μs, Δt$_1^b$=μs, Δt$_1^c$=μs. Hence, the fractional increase of the semi constant-time period with t$_1$ equals to λ=1+Δt$_1^c$/Δt$_1^a$=0.58. The duration and strengths of the pulsed z-field gradients (PFGs) are: G$_1$ (1 ms, 22 G/cm); G$_2$ (500 μs, 6 G/cm); G$_3$ (1 ms, 20 G/cm); G$_4$ (500 μs, 6 G/cm); G$_5$ (2.0 ms, 15 G/cm); G$_6$ (2.0 ms, 15 G/cm); G$_7$ (2.0 ms, 20 G/cm); G$_8$ (2.0 ms, −20 G/cm). All PFG pulses are of rectangular shape. The delays are: τ$_1$=1.8 ms, τ$_2$=0.6 ms, τ$_3$=2.4 ms, τ$_m$=70 ms. Phase cycling: φ$_1$=x; φ$_2$=x; φ$_3$=x,−x; φ$_4$=x,−x; φ$_5$(receiver)=x,−x,−x,x. Quadrature detection in t$_1$($^1$H) is accomplished by altering the phase φ$_2$ according to States-TPPI. GFT-NMR super phase-cycling scheme for recording the two basic spectra is: φ$_1$=x,y.

Figure 45:
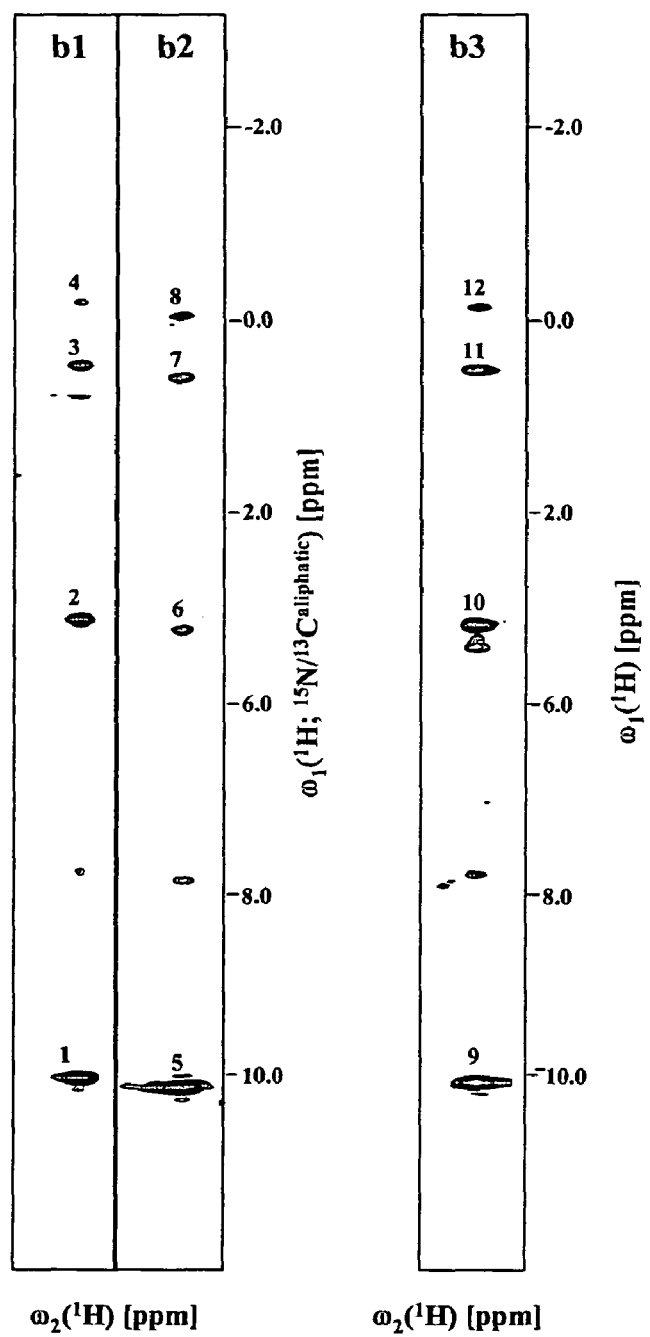
Figure 46:
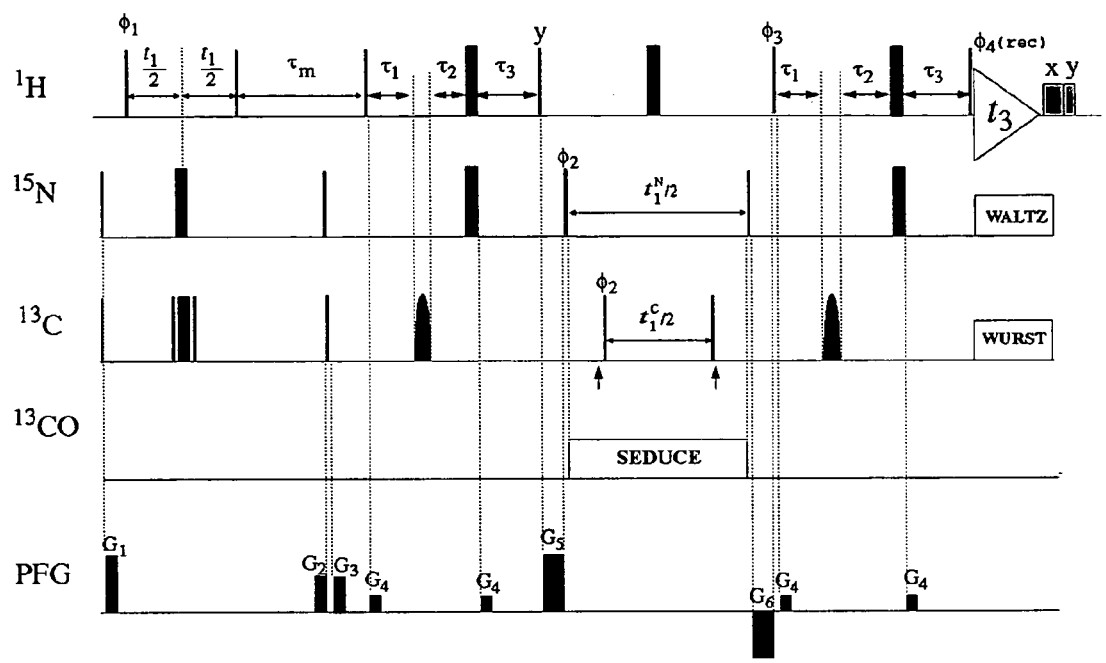

FIG. 45 shows composite plots of [ω$_1$($^1$H; $^{15}$N/$^{13}$C$^{aliph}$), ω$_2$($^1$H)] strips taken from the basic and first order central peak spectra of (3,2)D $^{15}$N/$^{13}$C$^{aliph}$ resolved [$^1$H, $^1$H] NOESY. The basic spectra (labeled "b1"-"b2") and the first order central peak spectra (labeled "b3") are centered on the respective ω$_2$($^1$H) chemical shifts. Strips have been taken at ω$_1$($^1$HN) chemical shift of residue Thr 67. The peaks labeled 1-12 correspond to the following linear combination of chemical shifts along ω$_1$ (i=Thr 67; i−1=Thr 67):

1. $\Omega_0(^1H^N_i)+\Omega_1(^{15}N_i)/2.0$
2. $\Omega_0(^1H^\alpha_{i-1})+\Omega_1(^{15}N_i)/2.0$
3. $\Omega_0(^1H^{\gamma2}_i)+\Omega_1(^{15}N_i)/2.0$
4. $\Omega_0((^1H^{\delta1}_{i-1})_3)+\Omega_1(^{15}N_i)/2.0$
5. $\Omega_0(^1H^N_i)-\Omega_1(^{15}N_i)/2.0$
6. $\Omega_0(^1H^\alpha_{i-1})-\Omega_1(^{15}N_i)/2.0$
7. $\Omega_0(^1H^{\gamma2}_i)-\Omega_1(^{15}N_i)/2.0$
8. $\Omega_0((^1H^{\delta1}_{i-1})_3)-\Omega_1(^{15}N_i)/2.0$
9. $\Omega_0(^1H^N_i)$
10. $\Omega_0(^1H^\alpha_{i-1})$
11. $\Omega_0(^1H^{\gamma2}_i)$
12. $\Omega_0((^1H^{\delta1}_{i-1})_3)$ FIG. 46 depicts the r.f. pulse scheme of (3,2)D $^{15}$N/$^{13}$C$^{aliphatic}$-resolved [$^1$H, $^1$H]-NOESY. Rectangular 90° and 180° pulses are indicated by thin and thick vertical bars, respectively, and phases are indicated above the pulses. Where no r.f. phase is marked, the pulse is applied along x. High-power 90° pulse lengths are: 9.0 μs for $^1$H, 17.0 μs for $^{13}$C and 40 μs for $^{15}$N. SEDUCE is used for decoupling of $^{13}$C' during t$_1$($^{13}$C/$^{15}$N) and t$_2$($^{13}$C/$^{15}$N) (r.f. field strength=1 kHz). WURST is used for decoupling of $^{13}$C during acquisition and $^{13}$C decoupling during t$_1$($^1$H) is achieved using a (90°$_x$-180°$_y$-90°$_x$) composite pulse. WALTZ16 is employed to decouple $^{15}$N (r.f.=1.70 kHz) during acquisition. The duration of $^1$H spin-lock purge pulses applied immediately after acquisition for suppression of the water line are: SL$_x$, 4.9 ms; SL$_y$: 2.6 ms. The $^1$H r.f. carrier position is placed at 4.78 ppm. The $^{15}$N and $^{13}$C carrier positions are set to 118.0 ppm and 36 ppm, respectively. The duration and strengths of the pulsed z-field gradients (PFGs) are: G$_1$ (1 ms, 22 G/cm); G$_2$ (1 ms, 8 G/cm); G$_3$ (1 ms, 20 G/cm); G$_4$ (500 μs, 6 G/cm); G$_5$ (2.0 ms, 15 G/cm); G$_6$ (2.0 ms, 15 G/cm). All PFG pulses are of rectangular shape. The delays are: τ$_1$=1.8 ms, τ$_2$=0.6 ms, τ$_3$=2.4 ms, $\tau_m$=70 ms. Phase cycling: $\phi_1$=2(x), 2(y); $\phi_2$=x, -x; $\phi_3$=4(x), 4(y), 4(-x), 4(-y); $\phi_4$ (receiver)=x,-x,-x,x,-y,y,y,-y,-x,x, x,-x,y,-y,-y,y. Quadrature detection in $t_1$($^1$H) is accomplished by altering the phase $\phi_1$ according to States-TPPI. GFT NMR super phase-cycling scheme for recording the two basic spectra is: $\phi_2$=x,y.

Figure 47:
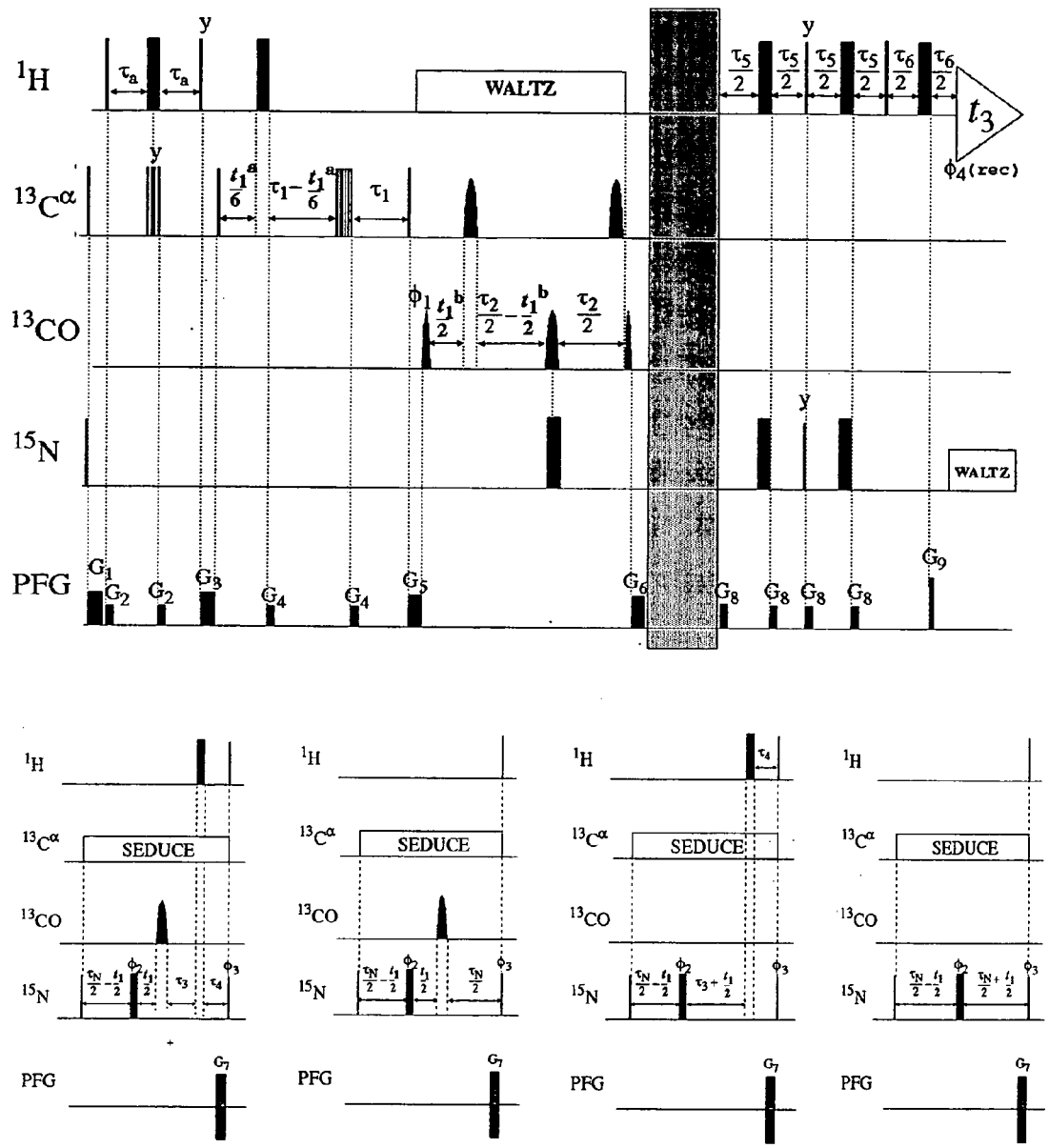

FIG. 47 depicts the r.f. pulse scheme of J-GFT (6,2)D (H$^\alpha$—C$^\alpha$—CO)—N—HN for the measurement of RDCs. Rectangular 90° and 180° pulses are indicated by thin and thick vertical bars, respectively, and phases are indicated above the pulses. Where no r.f. phase is marked, the pulse is applied along x. The shaded portion of the sequence is shown as an expansion in the figure with different modulation schemes of the coupling constants. The high power 90° pulse lengths were: 5.8 μs for $^1$H and 15.4 μs for $^{13}$C, and 38 μs for $^{15}$N. The $^{15}$N r.f. carrier is set to 120.9 ppm. The $^{13}$C carrier is set to 56 ppm initially and shifted to 176 ppm before the first pulse on $^{13}$C'. Pulses on $^{13}$C prior to $t_1^a$ are applied at high power, and $^{13}$C coupling during the $^1$H—$^{13}$C$^\alpha$ INEPT (Cavanagh et al., *Protein NMR Spectroscopy* Academic Press: San Diego, Calif. (1996), which is hereby incorporated by reference in its entirety) is achieved using a (90°$_x$-180°$_y$-90°$_x$) composite pulse. Subsequently, the 90° and 180° pulse lengths of $^{13}$C$^\alpha$ are adjusted to 51.5 μs and 46 μs (at a $^1$H resonance frequency of 600 MHz), respectively, to minimize perturbation of the $^{13}$C' spins. A six-pulse composite sequence (Shaka, *Chem. Phy. Lett.* 120:201-205 (1985), which is hereby incorporated by reference in its entirety) is used to simultaneously invert/refocus $^{13}$C$^\alpha$/$^{13}$C' magnetization during $^{13}$C$^\alpha$—$^{13}$C' polarization transfer. The width of the 90° SEDUCE pulses (Cavanagh et al., *Protein NMR Spectroscopy* Academic Press: San Diego, Calif. (1996), which is hereby incorporated by reference in its entirety) applied to $^{13}$C' pulse is 200 μs and the corresponding 180° pulses are applied with same power. WALTZ16 (Cavanagh et al., *Protein NMR Spectroscopy* Academic Press: San Diego, Calif. (1996), which is hereby incorporated by reference in its entirety) is employed to decouple $^1$H (r.f. field strength=9.2 kHz) during the heteronuclear magnetization transfers as well as to decouple $^{15}$N during acquisition (r.f.=1.78 kHz). The off-resonance SEDUCE sequence (Cavanagh et al., *Protein NMR Spectroscopy* Academic Press: San Diego, Calif. (1996), which is hereby incorporated by reference in its entirety) is used for decoupling of $^{13}$C$^\alpha$ during the $^{15}$N chemical shift evolution period (adiabatic decoupling of aliphatic $^1$H during signal detection could be employed for enhancing sensitivity (Vander Kooi et al., *J. Biomol. NMR* 15:335-338 (1999), which is hereby incorporated by reference in its entirety). The $^1$H r.f. carrier is placed at the position of the solvent line at 4.78 ppm. The duration and strengths of the pulsed z-field gradients (PFGs) are: G1 (1 ms, 24 G/cm); G2 (100 μs, 8 G/cm); G3 (1 ms, 20 G/cm); G4 (500 μs, 8 G/cm); G5 (1.0 ms, 20 G/cm); G6 (1.0 ms, 20 G/cm); G7 (1.25 ms, 30 G/cm); G8 (500 μs, 8 G/cm); G9 (125 μs, 29.5 G/cm). All PFG pulses are of rectangular shape. The delays are: $\tau_a$=1.7 ms, $\tau_1$=4.5 ms, $\tau_2$=24.0 ms, $\tau_3$=27.3 ms, $\tau_4$=2.7 ms, $\tau_5$=4.6 ms, $\tau_6$=1.0 ms, $\tau_N$=30 ms. Phase cycling: $\phi_1$=x, -x; $\phi_2$=2(x), 2(-x); $\phi_3$=x; $\phi_4$(receiver)=x, -x. A sensitivity enhancement scheme (Kay et al., *J. Am. Chem. Soc.* 114:10663-10665 (1992), which is hereby incorporated by reference in its entirety) is employed, i.e., the sign of G7 is inverted in concert with a 180° shift of $\phi_5$. Quadrature detection of $t_1$($^{15}$N) is achieved via gradient selection of coherences using G7. GFT NMR super phase-cycling scheme for recording the basic spectra is described briefly below:

| | |
|---|---|
| (i) Detection of $^1$J($^1$H$^\alpha$—$^{13}$C$^\alpha$): | |
| Cosine modulation: | $t_1^a$/6.0 = $t_1$/6.0 + 1.7 ms |
| Sine modulation: | $t_1^a$/6.0 = $t_1$/6.0 |
| (ii) Detection of $^1$J($^{13}$C$^\alpha$—$^{13}$C'): | |
| Cosine modulation: | $t_1^b$/2.0 = $t_1$/2.0 + 4.5 ms |
| Sine modulation: | $t_1^b$/2.0 = $t_1$/2.0 |
| (iii) Detection of $^1$J($^{15}$N—$^{13}$C'): | |
| Cosine modulation: | Scheme (a) or (b) |
| Sine modulation: | Scheme (c) or (d) |
| (iv) Detection of $^1$J($^{15}$N—$^1$H): | |
| Cosine modulation: | Scheme (a) or (c) |
| Sine modulation: | Scheme (b) or (d) |

The central peak spectra are acquired by successively omitting the coupling evolution in the order (i) to (iv) shown above, using the same r.f. pulse scheme.

Figure 48:
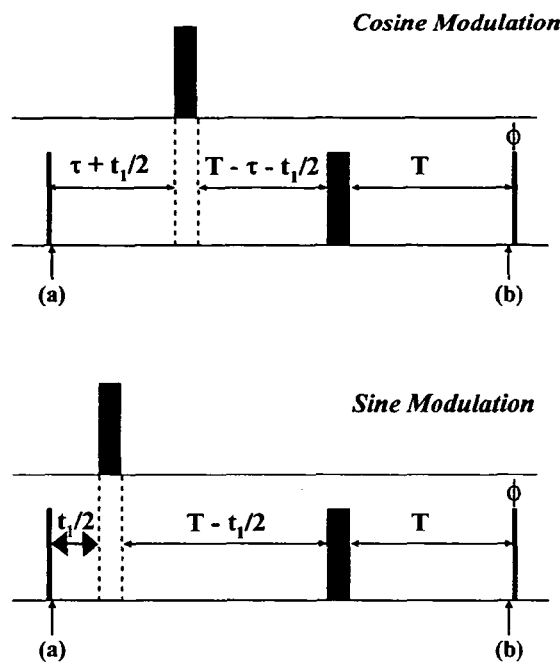

FIG. 48 is a schematic diagram of the r.f. pulse module used for detecting the cosine and sine modulation of the transfer amplitude for a given pair of nuclei, I-S, in J-GFT (6,2)D (H$^\alpha$—C$^\alpha$—CO)—N—HN. This module is repeatedly incorporated for simultaneous measurement of multiple RDCs during polarization transfers (FIG. 47). Rectangular 90° and 180° pulses are indicated by thin and thick vertical bars, respectively. The delay 'τ' is set to ½J$_{IS}$, where J$_{IS}$ is the one-bond scalar coupling constant under isotropic conditions. The relevant product operator terms at points a and b are described in Example 26.

Figure 49:
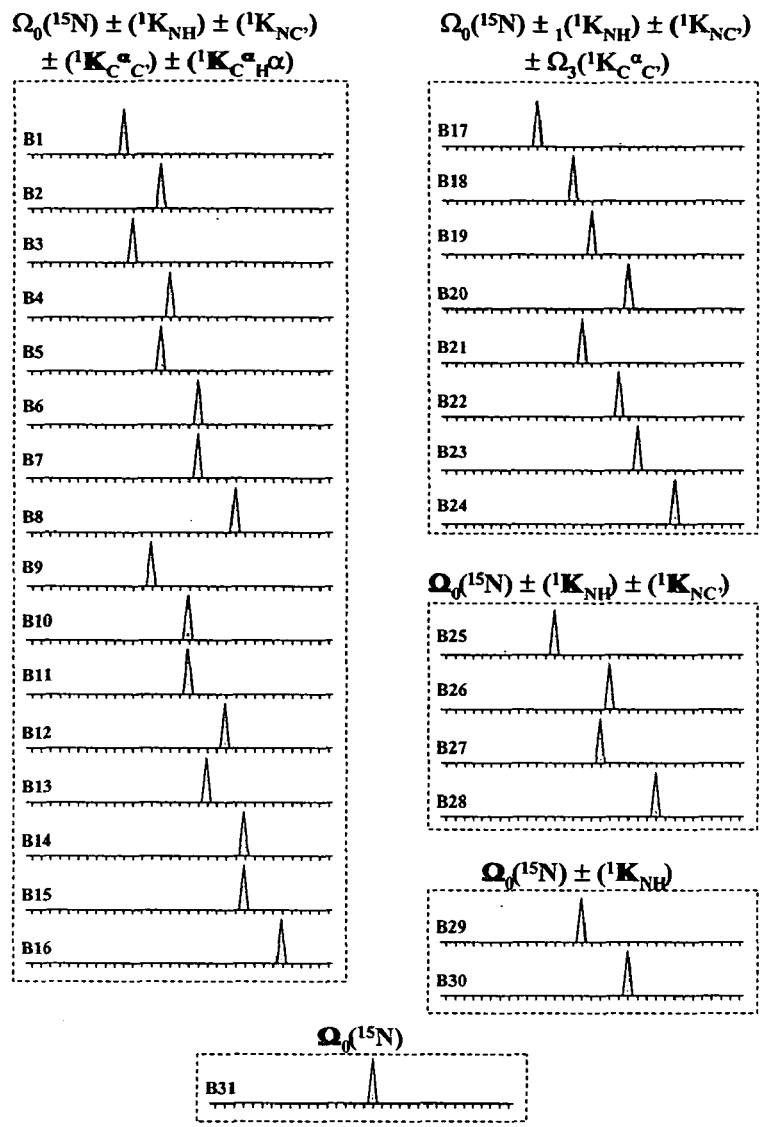

FIG. 49 is a schematic depiction of the peak pattern observed in J-GFT (6,2)D (H$^\alpha$—C$^\alpha$—CO)—N—HN spectra. The subspectra are grouped into basic, first-, second-, and third-order central peaks. The fourth-order central peak is represented by a peak in the 2D [$^{15}$N—$^1$H] HSQC. The linear combination of the couplings observed in each group of subspectra is shown.

Figure 50:
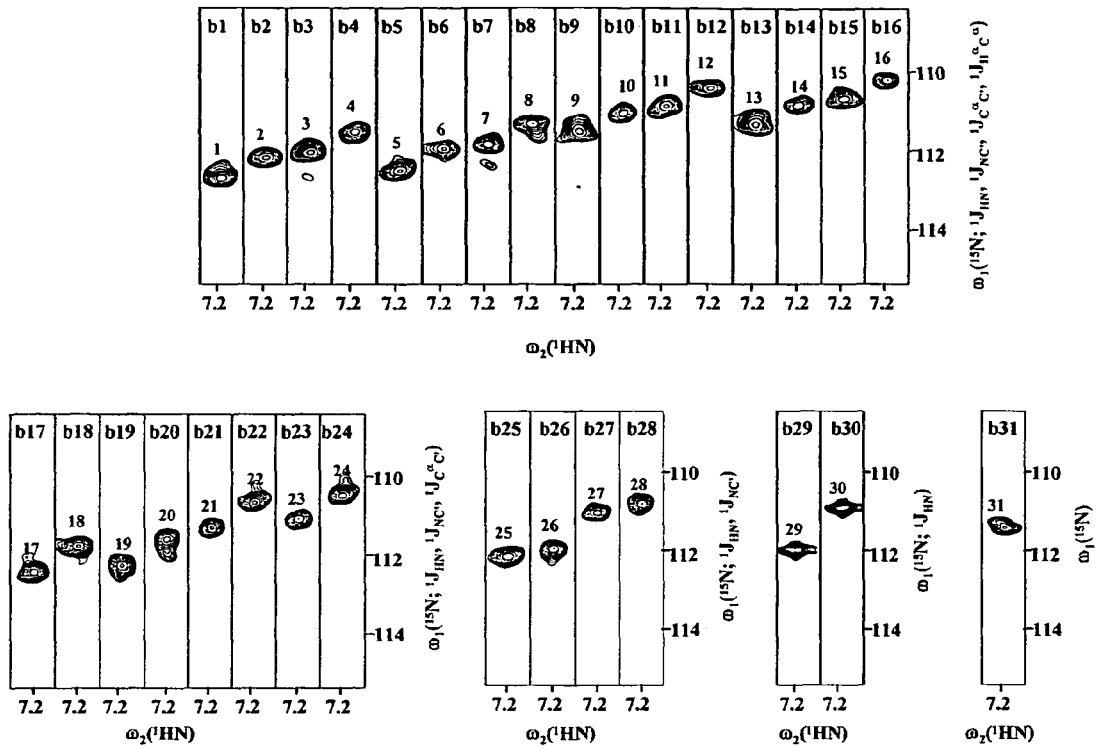
Figure 50:
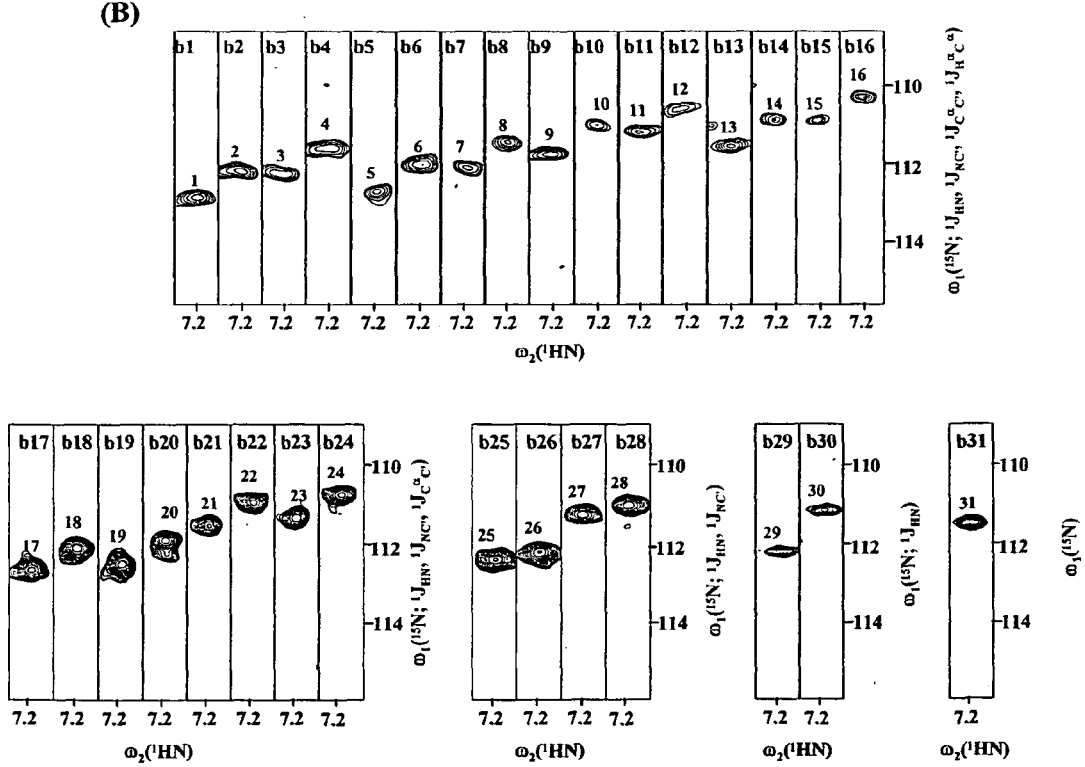

FIG. 50 shows composite plots of [ω$_1$($^{15}$N; $^1$J$_{HN}$, $^1$J$_{NC'}$, $^1$J$_{C^\alpha C'}$, $^1$J$_{H^\alpha C^\alpha}$), ω$_2$($^1$H)] strips taken from the basic spectra (labeled b1-b16), first order central peak spectra (labeled b17-b24), second order central peak spectra (labeled b25-b28), third order central peak spectra (labeled b29-b30) and fourth order central peak spectra (labeled b31) of the (6,2)D ($^1$H$^\alpha$—$^{13}$C$^\alpha$—$^{13}$CO)—N—HN recorded for Z-domain in (A) isotropic and (B) liquid-crystalline (Pf1 phage aligned) medium at 25° C. The strips are centered about their backbone $^1$HN chemical shifts. As an example, strips corresponding to ω$_2$($^1$H$^N$) chemical shifts for residue Leu 32 of protein Z-domain are shown. The following notation has been used for representing one-bond scalar and residual dipolar coupling constants, where the subscript 'i' refers to the residue number:

In (A): $J_{HN}$=$^1$J$_{H(i)N(i)}$; $J_{NC'}$=$^1$J$_{N(i)C'(i-1)}$; $J_{C'C'}^\alpha$=$^1$J$_{C^\alpha(i-1)C'(i-1)}$;

$J_{H^\alpha C^\alpha}$=$^1$J$_{H^\alpha(i-1)C^\alpha(i-1)}$;

In (B): $J_{HN}$=$^1$J$_{H(i)N(i)}$+$^1$J$^D_{H(i)N(i)}$; $J_{NC'}$=$^1$J$_{N(i)C'(i-1)}$+$^1$J$^D_{N(i)C(i)}$;

$J_{C^\alpha C'}$=$^1$J$_{C^\alpha(i-1)C'(i-1)}$+$^1$J$^D_{C^\alpha(i-1)C'(i-1)}$; $J_{H^\alpha C^\alpha}$=$^1$J$_{H^\alpha(i-1)C^\alpha(i-1)}$+$^1$J$^D_{H^\alpha(i-1)C^\alpha(i-1)}$)

Peaks labeled 1-31 correspond to the following linear combination of chemical shifts in both (A) and (B):

1. Ω$_0$($^{15}$N)+$J_{HN}$/2.0+$^1$J$_{NC'}$/2.0+$J_{C^\alpha C'}^\alpha$/2.0+$J_{H^\alpha C^\alpha}$/6.0
2. Ω$_0$($^{15}$N)+$J_{HN}$/2.0+$^1$J$_{NC'}$/2.0+$J_{C^\alpha C'}^\alpha$/2.0−$J_{H^\alpha C^\alpha}$/6.0
3. Ω$_0$($^{15}$N)+$J_{HN}$/2.0+$^1$J$_{NC'}$/2.0−$J_{C^\alpha C'}^\alpha$/2.0+$J_{H^\alpha C^\alpha}$/6.0
4. Ω$_0$($^{15}$N)+$J_{HN}$/2.0+1JNC'/2.0−$J_{C^\alpha C'}^\alpha$/2.0−$J_{H^\alpha C^\alpha}$/6.0
5. Ω$_0$($^{15}$N)+$J_{HN}$/2.0−1JNC'/2.0+$J_{C^\alpha C'}^\alpha$/2.0+$J_{H^\alpha C^\alpha}$/6.0
6. Ω$_0$($^{15}$N)+$J_{HN}$/2.0−1JNC'/2.0+$J_{C^\alpha C'}^\alpha$/2.0−$J_{H^\alpha C^\alpha}$/6.0
7. Ω$_0$($^{15}$N)+$J_{HN}$/2.0−1JNC'/2.0−$J_{C^\alpha C'}^\alpha$/2.0+$J_{H^\alpha C^\alpha}$/6.0
8. Ω$_0$($^{15}$N)+$J_{HN}$/2.0−1JNC'/2.0−$J_{C^\alpha C'}^\alpha$/2.0−$J_{H^\alpha C^\alpha}$/6.0
9. Ω$_0$($^{15}$N)−$J_{HN}$/2.0+1JNC'/2.0+$J_{C^\alpha C'}^\alpha$/2.0+$J_{H^\alpha C^\alpha}$/6.0

10. $\Omega_0(^{15}N) - J_{HN}/2.0 + 1JNC'/2.0 + J_{C^\alpha C'}/2.0 - J_{H^\alpha C^\alpha}/6.0$
11. $\Omega_0(^{15}N) - J_{HN}/2.0 + 1JNC'/2.0 - J_{C^\alpha C'}/2.0 + J_{H^\alpha C^\alpha}/6.0$
12. $\Omega_0(^{15}N) - J_{HN}/2.0 + 1JNC'/2.0 - J_{C^\alpha C'}/2.0 - J_{H^\alpha C^\alpha}/6.0$
13. $\Omega_0(^{15}N) - J_{HN}/2.0 - 1JNC'/2.0 + J_{C^\alpha C'}/2.0 + J_{H^\alpha C^\alpha}/6.0$
14. $\Omega_0(^{15}N) - J_{HN}/2.0 - 1JNC'/2.0 + J_{C^\alpha C'}/2.0 - J_{H^\alpha C^\alpha}/6.0$
15. $\Omega_0(^{15}N) - J_{HN}/2.0 - 1JNC'/2.0 - J_{C^\alpha C'}/2.0 + J_{H^\alpha C^\alpha}/6.0$
16. $\Omega_0(^{15}N) - J_{HN}/2.0 - 1JNC'/2.0 - J_{C^\alpha C'}/2.0 - J_{H^\alpha C^\alpha}/6.0$
17. $\Omega_0(^{15}N) + J_{HN}/2.0 + 1JNC'/2.0 + J_{C^\alpha C'}/2.0$
18. $\Omega_0(^{15}N) + J_{HN}/2.0 + ^1J_{NC}/2.0 - J_{C^\alpha C'}/2.0$
19. $\Omega_0(^{15}N) + J_{HN}/2.0 - ^1J_{NC}/2.0 + J_{C^\alpha C'}/2.0$
20. $\Omega_0(^{15}N) + J_{HN}/2.0 - ^1J_{NC}/2.0 - J_{C^\alpha C'}/2.0$
21. $\Omega_0(^{15}N) - J_{HN}/2.0 + ^1J_{NC}/2.0 + J_{C^\alpha C'}/2.0$
22. $\Omega_0(^{15}N) - J_{HN}/2.0 + ^1J_{NC}/2.0 - J_{C^\alpha C'}/2.0$
23. $\Omega_0(^{15}N) - J_{HN}/2.0 - ^1J_{NC}/2.0 + J_{C^\alpha C'}/2.0$
24. $\Omega_0(^{15}N) - J_{HN}/2.0 - ^1J_{NC}/2.0 - J_{C^\alpha C'}/2.0$
25. $\Omega_0(^{15}N) + J_{HN}/2.0 + ^1J_{NC}/2.0$
26. $\Omega_0(^{15}N) + J_{HN}/2.0 - ^1J_{NC}/2.0$
27. $\Omega_0(^{15}N) - J_{HN}/2.0 + ^1J_{NC}/2.0$
28. $\Omega_0(^{15}N) - J_{HN}/2.0 - ^1J_{NC}/2.0$
29. $\Omega_0(^{15}N) + J_{HN}/2.0$
30. $\Omega_0(^{15}N) - J_{HN}/2.0$
31. $\Omega_0(15N)$

DETAILED DESCRIPTION OF THE INVENTION

G$^2$FT NMR: Design Principles, Theory, and Data Processing

The present application discloses novel "G$^2$FT NMR experiments" in which two G-matrix transformations are applied. This allows one to jointly sample shifts solely serving to provide increased resolution separately from those also providing sequential connectivities. As a result, one obtains data sets in which spin system identification can be based on (3,2)D GFT NMR in the first GFT dimension, for example, while previously described peak patterns (Atreya et al., *Proc. Natl. Acad. Sci. USA* 101:9642-9647 (2004), which is hereby incorporated by reference in its entirety) for sequential assignment are retained in the second GFT dimension.

Previously described $^{15}N$, $^1H^N$-resolved triple resonance (4,3)D GFT NMR experiments (Kim et al., *J. Biomol. NMR* 28:117-130 (2004); Atreya et al., *Proc. Natl. Acad. Sci. USA* 101:9642-9647 (2004), which are hereby incorporated by reference in their entirety) contain a single "GFT dimension" used for establishing sequential links based on $^{13}C^{\alpha/\beta}$ and/or $^1H^\alpha$ shifts. In the second indirect dimension (the "resolving dimension") $^{15}N$ shifts are measured, which solely serve to provide signal dispersion. In cases of high $^{15}N$—$^1H^N$ shift degeneracy, overlap occurs in this dimension. Spectral resolution can be improved if shifts of other nuclei (e.g., $^{13}C'_{i-1}$) are measured in addition to $^{13}C^{\alpha\beta}$ or $^{13}C^\alpha/^1H^\alpha$ and $^{15}N$ shifts in the indirect dimensions. This can serve to separate two spin systems which have degenerate $^{13}C^\alpha/^{13}C^\beta$ or/and $^{15}N/^1H^N$ shifts but non-degenerate $^{13}C'_{i-1}$ chemical shifts. This can be accomplished in two ways: (i) jointly sample the $^{13}C'_{i-1}$ shift in the GFT dimension of the (4,3)D experiments along with the $^{13}C^\alpha/^{13}C^\beta$ shifts, or (ii) jointly sample the $^{13}C'_{i-1}$ shift along with the $^{15}N$ shift in the resolving dimension. Importantly, the first approach "scrambles" the GFT peak pattern of the (4,3)D experiments, since the $^{13}C'_{i-1}$ shifts are linearly combined with those of $^{13}C^\alpha_i/^{13}C^\beta_i$ and $^{13}C^\alpha_{i-1}/^{13}C^\beta_{i-1}$. On the other hand, combining $^{13}C'_{i-1}$ and $^{15}N$ shifts allows one to jointly sample those shifts which solely serve to provide increased resolution separately from those providing sequential connectivities. Then, each of the two indirect dimensions serve for joint sampling of a distinct set of shifts, and the processing of such data sets requires employment of two G-matrix transformations. Hence, these experiments are named "G$^2$FT NMR" experiments. Such grouping of jointly sampled shifts (i) provides increased spectral resolution by increasing signal dispersion in both the indirect dimensions (See Atreya et al., *Proc. Natl. Acad. Sci. USA* 101:9642-9647 (2004), which is hereby incorporated by reference in its entirety), (ii) allows one to pursue spin system identification based on 3D spectral information obtained from (3,2)D GFT NMR, (iii) allows one to match peak pattern ("C$^{\alpha\beta}$C$^\alpha$ or C$^\alpha$H$^\alpha$-pattern") manifested in the second GFT dimension in order to establish sequential connectivites. To minimize loss of sensitivity, additional frequency labeling is preferably accomplished in a constant time manner (Wüthrich, *NMR of Proteins and Nucleic Acids* Wiley: New York (1986), which is hereby incorporated by reference in its entirety) during delays required for magnetization transfer. This has two advantages: (i) no additional signal losses due to transverse relaxation occur, and (ii) lines do not broaden because of the joint sampling of multiple shifts (Kim et al., *J. Am. Chem. Soc.* 125:1385-1393 (2003), which is hereby incorporated by reference in its entirety). Based on these considerations, (5,3)D HN{N,CO}{C$^{\alpha\beta}$C$^\alpha$} and (5,3)D HN{NCO}{C$^{\alpha\beta}$C$^\alpha$} were designed. For systems with high $^{13}C^\alpha/^{13}C^\beta$ shift degeneracy, precluding efficient linking of spins systems, (5,3)D HN{N, CO}{C$^\alpha$H$^\alpha$}/HN{NCO}{C$^\alpha$H$^\alpha$} were designed to additionally employ H$^\alpha$ shifts for establishing sequential connectivities. In the same spirit, one can combine $^{13}C^\alpha_{i/i-1}$ and $^{15}N$ shifts in the "resolving-dimension". This offers an alternative way to break spectral overlap in systems with very high shift degeneracy, and leads to the implementation of (5,3)D G$^2$FT HN{NC$^\alpha$}{C$^{\alpha\beta}$C$^\alpha$} and HN{N(CO)C$^\alpha$}{C$^{\alpha\beta}$C$^\alpha$}. A novel feature of (5,3)D G$^2$FT HN{NC$^\alpha$}{C$^{\alpha\beta}$C$^\alpha$} is that intraresidue and sequential peaks are located in different planes (since the $^{15}N_i$ shift is combined with $^{13}C^\alpha_{i/i-1}$), that is, in cases of multiple sequential shift degeneracy, this experiment allows one to unambiguously confirm the presence of both the intra- and sequential peaks associated with a given backbone NH moiety.

A (N,N-K)D GFT NMR experiment enables phase sensitive joint sampling of K+1 chemical shifts in a single indirect dimension named the "GFT dimension" (Kim et al., *J. Am. Chem. Soc.* 125:1385-1393 (2003); Kim et al., *J. Biomol. NMR* 28:117-130 (2004); Atreya et al., *Proc. Natl. Acad. Sci. USA* 101:9642-9647 (2004), which are hereby incorporated by reference in their entirety). The other N−1 dimensions are conventionally sampled (Cavanagh et al., *Protein NMR Spectroscopy* Academic Press: San Diego (1996), which is hereby incorporated by reference in its entirety). The joint sampling of K+1 chemical shift evolution periods generates chemical shift multiplets with $2^K$ components located at $\Omega_0 \pm \Omega_1 \ldots \pm \Omega_K$. These multiplets are edited into $2^K$ different subspectra by G-matrix transformation (Kim et al., *J. Am. Chem. Soc.* 125:1385-1393 (2003); Kim et al., *J. Biomol. NMR* 28:117-130 (2004); Atreya et al., *Proc. Natl. Acad. Sci. USA* 101: 9642-9647 (2004), which are hereby incorporated by reference in their entirety) of $2^K$ data sets each containing the chemical shift multiplets with a different in-phase/anti-phase pattern. Considering both real and an imaginary part of these $2^K$ data sets, a total of $2^{K+1}$ data sets with varying sine and cosine modulation of shifts have to be linearly combined. These can be written as a $2^{K+1}$ dimensional vector:

$$\hat{S}(K) \propto \begin{bmatrix} C_K \\ S_K \end{bmatrix} \otimes \ldots \otimes \begin{bmatrix} C_l \\ S_l \end{bmatrix} \otimes \begin{bmatrix} C_0 \\ S_0 \end{bmatrix} \quad (1)$$

where $c_j = \cos(\Omega_j t)$ and $s_j = \sin(\Omega_j t)$, and t represents the evolution time in the indirect GFT dimension. The G-matrix is defined as a $2^K \times 2^{K+1}$ complex matrix (Kim et al., *J. Am. Chem. Soc.* 125:1385-1393 (2003), which is hereby incorporated by reference in its entirety):

$$\hat{G}(K) = \begin{bmatrix} 1 & i \\ 1 & -i \end{bmatrix}_1 \otimes \ldots \otimes \begin{bmatrix} 1 & i \\ 1 & -i \end{bmatrix}_K \otimes \begin{bmatrix} 1 & i \end{bmatrix} \quad (2)$$

Multiplication of $\hat{S}(K)$ with the G-matrix according to $$T(K) = \hat{G}(K) \cdot \hat{S}(K) \quad (3)$$

yields the vector T(K) containing the edited subspectra. Those are subsequently Fourier transformed yielding the desired $2^K$ frequency domain subspectra (Kim et al., *J. Am. Chem. Soc.* 125:1385-1393 (2003), which is hereby incorporated by reference in its entirety).

The concept of GFT NMR data acquisition can be extended to the joint sampling of two sets of K'+1 and K"+1 different chemical shifts in two separate indirect dimensions (FIG. 1(a)). This results in shift multiplets with $2^{K'}$ and $2^{K''}$ components, respectively, in the two GFT dimensions, yielding detection of a total of $2^M$ (M=K'+K") linear combination of chemical shifts [e.g., $\omega_1:(\Omega_0, \pm\Omega_1, \ldots \pm\Omega_{K'}) \otimes \omega_2:(\Omega_{0''}, \pm\Omega_{1''} \ldots \pm\Omega_{K''})$] Those can be edited into $2^M$ different subspectra as described in the following.

Each data set is collected by jointly incrementing K'+1 and K"+1 shifts in the two GFT dimensions along with systematic variation of the phases of r.f. pulses exciting spins of type i or j (i=1 ... K'+1; j=1 ... K"+1) between 0° and 90° in order to register both cosine and sine modulated data sets (Kim et al., *J. Am. Chem. Soc.* 125:1385-1393 (2003), which is hereby incorporated by reference in its entirety) resulting in a total of $2^{K'+K''+2}$ data sets. These form a $2^{K'+1} * 2^{K''+1}$ dimensional vector, which can be obtained by tensor product formation according to:

$$\hat{S}(K', K'') = \hat{S}(K') \otimes \hat{S}(K'') \quad (4)$$

$\hat{S}(K', K'')$ shall be transformed by employment of G-matrix transformation into T(K', K"), which contains the $2^M$ (M=K'+K") edited time domain subspectra.

With $T(K', K'') = T(K') \otimes T(K'') \quad (5)$ and Equation 3, one obtains $$T(K', K'') = [\hat{G}(K') \cdot \hat{S}(K')] \otimes [\hat{G}(K'') \cdot \hat{S}(K'')] \quad (6),$$

which can be rearranged to:

$$T(K', K'') = [\hat{G}(K') \otimes \hat{G}(K'')] \cdot [\hat{S}(K') \otimes S(K'')] \quad (7)$$

$$= [\hat{G}(K') \otimes \hat{G}(K'')] \cdot \hat{S}(K', K''). \quad (8)$$

Hence, $\hat{G}(K', K'') = \hat{G}(K') \otimes \hat{G}(K'')$ represents the required G-matrix. In the case of K=K'=K", $\hat{G}(K', K'')$ corresponds to the tensor product of $\hat{G}(K)$ with itself, which can be written as $G^2(K) = \hat{G}(K) \otimes \hat{G}(K)$. This relation gives rise to the name "$G^2$FT NMR experiments". If K'≠K", the experiment has to be denoted as a "G'G"FT NMR experiment" [e.g., (6,3)D { $H^{\alpha\beta}C^{\alpha\beta}C^{\alpha}$}{CON}HN; FIGS. 24 and 25].

The data sets T(K',K") are Fourier transformed along both GFT dimensions to yield the $2^M$ (N,N-M)D frequency domain subspectra. As examples, the real $\hat{G}(K', K'')$ matrices used for processing the (5,3)D and (6,3)D data described in Examples 1 to 4 (FIG. 10; Table 1) are provided below. For (5,3)D: K'=K"=1 and for (6,3)D: K'=2; K"=1. Hence:

$$\hat{G}(1) = \begin{pmatrix} 1 & 0 & 0 & -1 \\ 0 & 1 & 1 & 0 \\ 1 & 0 & 0 & 1 \\ 0 & 1 & -1 & 0 \end{pmatrix} \hat{G}(2) = \begin{pmatrix} 1 & 0 & 0 & -1 & 0 & -1 & -1 & 0 \\ 0 & 1 & 1 & 0 & 1 & 0 & 0 & -1 \\ 1 & 0 & 0 & 1 & 0 & -1 & 1 & 0 \\ 0 & 1 & -1 & 0 & 1 & 0 & 0 & 1 \\ 1 & 0 & 0 & 1 & 0 & 1 & 1 & 0 \\ 0 & 1 & 1 & 0 & -1 & 0 & 0 & 1 \\ 1 & 0 & 0 & 1 & 0 & 1 & -1 & 0 \\ 0 & 1 & -1 & 0 & -1 & 0 & 0 & 1 \end{pmatrix} \quad (9)$$

$$\hat{G}(1,1) = \hat{G}(1) \otimes \hat{G}(1) = \begin{pmatrix} 1 & 0 & 0 & -1 & 0 & 0 & 0 & 0 & 0 & 0 & 0 & -1 & 0 & 0 & 1 \\ 0 & 1 & 1 & 0 & 0 & 0 & 0 & 0 & 0 & 0 & 0 & 0 & -1 & -1 & 0 \\ 1 & 0 & 0 & 1 & 0 & 0 & 0 & 0 & 0 & 0 & 0 & -1 & 0 & 0 & -1 \\ 0 & 1 & -1 & 0 & 0 & 0 & 0 & 0 & 0 & 0 & 0 & 0 & -1 & 1 & 0 \\ 0 & 0 & 0 & 0 & 1 & 0 & 0 & -1 & 1 & 0 & 0 & -1 & 0 & 0 & 0 & 0 \\ 0 & 0 & 0 & 0 & 0 & 1 & 1 & 0 & 0 & 1 & 1 & 0 & 0 & 0 & 0 & 0 \\ 0 & 0 & 0 & 0 & 1 & 0 & 0 & 1 & 1 & 0 & 0 & 1 & 0 & 0 & 0 & 0 \\ 0 & 0 & 0 & 0 & 0 & 1 & -1 & 0 & 0 & 1 & -1 & 0 & 0 & 0 & 0 & 0 \\ 1 & 0 & 0 & -1 & 0 & 0 & 0 & 0 & 0 & 0 & 0 & 1 & 0 & 0 & -1 \\ 0 & 1 & 1 & 0 & 0 & 0 & 0 & 0 & 0 & 0 & 0 & 0 & 1 & 1 & 0 \\ 1 & 0 & 0 & 1 & 0 & 0 & 0 & 0 & 0 & 0 & 0 & 1 & 0 & 0 & 1 \\ 0 & 1 & -1 & 0 & 0 & 0 & 0 & 0 & 0 & 0 & 0 & 0 & 1 & -1 & 0 \\ 0 & 0 & 0 & 0 & 1 & 0 & 0 & -1 & -1 & 0 & 0 & 1 & 0 & 0 & 0 & 0 \\ 0 & 0 & 0 & 0 & 0 & 1 & 1 & 0 & 0 & -1 & -1 & 0 & 0 & 0 & 0 & 0 \\ 0 & 0 & 0 & 0 & 1 & 0 & 0 & 1 & -1 & 0 & 0 & -1 & 0 & 0 & 0 & 0 \\ 0 & 0 & 0 & 0 & 0 & 1 & -1 & 0 & 0 & -1 & 1 & 0 & 0 & 0 & 0 & 0 \end{pmatrix} \quad (10)$$

$$\hat{G}(2,1) = \hat{G}(2) \otimes \hat{G}(1) = \quad (11)$$

```
⎛ 1 0  0 -1  0  0  0  0  0  0  0 -1  0  0  1  0  0  0  0 -1  0  0  1 -1  0  0  1  0  0  0  0 ⎞
⎜ 0 1  1  0  0  0  0  0  0  0  0 -1 -1  0  0  0  0  0  0 -1 -1  0  0 -1 -1  0  0  0  0  0  0 ⎟
⎜ 1 0  0  1  0  0  0  0  0  0  0 -1  0  0 -1  0  0  0  0 -1  0  0 -1 -1  0  0 -1  0  0  0  0 ⎟
⎜ 0 1 -1  0  0  0  0  0  0  0  0 -1  1  0  0  0  0  0  0 -1  1  0  0 -1  1  0  0  0  0  0  0 ⎟
⎜ 0 0  0  0  1  0  0 -1  1  0  0 -1  0  0  0  0  1  0  0 -1  0  0  0  0  0  0  0  0 -1  0  0  1 ⎟
⎜ 0 0  0  0  0  1  1  0  0  1  1  0  0  0  0  0  0  1  1  0  0  0  0  0  0  0  0  0 -1 -1  0 ⎟
⎜ 0 0  0  0  1  0  1  1  0  0  1  0  0  0  0  1  0  0  1  0  0  0  0  0  0  0  0 -1  0  0 -1 ⎟
⎜ 0 0  0  0  0  1 -1  0  0  1 -1  0  0  0  0  0  0  1 -1  0  0  0  0  0  0  0  0  0 -1  1  0 ⎟
⎜ 1 0  0 -1  0  0  0  0  0  0  1  0  0 -1  0  0  0  0 -1  0  0  1  1  0  0 -1  0  0  0  0  0 ⎟
⎜ 0 1  1  0  0  0  0  0  0  0  1  1  0  0  0  0  0  0 -1 -1  0  0  1  1  0  0  0  0  0  0  0 ⎟
⎜ 1 0  0  1  0  0  0  0  0  0  1  0  0  1  0  0  0  0 -1  0  0 -1  1  0  0  1  0  0  0  0  0 ⎟
⎜ 0 1 -1  0  0  0  0  0  0  0  1 -1  0  0  0  0  0  0 -1  1  0  0  1 -1  0  0  0  0  0  0  0 ⎟
⎜ 0 0  0  0  1  0 -1 -1  0  0  1  0  0  0  0  1  0  0 -1  0  0  0  0  0  0  0  0  0  1  0  0 -1 ⎟
⎜ 0 0  0  0  0  1  1  0  0 -1 -1  0  0  0  0  0  0  1  1  0  0  0  0  0  0  0  0  0  1  1  0 ⎟
⎜ 0 0  0  0  1  0  1 -1  0  0 -1  0  0  0  0  1  0  0  1  0  0  0  0  0  0  0  0  0  1  0  0  1 ⎟
⎜ 0 0  0  0  0  1 -1  0 -1  1  0  0  0  0  0  0  1 -1  0  0  0  0  0  0  0  0  0  0  1 -1  0 ⎟
⎜ 1 0  0 -1  0  0  0  0  0  0  0 -1  0  0  1  0  0  0  0  1  0  0 -1  1  0  0 -1  0  0  0  0 ⎟
⎜ 0 1  1  0  0  0  0  0  0  0  0 -1 -1  0  0  0  0  0  0  1  1  0  0  1  1  0  0  0  0  0  0 ⎟
⎜ 1 0  0  1  0  0  0  0  0  0  0 -1  0  0 -1  0  0  0  0  1  0  0  1  1  0  0  1  0  0  0  0 ⎟
⎜ 0 1 -1  0  0  0  0  0  0  0  0 -1  1  0  0  0  0  0  0  1 -1  0  0  1 -1  0  0  0  0  0  0 ⎟
⎜ 0 0  0  0  1  0 -1  1  0  0 -1  0  0  0  0 -1  0  0  1  0  0  0  0  0  0  0  0  0  1  0  0 -1 ⎟
⎜ 0 0  0  0  0  1  1  0  1  1  0  0  0  0  0 -1 -1  0  0  0  0  0  0  0  0  0  0  0  1  1  0 ⎟
⎜ 0 0  0  0  1  0  1  1  0  0  1  0  0  0  0 -1  0  0 -1  0  0  0  0  0  0  0  0  0  1  0  0  1 ⎟
⎜ 0 0  0  0  0  1 -1  0  1 -1  0  0  0  0  0 -1  1  0  0  0  0  0  0  0  0  0  0  0  1 -1  0 ⎟
⎜ 1 0  0 -1  0  0  0  0  0  0  1  0  0 -1  0  0  0  0  1  0  0 -1 -1  0  0  1  0  0  0  0  0 ⎟
⎜ 0 1  1  0  0  0  0  0  0  0  1  1  0  0  0  0  0  0  1  1  0  0 -1 -1  0  0  0  0  0  0  0 ⎟
⎜ 1 0  0  1  0  0  0  0  0  0  1  0  0  1  0  0  0  0  1 -1  0  0 -1  0  0  0  0  0  0  0  0 ⎟
⎜ 0 1 -1  0  0  0  0  0  0  0  1 -1  0  0  0  0  0  0  1 -1  0  0 -1  1  0  0  0  0  0  0  0 ⎟
⎜ 0 0  0  0  1  0 -1 -1  0  0  1  0  0  0  0 -1  0  0  1  0  0  0  0  0  0  0  0  0 -1  0  0  1 ⎟
⎜ 0 0  0  0  0  1  1  0  0 -1 -1  0  0  0  0 -1 -1  0  0  0  0  0  0  0  0  0  0  0 -1 -1  0 ⎟
⎜ 0 0  0  0  1  0  1 -1  0  0 -1  0  0  0  0 -1  0  0 -1  0  0  0  0  0  0  0  0  0 -1  0  0 -1 ⎟
⎝ 0 0  0  0  0  1 -1  0 -1  1  0  0  0  0  0 -1  1  0  0  0  0  0  0  0  0  0  0  0 -1  1  0 ⎠
```

The present invention discloses the following G²FT NMR experiments: (i) G²FT (5,3)D [HN{N,CO}{C$^{\alpha\beta}$C$^{\alpha}$}]NMR; (ii) G²FT (5,3)D [HN{NCO}{C$^{\alpha\beta}$C$^{\alpha}$}] NMR; (iii) G²FT (5,3)D [HN{NC$^{\alpha}$}{C$^{\alpha\beta}$C$^{\alpha}$}]NMR; (iv) G²FT (5,3)D [HN{N(CO)C$^{\alpha}$}{C$^{\alpha\beta}$C$^{\alpha}$}]NMR; (v) G²FT (5,3)D [HN{N,CO}{C$^{\alpha}$H$^{\alpha}$}]NMR; (vi) G²FT (5,3)D [{H$^{\alpha}$C$^{\alpha}$}{CON}HN]NMR; and (vii) G²FT (6,3)D [{H$^{\alpha\beta}$C$^{\alpha\beta}$C$^{\alpha}$}{CON}{HN}] NMR. Experiments (i) and (iii), as well as (ii) and (iv), can form a pair to sequentially assign backbone $^{13}$C$^{\alpha}$ and sidechain $^{13}$C$^{\beta}$ resonances in proteins. Experiment (v) and (vi) can form a pair to sequentially assign backbone $^{13}$C$^{\alpha}$ and $^{1}$H$^{\alpha}$ resonances. Using these chemical shifts, experiment (vii) provides information on $^{1}$H$^{\alpha/\beta}$ chemical shifts. The curly brackets group jointly sampled shifts represented by underlined letters (Kim et al., *J. Am. Chem. Soc.* 125:1385-1393 (2003), which is hereby incorporated by reference in its entirety); in (5,3)D HN{N,CO}{C$^{\alpha\beta}$C$^{\alpha}$} and (5,3)D HN{N,CO}{C$^{\alpha}$H$^{\alpha}$}, the comma indicates a bifurcated $^{13}$C'$_{i-1}$←$^{15}$N$_{i}$→$^{13}$C$^{\alpha}_{i}$ transfer (Szyperski et al., *J. Magn. Reson.* B 109:229-233 (1995); Konrat et al., *J. Biomol. NMR* 15:309-313 (1999); Szyperski et al., *J. Am. Chem. Soc.* 118:8147-8148 (1996); Szyperski et al., *J. Biomol. NMR* 11:387-405 (1998), which are hereby incorporated by reference in their entirety).

Thus, the present invention relates to a method of conducting a (5,3) dimensional (D) [HN{N,CO}{C$^{\alpha\beta}$C$^{\alpha}$}] G-matrix Fourier transformation (GFT) nuclear magnetic resonance (NMR) experiment. The method involves providing a sample, where the sample is a protein molecule having two consecutive amino acid residues, i−1 and i, and the chemical shift values for the following nuclei are measured: (1) α- and β-carbons of amino acid residues i and i−1, $^{13}$C$^{\alpha/\beta}_{i/i-1}$; (2) a polypeptide backbone amide nitrogen of amino acid residue i, $^{15}$N$_i$; (3) a polypeptide backbone carbonyl carbon of amino acid residue i−1, $^{13}$C'$_{i-1}$; and (4) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^{13}C^{\alpha/\beta}_{i/i-1}$ and $^{13}C^\alpha_{i/i-1}$, is selected. Next, the first set of 2 indirect chemical shift evolution periods is jointly sampled in a first indirect time domain dimension, $t_1(^{13}C^{\alpha/\beta}_{i/i-1}, ^{13}C^\alpha_{i/i-1})$. Then, a second set of 2 indirect chemical shift evolution periods of the 5D FT NMR experiment, $^{15}N_i$ and $^{13}C'_{i-1}$, is selected. Next, the second set of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^{13}C^{\alpha/\beta}, ^{13}C^\alpha)$, giving rise to 2 chemical shift doublet components in a second frequency domain dimension, $\omega_2(^{15}N, ^{13}C')$ thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components. One specific embodiment of this method, (5,3)D HN{N,CO}{$C^{\alpha\beta}C^\alpha$}, involves applying radiofrequency pulses for a 5D FT NMR experiment according to the scheme shown in FIG. 5.

Another aspect of the present invention relates to a method of conducting a (5,3) dimensional (D) [HN{NCO}{$C^{\alpha\beta}C^\alpha$}] G-matrix Fourier transformation (GFT) nuclear magnetic resonance (NMR) experiment. The method involves providing a sample, where the sample is a protein molecule having two consecutive amino acid residues, i−1 and i, and the chemical shift values for the following nuclei are measured: (1) α- and β-carbons of amino acid residue i−1, $^{13}C^{\alpha/\beta}_{i-1}$; (2) a polypeptide backbone amide nitrogen of amino acid residue i, $^{15}N_i$; (3) a polypeptide backbone carbonyl carbon of amino acid residue i−1, $^{13}C'_{i-1}$; and (4) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^{13}C^{\alpha/\beta}_{i-1}$ and $^{13}C^\alpha_{i-1}$, is selected. Next, the first set of 2 indirect chemical shift evolution periods is jointly sampled in a first indirect time domain dimension, $t_1(^{13}C^{\alpha/\beta}_{i-1}, ^{13}C^\alpha_{i-1})$. Then, a second set of 2 indirect chemical shift evolution periods of the 5D FT NMR experiment, $^{15}N_i$ and $^{13}C'_{i-1}$, is selected. Next, the second set of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^{13}C^{\alpha/\beta}, ^{13}C^\alpha)$, giving rise to 2 chemical shift doublet components in a second frequency domain dimension, $\omega_2(^{15}N, ^{13}C')$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components. One specific embodiment of this method, (5,3)D HN{NCO}{$C^{\alpha\beta}C^\alpha$}, involves applying radiofrequency pulses for a 5D FT NMR experiment according to the scheme shown in FIG. 6.

Another aspect of the present invention relates to a method of conducting a (5,3) dimensional (D) [HN{$NC^\alpha$}{$C^{\alpha\beta}C^\alpha$}] G-matrix Fourier transformation (GFT) nuclear magnetic resonance (NMR) experiment. The method involves providing a sample, where the sample is a protein molecule having two consecutive amino acid residues, i−1 and i, and chemical shift values for the following nuclei are measured: (1) α- and β-carbons of amino acid residue i and i−1, $^{13}C^{\alpha/\beta}_{i/i-1}$; (2) a polypeptide backbone amide nitrogen of amino acid residue i, $^{15}N_i$; and (3) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^{13}C^{\alpha/\beta}_{i/i-1}$ and $^{13}C^\alpha_{i/i-1}$, is selected. Next, the first set of 2 indirect chemical shift evolution periods is jointly sampled in a first indirect time domain dimension, $t_1(^{13}C^{\alpha/\beta}_{i/i-1}, ^{13}C^\alpha_{i/i-1})$. Then, a second set of 2 indirect chemical shift evolution periods of the 5D FT NMR experiment, $^{15}N_i$ and $^{13}C^\alpha_{i/i-1}$, is selected. Next, the second set of 2 indirect chemical shift evolution periods is jointly sampled in a second indirect time domain dimension, $t_2(^{15}N_i, ^{13}C^\alpha_{i/i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^{13}C^{\alpha/\beta}, ^{13}C^\alpha)$, giving rise to 2 chemical shift doublet components in a second frequency domain dimension, $\omega_2(^{15}N, ^{13}C^\alpha)$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components. One specific embodiment of this method, (5,3)D HN{$NC^\alpha$}{$C^{\alpha\beta}C^\alpha$}, involves applying radiofrequency pulses for a 5D FT NMR experiment according to the scheme shown in FIG. 13.

Another aspect of the present invention relates to a method of conducting a (5,3) dimensional (D) [HN{N(CO)$C^\alpha$}{$C^{\alpha\beta}C^\alpha$}] G-matrix Fourier transformation (GFT) nuclear magnetic resonance (NMR) experiment. The method involves providing a sample, where the sample is a protein molecule having two consecutive amino acid residues, i−1 and i, and the chemical shift values for the following nuclei are measured: (1) α- and β-carbons of amino acid residue i−1, $^{13}C^{\alpha/\beta}_{i-1}$; (2) a polypeptide backbone amide nitrogen of amino acid residue i, $^{15}N_i$; and (3) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^{13}C^{\alpha/\beta}_{i-1}$ and $^{13}C^\alpha_{i-1}$, is selected. Next, the first set of 2 indirect chemical shift evolution periods is jointly sampled in a first indirect time domain dimension, $t_1(^{13}C^{\alpha/\beta}_{i-1}, ^{13}C^\alpha_{i-1})$. Then, a second set of 2 indirect chemical shift evolution periods of the 5D FT NMR experiment, $^{15}N_i$ and $^{13}C^\alpha_{i-1}$, is selected. Next, the second set of 2 indirect chemical shift evolution periods is jointly sampled in a second indirect time domain dimension, $t_2(^{15}N_i, ^{13}C^\alpha_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^{13}C^{\alpha/\beta}, ^{13}C^\alpha)$, giving rise to 2 chemical shift doublet components in a second frequency domain dimension, $\omega_2(^{15}N, ^{13}C^\alpha)$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components. One specific embodiment of this method, (5,3)D HN{N(CO)C$^\alpha$}{C$^{\alpha\beta}$C$^\alpha$}, involves applying radiofrequency pulses for a 5D FT NMR experiment according to the scheme shown in FIG. 14.

Another aspect of the present invention relates to a method of conducting a (5,3) dimensional (D) [HN{N,CO}{C$^\alpha$H$^\alpha$}] G-matrix Fourier transformation (GFT) nuclear magnetic resonance (NMR) experiment. The method involves providing a sample, where the sample is a protein molecule having two consecutive amino acid residues, i−1 and i, and the chemical shift values for the following nuclei are measured: (1) α-carbon of amino acid residues i and i−1, $^{13}C^\alpha_{i/i-1}$; (2) α-proton of amino acid residues i and i−1, $^1H^\alpha_{i/i-1}$; (3) a polypeptide backbone amide nitrogen of amino acid residue i, $^{15}N_i$; (4) a polypeptide backbone carbonyl carbon of amino acid residue i−1, $^{13}C'_{i-1}$; and (5) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^1H^\alpha_{i/i-1}$ and $^{13}C^\alpha_{i/i-1}$, is selected. Next, the first set of 2 indirect chemical shift evolution periods is jointly sampled in a first indirect time domain dimension, $t_1(^1H^\alpha_{i/i-1}, ^{13}C^\alpha_{i/i-1})$. Then, a second set of 2 indirect chemical shift evolution periods of the 5D FT NMR experiment, $^{15}N_i$ and $^{13}C'_{i-1}$, is selected. Next, the second set of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^1H^\alpha, ^{13}C^\alpha)$, giving rise to 2 chemical shift doublet components in a second frequency domain dimension, $\omega_2(^{15}N, ^{13}C')$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components. One specific embodiment of this method, (5,3)D {H$^\alpha$C$^\alpha$}{CON}HN, involves applying radiofrequency pulses for a 5D FT NMR experiment according to the scheme shown in FIG. 18.

Another aspect of the present invention relates to a method of conducting a (5,3) dimensional (D) [{H$^\alpha$C$^\alpha$}{CON}HN] G-matrix Fourier transformation (GFT) nuclear magnetic resonance (NMR) experiment. The method involves providing a sample, where the sample is a protein molecule having two consecutive amino acid residues, i−1 and i, and chemical shift values for the following nuclei are measured: (1) α-carbon of amino acid residue i−1, $^{13}C^\alpha_{i-1}$; (2) α-proton of amino acid residue i−1, $^1H^\alpha_{i-1}$; (3) a polypeptide backbone amide nitrogen of amino acid residue i, $^{15}N_i$; (4) a polypeptide backbone carbonyl carbon of amino acid residue i−1, $^{13}C'_{i-1}$; and (5) a polypeptide backbone amide proton of amino acid residue i, $^1H^N_i$. Next, radiofrequency pulses for a 5D FT NMR experiment are applied to the sample. Then, a first set of 2 indirect chemical shift evolution periods of the 5D FT NMR experiment, $^1H^\alpha_{i-1}$ and $^{13}C^\alpha_{i-1}$, is selected. Next, the first set of 2 indirect chemical shift evolution periods is jointly sampled in a first indirect time domain dimension, $t_1(^1H^\alpha_{i-1}, ^{13}C^\alpha_{i-1})$. Then, a second set of 2 indirect chemical shift evolution periods of the 5D FT NMR experiment, $^{15}N_i$ and $^{13}C'_{i-1}$, is selected. Next, the second set of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 4 components resulting from each of 2 chemical shift doublet components in a first frequency domain dimension, $\omega_1(^1H^\alpha, ^{13}C^\alpha)$, giving rise to 2 chemical shift doublet components in a second frequency domain dimension, $\omega_2(^{15}N, ^{13}C')$, thereby enabling phase-sensitive sampling of all jointly sampled 4 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components. One specific embodiment of this method, (5,3)D {H$^\alpha$C$^\alpha$}{CON}HN, involves applying radiofrequency pulses for a 5D FT NMR experiment according to the scheme shown in FIG. 19.

For the above six G$^2$FT NMR experiments, the step of transforming the 3D basic NMR spectra into 3D phase-sensitively edited basic NMR spectra can be carried out by applying a G-matrix defined as $$\hat{G}(1) = \begin{bmatrix} 1 & i \\ 1 & -i \end{bmatrix} \otimes [1 \ i],$$

where $i=\sqrt{-1}$, along the first and second indirect time domain dimensions under conditions effective to edit the chemical shift multiplet components in the time domain. Alternatively, the transforming can be carried out by applying a F-matrix defined as $$\hat{F}(1) = \begin{bmatrix} 1 & 1 \\ 1 & -1 \end{bmatrix}$$

along the first and second frequency domain dimensions under conditions effective to edit the chemical shift multiplet components in the frequency domain.

Another aspect of the present invention relates to a method of conducting a (6,3) dimensional (D) [{H$^{\alpha\beta}$C$^{\alpha\beta}$C$^\alpha$}{CON}HN] G-matrix Fourier transformation (GFT) nuclear magnetic resonance (NMR) experiment. The method involves providing a sample, where the sample is a protein molecule having two consecutive amino acid residues, i−1 and i, and the chemical shift values for the following nuclei are measured: (1) α- and β-carbons of amino acid residue i−1, $^{13}C^{\alpha/\beta}_{i-1}$; (2) α- and β-protons of amino acid residue i−1, $^1H^{\alpha/\beta}_{i-1}$; (3) a polypeptide backbone carbonyl carbon of amino acid residue i−1, $^{13}C'_{i-1}$; (4) a polypeptide backbone amide nitrogen of amino acid residue i, $^{15}N_i$; and (5) a polypeptide backbone amide proton of amino acid residue i, $^{1}H^{N}_i$. Next, radiofrequency pulses for a 6D FT NMR experiment are applied to the sample. Then, a first group of 3 indirect chemical shift evolution periods of the 6D FT NMR experiment, $^{1}H^{\alpha/\beta}_{i-1}$, $^{13}C^{\alpha/\beta}_{i-1}$ and $^{13}C^{\alpha}_{i-1}$, is selected. Next, the first group of 3 indirect chemical shift evolution periods is jointly sampled in a first indirect time domain dimension, $t_1(^{1}H^{\alpha/\beta}_{i-1}, ^{13}C^{\alpha/\beta}_{i-1}, ^{13}C^{\alpha}_{i-1})$. Then, a second group of 2 indirect chemical shift evolution periods of the 6D FT NMR experiment, $^{15}N_i$ and $^{13}C'_{i-1}$, is selected. Next, the second group of 2 indirect chemical shift evolution periods is jointly sampled in a second indirect time domain dimension, $t_2(^{15}N_i, ^{13}C'_{i-1})$. Then, NMR signals detected in a direct dimension are independently cosine and sine modulated to generate 3D basic NMR spectra containing frequency domain signals having a chemical shift multiplet with 8 components resulting from each of 4 chemical shift doublet components in a first frequency domain dimension, $\Omega_1(^{13}C^{\alpha/\beta}, ^{13}C^{\alpha})$, giving rise to 2 chemical shift doublet components in a second frequency domain dimension, $\omega_2(^{15}N, ^{13}C')$, thereby enabling phase-sensitive sampling of all jointly sampled 5 indirect chemical shift evolution periods. Finally, the 3D basic NMR spectra are transformed into 3D phase-sensitively edited basic NMR spectra, where the 8 chemical shift multiplet components of the 3D basic NMR spectra are edited to yield 3D phase-sensitively edited basic NMR spectra having individual chemical shift multiplet components. One specific embodiment of this method, (6,3)D $\{H^{\alpha\beta}C^{\alpha\beta}C^{\alpha}\}\{CON\}HN$, involves applying radiofrequency pulses for a 6D FT NMR experiment according to the scheme shown in FIG. 24.

For the above (6,3)D [$\{H^{\alpha\beta}C^{\alpha\beta}C^{\alpha}\}\{CON\}HN$] G²FT NMR experiment, the step of transforming the 3D basic NMR spectra into 3D phase-sensitively edited basic NMR spectra can be carried out by applying a G-matrix defined as $$\hat{G}(2) = \begin{bmatrix} 1 & i \\ 1 & -i \end{bmatrix} \otimes \begin{bmatrix} 1 & i \\ 1 & -i \end{bmatrix} \otimes [1 \; i],$$

where $i=\sqrt{-1}$, along the first indirect time domain dimension and applying a G-matrix defined as $$\hat{G}(1) = \begin{bmatrix} 1 & i \\ 1 & -i \end{bmatrix} \otimes [1 \; i]$$

along the second indirect time domain dimension under conditions effective to edit the chemical shift multiplet components in the time domain. Alternatively, the transforming can be carried out by applying a F-matrix defined as $\hat{F}(2)=\hat{F}(1)\otimes\hat{F}(1)$, where $$\hat{F}(1) = \begin{bmatrix} 1 & 1 \\ 1 & -1 \end{bmatrix},$$

along the first frequency domain dimension and applying a F-matrix defined as $$\hat{F}(1) = \begin{bmatrix} 1 & 1 \\ 1 & -1 \end{bmatrix}$$

along the second frequency domain dimension under conditions effective to edit the chemical shift multiplet components in the frequency domain.

With the information of $^{1}H^{\alpha\beta}$ and $^{13}C^{\alpha\beta}$ chemical shifts obtained in the above G²FT NMR experiments, a (5,3)D [HC(C)C—CH] GFT NMR experiment can be conducted to assign the more peripheral spins of the aliphatic side chain of a given amino acid residue, where the hyphen represents the fact that $^{13}C^{coupled}$ is frequency labeled twice while, for nuclei in parentheses, chemical shift evolution is omitted.

Thus, yet another aspect of the present invention relates to a method of conducting a (5,3) dimensional (D) [HC(C)C—CH] G-matrix Fourier transformation (GFT) nuclear magnetic resonance (NMR) experiment. The method involves providing a sample, where the sample is a protein molecule and the chemical shift values for the following nuclei are measured: (1) a proton, $^{1}H$; (2) a carbon coupled to $^{1}H$, $^{13}C$; (3) a carbon coupled, via another carbon, to $^{13}C$, $^{13}C^{coupled}$; and (4) a proton coupled to $^{13}C^{coupled}$, $^{1}H^{coupled}$, where the chemical shift of $^{13}C^{coupled}$ provides signal dispersion in an indirect dimension. Next, radiofrequency pulses for a 5D FT NMR experiment are applied to the sample. Then, 3 indirect chemical shift evolution periods of the 5D FT NMR experiment, $^{1}H$, $^{13}C$, and $^{13}C^{coupled}$, are selected. Next, the 3 indirect chemical shift evolution periods are jointly sampled in an indirect time domain dimension, $t_1(^{1}H, ^{13}C, ^{13}C^{coupled})$. Then, NMR signals detected in a direct dimension are independently cosine and sine modulated to generate 3D basic NMR spectra containing frequency domain signals with 4 chemical shift multiplet components, thereby enabling phase-sensitive sampling of all jointly sampled 3 indirect chemical shift evolution periods. Finally, the 3D basic NMR spectra are transformed into 3D phase-sensitively edited basic NMR spectra, where the 4 chemical shift multiplet components of the 3D basic NMR spectra are edited to yield 3D phase-sensitively edited basic NMR spectra having individual chemical shift multiplet components. One specific embodiment of this method, (5,3)D HC(C)C—CH, involves applying radiofrequency pulses for a 5D FT NMR experiment according to the scheme shown in FIG. 27.

In another embodiment, the method of conducting a (5,3)D [HC(C)C—CH] GFT NMR experiment can further involve repeating once the steps of jointly sampling, independently cosine and sine modulating, and transforming, where the jointly sampling involves jointly sampling 2 indirect chemical shift evolution periods out of the 3 indirect chemical shift evolution periods, under conditions effective to generate a first order central peak NMR spectrum.

In another embodiment for the above method of conducting a (5,3)D [HC(C)C—CH] GFT NMR experiment, the step of transforming the 3D basic NMR spectra into 3D phase-sensitively edited basic NMR spectra can be carried out by applying a G-matrix defined as $$\hat{G}(2) = \begin{bmatrix} 1 & i \\ 1 & -i \end{bmatrix} \otimes \begin{bmatrix} 1 & i \\ 1 & -i \end{bmatrix} \otimes [1i],$$

where $i=\sqrt{-1}$, under conditions effective to edit the chemical shift multiplet components in a time domain. Alternatively, the transforming can be carried out by applying a F-matrix defined as $\hat{F}(2)=\hat{F}(1)\otimes\hat{F}(1)$, where $$\hat{F}(1) = \begin{bmatrix} 1 & 1 \\ 1 & -1 \end{bmatrix},$$

under conditions effective to edit the chemical shift multiplet components in a frequency domain.

L-GFT NMR of Proteins with Aromatic Rings

The present application discloses aromatic L-GFT and L-GFT-TROSY (4,3)D [HCCH] (as well as (4,3)D [HCCH] and (4,3)D [HCCH]). Sensitivity is maximized by using (i) newly introduced longitudinal relaxation (L-)optimization (Pervushin et al., *J. Am. Chem. Soc.* 124:12898-12902 (2002), which is hereby incorporated by reference in its entirety) for aromatic protons ($^1H^{aromatic}$), (ii) pulsed field gradient (PFG) selection of coherences with preservation of equivalent pathways (PEP) (Cavanagh et al., *Protein NMR Spectroscopy: Principles and Practice* Academic Press: San Diego (1996); Kay et al., *J. Am. Chem. Soc.* 114:10663-10665 (1992), which are hereby incorporated by reference in their entirety), (iii) (semi-) constant time (ct) frequency labeling (Cavanagh et al., *Protein NMR Spectroscopy: Principles and Practice* Academic Press: San Diego (1996), which is hereby incorporated by reference in its entirety), and (iv) employment of transverse relaxation optimized spectroscopy (TROSY; Pervushin et al., *Proc. Natl. Acad. Sci. USA* 94:12366-12371 (1997); Pervushin et al., *J. Am. Chem. Soc.* 120:6394-6400 (1998); Meissner et al., *J. Magn. Reson.* 139:447-450 (1999), which are hereby incorporated by reference in their entirety). Rapid sampling is accomplished by use of G-matrix FT (GFT) NMR (Kim et al., *J. Am. Chem. Soc.* 125:1385-1393 (2003), which is hereby incorporated by reference in its entirety) combined (Atreya et al., *Proc. Natl. Acad. Sci. USA* 101:9642-9647 (2004); Atreya et al., *Method Enzymol.* 394:78-108 (2005), which are hereby incorporated by reference in their entirety) with L-optimization, which thus serves to enhance sensitivity (Pervushin et al., *J. Am. Chem. Soc.* 124:12898-12902 (2002), which is hereby incorporated by reference in its entirety) and/or shorten relaxation delays (Atreya et al., *Proc. Natl. Acad. Sci. USA* 101:9642-9647 (2004), which is hereby incorporated by reference in its entirety). $^1H^{aromatic}$ L-optimization is feasible since (i) $^1H^{aromatic}/^1H_2O$ and $^1H^{aliphatic}$ chemical shift ranges do not overlap, which enables selective "flipping" of $^1H^{aliphatic}/^1H_2O$ magnetization while $^1H^{aromatic}$ magnetization is along z, and (ii) a large number of dipolar $^1H^{aromatic}$—$^1H^{aliphatic}$ and Tyr $^1H^{aromatic}$—$^1H^{hydroxyl}$ interactions can increase $R_1$ of $^1H^{aromatic}$.

Thus, the present invention relates to a method of conducting a longitudinal aromatic proton relaxation optimized (4,3) dimensional (D) [HCCH] G-matrix Fourier transformation (GFT) nuclear magnetic resonance (NMR) experiment. The method involves providing a sample, where the sample is a protein molecule and the chemical shift values for the following nuclei are measured: (1) an aromatic proton, $^1H$; (2) an aromatic carbon coupled to $^1H$, $^{13}C$; (3) a carbon coupled to $^{13}C$, $^{13}C^{coupled}$; and (4) a proton coupled to $^{13}C^{coupled}$, $^1H^{coupled}$. Next, radiofrequency pulses for a 4D FT NMR experiment are applied to the sample under conditions effective to allow longitudinal relaxation optimization of the aromatic protons. Then, 2 indirect chemical shift evolution periods of the 4D FT NMR experiment, $^1H$ and $^{13}C$, are selected. Next, the 2 indirect chemical shift evolution periods are jointly sampled in an indirect time domain dimension, $t_1(^1H, ^{13}C)$. Then, NMR signals detected in a direct dimension are independently cosine and sine modulated to generate 3D basic NMR spectra containing frequency domain signals with 2 chemical shift doublet components, thereby enabling phase-sensitive sampling of the jointly sampled 2 indirect chemical shift evolution periods. Finally, the 3D basic NMR spectra are transformed into 3D phase-sensitively edited basic NMR spectra, where the 2 chemical shift doublet components of the 3D basic NMR spectra are edited to yield 3D phase-sensitively edited basic NMR spectra having individual chemical shift doublet components. One specific embodiment of this method, (4,3)D HCCH, involves applying radiofrequency pulses for a 4D FT NMR experiment according to the scheme shown in FIG. 32.

Another aspect of the present invention relates to a method of conducting a longitudinal aromatic proton relaxation optimized (4,3) dimensional (D) [HCCH] G-matrix Fourier transformation (GFT) nuclear magnetic resonance (NMR) experiment. The method involves providing a sample, where the sample is a protein molecule and the chemical shift values for the following nuclei are measured: (1) an aromatic proton, $^1H$; (2) an aromatic carbon coupled to $^1H$, $^{13}C$; (3) a carbon coupled to $^{13}C$, $^{13}C^{coupled}$; and (4) a proton coupled to $^{13}C^{coupled}$, $^1H^{coupled}$. Next, radiofrequency pulses for a 4D FT NMR experiment are applied to the sample under conditions effective to allow longitudinal relaxation optimization of the aromatic protons. Then, 2 indirect chemical shift evolution periods of the 4D FT NMR experiment, $^{13}C$ and $^{13}C^{coupled}$, are selected. Next, the 2 indirect chemical shift evolution periods are jointly sampled in an indirect time domain dimension, $t_1(^{13}C, ^{13}C^{coupled})$. Then, NMR signals detected in a direct dimension are independently cosine and sine modulated to generate 3D basic NMR spectra containing frequency domain signals with 2 chemical shift doublet components, thereby enabling phase-sensitive sampling of the jointly sampled 2 indirect chemical shift evolution periods. Finally, the 3D basic NMR spectra are transformed into 3D phase-sensitively edited basic NMR spectra, where the 2 chemical shift doublet components of the 3D basic NMR spectra are edited to yield 3D phase-sensitively edited basic NMR spectra having individual chemical shift doublet components.

Another aspect of the present invention relates to a method of conducting a longitudinal aromatic proton relaxation optimized (4,3) dimensional (D) [HCCH] G-matrix Fourier transformation (GFT) nuclear magnetic resonance (NMR) experiment. The method involves providing a sample, where the sample is a protein molecule and the chemical shift values for the following nuclei are measured: (1) an aromatic proton, $^1H$; (2) an aromatic carbon coupled to $^1H$, $^{13}C$; (3) a carbon coupled to $^{13}C$, $^{13}C^{coupled}$; and (4) a proton coupled to $^{13}C^{coupled}$, $^1H^{coupled}$. Next, radiofrequency pulses for a 4D FT NMR experiment are applied to the sample under conditions effective to allow longitudinal relaxation optimization of the aromatic protons. Then, 2 indirect chemical shift evolution periods of the 4D FT NMR experiment, $^1H$ and $^{13}C^{coupled}$, are selected. Next, the 2 indirect chemical shift evolution periods are jointly sampled in an indirect time domain dimension, $t_1(^1H, ^{13}C^{coupled})$. Then, NMR signals detected in a direct dimension are independently cosine and sine modulated to generate 3D basic NMR spectra containing frequency domain signals with 2 chemical shift doublet components, thereby enabling phase-sensitive sampling of the jointly sampled 2 indirect chemical shift evolution periods. Finally, the 3D basic NMR spectra are transformed into 3D phase-sensitively edited basic NMR spectra, where the 2 chemical shift doublet components of the 3D basic NMR spectra are edited to yield 3D phase-sensitively edited basic NMR spectra having individual chemical shift doublet components.

For the above three L-GFT (4,3)D NMR experiments, the step of transforming the 3D basic NMR spectra into 3D phase-sensitively edited basic NMR spectra can be carried out by applying a G-matrix defined as $$\hat{G}(1) = \begin{bmatrix} 1 & i \\ 1 & -i \end{bmatrix} \otimes [1\,i],$$

where $i=\sqrt{-1}$, under conditions effective to edit the chemical shift doublet components in a time domain. Alternatively, the transforming can be carried out by applying a F-matrix defined as $$\hat{F}(1) = \begin{bmatrix} 1 & 1 \\ 1 & -1 \end{bmatrix},$$

under conditions effective to edit the chemical shift doublet components in a frequency domain.

GFT NOESY NMR Experiments

The present application discloses a through-bond GFT NMR based resonance assignment protocol (Atreya et al., Proc. Natl. Acad. Sci. USA 101:9642-9647 (2004); Kim et al., J. Am. Chem. Soc. 125:1385-1393 (2003); Kim et al., J. Biomol. NMR 28:117-130 (2004), which are hereby incorporated by reference in their entirety) used in conjunction with a newly implemented NOESY experiment combining simultaneous (Farmer et al., J. Biomol. NMR 4:673-687 (1994); Pascal et al., J. Magn. Reson. 103:197-201 (1994); Jerala et al., J. Magn. Reson. B108:294-298 (1995); Uhrin et al., J. Biomol. NMR 18:253-259 (2000); Xia et al., J. Biomol. NMR 27:193-203 (2003), which are hereby incorporated by reference in their entirety) and GFT (Atreya et al., Proc. Natl. Acad. Sci. USA 101:9642-9647 (2004); Kim et al., J. Am. Chem. Soc. 125:1385-1393 (2003); Kim et al., J. Biomol. NMR 28:117-130 (2004), which are hereby incorporated by reference in their entirety) NMR data acquisition. One of the experiments is named "GFT (4,3)D [$HC^{ali}$/HN]-NOESY-[$CH^{ali}$/NH]", where the underlined letters denote nuclei for which the shifts are jointly sampled. The NOESY experiment encodes in two subspectra, the information of 4D $^{15}N/^{15}N$-, $^{13}C^{alipahtic}/^{15}N$-, and $^{13}C^{aliphatic}/^{13}C^{aliphatic}$-resolved [$^1H$, $^1H$]-NOESY. Each of the subspectra contain one component of a chemical shift doublet manifested along the GFT dimension at $\omega_1:\Omega(^1H)\pm\Omega(X)$ [$X=^{15}N, ^{13}C^{aliphatic}$]. A third subspectrum, containing peaks located at the centers of the shift doublets at $\omega_1:\Omega(^1H)$, encodes the information of 3D $^{15}N$- and $^{13}C^{aliphatic}$-resolved [$^1H$, $^1H$]-NOESY. Preferably, central peaks are recorded in simultaneous 3D $^{15}N/^{13}C^{aliphatic}/^{13}C^{aromatic}$-resolved [$^1H$, $^1H$]-NOESY (named here for brevity 3D [H]-NOESY-[$CH^{ali}/CH^{aro}$/NH]); this allows one to detect NOEs on aromatic protons along with the desired central peaks.

The impact of the simultaneous GFT NOESY data collection strategy is described herein in detail, since it is a priori not straightforward to identify sampling-limited (Szyperski et al., Proc. Natl. Acad. Sci. USA. 99:8009-8014 (2002), which is hereby incorporated by reference in its entirety) NOESY data acquisition. Longer measurement times and the resulting increased S/N ratios lead to detection of additional NOEs corresponding to longer $^1H$—$^1H$ distances. This may have significant impact on the precision of the final NMR structure, and the sole analysis of S/N ratio distributions (for example, of intraresidue and sequential NOEs) is not sufficient. Hence, one has to assess for (4,3)D NOESY: (i) the relative sensitivity of chemical shift doublet versus central peak detection, (ii) the increase in the fraction of central peak NOEs that can be assigned directly based on chemical shift data when having the additional information encoded in shift doublets, (iii) its impact on precision and accuracy of initial NMR structures obtained based on chemical shift data only, (iv) its value relative to computational techniques for generating initial structures from central peaks detected in 3D NOESY without reference to an initial structure, and (v) the number of additionally resolved and assigned NOEs allowing one to obtain a well-refined NMR structure. These criteria are central for establishing the role of (4,3)D [$HC^{ali}$/HN]-NOESY-[$CH^{ali}$/NH] for efficient NOE-based structure determination.

Thus, the present invention relates to a method of conducting a (3,2) dimensional (D) <[$^1H^XX$]-nuclear Overhauser enhancement spectroscopy (NOESY)-[$^1H$]> G-matrix Fourier transformation (GFT) nuclear magnetic resonance (NMR) experiment. The method involves providing a sample, where the sample is a protein molecule and the chemical shift values for the following nuclei are measured: (1) a proton, $^1H$; (2) X, wherein X is an aliphatic carbon, $^{13}C^{ali}$, an aromatic carbon, $^{13}C^{aro}$, or a nitrogen, $^{15}N$; and (3) a proton bound to X, $1H^X$. Next, radiofrequency pulses for a first 3D NOESY FT NMR experiment are applied to the sample. Then, a first set of 2 indirect chemical shift evolution periods of the 3D NOESY FT NMR experiment, $^1H^X$ and X, is jointly sampled in an indirect time domain dimension, $t_1(^1H^X,X)$. Next, NMR signals detected in a direct dimension are independently cosine and sine modulated to generate 2D basic NMR spectra containing frequency domain signals with 2 chemical shift doublet components, thereby enabling phase-sensitive sampling of the jointly sampled first set of 2 indirect chemical shift evolution periods. Finally, the 2D basic NMR spectra are transformed into 2D phase-sensitively edited basic NMR spectra, where the 2 chemical shift doublet components of the 2D basic NMR spectra are edited to yield 2D phase-sensitively edited basic NMR spectra having individual chemical shift doublet components.

In another embodiment, the above method involves further measuring chemical shift values for the following nuclei to conduct a (3,2)D <[$^1H^XX/^1H^YY$]-NOESY-[$^1H$]> GFT NMR experiment: (1) Y, where Y is an aliphatic carbon, $^{13}C^{ali}$, an aromatic carbon, $^{13}C^{aro}$, or a nitrogen, $^{15}N$, and (2) $^1H^Y$, a proton bound to Y, where (a) the step of applying further involves simultaneously applying radiofrequency pulses for a second 3D NOESY FT NMR experiment to the sample, (b) the step of jointly sampling further involves simultaneously jointly sampling a second set of 2 indirect chemical shift evolution periods of the 3D NOESY FT NMR experiment, $^1H^Y$ and Y, and (c) the step of independently cosine and sine modulating further involves simultaneous phase-sensitive sampling of the jointly sampled second set of indirect chemical shift evolution periods.

In another embodiment, the above method involves further measuring chemical shift values for the following nuclei to conduct a (3,2)D <[$^1H^XX/^1H^YY/^1H^ZZ$]-NOESY-[$^1H$]> GFT NMR experiment: (1) Z, where Z is an aliphatic carbon, $^{13}C^{ali}$, an aromatic carbon, $^{13}C^{aro}$, or a nitrogen, $^{15}N$, and (2) $^1H^Z$, a proton bound to Z, where (a) the step of applying further involves simultaneously applying radiofrequency pulses for a third 3D NOESY FT NMR experiment to the sample, (b) the step of jointly sampling further involves simultaneously jointly sampling a third set of 2 indirect chemical shift evolution periods of the 3D NOESY FT NMR experiment, $^1H^Z$ and Z, and (c) the step of independently cosine and sine modulating further involves simultaneous phase-sensitive sampling of the jointly sampled third set of indirect chemical shift evolution periods. One specific embodiment of this method, (3,2)D [$^1\underline{H^XX}/^1\underline{H^Y}Y/^1H^Z$ Z]-NOESY-[$^1H$], involves applying radiofrequency pulses for a 4D FT NMR experiment according to the scheme shown in FIG. 46.

Another aspect of the present invention relates to a method of conducting a (4,3) dimensional (D) <[1HXX]-nuclear Overhauser enhancement spectroscopy (NOESY)-[$Y^1H^Y$]> G-matrix Fourier transformation (GFT) nuclear magnetic resonance (NMR) experiment. The method involves providing a sample, where the sample is a protein molecule and the chemical shift values for the following nuclei are measured: (1) X, wherein X is an aliphatic carbon, $^{13}C^{ali}$, an aromatic carbon, $^{13}C^{aro}$, or a nitrogen, $^{15}N$; (2) a proton bound to X, $^1H^X$; (3) Y, wherein Y is an aliphatic carbon, $^{13}C^{ali}$, an aromatic carbon, $^{13}C^{aro}$, or a nitrogen, $^{15}N$; and (4) a proton bound to Y, $^1H^Y$. Next, radiofrequency pulses for a first 4D NOESY FT NMR experiment are applied to the sample. Then, a first set of 2 indirect chemical shift evolution periods of the 4D NOESY FT NMR experiment, $^1H^X$ and X, is selected. Next, the first set of 2 indirect chemical shift evolution periods is jointly sampled in an indirect time domain dimension, $t_1(^1H^X,X)$. Then, NMR signals detected in a direct dimension are independently cosine and sine modulated to generate 3D basic NMR spectra containing frequency domain signals with 2 chemical shift doublet components, thereby enabling phase-sensitive sampling of the jointly sampled 2 indirect chemical shift evolution periods. Finally, the 3D basic NMR spectra are transformed into 3D phase-sensitively edited basic NMR spectra, where the 2 chemical shift doublet components of the 3D basic NMR spectra are edited to yield 3D phase-sensitively edited basic NMR spectra having individual chemical shift doublet components.

In another embodiment, the above method involves further measuring chemical shift values for the following nuclei to conduct a (4,3)D <[$^1\underline{H^XX}/^1\underline{H^{X'}X'}$]-NOESY-[$Y^1H^Y/Y'^1H^{Y'}$]> GFT NMR experiment: (1) X', where X' is an aliphatic carbon, $^{13}C^{ali}$, an aromatic carbon, $^{13}C^{aro}$, or a nitrogen, $^{15}N$; (2) a proton bound to X', $^1H^{X'}$; (3) Y', where Y' is an aliphatic carbon, $^{13}C^{ali}$, an aromatic carbon, $^{13}C^{aro}$, or a nitrogen, $^{15}N$; and (4) a proton bound to Y', $^1H^{Y'}$, where (a) the step of applying further involves simultaneously applying radiofrequency pulses for a second 4D NOESY FT NMR experiment to the sample, (b) the step of jointly sampling further involves simultaneously jointly sampling a second set of 2 indirect chemical shift evolution periods of the 4D NOESY FT NMR experiment, $^1H^Y$ and Y, and (c) the step of independently cosine and sine modulating further involves simultaneous phase-sensitive sampling of the jointly sampled second set of indirect chemical shift evolution periods. One specific embodiment of this method, (4,3)D [$^1H^XX/^1H^{X'}$ X']-NOESY-[$Y^1H^Y/Y'^1H^{Y'}$], involves applying radiofrequency pulses for a simultaneous 4D NOESY FT NMR experiment according to the scheme shown in FIG. 36(a).

For the above GFT NOESY NMR experiments, the step of transforming the 3D basic NMR spectra into 3D phase-sensitively edited basic NMR spectra can be carried out by applying a G-matrix defined as $$\hat{G}(1) = \begin{bmatrix} 1 & i \\ 1 & -i \end{bmatrix} \otimes [1\,i],$$

where $i=\sqrt{-1}$, under conditions effective to edit the chemical shift doublet components in a time domain. Alternatively, the transforming can be carried out by applying a F-matrix defined as $$\hat{G}(1) = \begin{bmatrix} 1 & i \\ 1 & -i \end{bmatrix} \otimes [1\,i],$$

under conditions effective to edit the chemical shift doublet components in a frequency domain.

Another aspect of the present invention relates to a method of conducting a (4,2) dimensional (D) <[$^1H^XX$]-nuclear Overhauser enhancement spectroscopy (NOESY)-[$Y^1H^Y$]> G-matrix Fourier transformation (GFT) nuclear magnetic resonance (NMR) experiment. The method involves providing a sample, where the sample is a protein molecule and the chemical shift values for the following nuclei are measured: (1) X, where X is an aliphatic carbon, $^{13}C^{ali}$, an aromatic carbon, $^{13}C^{aro}$, or a nitrogen, $^{15}N$; (2) a proton bound to X, $^1H^X$; (3) Y, where Y is an aliphatic carbon, $^{13}C^{ali}$, an aromatic carbon, $^{13}C^{aro}$, or a nitrogen, $^{15}N$; and (4) a proton bound to Y, $^1H^Y$. Next, radiofrequency pulses for a first 4D NOESY FT NMR experiment are applied to the sample. Then, a first group of 3 indirect chemical shift evolution periods of the 4D NOESY FT NMR experiment, $^1H^X$, X, and Y, is selected. Next, the first group of 3 indirect chemical shift evolution periods is jointly sampled in an indirect time domain dimension, $t_1(^1H^X,X,Y)$. Then, NMR signals detected in a direct dimension are independently cosine and sine modulated to generate 2D basic NMR spectra containing frequency domain signals with 4 chemical shift multiplet components, thereby enabling phase-sensitive sampling of all jointly sampled 3 indirect chemical shift evolution periods. Finally, the 2D basic NMR spectra are transformed into 2D phase-sensitively edited basic NMR spectra, where the 4 chemical shift multiplet components of the 2D basic NMR spectra are edited to yield 2D phase-sensitively edited basic NMR spectra having individual chemical shift multiplet components. One specific embodiment of this method, (4,2)D [$^1H^X$ X]-NOESY-[$Y^1H^Y$], involves applying radiofrequency pulses for a simultaneous 4D NOESY FT NMR experiment according to the scheme shown in FIG. 44.

In another embodiment, the above method involves further measuring chemical shift values for the following nuclei to conduct a (4,2)D <[$^1H^XX/^1H^{X'}X'$]-NOESY-[$Y^1H^Y/Y'^1H^{Y'}$]> GFT NMR experiment: (1) X', where X' is an aliphatic carbon, $^{13}C^{ali}$, an aromatic carbon, 13Caro, or a nitrogen, $^{15}N$; (2) a proton bound to X', $^1H^{X'}$; (3) Y', where Y' is an aliphatic carbon, $^{13}C^{ali}$, an aromatic carbon, $^{13}C^{aro}$, or a nitrogen, $^{15}N$; and (4) a proton bound to Y', $^1H^{Y'}$, where (a) the step of applying further involves simultaneously applying radiofrequency pulses for a second 4D NOESY FT NMR experiment to the sample, (b) the step of jointly sampling further involves simultaneously jointly sampling a second group of 3 indirect chemical shift evolution periods of the 4D NOESY FT NMR experiment, $^1H^{X'}$, X', and Y', and (c) the step of independently cosine and sine modulating further involves simultaneous phase-sensitive sampling of the jointly sampled second group of indirect chemical shift evolution periods.

For the above GFT NOESY NMR experiments, the step of transforming the 3D basic NMR spectra into 3D phase-sensitively edited basic NMR spectra can be carried out by applying a G-matrix defined as $$\hat{G}(2) = \begin{bmatrix} 1 & i \\ 1 & -i \end{bmatrix} \otimes \begin{bmatrix} 1 & i \\ 1 & -i \end{bmatrix} \otimes [1\,i],$$

where $i=\sqrt{-1}$, under conditions effective to edit the chemical shift multiplet components in a time domain. Alternatively, the transforming can be carried out by applying a F-matrix defined as $\hat{F}(2)=\hat{F}(1)\otimes\hat{F}(1)$, wherein $$\hat{F}(1) = \begin{bmatrix} 1 & 1 \\ 1 & -1 \end{bmatrix},$$

under conditions effective to edit the chemical shift multiplet components in a frequency domain.

In another embodiment, the above methods further involve repeating once the step of jointly sampling, independently cosine and sine modulating, and transforming, where the step of jointly sampling involves jointly sampling 2 indirect chemical shift evolution periods out of the 3 indirect chemical shift evolution periods, under conditions effective to generate a first order central peak NMR spectrum.

J-GFT NMR Experiments

The present application discloses a constant-time (ct) G-matrix Fourier transform (GFT) NMR experiment (Kim et al., *J. Am. Chem. Soc.* 125:1385-1393 (2003), which is hereby incorporated by reference in its entirety), which circumvents the drawbacks aforementioned in the Background of the Invention section for simultaneous and precise measurement of multiple correlated RDCs in proteins. GFT NMR has been previously shown to yield highly precise multi-dimensional spectral information rapidly for protein resonance assignments (Kim et al., *J. Am. Chem. Soc.* 125:1385-1393 (2003); Atreya et al., *Proc. Natl. Acad. Sci. USA* 101:9642-9647 (2004); Kim et al., *J. Biomol. NMR* 28:117-130 (2004); Atreya et al., *J. Am. Chem. Soc.* 127:4554-4555 (2005); Shen et al., *J. Am. Chem. Soc.* 127:9085-9099 (2005), which are hereby incorporated by reference in their entirety) by phase sensitive joint chemical shift sampling of several nuclei in a single indirect dimension called the GFT-dimension (Kim et al., *J. Am. Chem. Soc.* 125:1385-1393 (2003); Atreya et al., *Proc. Natl. Acad. Sci. USA* 101:9642-9647 (2004), which are hereby incorporated by reference in their entirety). Such a scheme is employed in the present invention for simultaneous measurement of several scalar and dipolar couplings in proteins. Four mutually correlated one-bond couplings, namely, $^{13}C^\alpha$—$^1H^\alpha$ ($^1J_{C_\alpha H_\alpha}/^1D_{C_\alpha H_\alpha}$), $^{13}C^\alpha$—$^{13}C'$ ($^1J_{C_\alpha C'}/^1D_{C_\alpha C'}$), $^{15}N$—$^{13}C'$ ($^1J_{NC'}/^1D_{NC'}$), and $^{15}N$—$^1H^N$ ($^1J_{NH}/^1D_{NH}$) are simultaneously measured in conjunction with $^{15}N$ and $^1H^N$ chemical shifts. The novel experiment is named "J-GFT (6,2)D [($H^\alpha$—$C^\alpha$—CO)—N—HN]", where each hyphen represents one of the measured (scalar/residual dipolar) one-bond couplings while, for nuclei in parentheses, chemical shift evolution is omitted.

Thus, the present invention also relates to a method of conducting a (6,2) dimensional (D) [($H^\alpha$—$C^\alpha$—CO)—N—HN] G-matrix Fourier transformation (GFT) nuclear magnetic resonance (NMR) experiment. The method involves providing a sample, where the sample is a protein molecule having two consecutive amino acid residues, i–1 and i, and the chemical shift values for the following nuclei: (1) a polypeptide backbone amide nitrogen of amino acid residue i, $^{15}N_i$; and (2) a polypeptide backbone amide proton of amino acid residue i, $^1H^N_i$, are measured in combination with four spin-spin couplings between (1) an α-proton of amino acid residue i–1, $^1H^\alpha_{i-1}$, and an α-carbon of amino acid residue i–1, $^{13}C^\alpha_{i-1}$; (2) an α-carbon of amino acid residue i–1, $^{13}C^\alpha_{i-1}$, and a polypeptide backbone carbonyl carbon of amino acid residue i–1, $^{13}C'_{i-1}$; (3) a polypeptide backbone carbonyl carbon of amino acid residue i–1, $^{13}C'_{i-1}$, and a polypeptide backbone amide nitrogen of amino acid residue i, $^{15}N_i$; (4) a polypeptide backbone amide nitrogen of amino acid residue i, $^{15}N_i$, and a polypeptide backbone amide proton of amino acid residue i, $^1H^N_i$. Next, radiofrequency pulses for a 6D FT NMR experiment are applied to the sample. Then, an indirect chemical shift evolution period of the 6D FT NMR experiment, $^{15}N_i$, is selected. Next, the indirect chemical shift evolution period is jointly sampled with four indirect spin-spin coupling evolution periods resulting from sampling the four spin-spin couplings. Then, NMR signals detected in a direct dimension resulting from time evolution of the indirect chemical shift and the four spin-spin couplings are independently cosine and sine modulated to generate 2D basic NMR spectra containing frequency domain signals with 16 multiplet components, thereby enabling phase-sensitive sampling of the indirect chemical shift evolution period and the indirect spin-spin coupling evolution periods. Finally, the 2D basic NMR spectra are transformed into 2D phase-sensitively edited basic NMR spectra, where the 16 multiplet components of the 2D basic NMR spectra are edited to yield 2D phase-sensitively edited basic NMR spectra having individual multiplet components. One specific embodiment of this method, (6,2)D ($H^\alpha$—$C^\alpha$—CO)—N—HN, involves applying radiofrequency pulses for a 6D FT NMR experiment according to the scheme shown in FIG. 47.

For the above J-GFT NMR experiments, the step of transforming the 2D basic NMR spectra into 2D phase-sensitively edited basic NMR spectra can be carried out by applying a G-matrix defined as $$\hat{G}(4) = \begin{bmatrix} 1 & i \\ 1 & -i \end{bmatrix} \otimes \begin{bmatrix} 1 & i \\ 1 & -i \end{bmatrix} \otimes \begin{bmatrix} 1 & i \\ 1 & -i \end{bmatrix} \otimes \begin{bmatrix} 1 & i \\ 1 & -i \end{bmatrix} \otimes [1\,i],$$

where $i=\sqrt{-1}$, under conditions effective to edit the multiplet components in a time domain. Alternatively, the transforming can be carried out by applying a F-matrix defined as $\hat{F}(4)=\hat{F}(1)\otimes\hat{F}(1)\otimes\hat{F}(1)\otimes\hat{F}(1)$, wherein $$\hat{F}(1) = \begin{bmatrix} 1 & 1 \\ 1 & -1 \end{bmatrix},$$

under conditions effective to edit the multiplet components in a frequency domain.

In addition, a further aspect of the present invention relates to conducting other (6,2)D GFT NMR experiments (e.g., (6,2)D [$H^\alpha$—($C^\alpha$—CO—N)—HN], (6,2)D [$H^\alpha$—$C^\alpha$—(CO—N—HN)], etc.), where chemical shift values for different selections of 2 nuclei (e.g., $^{13}H^\alpha_{i-1}$ and $^1H^N_i$, $^1H^\alpha_{i-1}$ and $^{13}C^\alpha_{i-1}$, etc.) are measured in combination with the four spin-spin couplings.

Another aspect of the present invention relates to conducting (7,2)D GFT NMR experiments (e.g., (7,2)D [($H^\alpha$—$C^\alpha$)—CO—N—HN], (7,2)D [$H^\alpha$—($C^\alpha$—CO)—N—HN], (7,2)D [H$^\alpha$—C$^\alpha$—(CO—N)—HN], (7,2)D [H$^\alpha$—C$^\alpha$—CO—(N—HN)], etc.), where chemical shift values for any selection of 3 nuclei (e.g., $^{13}$C'$_{i-1}$, $^{15}$N$_i$, and $^1$H$^N_i$; $^{13}$H$^\alpha_{i-1}$, $^{15}$N$_i$, and $^1$H$^N_i$; $^{13}$H$^\alpha_{i-1}$, $^{13}$C$^\alpha_{i-1}$, and $^1$H$^N_i$; $^{13}$H$^\alpha_{i-1}$, $^{13}$C$^\alpha_{i-1}$, and $^{13}$C'$_{i-1}$, etc.) are measured in combination with the four spin-spin couplings.

Another aspect of the present invention relates to conducting (8,2)D GFT NMR experiments (e.g., (8,2)D [(H$^\alpha$)—C$^\alpha$—CO—N—HN], (8,2)D [H$^\alpha$—(C$^\alpha$)—CO—N—HN], (8,2)D [H$^\alpha$—C$^\alpha$—CO—(N)—HN], (8,2)D [H$^\alpha$—C$^\alpha$—CO—N—(HN)], etc.), where chemical shift values for any selection of 4 nuclei (e.g., $^{13}$C$^\alpha_{i-1}$, $^{13}$C'$_{i-1}$, $^{15}$N$_i$, and $^1$H$^N_i$; $^{13}$H$^\alpha_{i-1}$, $^{13}$C'$_{i-1}$, $^{15}$N$_i$, and $^1$H$^N_i$; $^{13}$H$^\alpha_{i-1}$, $^{13}$C$^\alpha_{i-1}$, $^{13}$C'$_{i-1}$, and $^1$H$^N_i$; $^{13}$H$^\alpha_{i-1}$, $^{13}$C$^\alpha_{i-1}$, $^{13}$C'$_{i-1}$, and $^1$H$^N_i$, etc.) are measured in combination with the four spin-spin couplings.

Another aspect of the present invention relates to conducting a (9,2)D GFT NMR experiment (i.e., (9,2)D [H$^\alpha$—C$^\alpha$—CO—N—HN]), where chemical shift values for all 5 nuclei (i.e., $^{13}$H$^\alpha_{i-1}$, $^{13}$C$^\alpha_{i-1}$, $^{13}$C'$_{i-1}$, $^{15}$N$_i$, and $^1$H$^N_i$) are measured in combination with the four spin-spin couplings.

In addition, the present invention relates to conducting (5,2)D GFT NMR experiments (e.g., (5,2)D [(H$^\alpha$C$^\alpha$—CO)—N—HN], (5,2)D [(H$^\alpha$—C$^\alpha$CO)—N—HN], (5,2)D [(H$^\alpha$—C$^\alpha$—CO)N—HN], etc.), where chemical shift values for any selection of the nuclei are measured in combination with 3 spin-spin couplings (e.g., between $^{13}$C$^\alpha_{i-1}$ and $^{13}$C'$_{i-1}$, $^{13}$C'$_{i-1}$ and $^{15}$N$_i$, and $^{15}$N$_i$ and $^1$H$^N_i$; between $^{13}$H$^\alpha_{i-1}$ and $^{13}$C$^\alpha_{i-1}$, $^{13}$C'$_{i-1}$ and $^{15}$N$_i$, and $^{15}$N$_i$ and $^1$H$^N_i$; between $^{13}$H$^\alpha_{i-1}$ and $^{13}$C$^\alpha_{i-1}$, $^{13}$C$^\alpha_{i-1}$ and $^{13}$C'$_{i-1}$, and $^{15}$N$_i$ and $^1$H$^N_i$, etc.).

In addition, the present invention relates to conducting (4,2)D GFT NMR experiments (e.g., (4,2)D [(H$^\alpha$C$^\alpha$CO)—N—HN], (4,2)D [(H$^\alpha$—C$^\alpha$CO)N—HN], (4,2)D [(H$^\alpha$—C$^\alpha$—CO)NHN], etc.), where chemical shift values for any selection of the nuclei are measured in combination with 2 spin-spin couplings (e.g., between $^{13}$C'$_{i-1}$ and $^{15}$N$_i$, and $^{15}$N$_i$ and $^1$H$^N_i$; between $^{13}$H$^\alpha_{i-1}$ and $^{13}$C$^\alpha_{i-1}$, and $^{15}$N$_i$ and $^1$H$^N_i$; between $^{13}$H$^\alpha_{i-1}$ and $^{13}$C$^\alpha_{i-1}$, and $^{13}$C$^\alpha_{i-1}$ and $^{13}$C'$_{i-1}$, etc.).

EXAMPLES

The following examples are provided to illustrate embodiments of the present invention but are by no means intended to limit its scope.

Example 1

G$^2$FT (5,3)D HN{N,CO}{C$^{\alpha\beta}$C$^\alpha$} and G$^2$FT (5,3)D HN{NCO}{C$^{\alpha\beta}$C$^\alpha$}/(5,3)D {C$^{\alpha\beta}$C$^\alpha$}{CON}HN NMR Experiments NMR assignments of proteins are obtained by combining several multidimensional experiments (Cavanagh et al., *Protein NMR Spectroscopy* Academic Press: San Diego (1996), which is hereby incorporated by reference in its entirety). $^{15}$N, $^1$H$^N$-resolved triple resonance experiments sequentially linking $^{13}$C$^{\alpha/\beta}$ and/or $^1$H$^\alpha$ shifts are the most widely used (Cavanagh et al., *Protein NMR Spectroscopy* Academic Press: San Diego (1996), which is hereby incorporated by reference in its entirety). For (partly) unfolded or α-helical (membrane) proteins, spectral analysis is, however, impeded by very high shift degeneracy, so that novel methodology for their efficient assignment is required. $^{15}$N, $^1$H$^N$-degeneracy can be largely removed in $^{13}$C'$_{i-1}$, $^{15}$N$_i$, $^1$H$^N_i$-resolved experiments (i is a residue number) (Szyperski et al., *J. Magn. Reson. B* 109:229-233 (1995); Konrat et al., *J. Biomol. NMR* 15:309-313 (1999), which are hereby incorporated by reference in their entirety). When using correlated $^{13}$C$^{\alpha\beta}$ or $^{13}$C$^\alpha$/$^1$H$^\alpha$ shifts to establish connectivities, conventional NMR (Cavanagh et al., *Protein NMR Spectroscopy* Academic Press: San Diego (1996), which is hereby incorporated by reference in its entirety) would require recording of 5D spectra. Measurement times for such spectra are prohibitively long or lead to "sampling limited" data collection (Szyperski et al., *Proc. Natl. Acad. Sci. USA*, 99:8009-8014 (2002), which is hereby incorporated by reference in its entirety). G-matrix FT (GFT) NMR (Kim et al., *J. Am. Chem. Soc.* 125:1385-1393 (2003); Kim et al., *J. Biomol. NMR* 28:117-130 (2004); Atreya et al., *Proc. Natl. Acad. Sci. USA* 101: 9642-9647 (2004), which are hereby incorporated by reference in their entirety), rooted in reduced-dimensionality NMR (Szyperski et al., *J. Am. Chem. Soc.* 115:9307-9308 (1993); Brutscher et al., *J. Magn. Reson.* B109:238-242 (1995); Szyperski et al., *J. Am. Chem. Soc.* 118:8147-8148 (1996); Löhr et al., *J. Biomol. NMR* 6:189-195 (1995); Szyperski et al., *J. Biomol. NMR* 11:387-405 (1998), which are hereby incorporated by reference in their entirety) and related to accordion spectroscopy (Bodenhausen et al., *J. Magn. Reson.* 45:367-373 (1981); Atreya et al., *Methods Enzymol.* 394:78-108 (2005), which are hereby incorporated by reference in their entirety), can (i) rapidly provide precise high-dimensional spectral information and (ii) serve to reconstruct higher-dimensional spectra (Kupce et al., *J. Am. Chem. Soc.* 125:13958-13959 (2003); Coggins et al., *J. Am. Chem. Soc.* 126:1000-1001 (2004), which are hereby incorporated by reference in their entirety). Previously published (4,3)D GFT experiments (Atreya et al., *Proc. Natl. Acad. Sci. USA* 101:9642-9647 (2004), which is hereby incorporated by reference in its entirety) have greatly increased the speed of NMR structure determination, but are not optimally tailored for proteins with very high shift degeneracy.

Figure 1:
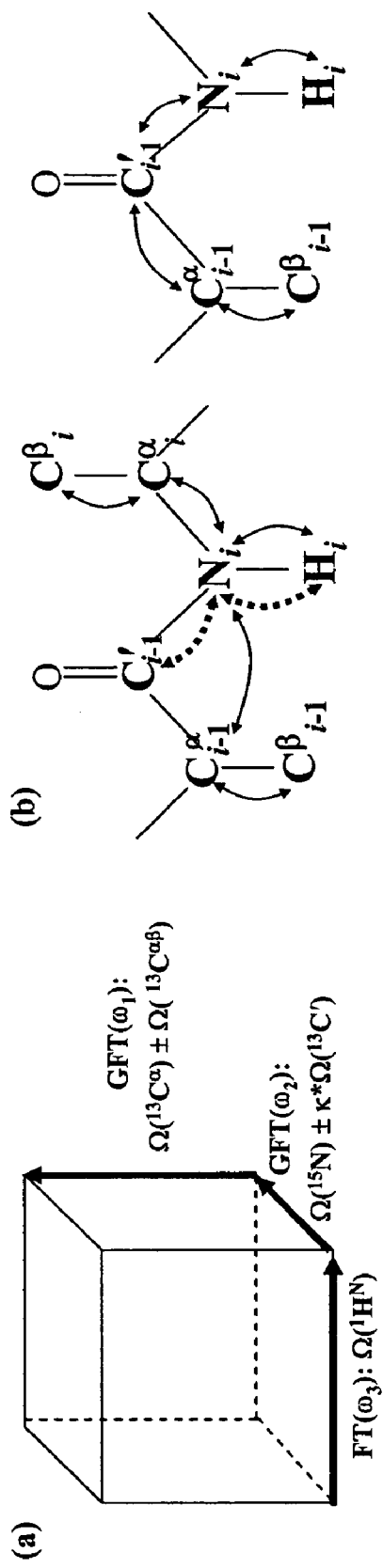
FIG. 1(a) illustrates $^{13}C'_{i-1}$, $^{15}N$, $^{1}H^N$-resolved (5,3)D G²FT NMR.
FIG. 1(b) illustrates magnetization transfers of HN{N,CO}{C$^{\alpha\beta}$C$^\alpha$} (left) and HN{NCO}{C$^{\alpha\beta}$C$^\alpha$} (right). Double-arrows indicate bidirectional transfers via one-bond scalar couplings. The "intraresidue" experiment (left) also yields sequential connectivities via smaller (Cavanagh et al., *Protein NMR Spectroscopy* Academic Press: San Diego (1996), which is hereby incorporated by reference in its entirety) two-bond $J_{CN}$ couplings.

This example (as well as Examples 2, 3, and 4) discloses "G$^2$FT NMR experiments" in which two G-matrix transformations were applied. First, $^{13}$C'$_{i-1}$, $^{15}$N$_i$, $^1$H$^N_i$-resolved experiments were implemented (FIG. 1). $^{15}$N$_i$ and $^{13}$C'$_{i-1}$ shifts were jointly sampled for breaking $^{15}$N, $^1$H$^N$-shift degeneracy (Szyperski et al., *J. Magn. Reson.* B 109:229-233 (1995); Konrat et al., *J. Biomol. NMR* 15:309-313 (1999), which are hereby incorporated by reference in their entirety), and $^{13}$C$^{\alpha/\beta}$ and $^{13}$C$^\alpha$ shifts were jointly sampled for sequentially linking spin systems (Atreya et al., *Proc. Natl. Acad. Sci. USA* 101:9642-9647 (2004), which is hereby incorporated by reference in its entirety). Resulting (5,3)D HN{N, CO}{C$^{\alpha\beta}$C$^\alpha$} and HN{NCO}{C$^{\alpha\beta}$C$^\alpha$} provided, respectively, intraresidue and sequential connectivities via one-bond scalar couplings (FIG. 1) based on 2*Ω($^{13}$C$^\alpha$), Ω($^{13}$C$^\alpha$)+Ω($^{13}$C$^\beta$) and Ω($^{13}$C$^\alpha$)−Ω($^{13}$C$^\beta$) (Atreya et al., *Proc. Natl. Acad. Sci. USA* 101:9642-9647 (2004), which is hereby incorporated by reference in its entirety). The curly brackets group jointly sampled shifts represented by underlined letters (Kim et al., *J. Am. Chem. Soc.* 125:1385-1393 (2003), which is hereby incorporated by reference in its entirety), and in (5,3)D HN{N,CO}{C$^{\alpha\beta}$C$^\alpha$} the comma indicates a bifurcated $^{13}$C'$_{i-1}$←$^{15}$N$_i$→$^{13}$C$^\alpha_i$ transfer (Szyperski et al., *J. Magn. Reson.* B 109:229-233 (1995); Konrat et al., *J. Biomol. NMR* 15:309-313 (1999); Szyperski et al., *J. Am. Chem. Soc.* 118:8147-8148 (1996); Szyperski et al., *J. Biomol. NMR* 11:387-405 (1998), which are hereby incorporated by reference in their entirety).

Figure 2:
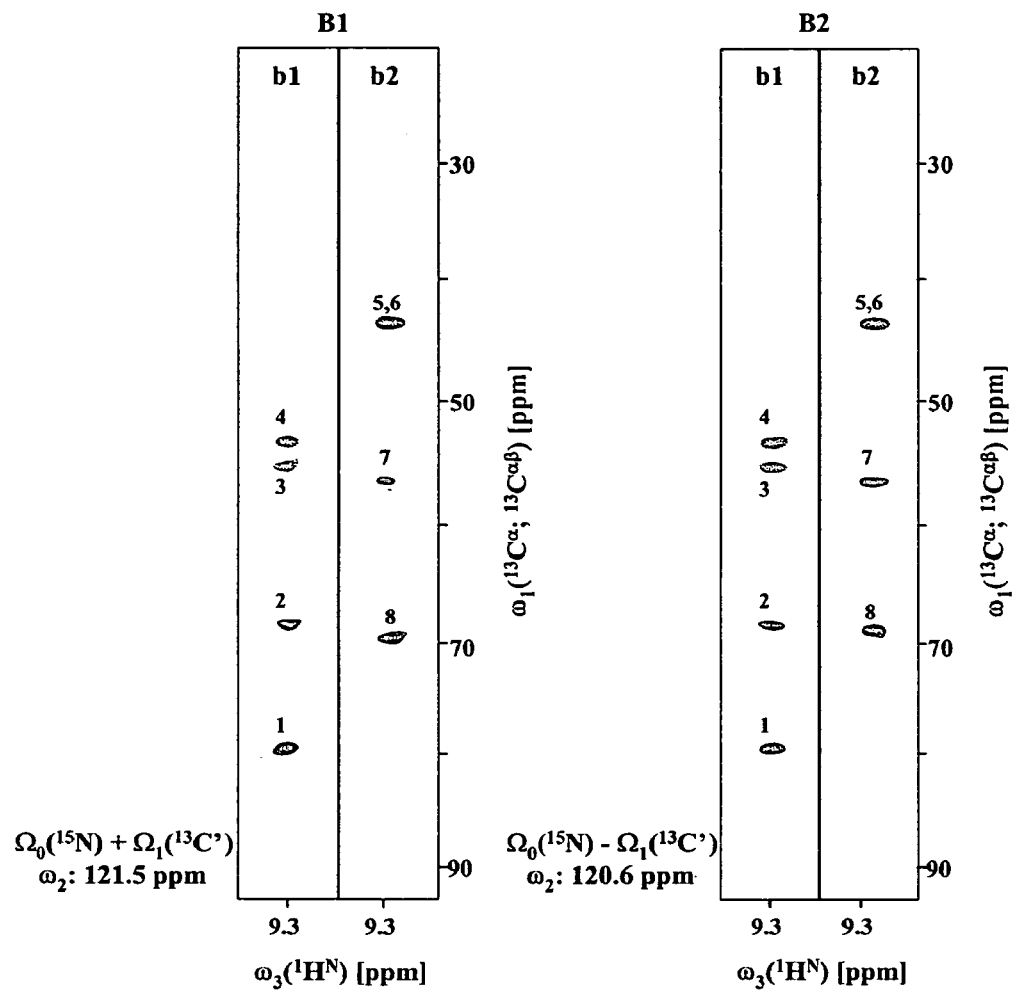
FIG. 2 shows composite plots of [$\omega_1$($^{13}C^\alpha$; $^{13}C^{\alpha\beta}$), $\omega_3$($^1H^N$)] strips taken from the basic spectra of G$^2$FT (5,3)D HN{N,CO}{$C^{\alpha\beta}C^\alpha$}. The four basic spectra are grouped into two sets, B1 and B2, comprising peaks at $\Omega_0$($^{15}N_i$)+$\Omega_1$($^{13}C'_{i-1}$) and $\Omega_0$($^{15}N_i$)−$\Omega_1$($^{13}C'_{i-1}$) along $\omega_2$, respectively. B1 and B2 each contain two spectra (labeled as "b1" and "b2") comprising peaks at $\omega_0$($^{13}C^\alpha_{i/i-1}$)±$\Omega_1$($^{13}C^{\alpha/\beta}_{i/i-1}$) along $\omega_1$. Positive and negative peaks are shown, respectively, with solid and dotted contour lines. As an example, strips are shown for the residue Val 5 of the 8.6 kDa protein Ubiquitin. Peaks labeled 1-4 in "b1" and 5-8 in "b2" correspond to the following linear combination of chemical shifts along $\omega_1$: (i=Val 5; i−1=Phe 4)

More specifically, in G$^2$FT (5,3)D HN{N,CO}{C$^{\alpha\beta}$C$^\alpha$}, magnetization from $^{15}$N nucleus of residue i was simultaneously transferred to $^{13}$C' ($^{13}$CO) of residue i−1 and the $^{13}$C$^\alpha$ of residues i and i−1 (hereafter referred to as i/i−1). Subsequently, $^{13}$C'$_{i-1}$ was frequency labeled jointly with $^{15}$N$_i$ during t$_2$(ω$_2$), with the latter being detected in quadrature. After independent frequency labeling of $^{13}C^\alpha{}_{i/i\text{-}1}$ and $^{13}C^\beta{}_{i/i\text{-}1}$ spins during $t_1(\omega_1)$, magnetization was transferred to the respective $^{13}C^\alpha{}_{i/i\text{-}1}$ spin, which was then frequency labeled and detected in quadrature during $t_1(\omega_1)$. Sequential application of G-matrix transformations along $\omega_1$ and $\omega_2$ yielded four basic spectra which can be grouped into two sets, B1 and B2, comprising peaks at $\Omega_0(^{15}N_i)\pm\Omega_1(^{13}C'_{i\text{-}1})$ along $\omega_2$. B1 and B2 each contained 2 basic spectra comprising peaks at $\Omega_0(^{13}C^\alpha{}_i)\pm\Omega_1(^{13}C^{\alpha/\beta}{}_i)$ and $\Omega_0(^{13}C^\alpha{}_{i\text{-}1})\pm\Omega_1(^{13}C^{\alpha/\beta}{}_{i\text{-}1})$ along $\omega_1$. Such a peak pattern is illustrated in FIG. 2.

In G²FT (5,3)D HN{NCO}{C$^{\alpha\beta}$C$^\alpha$}, as well as G²FT (5,3)D {C$^{\alpha\beta}$C$^\alpha$}{CON}HN, after independent frequency labeling of $^{13}C^\alpha{}_{i\text{-}1}$ and $^{13}C^\beta{}_{i\text{-}1}$ spins during $t_1(\omega_1)$, magnetization was transferred to the respective $^{13}C^\alpha{}_{i\text{-}1}$ spin, which was then frequency labeled and detected in quadrature during $t_1(\omega_1)$. Subsequently, $^{13}C'_{i\text{-}1}$ was frequency labeled in conjunction with $^{15}N_i$ during $t_2(\omega_2)$. Sequential application of G-matrix transformations along $\omega_1$ and $\omega_2$ yielded four basic spectra as in G²FT (5,3)D HN{N,CO}{C$^{\alpha\beta}$C$^\alpha$} above, which can be grouped into two sets, B1 and B2 comprising peaks at $\Omega_0(^{15}N_i)\pm\Omega_1(^{13}C'_{i\text{-}1})$ along $\omega_2$. B1 and B2 each contained 2 basic spectra comprising peaks at $\Omega_0(^{13}C^\alpha{}_{i\text{-}1})\pm\Omega_1(^{13}C^{\alpha/\beta}{}_{i\text{-}1})$ along $\omega_1$. Such a peak pattern is illustrated in FIGS. 3 and 4. (5,3)D HN{NCO}{C$^{\alpha\beta}$C$^\alpha$} is an "out-and-back" type of experiment, while (5,3)D {C$^{\alpha\beta}$C$^\alpha$}{CON}HN is of "out-and-stay" type.

The r.f. pulse schemes of G²FT (5,3)D HN{N,CO}{C$^{\alpha\beta}$C$^\alpha$}) (FIG. 5) and G²FT (5,3)D HN{NCO}{C$^{\alpha\beta}$C$^\alpha$} (FIG. 6) yielded "out-and-back" transfers. This allowed employment of GFT (Kim et al., *J. Am. Chem. Soc.* 125:1385-1393 (2003), which is hereby incorporated by reference in its entirety)- TROSY (Pervushin et al., *Proc. Natl. Acad. Sci.* 94:12366-12371 (1997), which is hereby incorporated by reference in its entirety) for (large) deuterated (Gardner et al., *Annu. Rev. Biophys. Biomol. Struct.* 27:307-318 (1998), which is hereby incorporated by reference in its entirety) proteins (embedded in membrane mimics), and enabled longitudinal $^1H$ relaxation (L-) optimization (Pervushin et al., *J. Am. Chem. Soc.* 124:12898-12902 (2002), which is hereby incorporated by reference in its entirety). (5,3)D HN{N,CO}{C$^{\alpha\beta}$C$^\alpha$} and HN{NCO}{C$^{\alpha\beta}$C$^\alpha$} L-G²FT NMR experiments were performed (Table 1), respectively, in 24 and 20 hours for a ~0.8 mM solution of $^{15}N$, $^{13}C$ doubly labeled 17 kDa protein yqbG, target of the Northeast Structural Genomics consortium, at 25° C. on a Varian INOVA 600 spectrometer (Palo Alto, Calif.) equipped with a cryogenic probe. Processing yielded four subspectra. Each contained one peak of a quartet at $\omega_1:\Omega(^{13}C^\alpha)\pm\Omega(^{13}C^{\alpha\beta})/\omega_2:\Omega(^{15}N)\pm\kappa\Omega(^{13}C')$. Assignments were accomplished in three steps. First, peak pairs at $\omega_1:\Omega(^{15}N)\pm\kappa\Omega(^{13}C')$ in (3,2)D HNNCO (FIG. 7; Table 1) were centered about peaks in 2D [$^{15}N$, $^1H$]-HSQC and provided spin system identification. Next, peak pair positions were transferred to (5,3)D G²FT subspectra, where the same $\omega_1$ pattern was observed at $\omega_2:\Omega(^{15}N)\pm\kappa\Omega(^{13}C')$. Signals at $\omega_1:2*\Omega(^{13}C^\alpha)$ were "central peaks" for pair identification at $\omega_1:\Omega(^{13}C)\pm\Omega(^{13}C^\beta)$ (Atreya et al., *Proc. Natl. Acad. Sci. USA* 101:9642-9647 (2004), which is hereby incorporated by reference in its entirety), which profited from increased dispersion along $\omega_1$ due to C$^{\alpha\beta}$C$^\alpha$ frequency labeling (Atreya et al., *Proc. Natl. Acad. Sci. USA* 101:9642-9647 (2004), which is hereby incorporated by reference in its entirety). Lastly, "sequential walks" at $\omega_2:\Omega(^{15}N)\pm\kappa\Omega(^{13}C')$ in two sets of subspectra yielded three connectivities each, i.e., a total of six.

TABLE 1

Acquisition Parameters for the G²FT NMR Experiments

| Figure number for r.f. pulse scheme | G²FT NMR Experiments Magnetization transfer pathway | Protein | Indirect dimension: $t_{max}$(ms); Complex points; Digital Resolution (Hz/Pt)[a] | Peak Measurement Time (hrs) | Detection Yield (%) |
|---|---|---|---|---|---|
| 5 | L-(5,3)D HN{N,CO}{C$^{\alpha\beta}$C$^\alpha$}[b]<br><br>$^1HN_i \to {}^{15}N_i \to {}^{13}C^\alpha{}_{i/i\text{-}1} \to {}^{13}C^{\alpha\beta}{}_{i/i\text{-}1} \to {}^{13}C^\alpha{}_{i/i\text{-}1} \to {}^{15}N_i \to {}^1HN_i$<br>    (t$_1$)         (t$_1$)         (t$_2$)      (t$_3$)<br>    $\cdots\to {}^{13}C'_{i\text{-}1} \cdots$<br>         (t$_2$) | yqbG | $\omega_1(^{13}C^\alpha; {}^{13}C^{\alpha\beta})$: 6.5; 72; 22<br>$\omega_2(^{15}N; {}^{13}C')$: 24.0; 36; 24 | 24 | 93 |
|  |  | rps24e | $\omega_1(^{13}C^\alpha; {}^{13}C^{\alpha\beta})$: 6.5; 90; 27<br>$\omega_2(^{15}N; {}^{13}C')$: 24.0; 40; 27 | 7 | 95 |
| 6 | L-(5,3)D HN{NCO}{C$^{\alpha\beta}$C$^\alpha$}<br><br>$^1HN_i \to {}^{15}N_i \to {}^{13}C'_{i\text{-}1} \to {}^{13}C^\alpha{}_{i\text{-}1} \to {}^{13}C^{\alpha\beta}{}_{i\text{-}1} \to {}^{13}C^\alpha{}_{i\text{-}1} \to$<br>         (t$_1$)       (t$_1$)<br>$\to {}^{13}C'_{i\text{-}1} \to {}^{15}N_i \to {}^1HN_i$<br>     (t$_2$)     (t$_2$)    (t$_3$) | yqbG | $\omega_1(^{13}C^\alpha; {}^{13}C^{\alpha\beta})$: 6.5; 72; 22<br>$\omega_2(^{15}N; {}^{13}C')$: 24.0; 36; 24 | 20 | 97 |
|  |  | rps24e | $\omega_1(^{13}C^\alpha; {}^{13}C^{\alpha\beta})$: 6.5; 90; 27<br>$\omega_2(^{15}N; {}^{13}C')$: 24.0; 40; 27 | 7 | 100 |

TABLE 1-continued

Acquisition Parameters for the G$^2$FT NMR Experiments

| Figure number for r.f. pulse scheme | G$^2$FT NMR Experiments Magnetization transfer pathway | Protein | Indirect dimension: t$_{max}$(ms); Complex points; Digital Resolution (Hz/Pt)$^a$ | Peak Measurement Time (hrs) | Detection Yield (%) |
|---|---|---|---|---|---|
| 11 | (5,3)D {C$^{\alpha\beta}$C$^\alpha$}{CON}HN<br><br>$^1$H$^{\alpha\beta}_{i-1}$→$^{13}$C$^{\alpha\beta}_{i-1}$→$^{13}$C$^\alpha_{i-1}$→$^{13}$C'$_{i-1}$→$^{15}$N$_i$→$^1$HN$_i$<br>(t$_1$)    (t$_1$)    (t$_2$)    (t$_2$)    (t$_3$) | yqbG | $\omega_1$($^{13}$C$^\alpha$; $^{13}$C$^{\alpha\beta}$):<br>6.5; 72; 22<br>$\omega_2$($^{15}$N; $^{13}$C'):<br>24.0; 36; 24 | 13.5 | 110 |
| 18 | (5,3)D HN{N,CO}{C$^\alpha$H$^\alpha$}<br><br>$^1$HN$_i$→$^{15}$N$_i$→$^{13}$C$^\alpha_{i/i-1}$→$^1$H$^\alpha_{i/i-1}$→$^{13}$C$^\alpha_{i/i-1}$→$^{15}$N$_i$→$^1$HN$_i$<br>           (t$_1$)       (t$_1$)       (t$_2$)    (t$_3$)<br>└----→ $^{13}$C'$_{i-1}$ ----------┘<br>              (t$_2$) | Z-domain | $\omega_1$($^{13}$C$^\alpha$; $^1$H$^\alpha$):<br>6.5; 78; 23<br>$\omega_2$($^{15}$N; $^{13}$C'):<br>16.0; 46; 44 | 16 | 100 |
| 19 | (5,3)D {H$^\alpha$C$^\alpha$}{CON}HN<br><br>$^1$H$^\alpha_{i-1}$→$^{13}$C$^\alpha_{i-1}$→$^{13}$C'$_{i-1}$→$^{15}$N$_i$→$^1$HN$_i$<br>(t$_1$)    (t$_1$)    (t$_2$)    (t$_2$)    (t$_3$) | Z-domain | $\omega_1$($^{13}$C$^\alpha$; $^{13}$C$^{\alpha\beta}$):<br>6.5; 28; 23<br>$\omega_2$($^{15}$N; $^{13}$C'):<br>16.0; 46; 44 | 13 | 100 |
| 24 | (6,3)D {H$^{\alpha\beta}$C$^{\alpha\beta}$C$^\alpha$}{CON}HN<br><br>$^1$H$^{\alpha\beta}_{i-1}$→$^{13}$C$^{\alpha\beta}_{i-1}$→$^{13}$C$^\alpha_{i-1}$→$^{13}$C'$_{i-1}$→$^{15}$N$_i$→$^1$HN$_i$<br>(t$_1$)    (t$_1$)    (t$_2$)    (t$_2$)    (t$_3$) | Ubiquitin | $\omega_1$($^{13}$C$^\alpha$; $^{13}$C$^{\alpha\beta}$, H$^{\alpha\beta}$):<br>6.5; 98; 34<br>$\omega_2$($^{15}$N; $^{13}$C'):<br>10.0; 30; 47 | 24 | 100 |
| 13 | L-(5,3)D HN{N,C$^\alpha$}{C$^{\alpha\beta}$C$^\alpha$}<br><br>$^1$HN$_i$→$^{15}$N$_i$→$^{13}$C$^\alpha_{i/i-1}$→$^{13}$C$^{\alpha\beta}_{i/i-1}$→$^{13}$C$^\alpha_{i/i-1}$→$^{15}$N$_i$→$^1$HN$_i$<br>(t$_2$)    (t$_1$)    (t$_1$)    (t$_2$)    (t$_3$) | rps24e | $\omega_1$($^{13}$C$^\alpha$; $^{13}$C$^{\alpha\beta}$):<br>6.5; 90; 23<br>$\omega_2$($^{15}$N; $^{13}$C$^\alpha$):<br>13.0; 40; 47 | 13 | |
| 14 | L-(5,3)D HN{N(CO)C$^\alpha$}{C$^{\alpha\beta}$C$^\alpha$}<br><br>$^1$HN$_i$→$^{15}$N$_i$→$^{13}$C'$_{i-1}$→$^{13}$C$^\alpha_{i-1}$→$^{13}$C$^{\alpha\beta}_{i-1}$→$^{13}$C$^\alpha_{i-1}$→<br>           (t$_2$)    (t$_1$)    (t$_1$)<br>→$^{13}$C'$_{i-1}$→$^{15}$N$_i$→$^1$HN$_i$<br>     (t$_2$)    (t$_3$) | rps24e | $\omega_1$($^{13}$C$^\alpha$; $^{13}$C$^{\alpha\beta}$):<br>6.5; 90; 23<br>$\omega_2$($^{15}$N; $^{13}$C$\alpha$):<br>13.0; 40; 47 | 13 | |

$^a$Direct dimension: $\omega_3$($^1$H$^N$): 64; 512; 20
$^b$Includes a 2D [$^{15}$N-$^1$H$^N$]HSQC ($\omega_1$($^{15}$N): 80; 128; 15 min) and (3,2)D HNNCO[$\omega_1$($^{15}$N; $^{13}$C'): 40; 64; 1.5 hrs]

α-Helical protein yqbG exhibited $^{15}$N, $^1$H$^N$-shift degeneracy in 2D [$^{15}$N, $^1$H]-HSQC (FIGS. 8(a) and 9(a)). This was aggravated at the lower resolution of 3D spectra (FIGS. 8(b) and 9(b)) where complete degeneracy was observed for eight residues. In contrast, at least one of the two peaks at $\omega_2$:Ω ($^{15}$N)±κΩ($^{13}$C') (FIGS. 8(c)-(d) and 9(c)-(d)) were resolved for all residues. This allowed efficient sequential assignment using the (5,3)D HN{N,CO}{C$^{\alpha\beta}$C$^\alpha$} (peak detection yield: 93%)/HN{NCO}{C$^{\alpha\beta}$C$^\alpha$} (yield: 95%) experiments (FIG. 10). (For nondeuterated proteins, (5,3)D {C$^{\alpha\beta}$C$^\alpha$}{CON}HN (FIGS. 11 and 12) is often more sensitive then the out-and-back implementation.)

L-optimization (FIG. 5; Pervushin et al., J. Am. Chem. Soc. 124:12898-12902 (2002), which is hereby incorporated by reference in its entirety) can increase sampling speed of out-and-back experiments without loss of intrinsic sensitivity (Atreya et al., Proc. Natl. Acad. Sci. USA 101:9642-9647 (2004), which is hereby incorporated by reference in its entirety), yielding minimal measurement times of ~7 h for (5,3)D HN{N,CO}{C$^{\alpha\beta}$C$^\alpha$}/HN{NCO}{C$^{\alpha\beta}$C$^\alpha$} (Table 1).

A further reduction of measurement time can be achieved by maximum entropy reconstruction of nonlinearly sampled data (Atreya et al., Methods Enzymol. 394:78-108 (2005); Hoch et al., NMR Data Processing Wiley-Liss: New York (1996); Rovnyak et al., J. Magn. Reson. 170:15-21 (2004), which are hereby incorporated by reference in their entirety), as is demonstrated herein for 13.5 kDa protein rps24e, target of the Northeast Structural Genomics consortium. L-(5,3)D G$^2$FT HN{NCO}{C$^{\alpha\beta}$C$^\alpha$} data were recorded in 3.5 hours, making L-(5,3)D G$^2$FT NMR a viable option for high-throughput data collection in structural genomics (Montelione et al., Nature Struct. Biol. 7:982-984 (2002), which is hereby incorporated by reference in its entirety).

To enable assignment of systems with very high shift degeneracy, additional G$^2$FT NMR experiments were implemented (see Table 1 and Examples 2, 3, and 4). The (5,3)D G$^2$FT NMR experiments can be combined with $^{15}$N-resolved (4,3)D counterparts (Atreya et al., Proc. Natl. Acad. Sci. USA 101:9642-9647 (2004), which is hereby incorporated by reference in its entirety). ($^{15}$N-resolved (4,3)D GFT subspectra can be created by symmetrizing (Szyperski et al., *J. Magn. Reson.* B 109:229-233 (1995), which is hereby incorporated by reference in its entirety) pairs of corresponding (5,3)D G²FT subspectra along $\omega_1$($^{15}$N; $^{13}$C') about the position of $\Omega$($^{15}$N), accurately defined in (3,2)D HNNCO). This enables one to establish sequential walks at $\omega_2$:$\Omega$($^{15}$N)±κ$\Omega$($^{13}$C') or $\omega_2$:$\Omega$($^{15}$N)±κ$\Omega$($^{13}$C$^\alpha$) as well as $\omega_2$:$\Omega$($^{15}$N). (In the three sets of subspectra constituting (5,3)D HN{N,CO}{C$^{\alpha\beta}$C$^\alpha$}, (5,3)D HN{NCO}{C$^{\alpha\beta}$C$^\alpha$}, and (4,3)D HNNC$^{\alpha\beta}$C$^\alpha$, nine sequential walks were established (FIG. 9). Hence, combination of all three pairs of (5,3)D G²FT experiments described in the present application can provide a total of 24 independent sequential walks.) Taken together, the novel (5,3)D G²FT NMR experiments are powerful for efficiently assigning proteins with high shift degeneracy and promise to pave the way for NMR-based structural genomics of membrane proteins (Sorgen et al., *Proc. Natl. Acad. Sci. USA* 99:14037-14040 (2002), which is hereby incorporated by reference in its entirety).

Example 2

G²FT (5,3)D HN{NC$^\alpha$}{C$^{\alpha\beta}$C$^\alpha$} and G²FT (5,3)D HN{N(CO)C$^\alpha$}{C$^{\alpha\beta}$C$^\alpha$} NMR Experiments Experiments profiting from large $^{13}$C$^\alpha$ shift dispersion (Cavanagh et al., *Protein NMR Spectroscopy* Academic Press: San Diego (1996), which is hereby incorporated by reference in its entirety) were recorded for 13.5 kDa protein rps24e. G²FT (5,3)D HN{NC$^\alpha$}{C$^{\alpha\beta}$C$^\alpha$} NMR experiment (FIG. 13; 13 hrs.; 100%) and G²FT (5,3)D HN{N(CO)C$^\alpha$}{C$^{\alpha\beta}$C$^\alpha$} NMR experiment (FIG. 14; 13 hrs.; 100%) enabled $^{13}$C$^\alpha$, $^{15}$N, $^1$H$^N$-resolved sequential assignment of backbone $^{13}$C$^\alpha$ and sidechain $^{13}$C$^\beta$ resonances in proteins (FIG. 15).

In G²FT (5,3)D HN{NC$^\alpha$}{C$^{\alpha\beta}$C$^\alpha$}, magnetization from $^{15}$N$_i$ nucleus was transferred to $^{13}$C$^\alpha_i$ which was frequency labeled jointly with $^{15}$N$_i$ during $t_2$ ($\omega_2$), the latter being detected in quadrature. Subsequently, after independent frequency labeling of $^{13}$C$^\alpha_{i/i-1}$ and $^{13}$C$^\beta_{i/i-1}$ spins during $t_1$($\omega_1$), magnetization was transferred to the respective $^{13}$C$^\alpha_{i/i-1}$ spin, which was then frequency labeled and detected in quadrature during $t_1$($\omega_1$). Sequential application of G-matrix transformations along $\omega_1$ and $\omega_2$ yielded four basic spectra which can be grouped into two sets, B1 and B2, comprising peaks at $\Omega_0$($^{15}$N$_i$)±$\Omega_1$($^{13}$C$^\alpha_i$) along $\omega_2$. B1 and B2 each contained 2 basic spectra comprising peaks at $\omega_0$($^{13}$C$^\alpha_i$)±$\Omega_1$($^{13}$C$^{\alpha/\beta}_i$) and $\Omega_0$($^{13}$C$^\alpha_{i-1}$)±$\Omega_1$($^{13}$C$^{\alpha/\beta}_{i-1}$) along $\omega_1$. Such a peak pattern is illustrated in FIG. 16.

In G²FT (5,3)D HN{N(CO)C$^\alpha$}{C$^{\alpha\beta}$C$^\alpha$}, after independent frequency labeling of $^{13}$C$^\alpha_{i-1}$ and $^{13}$C$^\beta_{i-1}$ spins during $t_1$($\omega_1$), magnetization was transferred to the respective $^{13}$C$^\alpha_{i-1}$ spin, which was then frequency labeled and detected in quadrature during $t_1$($\omega_1$). Subsequently, $^{13}$C$^\alpha_{i-1}$ was frequency labeled in conjunction with $^{15}$N$_i$ during $t_2$($\omega_2$). Sequential application of G-matrix transformations along $\omega_1$ and $\omega_2$ yielded four basic spectra which can be grouped into two sets, B1 and B2, comprising peaks at $\Omega_0$($^{15}$N$_i$)±$\Omega_1$($^{13}$C$^\alpha_{i-1}$) along $\omega_2$. B1 and B2 each contained 2 basic spectra comprising peaks at $\Omega_0$($^{13}$C$^\alpha_{i-1}$)±$\Omega_1$($^{13}$C$^{\alpha/\beta}_{i-1}$) along $\omega_1$. Such a peak pattern is illustrated in FIG. 17.

Example 3

G²FT (5,3)D HN{N,CO}{C$^\alpha$H$^\alpha$} and G²FT (5,3)D {H$^\alpha$C$^\alpha$}{CON}HN NMR Experiments G²FT (5,3)D HN{N,CO}{C$^\alpha$H$^\alpha$} (FIG. 18; measurement time 16 hrs.; peak detection yield: 100%) and G²FT (5,3)D {H$^\alpha$C$^\alpha$}{CON}HN (FIG. 19; 13 hrs.; 100%) were recorded for 8 kDa protein Z-domain (Tashiro et al., *J. Mol. Biol.* 272:573-590 (1997), which is hereby incorporated by reference in its entirety), which allowed $^{13}$C'$_{i-1}$, $^{15}$N$_i$, $^1$H$^N_i$-resolved sequential assignment based on $\Omega$($^{13}$C$^\alpha$) and $\Omega$($^1$H$^\alpha$) (FIG. 20).

In G²FT (5,3)D HN{N,CO}{C$^\alpha$H$^\alpha$}, magnetization from $^{15}$N nucleus of residue i was simultaneously transferred to $^{13}$C' of residue i−1 and the $^{13}$C$^\alpha$ of residues i/i−1. Subsequently, $^{13}$C'$_{i-1}$ was frequency labeled jointly with $^{15}$N$_i$ during $t_2$($\omega_2$) with the latter detected in quadrature. $^{13}$C$^\alpha_{i/i-1}$ and $^1$H$^\alpha_{i/i-1}$ spins were jointly sampled during $t_1$($\omega_1$) with $^{13}$C$^\alpha$ being detected in quadrature. Sequential application of G-matrix transformations along $\omega_1$ and $\omega_2$ yielded four basic spectra which can be grouped into two sets, B1 and B2, comprising peaks at $\Omega_0$($^{15}$N$_i$)±$\Omega_1$($^{13}$C'$_{i-1}$) along $\omega_2$. B1 and B2 each contained 2 basic spectra comprising peaks at $\Omega_0$($^{13}$C$^\alpha_i$)±$\Omega_1$($^1$H$^\alpha_i$) and $\Omega_0$($^{13}$C$^\alpha_{i-1}$)±$\Omega_1$($^1$H$^\alpha_{i-1}$) along $\omega^1$. Such a peak pattern is illustrated in FIG. 21. Using the principle discussed above, the first order central peak spectra comprising peaks at $\Omega_0$($^{13}$C$^\alpha_i$) along $\omega_1$ was obtained using (4,3)D HN{N,CO}{C$^\alpha$}. In this experiment, the transfer of magnetization from $^{13}$C$^\alpha_{i/i-1}$ to $^1$H$^\alpha_{i/i-1}$ and back was omitted. The r.f. pulse scheme for (4,3)D HN{N,CO}{C$^\alpha$} is shown in FIG. 22.

In G²FT (5,3)D {H$^\alpha$C$^\alpha$}{CON}HN, $^1$H$^\alpha_{i-1}$ and $^{13}$C$^\alpha_{i-1}$ spins were jointly sampled during $t_1$($\omega_1$), with the latter being detected in quadrature. Subsequently, magnetization was transferred to $^{13}$C'$_{i-1}$ which was frequency labeled jointly with $^{15}$N$_i$ during $t_2$($\omega_2$). Sequential application of G-matrix transformations along $\omega_1$ and $\omega_2$ yielded four basic spectra which can be grouped into two sets, B1 and B2, comprising peaks at $\Omega_0$($^{15}$N$_i$)±$\Omega_1$($^{13}$C'$_{i-1}$) along $\omega_2$. B1 and B2 each contained 2 basic spectra comprising peaks at $\Omega_0$($^{13}$C$^\alpha_{i-1}$)±$\Omega_1$($^1$H$^\alpha_{i-1}$) along $\omega_1$. Such a peak pattern is illustrated in FIG. 23. The two first order central peak spectra can be obtained either by omission of $^1$H$^\alpha_{i-1}$ frequency labeling along $\omega_1$ or by using $^{13}$C steady-state magnetization.

Example 4

G²FT (6,3)D {H$^{\alpha\beta}$C$^{\alpha\beta}$C$^\alpha$}{CON}HN NMR Experiment Having obtained the chemical shifts of $^{13}$C$^{\alpha/\beta}$ spins for a given amino acid residue using the G²FT (5,3)D HN{N,CO}{C$^{\alpha\beta}$C$^\alpha$}, G²FT (5,3)D HN{NCO}{C$^{\alpha\beta}$C$^\alpha$}, G²FT (5,3)D HN{NC$^\alpha$}{C$^{\alpha\beta}$C$^\alpha$}, and G²FT (5,3)D HN{N(CO)C$^\alpha$}{C$^{\alpha\beta}$C$^\alpha$} NMR experiments, G²FT (6,3)D {H$^{\alpha\beta}$C$^{\alpha\beta}$C$^\alpha$}{CON}HN (FIGS. 24 and 25; 24 hrs.; 100%) was recorded for 9 kDa protein ubiquitin, which allowed the assignment of $^1$H$^{\alpha\beta}$.

In G²FT (6,3)D {H$^{\alpha\beta}$C$^{\alpha\beta}$C$^\alpha$}{CON}HN, frequency labeling of the $^1$H$^{\alpha/\beta}_{i-1}$ spin was carried out simultaneously with that of $^{13}$C$^{\alpha/\beta}_{i-1}$ and $^{13}$C$^\alpha_{i-1}$ spins. Subsequently, $^{13}$C'$_{i-1}$ was frequency labeled in conjunction with $^{15}$N$_i$ during $t_2$($\omega_2$). Sequential application of G-matrix transformations along $\omega_1$ and $\omega_2$ yielded eight basic spectra which can be grouped into two sets, B1 and B2, comprising peaks at $\Omega_0$($^{15}$N$_i$)±$\Omega_1$($^{13}$C'$_{i-1}$) along $\omega_2$. B1 and B2 each contained 4 basic spectra comprising peaks at $\Omega_0$($^{13}$C$^\alpha_{i-1}$)±$\Omega_1$($^{13}$C$^{\alpha/\beta}_{i-1}$)±$\Omega_2$($^1$H$^{\alpha/\beta}_{i-1}$) along $\omega_1$. The four first order central peak spectra were identical to the spectra from the above-described G²FT (5,3)D HN{NCO}{C$^{\alpha\beta}$C$^\alpha$} and were obtained either by omission of $^1$H$^{\alpha/\beta}_{i-1}$ frequency labeling along a), or by using $^{13}$C steady-state magnetization.

Example 5

GFT (5,3)D HC(C)C—CH NMR Experiment

As was shown for (4,3)D GFT congeners (Atreya et al., *Proc. Natl. Acad. Sci. USA* 101:9642-9647 (2004), which is hereby incorporated by reference in its entirety), $C^{\alpha\beta}C^{\alpha}$-type $G^2FT$ experiments can be combined with a GFT (5,3)D HC(C)C—CH NMR experiment for aliphatic side chain assignment. The peak patterns observed in a GFT (5,3)D HC(C)C—CH NMR experiment are illustrated in FIG. 26 and the r.f. pulse scheme for that experiment is shown in FIG. 27. Acquisition parameters for the GFT (5,3)D HC(C)C—CH NM experiment are shown in Table 2. $^{13}$C steady-state magnetization was used to obtain the two first order central peak spectra. The GFT (5,3)D HC(C)C—CH NMR experiment can also be used for assigning backbone sugar resonances in $^{13}$C-labeled oligonucleotides by tuning the constant time delay to a value suited for transferring magnetization between $^{13}$C-spins in nucleic acids.

TABLE 2

Acquisition Parameters for the GFT (5,3)D HC(C)C—CH NMR Experiment Recorded for 14 kDa Protein PfR13

| | GFT (5,3)D HC(C)C—CH |
|---|---|
| $^1$H resonance frequency | 750 MHz |
| No. of Points ($t_1$, $t_2$, $t_3$) Collected: | 140, 24, 512 |
| After LP: | 140, 24, 512 |
| After zero filling: | 512, 64, 1024 |
| Window functions: | sine 70/70/70 |
| No. of transients: | 2 |
| Spectral width ($\omega_1$, $\omega_2$, $\omega_3$; Hz) | 26000, 5600, 8000 |
| $t_{max}$ (ms) | 5.5, 4.2, 64.0 |
| Carrier Position ($\omega_1$, $\omega_2$, $\omega_3$; ppm) | 43/0.0, 43.0, 4.78 |
| Recycle delay(s) | 0.4 |
| Collection time (hrs) | 28.0 |

Example 6

Figure 28:
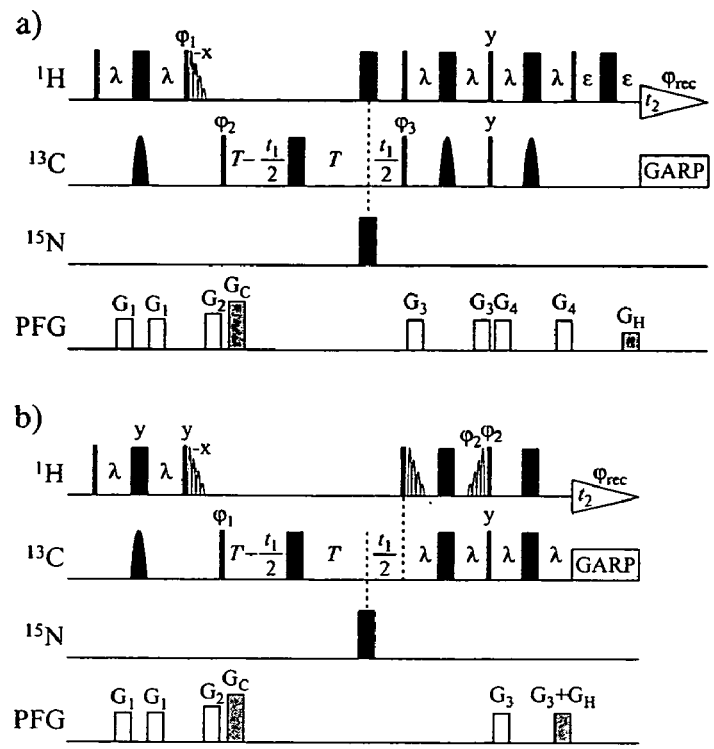
Figure 30:
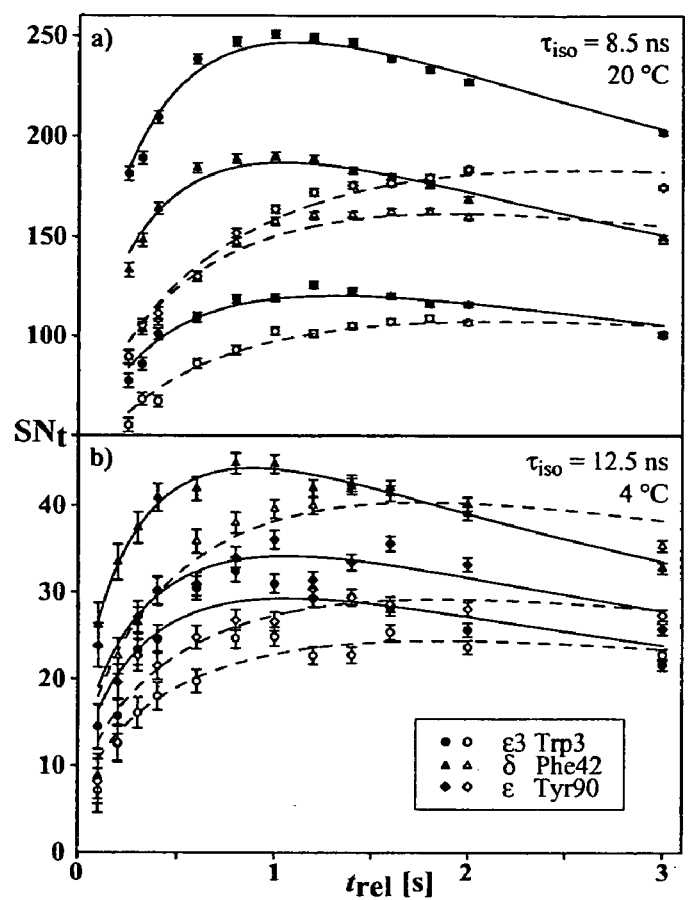

Longitudinal Proton Relaxation (L-) Optimization for $^1$H$^{aromatic}$—$^{13}$C$^{aromatic}$ Correlation Spectroscopy Explored by Use of 2D [$^{13}$C, $^1$H]-HSQC/TROSY $^1$H$^{aromatic}$ L-optimization was explored for a sample of a Northeast Structural Genomics Consortium (NESG) target protein PfR13 (14 kDa) at $^1$H resonance frequency of 750 MHz. Two series of experiments (with and without) L-optimization, L- and non-L-ct 2D [$^{13}$C, $^1$H]-HSQC/TROSY, were performed at 20° C. and 4° C., using pulsed field gradient (PFG)-preservation of equivalent pathways (PEP) sensitivity-enhanced (Cavanagh et al., *Protein NMR Spectroscopy: Principles and Practice* Academic Press: San Diego (1996), which is hereby incorporated by reference in its entirety) 2D [$^{13}$C, $^1$H]-HSQC and 2D [$^{13}$C, $^1$H]-TROSY r.f. pulse schemes (FIG. 28). (PFG-PEP is recommended for all but very large proteins; sensitivity is enhanced up to $\tau_{iso} \sim 35$ ns (FIG. 29) with excellent water suppression. TROSY is generally preferred in 2D ct [$^{13}$C, $^1$H]-spectroscopy since sensitivity can be enhanced by using $^{13}$C$^{aromatic}$ polarization (Pervushin et al., *J. Am. Chem. Soc.* 120:6394-6400 (1998), which is hereby incorporated by reference in its entirety). See Example 7.) The following $t_{rel}$ values were used at 4° C.: 0.1, 0.2, 0.3, 0.4, 0.6, 0.8, 1.0, 1.2, 1.4, 1.6, 2.0, and 3.0 s, and at 20° C.: 0.25, 0.32, 0.4, 0.6, 0.8, 1.0, 1.2, 1.4, 1.6, 2.0, and 3.0 s. HSQC spectra were recorded at 20° C. with varying relaxation delay between scans, where the approximate isotropic correlation time for overall tumbling of PfR13, $\tau_{iso}$, is 8.5 ns. TROSY spectra with suppression of signal contributions from $^{13}$C$^{aromatic}$ polarization were acquired at 4° C., where $\tau_{iso}$=12.5 ns. Signal-to-noise (S/N) ratios were measured as a function of the relaxation delay between scans, $t_{rel}$, and divided by the square-root of the measurement time, $t_{tot}$, thus yielding SN$_t$, a measure for intrinsic sensitivity. A least-squares fit of $$SN_t = A \frac{1 - \exp(-R_1(t_{rel} + t_{acq}))}{\sqrt{t_{rel} + t_{acq} + t_{seq}}} \quad (1)$$

to the experimental SN$_t$ values yielded $t_{rel}^{opt}$ at which, for a given proton, intrinsic sensitivity was maximal (Tables 3, 4, and 5). $t_{acq}$ and $t_{seq}$ represent the acquisition time and length of the pulsing period, respectively, while scaling factor A and effective longitudinal relaxation rate R$_1$ are fitted. Twenty two and twenty well-resolved cross-peaks were considered from the 20° C. and 4° C. spectra, respectively. Representative experimental data and fitted curves are shown in FIG. 30, and Tables 3 and 4 afford a listing of parameters for each of the analyzed $^1$H$^{aromatic}$ spins. Moreover, Table 5 provides a survey of parameters averaged according to residue type. Analysis of resolved peaks (Tables 3 and 4) revealed that at 20° C. (4° C.) (i) the average $t_{rel}^{opt}$=1.9 s (1.8 s) without is longer than the average $t_{rel}^{opt}$=1.1 s (1.0 s) with L-optimization, and (ii) the average gain in intrinsic sensitivity arising at $t_{rel}^{opt}$ due to L-optimization (FIG. 30) is ~20% (~15%). For the L-optimized experiment acquired at $t_{rel}^{match}$~0.4-0.6 s, intrinsic sensitivity matches the one of the non-L congener at its $t_{rel}^{opt}$, that is, L-optimization allows one to reach the maximum sensitivity achieved without L-optimization at about 4-fold increased sampling speed.

TABLE 3

Comparison of 2D [$^{13}$C, $^1$H]-HSQC Acquired for PfR13 at 20° C. with and without L-optimization

| Residue No. | Res. Type | Atom Type | Without L-optimization ||||| With L-optimization |||||| Ratio$^c$ of SN$_t$ at $t_{rel}^{opt}$ |
|---|---|---|---|---|---|---|---|---|---|---|---|---|---|
| | | | A | R$_1$ [s$^{-1}$] | $t_{rel}^{opt}$ [s] | SN$_t^a$ at $t_{rel}^{opt}$ | A | R$_1$ [s$^{-1}$] | $t_{rel}^{opt}$ [s] | SN$_t^a$ at $t_{rel}^{opt}$ | $t_{rel}^{match}$ [s]$^b$ | |
| 3 | Trp | H$^{\delta 1}$ | 334 ± 28 | 0.5 ± 0.06 | 2.6 | 146 | 259 ± 8 | 1.0 ± 0.06 | 1.3 | 162 | 0.5 | 1.10 |
| 3 | Trp | H$^{\epsilon 3}$ | 223 ± 11 | 0.6 ± 0.04 | 2.2 | 107 | 197 ± 6 | 0.9 ± 0.05 | 1.3 | 120 | 0.5 | 1.10 |
| 3 | Trp | H$^{\eta 2}$ | 272 ± 11 | 0.6 ± 0.04 | 2.1 | 133 | 240 ± 7 | 0.9 ± 0.05 | 1.4 | 145 | 0.6 | 1.10 |
| 3 | Trp | H$^{\zeta 2}$ | 303 ± 23 | 0.5 ± 0.06 | 2.4 | 139 | 251 ± 6 | 1.0 ± 0.04 | 1.2 | 160 | 0.5 | 1.15 |
| 3 | Trp | H$^{\zeta 3}$ | 393 ± 21 | 0.5 ± 0.04 | 2.4 | 181 | 344 ± 16 | 0.8 ± 0.06 | 1.5 | 193 | 0.8 | 1.05 |
| 11 | Phe | H$^{\delta}$ | 857 ± 6 | 0.9 ± 0.01 | 1.4 | 505 | 839 ± 10 | 1.3 ± 0.03 | 1.0 | 590 | 0.3 | 1.15 |
| 11 | Phe | H$^{\epsilon}$ | 1014 ± 6 | 0.9 ± 0.01 | 1.4 | 602 | 942 ± 13 | 1.2 ± 0.03 | 1.0 | 655 | 0.5 | 1.10 |
| 11 | Phe | H$^{\zeta}$ | 249 ± 8 | 0.8 ± 0.05 | 1.5 | 144 | 244 ± 6 | 1.2 ± 0.05 | 1.1 | 164 | 0.4 | 1.15 |

TABLE 3-continued

Comparison of 2D [$^{13}$C, $^{1}$H]-HSQC Acquired for PfR13 at 20° C. with and without L-optimization

| Residue No. | Res. Type | Atom Type | Without L-optimization | | | | With L-optimization | | | | $t_{rel}^{match}$ [s][b] | Ratio[c] of $SN_t$ at $t_{rel}^{opt}$ |
|---|---|---|---|---|---|---|---|---|---|---|---|---|
| | | | A | $R_1$ [s$^{-1}$] | $t_{rel}^{opt}$ [s] | $SN_t^a$ at $t_{rel}^{opt}$ | A | $R_1$ [s$^{-1}$] | $t_{rel}^{opt}$ [s] | $SN_t^a$ at $t_{rel}^{opt}$ | | |
| 21 | Tyr | H$^\delta$ | 110 ± 7 | 0.7 ± 0.06 | 1.8 | 58 | 104 ± 3 | 1.3 ± 0.08 | 1.0 | 73 | 0.3 | 1.25 |
| 21 | Tyr | H$^\epsilon$ | 477 ± 4 | 0.8 ± 0.01 | 1.6 | 264 | 472 ± 3 | 1.5 ± 0.02 | 0.9 | 355 | 0.2 | 1.35 |
| 42 | Phe | H$^\delta$ | 317 ± 13 | 0.7 ± 0.04 | 1.9 | 161 | 273 ± 5 | 1.2 ± 0.04 | 1.0 | 187 | 0.4 | 1.15 |
| 42 | Phe | H$^\epsilon$ | 232 ± 3 | 0.9 ± 0.02 | 1.4 | 138 | 220 ± 3 | 1.1 ± 0.03 | 1.1 | 147 | 0.6 | 1.05 |
| 60 | Phe | H$^\epsilon$ | 82 ± 6 | 0.6 ± 0.06 | 2.3 | 38 | 84 ± 6 | 0.8 ± 0.08 | 1.6 | 47 | 0.5 | 1.20 |
| 86 | Tyr | H$^\epsilon$ | 467 ± 4 | 0.7 ± 0.01 | 1.7 | 254 | 466 ± 3 | 1.4 ± 0.02 | 0.9 | 346 | 0.2 | 1.35 |
| 89 | Phe | H$^\delta$ | 186 ± 10 | 0.7 ± 0.05 | 1.9 | 95 | 173 ± 3 | 1.4 ± 0.06 | 0.9 | 128 | 0.2 | 1.35 |
| 89 | Phe | H$^\zeta$ | 79 ± 4 | 0.9 ± 0.07 | 1.4 | 47 | 84 ± 3 | 1.1 ± 0.06 | 1.2 | 54 | 0.4 | 1.15 |
| 90 | Tyr | H$^\delta$ | 442 ± 17 | 0.5 ± 0.03 | 2.4 | 203 | 397 ± 10 | 0.9 ± 0.04 | 1.3 | 240 | 0.5 | 1.20 |
| 90 | Tyr | H$^\epsilon$ | 415 ± 20 | 0.5 ± 0.03 | 2.6 | 183 | 370 ± 5 | 1.1 ± 0.03 | 1.1 | 247 | 0.2 | 1.35 |
| 98 | Tyr | H$^\delta$ | 924 ± 32 | 0.7 ± 0.04 | 1.9 | 474 | 874 ± 14 | 1.1 ± 0.04 | 1.1 | 580 | 0.3 | 1.20 |
| 98 | Tyr | H$^\epsilon$ | 1630 ± 41 | 0.7 ± 0.03 | 1.8 | 867 | 1667 ± 23 | 1.3 ± 0.03 | 1.00 | 1164 | 0.2 | 1.35 |
| 110 | Tyr | H$^\delta$ | 3371 ± 12 | 1.1 ± 0.01 | 1.1 | 2256 | 3316 ± 31 | 1.4 ± 0.03 | 0.9 | 2455 | 0.4 | 1.10 |
| 110 | Tyr | H$^\epsilon$ | 3746 ± 11 | 1.2 ± 0.01 | 1.1 | 2524 | 4009 ± 48 | 1.3 ± 0.03 | 0.9 | 2882 | 0.4 | 1.15 |

[a]The standard deviation of the noise of the spectra (assumed to be "white") was scaled to (an arbitrarily chosen) level of 100. Then, the peak height was taken and divided by the square-root of the measurement time (in seconds).
[b]$t_{rel}$ at which $SN_t$ in spectra acquired with L-optimization matches the maximum $SN_t$ at $t_{rel}^{opt}$ in spectra acquired without L-optimization.
[c]Ratio of $SN_t$ in L-optimized HSQC over that in HSQC without L-optimization at respective $t_{rel}^{opt}$.

TABLE 4

Comparison of 2D [$^{13}$C, $^{1}$H]-TROSY Acquired for PfR13 at 4° C. with and without L-optimization

| Residue No. | Res. | Atom Type | Without L-optimization | | | | With L-optimization | | | | $t_{rel}^{match}$ [s][b] | Ratio[c] of $SN_t$ at $t_{rel}^{opt}$ |
|---|---|---|---|---|---|---|---|---|---|---|---|---|
| | | | A | $R_1$ [s$^{-1}$] | $t_{rel}^{opt}$ [s] | $SN_t^a$ at $t_{rel}^{opt}$ | A | $R_1$ [s$^{-1}$] | $t_{rel}^{opt}$ [s] | $SN_t^a$ at $t_{rel}^{opt}$ | | |
| 3 | Trp | H$^{\delta1}$ | 36 ± 3 | 0.7 ± 0.09 | 1.8 | 19 | 27 ± 3 | 1.4 ± 0.22 | 0.9 | 20 | 0.5 | 1.05 |
| 3 | Trp | H$^{\epsilon3}$ | 47 ± 4 | 0.7 ± 0.09 | 1.9 | 24 | 43 ± 3 | 1.2 ± 0.14 | 1.1 | 29 | 0.4 | 1.20 |
| 3 | Trp | H$^{\eta2}$ | 59 ± 9 | 0.6 ± 0.14 | 2.1 | 29 | 52 ± 3 | 0.9 ± 0.09 | 1.4 | 31 | 0.7 | 1.05 |
| 3 | Trp | H$^{\zeta2}$ | 48 ± 3 | 0.7 ± 0.07 | 1.8 | 26 | 51 ± 4 | 0.9 ± 0.11 | 1.4 | 31 | 0.5 | 1.20 |
| 3 | Trp | H$^{\zeta3}$ | 80 ± 9 | 0.6 ± 0.10 | 2.0 | 40 | 70 ± 3 | 0.9 ± 0.07 | 1.3 | 43 | 0.7 | 1.10 |
| 11 | Phe | H$^\epsilon$ | 239 ± 9 | 0.8 ± 0.05 | 1.5 | 138 | 229 ± 5 | 1.3 ± 0.05 | 1.0 | 162 | 0.3 | 1.20 |
| 27 | Tyr | H$^\epsilon$ | 100 ± 4 | 0.9 ± 0.06 | 1.4 | 60 | 81 ± 1 | 1.6 ± 0.04 | 0.8 | 64 | 0.4 | 1.05 |
| 42 | Phe | H$^\delta$ | 76 ± 8 | 0.7 ± 0.11 | 1.8 | 40 | 60 ± 1 | 1.4 ± 0.04 | 0.9 | 44 | 0.4 | 1.10 |
| 42 | Phe | H$^\epsilon$ | 96 ± 6 | 0.7 ± 0.07 | 1.7 | 52 | 82 ± 5 | 1.1 ± 0.13 | 1.2 | 54 | 0.8 | 1.05 |
| 57 | Tyr | H$^\epsilon$ | 61 ± 4 | 0.9 ± 0.09 | 1.5 | 36 | 50 ± 1 | 1.6 ± 0.08 | 0.8 | 39 | 0.3 | 1.10 |
| 86 | Tyr | H$^\epsilon$ | 53 ± 2 | 0.8 ± 0.06 | 1.6 | 30 | 37 ± 2 | 1.9 ± 0.18 | 0.7 | 31 | 0.4 | 1.05 |
| 89 | Phe | H$^\delta$ | 29 ± 3 | 0.8 ± 0.15 | 1.5 | 17 | 25 ± 1 | 1.8 ± 0.17 | 0.7 | 21 | 0.2 | 1.25 |
| 89 | Phe | H$^\epsilon$ | 82 ± 10 | 0.7 ± 0.12 | 1.8 | 42 | 81 ± 4 | 1.1 ± 0.09 | 1.1 | 53 | 0.3 | 1.25 |
| 89 | Phe | H$^\zeta$ | 45 ± 3 | 0.8 ± 0.08 | 1.7 | 25 | 44 ± 3 | 0.9 ± 0.10 | 1.4 | 27 | 0.7 | 1.05 |
| 90 | Tyr | H$^\delta$ | 57 ± 10 | 0.5 ± 0.11 | 2.6 | 25 | 45 ± 2 | 1.1 ± 0.07 | 1.2 | 29 | 0.4 | 1.15 |
| 90 | Tyr | H$^\epsilon$ | 57 ± 6 | 0.7 ± 0.11 | 1.9 | 29 | 50 ± 3 | 1.2 ± 0.13 | 1.1 | 34 | 0.4 | 1.15 |
| 98 | Tyr | H$^\delta$ | 197 ± 14 | 0.7 ± 0.08 | 1.8 | 103 | 192 ± 5 | 1.1 ± 0.05 | 1.1 | 127 | 0.3 | 1.25 |
| 98 | Tyr | H$^\epsilon$ | 325 ± 16 | 0.7 ± 0.06 | 1.7 | 176 | 289 ± 6 | 1.3 ± 0.05 | 0.9 | 207 | 0.3 | 1.15 |
| 110 | Tyr | H$^\delta$ | 838 ± 47 | 0.9 ± 0.08 | 1.5 | 486 | 784 ± 30 | 1.2 ± 0.09 | 1.0 | 543 | 0.4 | 1.10 |
| 110 | Tyr | H$^\epsilon$ | 767 ± 25 | 0.9 ± 0.05 | 1.3 | 471 | 718 ± 17 | 1.4 ± 0.06 | 0.9 | 526 | 0.4 | 1.10 |

[a]The standard deviation of the noise of the spectra (assumed to be "white") was scaled to (an arbitrarily chosen) level of 100. Then, the peak height was taken and divided by the square-root of the measurement time (in seconds).
[b]$t_{rel}$ at which $SN_t$ in spectra acquired with L-optimization matches the maximum $SN_t$ at $t_{rel}^{opt}$ in spectra acquired without L-optimization.
[c]Ratio of $SN_t$ in L-optimized HSQC over that in HSQC without L-optimization at respective $t_{rel}^{opt}$.

TABLE 5

Parameters Averaged According to Residue Type

| Temp [° C.] | Residue Type | Without L-optimization $t_{rel}^{opt}$ [s] | With L-optimization $t_{rel}^{opt}$ [s] | $t_{rel}^{match}$ [s][a] | Ratio of $SN_t$ at $t_{rel}^{opt}$ |
|---|---|---|---|---|---|
| 20 | All[b] | 1.9 ± 0.4 | 1.2 ± 0.2 | 0.4 ± 0.2 | 1.20 ± 0.10 |
| | Phe | 1.7 ± 0.3 | 1.1 ± 0.2 | 0.4 ± 0.1 | 1.15 ± 0.09 |
| | Trp | 2.3 ± 0.2 | 1.4 ± 0.1 | 0.6 ± 0.1 | 1.10 ± 0.03 |
| | Tyr[b] | 2.0 ± 0.4 | 1.0 ± 0.2 | 0.3 ± 0.1 | 1.30 ± 0.07 |
| 4 | All[b] | 1.8 ± 0.3 | 1.1 ± 0.2 | 0.4 ± 0.2 | 1.15 ± 0.07 |
| | Phe | 1.7 ± 0.1 | 1.0 ± 0.2 | 0.5 ± 0.1 | 1.15 ± 0.09 |
| | Trp | 1.9 ± 0.1 | 1.2 ± 0.2 | 0.5 ± 0.2 | 1.10 ± 0.07 |
| | Tyr[b] | 1.8 ± 0.4 | 0.9 ± 0.2 | 0.4 ± 0.04 | 1.15 ± 0.07 |

[a]$t_{rel}$ at which $SN_t$ in spectra acquired with L-optimization matches the maximum $SN_t$ at $t_{rel}^{opt}$ in spectra acquired without L-optimization.
[b]The C-terminal residue Tyr 110 was excluded.

Example 7

Analysis of PFG-PEP and TROSY Based Sensitivity Enhancement

To assess the role of PFG-PEP and TROSY for sensitivity enhancement in $^1H^{aromatic}$—$^{13}C^{aromatic}$ correlation spectroscopy, theoretical calculations of nuclear spin relaxation rates were performed using semi-classical relaxation theory (Abragam, *Principles of Nuclear Magnetism* Oxford University Press: New York (1961), which is hereby incorporated by reference in its entirety).

Rates were estimated for a Phe $CH^{\epsilon/\zeta}$ moiety with bond lengths $r_{CH}$=1.38 Å and $r_{CC}$=1.09 Å (Weast, *CRC Handbook of Chemistry and Physics* CRC Press: Boca Raton, Fla. (1988), which is hereby incorporated by reference in its entirety), where $^1H^{aromatic}$ is dipolar coupled to two vicinal protons at $r_{HH}$=2.47 Å. The influence of "remotely located" protons was estimated by considering the NMR structure of PfR13 (PDB code: 1S04). On average, 15 remote protons were located within a sphere of 5 Å radius around $^1H^{aromatic}$, and "$<r^{-6}>$-averaging" revealed $<r_{HH}>$=3.1 Å. For chemical shift anisotropy (CSA) relaxation, the principal components of the CSA tensor of $^{13}C^{aromatic}$ were assumed to be (Veeman, *Prog. NMR Spectrosc.* 16:193-235 (1984), which is hereby incorporated by reference in its entirety): $\sigma_{11}$=255 ppm, $\sigma_{22}$=149 ppm, and $\sigma_{33}$=15 ppm.

For the calculations, the rigid-body approximation was used (Cavanagh et al., *Protein NMR Spectroscopy: Principles and Practice* Academic Press: San Diego (1996), which is hereby incorporated by reference in its entirety), that is, internal motional modes were neglected, and rates were obtained using the equations listed in Tables 5.5 and 5.7 of Cavanagh et al., *Protein NMR Spectroscopy: Principles and Practice* Academic Press: San Diego (1996), which is hereby incorporated by reference in its entirety, and equations from Pervushin et al., *J. Am. Chem. Soc.* 120:6394-6400 (1998), which is hereby incorporated by reference in its entirety:

$$R_2^C = \frac{1}{18}(\gamma_C B_0 \Delta\sigma_C)^2 \{J(0) + 3J(\omega_C)\} + \frac{1}{8}\left(\frac{\mu_0}{4\pi}\frac{\hbar\gamma_H\gamma_C}{r_{CH}^3}\right)^2 \quad (12)$$

$$\{4J(0) + J(\omega_H - \omega_C) + 3J(\omega_C) + 3J(\omega_H) + 6J(\omega_H + \omega_C)\}$$

$$R_2^{C,TROSY} = \frac{1}{18}(\gamma_C B_0 \Delta\sigma_C)^2 \{J(\omega_C) + 2J(2\omega_C)\} + \frac{1}{8}\left(\frac{\mu_0}{4\pi}\frac{\hbar\gamma_H\gamma_C}{r_{CH}^3}\right)^2 \quad (13)$$

$$\{4J(0) + J(\omega_H - \omega_C) + 3J(\omega_C) + 3J(\omega_H) + 6J(\omega_H + \omega_C)\} -$$

$$\frac{1}{12}(\gamma_C B_0 (\sigma_{33} + \sigma_{22} - 2\sigma_{11}))\left(\frac{\mu_0}{4\pi}\frac{\hbar\gamma_H\gamma_C}{r_{CH}^3}\right)\{4J(0) + 3J(\omega_C)\}$$

$$R_2^H = \frac{1}{8}\left(\frac{\mu_0}{4\pi}\frac{\hbar\gamma_H\gamma_C}{r_{CH}^3}\right)^2 \quad (14)$$

$$\{4J(0) + J(\omega_H - \omega_C) + 3J(\omega_C) + 3J(\omega_H) + 6J(\omega_H + \omega_C)\} +$$

$$\left(2\frac{1}{8}\left(\frac{\mu_0}{4\pi}\frac{\hbar\gamma_H^2}{r_{HH}^3}\right)^2 + 15\frac{1}{8}\left(\frac{\mu_0}{4\pi}\frac{\hbar\gamma_H^2}{<r_{HH}>^3}\right)^2\right)$$

$$\{5J(0) + 6J(\omega_H) + 6J(2\omega_H)\}$$

$$R_2^{MQ} = \frac{1}{18}(\gamma_C B_0 \Delta\sigma_C)^2 \{J(\omega_C) + 2J(2\omega_C)\} + \quad (15)$$

$$\left(2\frac{1}{8}\left(\frac{\mu_0}{4\pi}\frac{\hbar\gamma_H^2}{r_{HH}^3}\right)^2 + 15\frac{1}{8}\left(\frac{\mu_0}{4\pi}\frac{\hbar\gamma_H^2}{<r_{HH}>^3}\right)^2\right)$$

$$\{5J(0) + 6J(\omega_H) + 6J(2\omega_H)\},$$

with $$\Delta\sigma_C = \sqrt{(\sigma_{33} - \sigma_{11})^2 + (\sigma_{22} - \sigma_{11})^2 - (\sigma_{33} - \sigma_{11})(\sigma_{22} - \sigma_{11})}. \quad (16)$$

As expected, the dominant contributions to the $^{13}C^{aromatic}$ single-quantum relaxation rates ($R_2^C$, $R_2^{C,TROSY}$) were (i) $^{13}C^{aromatic}$ CSA and (ii) dipolar coupling to attached $^1H^{aromatic}$. The dominant contributions to $^1H^{aromatic}$ single-quantum relaxation ($R_2^H$) were dipolar couplings to the (i) attached $^{13}C^{aromatic}$, (ii) two vicinal $^1H^{aromatic}$ and (iii) "remote" $^1H$ spins (see above). The dominant contributions to $^1H^{aromatic}$—$^{13}C^{aromatic}$ multiple-quantum relaxation rate ($R_2^{MQ}$) were (i) $^{13}C$ CSA and (ii) dipolar couplings between $^1H^{aromatic}$ and the two vicinal and "remote" $^1H$. In the following, the impact of isotropic overall tumbling characterized by a single correlation time, $\tau_{iso}$, on efficiency of PFG-PEP and TROSY for $CH^{aromatic}$-moieties was assessed.

PFG-PEP

Neglecting transverse nuclear spin relaxation and signal de-phasing due to passive scalar couplings, PFG-PEP (Cavanagh et al., *Protein NMR Spectroscopy: Principles and Practice* Academic Press: San Diego (1996); Kay et al., *J. Am. Chem. Soc.* 114:10663-10665 (1992), which are hereby incorporated by reference in their entirety) increases sensitivity by $\sqrt{2}$ when compared to conventional data acquisition. When considering (i) de-phasing due to $^1J_{CC}$ (~50 Hz) and (ii) transverse relaxation for an isotropically reorienting rigid protein (see equations above), the sensitivity of a PFG-PEP experiment ($I_{SE}$) relative to the conventional experiment ($I_0$) is given by:

$$I_{SE}/I_0 = \sqrt{2} \cdot \left\{\frac{1}{2} + \frac{1}{2}\exp(-R_2^{MQ}\tau)\cos^2(\pi^1 J_{CC}\tau)\right\}\exp(-R_2^H \cdot 2\epsilon), \quad (17)$$

where $2\epsilon$ is the duration of the gradient echo period before the start of signal detection and $\tau$ is the delay for reverse INEPT (FIG. 28). Without PFG-PEP, $\tau$ is tuned for maximal polarization transfer according to $$\tau = \frac{1}{\pi^1 J_{CH}}\arctan\frac{\pi^1 J_{CH}}{R_2^C}, \quad (18)$$

where $^1J_{CH}$=160 Hz represents the one-bond $^{13}C^{aromatic}$—$^1H^{aromatic}$ scalar coupling.

Then, the sensitivity ratio $I_{SE}/I_0$ can be calculated as a function of $\tau_{iso}$ (FIG. 29). The calculations suggested that PFG-PEP yields a sensitivity gain for $\tau_{iso}$ up to ~35 ns (corresponding to ~70 kDa at ambient temperature in aqueous solution), provided that the gradient echo length $2\epsilon$ (FIG. 28) is minimized (e.g., set to 200 µs).

TROSY

For assessment of TROSY, a possible contribution to signals arising from $^{13}C^{aromatic}$ steady-state polarization was neglected (which can be used in GFT-TROSY (4,3)D HCCH for detecting central peaks but not for enhancing signals arising from $^1H$ polarization). The sensitivity gain over the non-TROSY experiment for a constant-time chemical shift evolution period 2T (FIG. 28) is then given by:

$$I_{TROSY}/I_{conv.} = \frac{1}{2} \frac{\exp(-R_2^{C,TROSY} \cdot 2T)}{\exp(-R_2^C \cdot 2T)}. \quad (19)$$

The factor ½ reflects the fact that only one of the two doublet components is selected in TROSY. FIG. 31 shows this ratio as a function of $\tau_{iso}$ for the two typically used values for the constant-time evolution period in HCCH. The calculations predict that TROSY becomes more sensitive at $\tau_{iso}$>23 ns and $\tau_{iso}$>8 ns when using 4.5 ms (¼$J_{CC}$) and 13.5 ms (¾$J_{CC}$) ct evolution periods, respectively (FIG. 31). Hence, non-TROSY was more sensitive with medium-sized proteins at the shorter period (¼$J_{CC}$) sufficient for GFT (4,3)D HCCH (see Example 8).

Example 8

(4,3)D HCCH Experiment: Implementation and Comparison

Exploration of L-optimization with 2D NMR (FIG. 30; Tables 3, 4, and 5) enabled implementation of L-GFT-TROSY (4,3)D HCCH, which is based on highly efficient $^1H^{(1)}(t_1) \rightarrow {}^{13}C^{(1)}(t_1) \rightarrow {}^{13}C^{(2)}(t_2) \rightarrow {}^1H^{(2)}(t_3)$ transfer via large $^1J\{^{13}C^{aromatic} - {}^{13}C^{aromatic}\}$ (~50 Hz) and $^1J\{^1H^{aromatic} - {}^{13}C^{aromatic}\}$ (~160 Hz) couplings. R.f. pulse schemes for L-GFT and L-GFT-TROSY (4,3)D HCCH are provided in FIG. 32.

An $S^3$-filter (Meissner et al., *J. Magn. Reson.* 139:447-450 (1999), which is hereby incorporated by reference in its entirety) was used for suppressing the faster relaxing ("anti-TROSY") component in L-GFT-TROSY (4,3)D HCCH. This filter turned out to be superior in terms of sensitivity when compared with the TROSY implementation of Pervushin et al., *J. Am. Chem. Soc.* 120:6394-6400 (1998), which is hereby incorporated by reference in its entirety. However, the $S^3$-filter led to a slight reduction in TROSY sensitivity enhancement due to partial exchange of the TROSY/anti-TROSY components in every alternate scan (FIG. 32). It is notable that "active" suppression of the anti-TROSY component can be omitted when employing the longer chemical shift evolution periods [e.g., $t_{1,max}(^{13}C/^1H)=13.5$ ms] for large proteins.

A technical comment relates to the line-shapes of peaks in the central peak subspectrum of L-GFT-TROSY which were derived from polarization of quaternary carbons (FIG. 33). For CH$^{aromatic}$-moieties, the two scans allowing cancellation of the anti-TROSY component can be briefly described as:

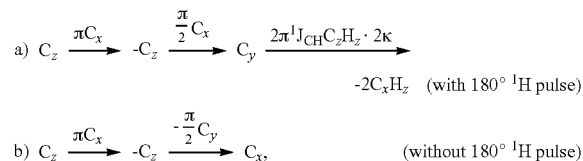

Quaternary carbon spins, however, do not evolve under $^1J_{CH}$ coupling and yield $C_y$ in every odd-numbered transient prior to $t_1(^{13}C)$. Hence, addition of the two scans yields a mixed phase resulting from the superposition of an absorptive and a dispersive signal.

The shifts of $^1H^{(1)}$ and $^{13}C^{(1)}$ were jointly sampled in a GFT dimension. Frequency labeling with the shifts of $^1H^{(1)}$, $^{13}C^{(1)}$ and $^{13}C^{(2)}$ was accomplished within only ~11.6-13.5 ms during polarization transfer. Short maximal evolution times of ~4.5 ms suffice in the GFT dimension since peaks are dispersed over the sum of $^1H^{aromatic}$ and $^{13}C^{aromatic}$ spectral widths (Atreya et al., *Proc. Natl. Acad. Sci. USA.* 101:9642-9647 (2004), which is hereby incorporated by reference in its entirety). At 4.5 ms ct delay, TROSY yielded higher sensitivity only for large proteins ($\tau_{iso}$>23 ns; FIG. 31), but allowed one to use $^{13}C^{(1)}$ polarization (Pervushin et al., *J. Am. Chem. Soc.* 120:6394-6400 (1998), which is hereby incorporated by reference in its entirety) for acquiring central peaks (Kim et al., *J. Am. Chem. Soc.* 125:1385-1393 (2003); Szyperski et al., *J. Am. Chem. Soc.* 118:8146-8147 (1996), which are hereby incorporated by reference in their entirety) without compromising on INEPT delays. (In aliphatic (4,3)D HCCH, central peaks can be derived from $^{13}C$ polarization since INEPT is tuned for CH, CH$_2$, and CH$_3$ groups (Cavanagh et al., *Protein NMR Spectroscopy: Principles and Practice* Academic Press: San Diego (1996), which is hereby incorporated by reference in its entirety). Aromatic spin systems contain only CH and delays are tuned to ½ $^1J$. Hence, $^{13}C$ polarization yields central peaks in aromatic non-TROSY (4,3)D HCCH only if sensitivity of basic spectra is compromised.) These peaks provided (H)CCH information defining centers of peak pairs at $\Omega(^{13}C^{(1)})\pm\Omega(^1H^{(1)})$ in basic spectra.

L-GFT-TROSY (4,3)D HCCH (data set "I") was recorded in 24 h with $t_{rel}$=1 s ($t_{rel}^{opt}$ for PfR13; Table 6) for 21 kDa protein HR41 (FIG. 33; 25° C.; $\tau_{iso}$~11 ns; 95% peak detection yield), an NESGC target for which data collection is sensitivity limited. For sensitivity comparison, L-GFT ("II"), GFT ("III"; $t_{rel}$=1.5 s with pre-saturation of water line), and L-GFT-TROSY with 13.5 ms ct delay (Pervushin et al., *J. Am. Chem. Soc.* 120:6394-6400 (1998); Meissner et al., *J. Magn. Reson.* 139:447-450 (1999), which are hereby incorporated by reference in their entirety) ("IV") were recorded. The relative intrinsic sensitivities of (4,3)D HCCH implementations (Table 6) are summarized in Table 7. The SN$_t$ values were determined for well resolved peaks and their ratios calculated. Table 7 provides the average ratios with standard deviations. The standard deviation for the comparison of L- versus non-L implementation reflects the varying density of non-aromatic protons located around a given $^1H^{aromatic}$. The relative sensitivity for basic spectra was ~2.5:3.8:2.1:1 (Table 7). Thus, at $\tau_{iso}$~11 ns, one has that (i) TROSY is ~20% less sensitive (Theory predicts that at ct delays of 4.5 and 13.5 ms, TROSY becomes more sensitive at $\tau_{iso}$>~23 ns and $\tau_{iso}$>~8 ns, respectively (FIG. 31).) when also taking into account that $^{13}C$ polarization yields central peaks in TROSY, (ii) L-optimization increases sensitivity by ~20-60% (the variation is due to non-uniform $^1H$ density), and (iii) $t_{1,max}(^{13}C^{(1)})$~4.5 ms versus 13.5 ms (often required without GFT) increases TROSY sensitivity ~2.5-fold.

TABLE 6

GFT NMR Data Acquisition and Processing Parameters

| (4,3)D HCCH Experiment | Protein | Indirect dimension: $t_{max}$(ms); Complex points; Digital Resolution [Hz/point]$^a$ | $t_{rel}$ [s] | Total Meas. Time [h] | Peak Detection Yield [%]$^b$ |
|---|---|---|---|---|---|
| L-GFT-TROSY ("I") (2T = 4.5 ms) | HR41 | $\omega_1(^{13}C; {}^{13}C, {}^1H)$: 4.5; 30; 27 $\omega_2(^{13}C)$: 4.5; 20; 70 | 1.0 | 23.3 | 94 (92) |
| L-GFT ("II") | HR41 | $\omega_1(^{13}C; {}^{13}C, {}^1H)$: 4.5; 30; 27 | 1.0 | 17.5 | 95 (97) |

TABLE 6-continued

GFT NMR Data Acquisition and Processing Parameters

| (4,3)D HCCH Experiment | Protein | Indirect dimension: $t_{max}$(ms); Complex points; Digital Resolution [Hz/point][a] | $t_{rel}$ [s] | Total Meas. Time [h] | Peak Detection Yield [%][b] |
|---|---|---|---|---|---|
| GFT ("III") | HR41 | $\omega_2$($^{13}$C): 4.5; 20; 70 $\omega_1$($^{13}$C; $^{13}$C, $^1$H): 4.5; 30; 27 $\omega_2$($^{13}$C): 4.5; 27; 97 | 1.5 | 17.5 | 88 (92) |
| L-GFT-TROSY ("IV") (2T = 13.5 ms) | HR41 | $\omega_1$($^{13}$C; $^{13}$C, $^1$H): 13.5; 90; 27 $\omega_2$($^{13}$C): 4.5; 20; 70 | 1.0 | 35.4 | 73 (70) |
| "previous" GFT ("V")[c] | HR41 | $\omega_1$($^{13}$C; $^{13}$C, $^1$H): 4.5; 30; 27 $\omega_2$($^{13}$C): 4.5; 27; 97 | 1.5 | 11.7[d] | 78[d] |
| GFT | MaR11 | $\omega_1$($^{13}$C; $^{13}$C, $^1$H): 4.5; 21; 19 $\omega_2$($^{13}$C): 4.5; 16; 59 | 0.3 | 0.4 | 87 (89) |
| L-GFT | MaR11 | $\omega_1$($^{13}$C; $^{13}$C, $^1$H): 4.5; 21; 19 $\omega_2$($^{13}$C): 4.5; 16; 59 | 0.3 | 0.4 | 91 (100) |

[a]direct dimension, $\omega_3$($^1$H): 57; 512; 9
[b]basic subspectra (central peak subspectrum)
[c]Shen et al., J. Am. Chem. Soc. 127: 9085-9099 (2005); Liu et al., Proc. Natl. Acad. Sci. USA 102: 10487-10492 (2005), which are hereby incorporated by reference in their entirety
[d]only basic spectra were recorded For GFT (4,3)D HCCH and L-GFT (4,3)D HCCH, two-thirds of the total measurement time is invested for acquiring basic spectra, while one third is required for central peak acquisition (by omitting the $^1$H chemical shift evolution). In TROSY congeners, the entire measurement time is utilized for recording both basic and central peak subspectra simultaneously, with the latter being derived from $^{13}$C steady-state polarization (FIG. 33; Szyperski et al., Proc. Natl. Acad. Sci. USA 99:8009-8014 (2002); Szyperski et al., J. Am. Chem. Soc. 118:8146-8147 (1996), which are hereby incorporated by reference in their entirety). Hence, the $SN_t$ values measured in the L-GFT-TROSY experiments can be multiplied with $\sqrt{1.5}=1.22$ in order to also consider the need to acquire the central peak subspectrum. Then, one has at $\tau_{iso}$~11 ns that TROSY (4.5 ms ct delay) is only ~20% less sensitive than the non-TROSY congener, and one would expect that TROSY becomes more sensitive at $\tau_{iso}$~15-20 ns (see FIG. 31).

Notably, the new L-GFT (4,3)D HCCH experiment (FIG. 32) was ~3 times more sensitive than a hitherto used scheme (Shen et al., J. Am. Chem. Soc. 127:9085-9099 (2005); Liu et al., Proc. Natl. Acad. Sci. U.S.A. 102:10487-10492 (2005), which are hereby incorporated by reference in their entirety) (see grey entries in Table 7).

HR41 contains 6 Phe, 6 Tyr and 6 Trp, and nearly complete aromatic resonance assignment (Liu et al., J. Biomol. NMR 32:261-261 (2005), which is hereby incorporated by reference in its entirety) enabled high-quality NMR structure determination (Shen et al., J. Am. Chem. Soc. 127:9085-9099 (2005); Liu et al., Proc. Natl. Acad. Sci. USA 102:10487-10492 (2005), which are hereby incorporated by reference in their entirety). Correlation of $^{13}$C$^\gamma$ and Tyr $^{13}$C$^\zeta$ shifts with, respectively, $^{13}$C$^\delta$/$^1$H$^\delta$ and Tyr $^{13}$C$^\epsilon$/$^1$H$^\epsilon$ shifts supported assignment of slowly flipping rings; the same C$^\gamma$/C$^\zeta$ shifts were detected on CH$^{\delta/\epsilon}$-moieties belonging to an immobilized ring (FIG. 33).

Nearly complete analysis of $^1$H-linewidths was afforded with (4,3)D HCCH (Tables 8 and 9), which was important to explore flipping of all rings in the protein. Comprehensive investigation of aromatic ring flipping requires (i) resonance

TABLE 7

Relative Sensitivity of Basic Spectra for (4,3)D HCCH Implementations

| Protein | Comparison | SN$_t$ ratio (basic spectra) | | SN$_t$ ratio (central peak spectra) $\Omega$($^{13}$C) (range)[a] |
|---|---|---|---|---|
| | | $\Omega$($^{13}$C) + $\Omega$($^1$H) (range)[a] | $\Omega$($^{13}$C) − $\Omega$($^1$H) (range)[a] | |
| HR41 | L-GFT ("II") versus L-GFT-TROSY ("I") (2T = 4.5 ms) | 1.6 ± 0.2 (1.1-2.2) | 1.5 ± 0.2 (1.1-2.3) | 6.5 ± 1.5 (3-9.5) |
| | L-GFT ("II") versus GFT ("III") | 1.7 ± 0.3 (1.2-2.4) | 1.8 ± 0.3 (1.1-2.8) | 1.9 ± 0.4 (1.3-3.3) |
| | L-GFT-TROSY ("I") (2T = 4.5 ms) versus L-GFT-TROSY("IV") (2T = 13.5 ms) | 2.6 ± 0.8 (1.2-4.9) | 2.5 ± 0.7 (1.5-4.8) | 2.5 ± 0.7 (0.7-4.1) |
| | L-GFT("II") versus "previous" GFT ("V")[b] | 3.0 ± 0.7 (1.4-4.4) | 2.9 ± 0.6 (1.5-4.9) | |
| MaR11 (FIG. 34) | L-GFT versus GFT | 1.3 ± 0.2 (1.0-1.9) | 1.3 ± 0.2 (1.0-1.7) | 1.4 ± 0.3 (1.0-2.0) |

[a]The minimum and maximum ratios of SN$_t$ values are indicated.
[b]Shen et al., J. Am. Chem. Soc. 127: 9085-9099 (2005); Liu et al., Proc. Natl. Acad. Sci. USA 102: 10487-10492 (2005), which are hereby incorporated by reference in their entirety assignment and structure determination, (ii) measurement of (all) $^1$H$^{aromatic}$-linewidths to identify rings for which a more detailed spectroscopic characterization of flipping kinetics is attractive (Wüthrich, NMR of proteins and Nucleic Acids Wiley: New York (1986); Wagner, Q. Rev. Biophys. 16:1-57 (1983); Skalicky et al., J. Am. Chem. Soc. 123:388-397 (2001), which are hereby incorporated by reference in their entirety), (iii) measurement of flipping rate constants, $k_{flip}$, and (iv) determination of activation parameters.

TABLE 8

$^1H^{aromatic}$ Line-Widths of HR41 at 25° C. from 2D [$^{13}$C, $^1$H] TROSY and (4,3)D HCCH

| | | | $^1$H linewidth [Hz] | | |
|---|---|---|---|---|---|
| Residue No. | Residue Type | Atom | 2D [$^{13}$C,$^1$H] TROSY | L-GFT (4,3)D HCCH | Average |
| 28 | Trp | H$^{δ1}$ | 32 | — | 32 |
| 28 | Trp | H$^{ε3}$ | 42 | 40 | 41 |
| 28 | Trp | H$^{η2}$ | 40 | 41 | 41 |
| 28 | Trp | H$^{ζ2}$ | 38 | — | 38 |
| 28 | Trp | H$^{ζ3}$ | — | 42 | 42 |
| 36 | Tyr | H$^δ$ | — | 21 | 21 |
| 36 | Tyr | H$^ε$ | — | 21 | 21 |
| 42 | Tyr | H$^δ$ | — | 35 | 35 |
| 42 | Tyr | H$^ε$ | — | 32 | 32 |
| 53 | Trp | H$^{δ1}$ | 35 | — | 35 |
| 53 | Trp | H$^{η2}$ | 43 | 41 | 42 |
| 53 | Trp | H$^{ζ2}$ | — | 35 | 35 |
| 53 | Trp | H$^{ζ3}$ | — | 39 | 39 |
| 54 | Phe | H$^ε$ | 52 | — | 52 |
| 54 | Phe | H$^ζ$ | 44 | — | 44 |
| 65 | Trp | H$^{δ1}$ | — | <37$^a$ | <37$^a$ |
| 65 | Trp | H$^{η2}$ | — | 39 | 39 |
| 65 | Trp | H$^{ζ2}$ | 38 | 34 | 36 |
| 66 | Phe | H$^δ$ | — | 25 | 25 |
| 66 | Phe | H$^ε$ | 27 | 24 | 25 |
| 66 | Phe | H$^ζ$ | 25 | 26 | 26 |
| 70 | Trp | H$^{δ1}$ | 33 | 39 | 36 |
| 70 | Trp | H$^{ε3}$ | — | 34 | 34 |
| 70 | Trp | H$^{η2}$ | — | 42 | 42 |
| 70 | Trp | H$^{ζ2}$ | — | 33 | 33 |
| 70 | Trp | H$^{ζ3}$ | — | <36$^a$ | <36$^a$ |
| 71 | Tyr | H$^δ$ | — | <29$^a$ | <29$^a$ |
| 71 | Tyr | H$^ε$ | — | <33$^a$ | <33$^a$ |
| 78 | Tyr | H$^ε$ | — | <35$^a$ | <35$^a$ |
| 80 | Phe | H$^δ$ | — | 32 | 32 |
| 80 | Phe | H$^ε$ | 41 | 41 | 41 |
| 80 | Phe | H$^ζ$ | 40 | — | 40 |
| 84 | Phe | H$^δ$ | 39 | 35 | 37 |
| 84 | Phe | H$^ε$ | 44 | 42 | 43 |
| 84 | Phe | H$^ζ$ | 44 | 45 | 45 |
| 90 | Tyr | H$^{δ1}$ | 45 | 34 | 39 |
| 90 | Tyr | H$^δ$ | — | 36 | 36 |
| 90 | Tyr | H$^{ε1}$ | — | 32 | 32 |
| 90 | Tyr | H$^{ε2}$ | 40 | 38 | 39 |
| 110 | Tyr | H$^δ$ | 31 | 27 | 29 |
| 110 | Tyr | H$^ε$ | — | 27 | 27 |
| 121 | Phe | H$^δ$ | — | <42$^a$ | <42$^a$ |
| 121 | Phe | H$^ε$ | — | <42$^a$ | <42$^a$ |
| 121 | Phe | H$^ζ$ | 39 | — | 39 |
| 125 | Trp | H$^{δ1}$ | 34 | 35 | 35 |
| 125 | Trp | H$^{η2}$ | — | <41$^a$ | <41$^a$ |
| 125 | Trp | H$^{ζ2}$ | — | <39$^a$ | <39$^a$ |
| 132 | Phe | H$^δ$ | 36 | 35 | 35 |
| 132 | Phe | H$^ε$ | 37 | 38 | 38 |
| 132 | Phe | H$^ζ$ | 39 | — | 39 |
| 145 | Trp | H$^{δ1}$ | 37 | 36 | 37 |
| 145 | Trp | H$^{ε3}$ | 51 | — | 51 |
| 145 | Trp | H$^{η3}$ | — | <36$^a$ | <36$^a$ |
| 145 | Trp | H$^{ζ2}$ | 43 | 44 | 43 |
| 145 | Trp | H$^{ζ3}$ | — | <48$^a$ | <48$^a$ |
| Completeness | | | 42% | 71% | 85% |

$^a$Upper limit only due to spectral overlap.

TABLE 9

Average $^1H^{aromatic}$-Linewidths of HR41 at 25° C.

| Proton type | $^1$H-linewidths [Hz] |
|---|---|
| All | 36 ± 7 |
| Phe (H$^δ$) | 32 ± 5 |

TABLE 9-continued

Average $^1H^{aromatic}$-Linewidths of HR41 at 25° C.

| Proton type | $^1$H-linewidths [Hz] |
|---|---|
| Phe (H$^ε$, H$^ζ$) | 39 ± 8 |
| Trp (H$^{δ1}$, H$^{ζ2}$) | 36 ± 3 |
| Trp (H$^{ε3}$, H$^{ζ3}$, H$^{η2}$) | 42 ± 4 |
| Tyr (H$^δ$, H$^ε$)$^a$ | 28 ± 6 |
| Tyr 90 (H$^δ$, H$^ε$) | 37 ± 3 |

$^a$Excluding Tyr 90.

For large proteins, measurement of $^1H^{aromatic}$-linewidths (which can provide estimates and/or bounds for flipping rates (Wüthrich, *NMR of Proteins and Nucleic Acids* Wiley: New York (1986); Wagner, *Q. Rev. Biophys.* 16:1-57 (1983); Skalicky et al., *J. Am. Chem. Soc.* 123:388-397 (2001), which are hereby incorporated by reference in their entirety) in ct 2D [$^{13}$C, $^1$H]-HSQC/TROSY can be hampered by spectral overlap and, thus, use of higher-dimensional NMR techniques is required. For 21 kDa HR41, only 42% of the linewidths could be obtained in 2D NMR. In contrast, combining ct 2D [$^{13}$C, $^1$H]-TROSY with (4,3)D HCCH (which allowed one to obtain 71% of the linewidths) yielded a largely complete (85%) analysis (Table 8).

In the slow exchange limit, excess line broadening, $ΔΔν$, provides an estimate for the rate constant (Skalicky et al., *J. Am. Chem. Soc.* 123:388-397 (2001), which is hereby incorporated by reference in its entirety). Comparison of the linewidths measured for Tyr 90 with those registered for the other aromatic protons (Table 9) thus allows one to derive a bound for the flipping rate constant of Tyr 90. With $ΔΔν<~5$ Hz, one obtains $k_{flip}<~π·ΔΔν~15$ s$^{-1}$. Consistently, neglecting a (small) contribution from dipolar interaction, one obtains from the ratio of $^1H^{δ1}$-$^1H^{δ2}$ cross peak and diagonal peak volume ratio in $^{13}C^{aromatic}$-resolved [$^1$H, $^1$H]-NOESY (Shen et al., *J. Am. Chem. Soc.* 127:9085-9099 (2005); Liu et al., *Proc. Natl. Acad. Sci. U.S.A.* 102:10487-10492 (2005), which are hereby incorporated by reference in their entirety) that $k_{flip}$~0.3 s$^{-1}$.

From $^{13}$C-resolved [$^1$H, $^1$H]-NOESY (Cavanagh et al., *Protein NMR Spectroscopy: Principles and Practice* Academic Press: San Diego (1996), which is hereby incorporated by reference in its entirety), $k_{flip}$(Tyr 90)~0.3 s$^{-1}$ reflected a slow motional mode on the seconds time scale, proving the absence of faster large amplitude motions enabling ring flipping. This indicated remarkable rigidity of the sub-structure in which the ring was embedded. Tyr 90 is conserved among ubiquitin-conjugating enzymes E2 (to which HR41 belongs as inferred from structure (Liu et al., *Proc. Natl. Acad. Sci. U.S.A.* 102:10487-10492 (2005), which is hereby incorporated by reference in its entirety)) and is located in spatial proximity to the interface between E2 and the ubiquitin-protein ligase E3 (Huang et al., *Science* 286:1321-1326 (1999); VanDemark et al., *Curr. Opin. Struct. Biol.* 12:822-830 (2002), which are hereby incorporated by reference in their entirety). Hence, the rigidity and/or the slow motional mode might be important for E2-E3 dimerization and, thus, for cellular protein degradation.

L-optimization for rapid data acquisition (FIG. 30) was also exemplified for 13 kDa protein MaR11 (Liu et al., *Proc. Natl. Acad. Sci. USA* 102:10487-10492 (2005), which is hereby incorporated by reference in its entirety) (1 mM; Table 6; FIG. 34), an NESG target for which data collection is sampling limited (With $t_{rel}$=0.3 s, the minimal measurement times of L-4D HCCH and L-GFT (4,2)D HCCH (Atreya et al., *Proc. Natl. Acad. Sci. USA* 101:9642-9647 (2004), which is hereby incorporated by reference in its entirety) were 4.9 hrs and 3 min, respectively.): L-GFT (4,3)D HCCH was acquired with $t_{rel}$=0.3 s in 25 min (Table 6; 94% peak detection yield).

Overall, for proteins up to ~25 kDa, PFG-PEP ct L-2D [$^{13}$C, $^{1}$H]-TROSY and L-GFT (4,3)D HCCH were most sensitive, while the TROSY congener was attractive for large proteins and slowly flipping (nearly stalled) rings, which are unique reporters of slow protein dynamics (Wüthrich, *NMR of proteins and Nucleic Acids* Wiley: NewYork, (1986); Wagner, *Q. Rev. Biophys.* 16:1-57 (1983); Skalicky et al., *J. Am. Chem. Soc.* 123:388-397 (2001), which are hereby incorporated by reference in their entirety). Aromatic L-optimization includes "flip-back" of $^{1}$H$_2$O polarization (Grzesiek et al., *J. Am. Chem. Soc.* 115:12593-12594 (1993), which is hereby incorporated by reference in its entirety), which is important for systems >100 kDa (Wider, *Method Enzymol.* 394:382-398 (2005), which is hereby incorporated by reference in its entirety). It is thus expected that L-GFT(-TROSY) (4,3)D HCCH NMR will play a key role for high-quality structure determination of large (membrane) (Atreya et al., *J. Am. Chem. Soc.* 127:4554-4555 (2005), which is hereby incorporated by reference in its entirety) proteins and for studying the quite unexplored (functional) dynamics of their molecular cores.

Example 9

GFT NOESY-Based Protocol—NMR Sample Characterization

NMR experiments were performed on a 600 MHz spectrometer equipped with a cryogenic probe (Styles et al., *Magn. Reson.* 60:397-404 (1994), which is hereby incorporated by reference in its entirety) for the 103-residue target protein YqfB of the Northeast Structural Genomics consortium (NESG; NESG ID: ET99). To ensure that results were representative for medium-sized proteins, NMR experiments were conducted with a 1 mM protein solution at ambient temperature 25° C.

Uniformly (U) $^{13}$C, $^{15}$N-labeled YqfB was produced as described in Yee et al., *Proc. Natl. Acad. Sci. USA* 99:1825-1830 (2002), which is hereby incorporated by reference in its entirety. The protein contained a 22-residue N-terminal tag with sequence MGTSHHHHHHSSGRENLYFQGH (SEQ ID NO:1) in order to facilitate purification. Thus, the polypeptide expressed for NMR structural studies had a molecular weight of 15.3 kDa and 14.5 kDa, respectively, with and without $^{13}$C/$^{15}$N double labeling. U-$^{13}$C, $^{15}$N YqfB was concentrated to an ~1 mM solution in 90% H$_2$O/10% $^2$H$_2$O (25 mM Na phosphate, pH=6.5, 400 mM NaCl, 1 mM DTT, 20 mM ZnCl$_2$, 0.01% NaN$_3$). The approximate isotropic overall rotational correlation time, $\tau_r$, of the protein was determined (at a $^1$H resonance frequency of 600 MHz) from $^{15}$N T$_1$/T$_{1\rho}$ nuclear spin relaxation time ratios, as was described in Szyperski et al., *Proc. Natl. Acad. Sci. USA* 99:8009-8014 (2002), which is hereby incorporated by reference in its entirety. In agreement with a molecular weight of 15.5 kDa for U-$^{13}$C, $^{15}$N YqfB, $\tau_r$~7.7 ns was obtained. This demonstrated that the protein was monomeric in solution.

Example 10

GFT NOESY-Based Protocol—Implementation of GFT (4,3)D [HC$^{ali}$/HN]-NOESY-[CH$^{ali}$/NH]

The chemical shift measurements and NOE transfers taking place in simultaneous GFT (4,3)D [HC$^{ali}$/HN]-NOESY-[CH$^{ali}$/NH] are shown in FIG. 35. Chemical shift doublets were registered in the GFT dimension at $\omega_1$:$\Omega$($^1$H)±κ·$\Omega$(X) [X=$^{15}$N, $^{13}$C$^{aliphatic}$], where κ represents a factor for scaling the projected chemical shift evolution (Szyperski et al., *J. Am. Chem. Soc.* 115:9307-9308 (1993), which is hereby incorporated by reference in its entirety). Proton polarization was transferred to the attached heteronucleus, frequency labeled with $\Omega$(X), transferred back to the proton and frequency labeled with $\Omega$($^1$H). The latter shift was detected in quadrature (Cavanagh et al., *Protein NMR Spectroscopy* Academic Press: San Diego (1996), which is hereby incorporated by reference in its entirety). Hence, with κ=0.5, one has that G-matrix transformation yields two subspectra with peaks located either at $\Omega$($^1$H)+0.5·$\Omega$(X) or $\Omega$($^1$H)–0.5·$\Omega$(X) [i.e., the peak separation matches $\Omega$(X)]. After NOE mixing, the polarization was transferred to the second heteronucleus for frequency labelling, and then transferred back to the attached proton for signal detection. As a result, polarization transfers and chemical shift measurements of 4D $^{15}$N/$^{15}$N-, $^{13}$C$^{alipahtic}$/$^{15}$N- and $^{13}$C$^{aliphatic}$/$^{13}$C$^{aliphatic}$-resolved [$^1$H, $^1$H]-NOESY occurred simultaneously. For detection of central peaks located at $\omega_1$:$\Omega$($^1$H), frequency labelling on the first heteronucleus was not required and hence the additional simultaneous heteronuclear polarization transfer was omitted (see below). It is advantageous to detect central peaks in conjunction with NOEs on aromatic protons. In this experiment, the polarization transfers of 3D $^{15}$N—, $^{13}$C$^{aliphatic}$ and $^{13}$C$^{aromatic}$-resolved [$^1$H, $^1$H]-NOESY occurred simultaneously. For uniformity of nomenclature, this experiment here was named as "3D [H]-NOESY-[CH$^{ali}$/CH$^{aro}$/NH]", where chemical shifts are measured for nuclei indicated in brackets.

The r.f. pulse scheme for the detection of shift doublets (FIG. 36(a)) was derived from simultaneous 3D $^{15}$N, $^{13}$C$^{aliphatic}$-resolved [$^1$H, $^1$H]-NOESY (Xia et al., *J. Biomol. NMR* 27:193-203 (2003), which is hereby incorporated by reference in its entirety) by inserting an additional simultaneous [$^1$H, $^{13}$C]/[$^1$H, $^{15}$N]-HSQC module (Cavanagh et al., *Protein NMR Spectroscopy* Academic Press: San Diego (1996), which is hereby incorporated by reference in its entirety) before NOE mixing. To minimize signal losses arising from T$_2$($^1$H) relaxation, $^1$H chemical shift evolution was implemented in a semiconstant time manner (Cavanagh et al., *Protein NMR Spectroscopy* Academic Press: San Diego (1996), which is hereby incorporated by reference in its entirety) during the reverse INEPT (Cavanagh et al., *Protein NMR Spectroscopy* Academic Press: San Diego (1996), which is hereby incorporated by reference in its entirety). To maximize intensity of $^1$H$^{aliphatic}$–$^1$H$^{aliphatic}$ NOEs, INEPT delays were tuned to ½$^1$J$_{CHaliphatic}$. Moreover, $^{13}$C and $^{15}$N chemical shift evolution in the GFT dimension was scaled (Szyperski et al., *J. Am. Chem. Soc.* 115:9307-9308 (1993), which is hereby incorporated by reference in its entirety) down with κ=0.5, limiting t$_{1,max}$($^{13}$C/$^{15}$N) to ~8 ms. This reduced the sensitivity loss arising from both transverse T$_2$($^{13}$C/$^{15}$N) relaxation and passive aliphatic one-bond $^{13}$C—$^{13}$C scalar couplings (~35 Hz). Likewise, starting from the scheme of 3D $^{15}$N, $^{13}$C$^{aliphatic}$-resolved [$^1$H, $^1$H]-NOESY (Xia et al., *J. Biomol. NMR* 27:193-203 (2003), which is hereby incorporated by reference in its entirety), 3D [H]-NOESY-[CH$^{ali}$/CH$^{aro}$/NH] was implemented for acquisition of central peaks and NOEs detected on aromatic protons. For completeness, the r.f. pulse scheme is shown in FIG. 36(b).

Example 11

GFT NOESY-Based Protocol—NMR Data Acquisition and Processing

NMR spectra for resonance assignment (Table 10) and structure determination (Tables 10 and 11) of YqfB were recorded at 25° C. on a Varian INOVA 600 spectrometer equipped with a cryogenic $^1$H{$^{13}$C, $^{15}$N} triple resonance probe, and processed using the program PROSA (Güntert et al., *J. Biomol. NMR* 2:619-629 (1992), which is hereby incorporated by reference in its entirety). The cryogenic probe used delivered a signal-to-noise ratio of 4,500:1 for the standard ethylbenzene sample (which is about four times larger than what is measured for the conventional $^1H\{^{13}C, ^{15}N\}$ probe). A detailed comparison pursued for 17 kDa NESG target protein YgdK dissolved in a 90% $H_2O$/10% $^2H_2O$ buffer (pH 6.5) containing 100 mM NaCl revealed that the cryogenic probe increased (on average) sensitivity by a factor of ~3 for double/triple resonance experiments and NOESY. Due to higher salt content (400 mM NaCl), the gain in sensitivity for the YqfB measurements was lowered to a factor of ~2. Hence, the NMR measurement times reported herein (Table 11) would have been about four times longer if conducted with a conventional probe.

GFT NMR data for resonance assignment were acquired in 16.9 hours (Table 11), while NOESY data were recorded with a total measurement time of 39 hours; (4,3)D [HC$^{ali}$/HN]-NOESY-[CH$^{ali}$/NH] shift doublets were acquired in 30 hours (hereafter referred to as "data set I") using the pulse scheme of FIG. 36(*a*) and central peaks were obtained from 3D [H]-NOESY-[CH$^{ali}$/CH$^{aro}$/NH] (FIG. 36(*b*)) acquired in 9.1 hours (Table 11). For comparison, a second data set ("data set II") comprising the shift doublets was acquired with twice the measurement time (60 hours; Table 11).

TABLE 10

Through-bond GFT NMR Experiments for Resonance Assignment of Protein YqfB

| Experiment | Polarization transfer pathway[a] | Linear combinations of chemical shifts observed along $\omega_1$ | Minimal measurement time (hrs)[b] GFT | non-GFT |
|---|---|---|---|---|
| (4,3)D HNNC$^{\alpha\beta}$C$^\alpha$ | $^1HN_i \to ^{15}N_i{}^{13}C^\alpha_{i/i-1} \to ^{13}C^{\alpha\beta}_{i/i-1} \to ^{13}C^\alpha_{i/i-1} \to ^{15}N_i \to ^1HN_i$ (t$_1$) (t$_1$) (t$_2$) (t$_3$) | $\Omega(^{13}C^\alpha_{i/i-1}) \pm \Omega(^{13}C^\alpha_{i/i-1})$ $\Omega(^{13}C^\alpha_{i/i-1}) \pm \Omega(^{13}C^\beta_{i/i-1})$ | 2.5 | 38 |
| (4,3)D C$^{\alpha\beta}$C$^\alpha$(CO)NHN | $^1H^\alpha_{i-1} \to ^{13}C^{\alpha\beta}_{i-1} \to ^{13}C^\alpha_{i-1} \to ^{13}C'_{i-1} \to ^{15}N_i \to ^1HN_i$ (t$_1$) (t$_1$) (t$_2$) (t$_3$) | $\Omega(^{13}C^\alpha_{i-1}) \pm \Omega(^{13}C^\alpha_{i-1})$ $\Omega(^{13}C^\alpha_{i-1}) \pm \Omega(^{13}C^\beta_{i-1})$ | 2.5 | 38 |
| (5,2)D HACACONHN | $^1H^\alpha_{i-1} \to ^{13}C^\alpha_{i-1} \to ^{13}C'_{i-1} \to ^{15}N_i \to ^1HN_i$ (t$_1$) (t$_1$) (t$_1$) (t$_1$) (t$_2$) | $\Omega(^{15}N_i) \pm \Omega(^{13}C'_{i-1})$ $\pm\Omega(^{13}C^\alpha_{i-1}) \pm \Omega(^1H^\alpha_{i-1})$ | 0.45[c] | 102 |
| (4,3)D HCCH aliphatic/aromatic | $^1H^{(1)} \to ^{13}C^{(1)} \to ^{13}C^{(2)} \to ^1H^{(2)}$ (t$_1$) (t$_1$) (t$_2$) (t$_3$) | $\Omega(^{13}C^{(1)}) \pm \Omega(^1H^{(1)})$ $\Omega(^{13}C^{(2)}) \pm \Omega(^1H^{(2)})$ | 1.9/0.63[c] | 31/2.2 |

[a]i−1 and i indicate two neighboring amino acid residues along the polypeptide chain. t$_1$, t$_2$, and t$_3$ denote the indirect evolution periods used for frequency labeling of the respective spins.
[b]The minimal measurement times for GFT and parent ("non-GFT") experiments were calculated by choosing the acquisition parameters of Table 11, and assuming that a single scan per "free induction decay" (FID) is recorded. Spectral widths: $^{13}C^\alpha$: 3,000 Hz; $^{13}C^{\alpha\beta}$: 9,000 Hz; $^{13}C^{aliphatic}$: 9,000 Hz; $^{13}C^{aromatic}$: 4,500 Hz; $^1H^{aromatic}$: 1,500 Hz; $^1H^{aliphatic}$: 6,000 Hz, $^1H^\alpha$: 1,800 Hz; $^{15}N$: 1,600 Hz; $^{13}C'$: 1,400 Hz. Delay between start of FID acquisitions ("recycle delays"): 0.55 s for (4,3)D HNNC$^{\alpha\beta}$C$^\alpha$ and (4,3)D C$^{\alpha\beta}$C$^\alpha$(CO)NHN; 0.95 s for (5,2)D HACACONHN, 0.39 s for (4,3)D HCCH (aliphatic) and 0.47 s for (4,3)D HCCH (aromatic). For experiments encoding K+1 shifts in the "GFT dimension", the spectral width along this dimension ($\omega_1$) is: (Kim et al., *J. Am. Chem. Soc.* 125: 1385-1393 (2003), which is hereby incorporated by reference in its entirety), $\Sigma^K_{j=0} SW_j$. The measurement times given includes the time required for recording both basic and central peak spectra. Note, that the third order central peak spectrum of (5,2)D HACACONHN is equivalent to 2D[$^{15}N,^1H$]HSQC.
[c]Assuming that central peak spectra are acquired by successive omission of indirect evolution periods.

TABLE 11

Acquisition Parameters of NMR Experiments

| Experiment | Indirect dimension: t$_{max}$ (ms); Complex points; Digital Resolution (Hz/Pt)[a] | Measurement time (hrs) |
|---|---|---|
| (4,3)D HNNC$^{\alpha\beta}$C$^\alpha$ | $\omega_1$($^{13}C^\alpha$; $^{13}C^{\alpha\beta}$): 6.4; 78; 23 $\omega_2$($^{15}N$): 15.6; 26; 25 | 5.0 |
| (4,3)D C$^{\alpha\beta}$C$^\alpha$(CO)NHN | $\omega_1$($^{13}C^\alpha$; $^{13}C^{\alpha\beta}$): 6.4; 78; 23 $\omega_2$($^{15}N$): 15.6; 26; 25 | 5.0 |
| (5,2)D HACACONHN | $\omega_1$($^{15}N$; $^{13}C'$, $^{13}C^\alpha$, $^1H^\alpha$): 6.3; 48; 14 | 1.5[b] |
| (4,3)D HCCH (aliphatic) | $\omega_1$($^{13}C$; $^1H$): 6.3; 95; 29 $\omega_2$($^{13}C$): 3.6; 16; 70 | 4.0[c] |
| (4,3)D HCCH (aromatic) | $\omega_1$($^{13}C$; $^1H$): 4.0; 25; 23 $\omega_2$($^{13}C$): 3.8; 16; 62 | 1.4[d] |
| 3D [H]-NOESY-[CH$^{ali}$/CH$^{aro}$/NH] | $\omega_1$($^1H$): 16; 128; 15 $\omega_2$($^{13}C$): 6.4; 28; 67 $\omega_2$($^{15}N$): 17; 28; 25 | 9.1 |
| Shift doublets of (4,3)D [HC$^{ali}$/HN]-NOESY-[CH$^{ali}$/NH] ("data sets I/II") | $\omega_1$($^1H$): 16; 200; 24.4 $\omega_1$($^{13}C/^{15}N$): 8; 200; 24.4 $\omega_2$($^{13}C$): 6.4; 28; 67 $\omega_2$($^{15}N$): 16.5; 28; 25 | 30/60[e] |

[a]Direct dimension: $\omega_3$($^1H$): 64; 512; 8. All spectra were recorded with 2 scans per FID unless indicated differently in a separate footnote. For "recycle delays" see footnote 'b' of Table 10.
[b]Includes 5 minutes to record a 2D [$^{15}N,^1H$]-HSQC, that is, third order central peak, spectrum with t$_{max}$($^{15}N$) = 24 ms and a single scan per FID. Other spectra were acquired with 4 scans per FID.
[c]Includes 12 minutes to record a 2D constant time [$^{13}C,^1H$] HSQC[7] with t$_{max}$($^{13}C$) = 28 ms.
[d]Includes 10 minutes to record a 2D constant time [$^{13}C,^1H$] HSQC[7] with t$_{max}$($^{13}C$) = 18 ms with 4 scans per FID.
[e]Data sets I and II were recorded with 2 and 4 scans per FID, respectively. Hence, the minimal measurement time is 15 hours.

Example 12

GFT NOESY-Based Protocol—Analysis of Through-Bond GFT NMR Correlation Spectra for Resonance Assignment As a salient feature, GFT NMR affords linear combinations of shifts encoded in chemical shift multiplets (Table 10), and G-matrix transformation warrants editing of the multiplet components into different subspectra (Atreya et al., *Proc. Natl. Acad. Sci. USA* 101:9642-9647 (2004); Kim et al., *J. Am. Chem. Soc.* 125:1385-1393 (2003); Kim et al., *J. Biomol. NMR* 28:117-130 (2004), which are hereby incorporated by reference in their entirety). Hence, the number of peaks per subspectrum does not increase when increasing the number of jointly sampled indirect chemical shift evolution periods. Concomitantly, the peak dispersion (and thus spectral resolution) increases when compared with conventional congeners (Cavanagh et al., *Protein NMR Spectroscopy* Academic Press: San Diego (1996), which is hereby incorporated by reference in its entirety) of the same dimensionality (Atreya et al., *Proc. Natl. Acad. Sci. USA* 101:9642-9647 (2004), which is hereby incorporated by reference in its entirety). Hence, the analysis of GFT NMR subspectra is quite generally less challenging than the analysis of the conventional congeners. For the present invention, the program XEASY (Bartels, *J. Biomol. NMR* 6:1-10 (1995), which is hereby incorporated by reference in its entirety) was used for data analysis. Importantly, XEASY can handle linear combinations of shifts by expanding chemical shift lists accordingly. This option was originally introduced for analysis of RD NMR spectra (Szyperski et al., *J. Am. Chem. Soc.* 115:9307-9308 (1993); Szyperski et al., *J. Magn. Reson.* B105:188-191 (1994); Brutscher et al., *J. Magn. Reson.* B105:77-82 (1994); Szyperski et al., *J. Magn. Reson.* B108:197-203 (1995); Szyperski et al., *J. Am. Chem. Soc.* 118:8146-8147 (1996); Szyperski et al., *J. Biomol. NMR* 11:387-405 (1998); Szyperski et al., *Proc. Natl. Acad. Sci. USA* 99:8009-8014 (2002); Bartels, *J. Biomol. NMR* 6:1-10 (1995), which are hereby incorporated by reference in their entirety) and allows one to assign linear combinations of shifts to peak positions. The chemical shifts are readily obtained from peak positions encoding the linear combinations by use of a simple linear least-squares fit (Kim et al., *J. Am. Chem. Soc.* 125:1385-1393 (2003), which is hereby incorporated by reference in its entirety). Visual inspection of matching linear combinations of shifts, either within one spectrum or between several spectra, was accomplished as for conventional spectra by use of XEASY. Peak picking was achieved by (i) generating peak lists from averaged shifts taken from the BioMagResBank or from shifts that were obtained at an earlier stage of the resonance assignment protocol, and (ii) manual adjustment of these lists.

Example 13

GFT NOESY-Based Protocol—Analysis of NOESY Data

NOESY spectra were analyzed using the program XEASY (Bartels, *J. Biomol. NMR* 6:1-10 (1995), which is hereby incorporated by reference in its entirety). 3D [H]-NOESY-[$CH^{ali}/CH^{aro}$/NH] comprises the central peaks of (4,3)D [$HC^{ali}$/HN]-NOESY-[$CH^{ali}$/NH] (FIG. 35) and was analyzed as described in the following. First, based on backbone and $^{13}C^\beta$ chemical shifts, the location of the regular secondary structure elements of YqfB was identified (Wishart et al., *Biochemistry* 31:1647-1650 (1994), which is hereby incorporated by reference in its entirety). Subsequently, an initial 3D NOESY peak list was generated that contained the expected intraresidue, sequential and medium range NOE peak positions. After manual adjustment of peak positions and identification of other, primarily long-range NOE peaks, all peaks were integrated. To confirm assignments of overlapped peaks, line shapes were compared visually. The final 3D [H]-NOESY-[$CH^{ali}/CH^{aro}$/NH] peak list, which yielded a high-quality structure of protein YqfB (PDB ID 1TE7; see Example 19), was used as a reference peak list to evaluate the impact of (4,3)D [$HC^{ali}$/HN]-NOESY-[$CH^{ali}$/NH]. First, it was determined how many peaks in 3D NOESY can be assigned based on chemical shift data only [matching tolerances: 0.02 ppm for $\Omega(^1H)$; 0.2 ppm for $\Omega(^{15}N)$ and $\Omega(^{13}C)$], that is, without reference to an (initial) structure. Second, the spectra comprising the doublets were analyzed as described in the following. (i) The two subspectra containing the shift doublets were assigned in a bottom-up manner (Kim et al., *J. Am. Chem. Soc.* 125:1385-1393 (2003), which is hereby incorporated by reference in its entirety) starting from the 3D [H]-NOESY-[$CH^{ali}/CH^{aro}$/NH] peak list; for each peak in 3D NOESY representing a central peak of (4,3)D [$HC^{ali}$/HN]-NOESY-[$CH^{ali}$/NH], the corresponding shift doublet was identified and the additionally encoded heteronuclear chemical shift was measured. It was then determined which peaks in 3D NOESY can be assigned unambiguously when having the additional, fourth chemical shift (with the matching tolerances indicated above). (ii) The subspectra containing the shift doublets were examined in order to identify "new" NOEs which could not be resolved and/or assigned in 3D [H]-NOESY-[$CH^{ali}/CH^{aro}$/NH], even with reference to a high-quality NMR structure. (iii) The S/N ratios of a large number of peaks were measured in order to assess the relative sensitivity of shift doublet compared to central peak detection. (iv) It was determined which fraction of the NOEs detected and assigned in 3D NOESY was likewise observed in the subspectra containing the shift doublets. This yielded a shift doublet detection yield relative to the (more sensitive) central peak detection.

Example 14

GFT NOESY-Based Protocol—NMR Structure Calculations

Cross-peak volumes measured in 3D [H]-NOESY-[$CH^{ali}/CH^{aro}$/NH] were converted into $^1H$—$^1H$ upper distance limit constraints by using the program DYANA (Güntert et al., *J. Mol. Biol.* 273:283-298 (1997), which is hereby incorporated by reference in its entirety). Cross peaks overlapping in 3D [H]-NOESY-[$CH^{ali}/CH^{aro}$/NH], but resolved in the shift doublet spectra of (4,3)D [$HC^{ali}$/HN]-NOESY-[$CH^{ali}$/NH], were interpreted conservatively and used to derive 5 Å distance limit constraints. Residues of regular secondary structure elements were initially identified by use of the chemical shift index method (Wishart et al., *Biochemistry* 31:1647-1650 (1994), which is hereby incorporated by reference in its entirety), and for polypeptide segments with three or more such identified consecutive residues, $\phi$ and $\psi$ backbone dihedral angle constraints were derived from the chemical shifts by use of the program TALOS (Cornilescu et al., *J. Biomol. NMR* 13:289-302 (1999), which is hereby incorporated by reference in its entirety). No hydrogen bond constraints were used. The final round of DYANA structure calculations employing torsion angle dynamics was started with 100 random conformers and 30,000 annealing steps, and the 20 structures with the lowest DYANA target functions were selected to represent the solution structure. Stereospecific assignments for calculating the refined reference structure were obtained using the FOUND and GLOMSA modules of DYANA (Güntert et al., *J. Mol. Biol.* 273:283-298 (1997), which is hereby incorporated by reference in its entirety). The Ramachandran map statistics of NMR structures was evaluated using the program PROCHECK (Laskowski et al., *J. Biomol. NMR* 8:477-486 (1996), which is hereby incorporated by reference in its entirety).

Example 15

GFT NOESY-Based Protocol—Automated NOE Assignment and Structure Calculation with CYANA Calculations with the program CYANA (Herrmann et al., *J. Mol. Biol.* 319:209-227 (2002), which is hereby incorporated by reference in its entirety) were performed for automated NOE assignment and structure calculation using the standard protocol with 7 cycles. (For the present invention, an evaluation using the program CYANA was best suited. This was because, for YqfB, all intraresidue, sequential and medium-range NOEs were assigned by predicting NOESY peak lists from chemical shift data and considering information on secondary structure elements. Hence, a top-down algorithm appeared to be the natural choice to complement the chemical shift based assignment protocol.) Matching tolerances for chemical shifts were set to 0.02 ppm for $\Omega(^1H)$ and to 0.2 ppm for $\Omega(^{13}C)$ and $\Omega(^{15}N)$. CYANA structure calculations were started with 100 random conformers and 30,000 annealing steps. The 20 conformers with lowest target function value were selected for the next cycle of NOE assignment. In routine applications, automatically obtained NOE peak assignments were confirmed by visual inspection of spectra. To assess the impact of network anchoring (Herrmann et al., *J. Mol. Biol.* 319:209-227 (2002), which is hereby incorporated by reference in its entirety) in a first cycle of a CYANA calculation, the entire 3D NOESY reference peak lists were provided as input and combined with $^1$H—$^1$H upper distance limit constraints derived from intraresidue, sequential, and medium-range NOEs (which were assigned as described in Example 13 above) and chemical shift derived (Cornilescu et al., *J. Biomol. NMR* 13:289-302 (1999), which is hereby incorporated by reference in its entirety) dihedral angle constraints. In addition, two CYANA calculations (referred to as (1) and (2) below) were performed to assess the impact of NOEs which could be assigned in (4,3)D [$\overline{HC^{ali}/HN}$]-NOESY-[$CH^{ali}$/NH] using chemical shift data only. In these calculations, a peak list containing only the remaining, unassigned long-range NOEs was provided as input. Specifically, calculations (1) and (2) were performed with the following input: (i) list of unassigned peaks of 3D [H]-NOESY-[$CH^{ali}/CH^{aro}$/NH] reference peak list, (ii) TALOS dihedral angle constraint list which yielded the reference structure of YqfB (1TE7; see Example 19), (iii) distance limit constraints representing intraresidue, sequential and medium-range NOEs (see above), and (iv) distance constraints representing long-range NOEs that were assigned in the 3D [H]-NOESY-[$CH^{ali}/CH^{aro}$/NH] reference peak list based on chemical shifts and (1) the shift doublets registered in the (4,3)D [$\overline{HC^{ali}/HN}$]-NOESY-[$CH^{ali}$/NH] subspectra of data set I (recorded in 30 hours), or (2) the shift doublet subspectra of data set II (recorded in 60 hours).

Example 16

GFT NOESY-Based Protocol—Evaluation of NOE Information Content with the Program QUEEN The program QUEEN (Nabuurs et al., *J. Am. Chem. Soc.* 125:12026-12034 (2003), which is hereby incorporated by reference in its entirety) affords quantitative evaluation of sets of NOEs using criteria originally developed for information theory. This program was used to analyze the information content of long-range NOEs assigned in (4,3)D [$\overline{HC^{ali}/HN}$]-NOESY-[$CH^{ali}$/NH] acquired with 3D [H]-NOESY-[$CH^{ali}/CH^{aro}$/NH] for central peak detection. For each constraint network, the total information content, $I_{total}$ (see equation 8 in Nabuurs et al., *J. Am. Chem. Soc.* 125:12026-12034 (2003), which is hereby incorporated by reference in its entirety), and for each individual constraint within a given network, the unique information, $I_{uni}$ (equation 10 in Nabuurs et al., *J. Am. Chem. Soc.* 125:12026-12034 (2003), which is hereby incorporated by reference in its entirety), and the average information, $I_{ave}$ (equation 11 in Nabuurs et al., *J. Am. Chem. Soc.* 125:12026-12034 (2003), which is hereby incorporated by reference in its entirety), were calculated. The long-range upper distance constraint networks derived from the following NOE peak lists were subject to such an analysis: (1) 3D [H]-NOESY-[$CH^{ali}/CH^{aro}$/NH] reference peak list, (2) list comprising peaks assigned in 3D [H]-NOESY-[$CH^{ali}/CH^{aro}$/NH] based on shift data only, (3) list comprising peaks assigned in 3D [H]-NOESY-[$CH^{ali}/CH^{aro}$/NH] based on shift data only but with reference to 4D information encoded in shift doublet data set I, and (4) same as (3) but with shift doublet data set II.

Example 17

GFT NOESY-Based Protocol—Resonance Assignment

Efficient analysis of NOESY spectra requires resonance assignments (Wüthrich, *NMR of Proteins and Nucleic Acids* Wiley: New York (1986), which is hereby incorporated by reference in its entirety). Inspection of the 2D [$^{15}$N, $^1$H] HSQC spectrum revealed that protein YqfB exhibited an overall good $^{15}$N/$^1$H$^N$ chemical shift dispersion. However, the central region of the spectrum was crowded, partly due to peaks arising from a 22-residue tag added to facilitate purification. Such $^{15}$N/$^1$H$^N$ chemical shift degeneracy posed a challenge for efficient backbone resonance assignment and made YqfB an attractive target for GFT NMR spectroscopy, which provides high dimensional spectral information (Atreya et al., *Proc. Natl. Acad. Sci. USA* 101:9642-9647 (2004); Kim et al., *J. Am. Chem. Soc.* 125:1385-1393 (2003); Kim et al., *J. Biomol. NMR* 28:117-130 (2004), which are hereby incorporated by reference in their entirety) to break shift degeneracy.

Figure 37:
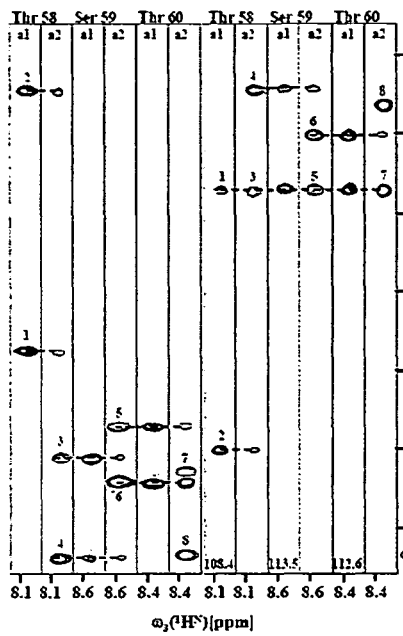
Figure 37:
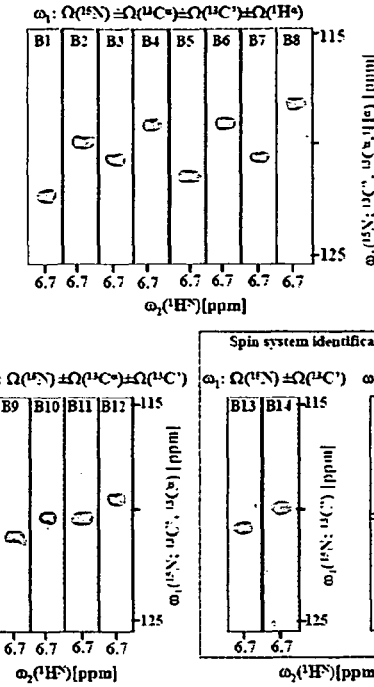
Figure 37:
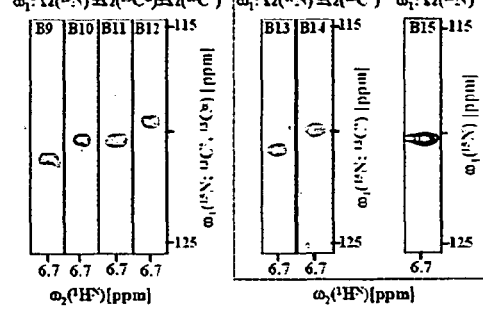
Figure 37:
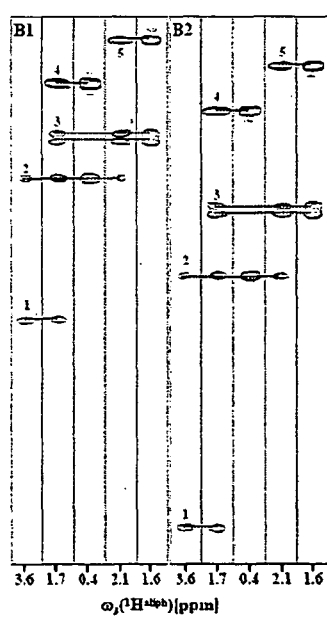
Figure 37:
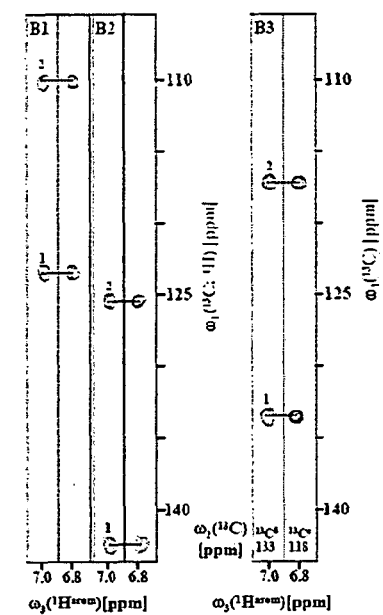

For obtaining (nearly) complete resonance assignments, a set of five through-bond GFT NMR experiments (Table 10) was performed in 16.9 hours (Table 11): (4,3)D HNNC$^{\alpha\beta}$C$^\alpha$ and C$^{\alpha\beta}$C$^\alpha$(CO)NHN for backbone and $^{13}$C$^\beta$ assignment (Atreya et al., *Proc. Natl. Acad. Sci. USA* 101:9642-9647 (2004), which is hereby incorporated by reference in its entirety), (5,2)D HACACONHN (Kim et al., *J. Am. Chem. Soc.* 125:1385-1393 (2003), which is hereby incorporated by reference in its entirety) for $^1$H$^\alpha$ assignment, and aliphatic/aromatic (4,3)D HCCH, derived from RD 3D HCCH (Szyperski et al., *Proc. Natl. Acad. Sci. USA* 99:8009-8014 (2002), which is hereby incorporated by reference in its entirety), for side chain spin system identification. FIG. 37 illustrates the resulting GFT NMR based resonance assignment strategy for protein YqfB. For backbone and $^{13}$C$^\beta$ resonance assignment, joint analysis of two subspectra of (4,3)D HNNC$^{\alpha\beta}$C$^\alpha$ and C$^{\alpha\beta}$C$^\alpha$(CO)NHN (Atreya et al., *Proc. Natl. Acad. Sci. USA* 101:9642-9647 (2004), which is hereby incorporated by reference in its entirety) proceeded conceptually as for 3D HNNCACB/CBCA(CO)NHN (Cavanagh et al., *Protein NMR Spectroscopy* Academic Press: San Diego (1996), which is hereby incorporated by reference in its entirety). The analysis of (5,2)D HACACONHN described previously (Kim et al., *J. Am. Chem. Soc.* 125:1385-1393 (2003), which is hereby incorporated by reference in its entirety) involved generating 15 2D peak lists from which >quintuples of chemical shifts were calculated. For side chain assignment, analysis of each of the three subspectra of (4,3)D HCCH proceeded conceptually as for conventional 3D H(C)CH (Cavanagh et al., *Protein NMR Spectroscopy* Academic Press: San Diego (1996), which is hereby incorporated by reference in its entirety). First, (4,3)D HCCH and 3D H(C)CH were indistinguishable in both the indirect carbon and direct proton dimensions. Second, $\omega_1:\Omega(^{13}C)+\Omega(^1H)$, $\omega_1:\Omega(^{13}C)-\Omega(^1H)$ (chemical shift doublets) and $\omega_1:\Omega(^{13}C)$ (central peaks) were detected along the GFT dimension in the three subspectra of (4,3)D HCCH (Table 10), while $\Omega(^1H)$ was detected along $\omega_1$ in 3D H(C)CH. Hence, spin system identification in (4,3)D HCCH can be visualized as "walking" into the side chains by use of (i) $\Omega(^{13}C)$, (ii) $\Omega(^{13}C+^1H)$, and (iii) $\Omega(^{13}C-^1H)$.

Through-bond GFT NMR (Atreya et al., *Proc. Natl. Acad. Sci. USA* 101:9642-9647 (2004); Kim et al., *J. Am. Chem.*

Soc. 125:1385-1393 (2003); Kim et al., *J. Biomol. NMR* 28:117-130 (2004), which are hereby incorporated by reference in their entirety) provided the spectral information of one 5D and four 4D conventional FT NMR spectra with high digital resolution (Table 11; FIG. 37), yielding nearly complete resonance assignments (98% of backbone and 95% of the side chain chemical shifts; BMRB ID 6207) with investment of 16.9 hours of instrument time. Importantly, the availability of the highest-dimensional spectral information ensured that data analysis was (i) robust with respect to occurrence of chemical shift degeneracies, (ii) highly reliable with respect to assignment yield and accuracy, and (iii) amenable to automated protocols due to increased peak dispersion and precision of shift measurements (Atreya et al., *Methods Enzymol.* 394:78-108 (2005); Atreya et al., *Proc. Natl. Acad. Sci. USA* 101:9642-9647 (2004); Kim et al., *J. Am. Chem. Soc.* 125:1385-1393 (2003); Kim et al., *J. Biomol. NMR* 28:117-130 (2004), which are hereby incorporated by reference in their entirety). Analysis of the two backbone experiments, (4,3)D HNNC$^{\alpha\beta}$C$^{\alpha}$/C$^{\alpha\beta}$C$^{\alpha}$(CO)NHN, greatly profited from (i) the intraresidue $^{13}$C$^{\alpha}$-$^{13}$C$^{\beta}$ shift correlations and (ii) the doubled dispersion manifested, for example, by peaks encoding 2·Ω($^{13}$C$^{\alpha}$) instead of ($^{13}$C$^{\alpha}$) (see FIG. S12 in Atreya et al., *Methods Enzymol.* 394:78-108 (2005), which is hereby incorporated by reference in its entirety). Moreover, it has been shown that 4D information encoded in RD 3D HCCH enables efficient assignment of the aliphatic side chains of proteins with molecular weights up to at least ~18 kDa (Shen et al., *J. Biomol. NMR* 29:549-550 (2004), which is hereby incorporated by reference in its entirety). That finding was confirmed here with the resonance assignment of YqfB using (4,3)D HCCH, the GFT NMR congener of RD 3D HCCH. Taken together, the through-bond GFT NMR (Atreya et al., *Proc. Natl. Acad. Sci. USA* 101:9642-9647 (2004); Kim et al., *J. Am. Chem. Soc.* 125:1385-1393 (2003); Kim et al., *J. Biomol. NMR* 28:117-130 (2004), which are hereby incorporated by reference in their entirety)-based resonance assignment protocol provides a suitable basis for subsequent NOE assignment.

Example 18

GFT NOESY-Based Protocol—NOE Peak Assignment and Distance Constraints

A single 3D [H]-NOESY-[CH$^{ali}$/CH$^{aro}$/NH] data set recorded in 9.1 hours (Table 11; corresponding to ~1.5-2 days with a conventional probe) provided the information of all three 3D NOESY experiments routinely acquired for structure determination of $^{13}$C/$^{15}$N labeled proteins. A total of 4708 NOEs were assigned and yielded 1453 $^1$H—$^1$H upper distance limit constraints (Table 12). Out of the 280 long-range constraints, only 53 (19%) involved aromatic protons. However, calculations with the program QUEEN (Nabuurs et al., *J. Am. Chem. Soc.* 125:12026-12034 (2003), which is hereby incorporated by reference in its entirety) confirmed (Wüthrich, *NMR of Proteins and Nucleic Acids* Wiley: New York (1986); Skalicky et al., *J. Am. Chem. Soc.* 123:388-397 (2001), which are hereby incorporated by reference in their entirety) that these aromatic constraints were highly valuable for the three-dimensional structure determination; 8 (27%) out of the 30 most informative constraints with the largest I$_{ave}$/I$_{total}$ [and 6 (40%) out of 15 most informative] involved aromatic rings (see also FIG. 38). This finding emphasized the importance of including aromatic protons into the simultaneous NOESY data acquisition (FIG. 36(*b*)) to enable high-quality NMR structure determination.

TABLE 12

Statistics of YqfB(1-103) Structure Calculations[a]

| | 1. without SSA | 2. PDB | 3. refined |
|---|---|---|---|
| Stereospecific assignments (SSA)[b] [%] | | | |
| $^\beta$CH$_2$ | — | 34 | 34 |
| Val and Leu isopropyl groups | — | 58 | 58 |
| Conformationally-restricting distance constraints[c] between residues i and j | | | |
| intra-residue [i = j] | 463 | 454 | 466 |
| sequential [i − j = 1] | 496 | 511 | 527 |
| medium range [1 < \|i − j\| <= 5] | 177 | 208 | 211 |
| long range [\|i − j\| > 5] | 304 | 280 | 289 |
| total | 1440 | 1453 | 1493 |
| Number of constraints per residue | 15.3 | 15.4 | 15.8 |
| Number of long-range constraints per residue | 2.9 | 2.7 | 2.8 |
| DYANA target function [Å$^2$] | 1.73 ± 0.17 | 1.89 ± 0.16 | 1.72 ± 0.20 |
| Average pairwise r.m.s.d. [Å] to the mean coordinates for residues 4-101 | | | |
| Backbone N, C$^\alpha$, C' | 0.97 ± 0.22 | 0.65 ± 0.18 | 0.69 ± 0.16 |
| All heavy atoms | 1.58 ± 0.24 | 1.19 ± 0.25 | 1.25 ± 0.21 |
| Backbone + best defined side-chains[d] | 1.05 ± 0.15 | 1.00 ± 0.11 | 0.79 ± 0.09 |
| Average number of distance constraint violations per DYANA conformer | | | |
| 0.2-0.5 Å | 1.0 | 1.1 | 1.0 |
| >0.5 Å | 0 | 0 | 0 |

TABLE 12-continued

Statistics of YqfB(1-103) Structure Calculations[a]

| | 1. without SSA | 2. PDB | 3. refined |
|---|---|---|---|
| Average number of dihedral-angle constraint violations per DYANA conformer >5° | 0 | 0 | 0 |
| Ramachandran map statistics | | | |
| Residues in most favored regions (%) | 71 | 73 | 73 |
| Residues in additional allowed regions (%) | 23 | 25 | 25 |
| Residues in generously allowed regions (%) | 5 | 2 | 2 |
| Residues in disallowed regions (%) | 1 | 0 | 0 |

[a]20 conformers with lowest DYANA target function values out of 100 calculated for YqfB (excluding the N-terminal 22-residue tag). 1. "PDB" is the reference structure deposited (1TE7) in the PDB (Berman et al., Nucleic Acids Res. 28: 235-242 (2000), which is hereby incorporated by reference in its entirety). 2. "without SSA" is the reference structure calculated with the constraint input of the PDB structure omitting the stereospecific assignments (SSA). 3. "refined" is PDB structure refined with NOEs resolved in the shift doublet spectra of (4,3)D [HC$^{ali}$/HN]-NOESY-[CH$^{ali}$/NH].
[b]Relative to pairs with non-degenerate chemical shifts.
[c]Note that the numbers vary for "without SSA" and "PDB" due to handling of stereospecific assignments (Guntert et al., J. Mol. Biol. 273: 283-298 (1997), which is hereby incorporated by reference in its entirety).
[d]Best-defined side-chains include residues 7, 16, 22-25, 35, 37-39, 52, 55-67, 71, 77, 79, 81, 84-86, 93, 97, 98.

Example 19

GFT NOESY-Based Protocol—YqfB Reference Structure Determination

A high-quality NMR structure of YqfB (PDB ID: 1TE7) was obtained with the distance constraints derived from 3D [H]-NOESY-[CH$^{ali}$/CH$^{aro}$/NH], as is evidenced (see middle column labeled PDB in Table 12) by (i) the small size and number of residual constraint violations, (ii) average r.m.s.d. values relative to the mean coordinates of 20 conformers of 0.65±0.18 Å for the backbone and 1.19±0.25 Å for all heavy atoms, (iii) a large fraction of stereospecific assignments for β-methylene and the Val and Leu isopropyl moieties, and (iv) the fact that all φ and Ψ dihedral angles were located in the allowed (most favored, additionally or generously allowed) regions of the Ramachandran map.

Example 20

GFT NOESY-Based Protocol—Sensitivity of NOE Detection in (4,3)D [HC$^{ali}$/HN]-NOESY-[CH$^{ali}$/NH]

Sensitivity of NOE detection was critical for identifying the optimal use of (4,3)D [HC$^{ali}$/HN]-NOESY-[CH$^{ali}$/NH]. First, the relative intrinsic sensitivity of 3D [H]-NOESY-[CH$^{ali}$/CH$^{aro}$/NH] and separately acquired 3D $^{15}$N-, $^{13}$C$^{aliphatic}$- and $^{13}$C$^{aromatic}$-resolved [$^1$H, $^1$H]-NOESY was evaluated. Complementing previous assessments (Farmer et al., J. Biomol. NMR 4:673-687 (1994); Pascal et al., J. Magn. Reson. 103:197-201 (1994); Jerala et al., J. Magn. Reson. B108:294-298 (1995); Uhrin et al., J. Biomol. NMR 18:253-259 (2000); Xia et al., J. Biomol. NMR 27:193-203 (2003), which are hereby incorporated by reference in their entirety), differences in sensitivity arose because (i) a $^{15}$N, $^1$H-sensitivity enhancement scheme (Cavanagh et al., Protein NMR Spectroscopy Academic Press: San Diego (1996), which is hereby incorporated by reference in its entirety) had not been integrated in simultaneous [$^{15}$N, $^1$H]/[$^{13}$C, $^1$H]-HSQC detection modules, which reduced the sensitivity of the $^{15}$N-resolved part to ~70% (~1/√2) compared to a sensitivity enhanced $^{15}$N-resolved [$^1$H, $^1$H]-NOESY, (ii) a compromise value was chosen for the $^{13}$C—$^1$H INEPT delay (FIG. 36) in order to enable simultaneous detection of NOEs on aliphatic and aromatic protons, which attenuated $^{13}$C—$^1$H detected signals by ~5%, and (iii) off-resonance effects of 90° r.f. pulses on $^{13}$C$^{aromatic}$ leading to a sensitivity reduction to ~75%. Additional smaller losses arose because (i) the $^1$H—$^{15}$N INEPT (Cavanagh et al., Protein NMR Spectroscopy Academic Press: San Diego (1996), which is hereby incorporated by reference in its entirety) delay (5.4 ms) was longer than the $^{13}$C—$^1$H INEPT delay (3.4 ms), which increased the signal loss for the $^{13}$C-resolved part due to $T_2$($^1$H) relaxation during an additional period of 4 ms, and (ii) of longer maximal evolution times in $t_2$ for $^{15}$N frequency (~16 ms) than for $^{13}$C$^{aliphatic}$/$^{13}$C$^{aromatic}$ frequency labeling (~6 ms), which requires that longitudinal two-spin order, $H_zC_z$, is present prior and after frequency $^{13}$C labeling leading to some signal loss for $^{13}$C—$^1$H detected signals due to $T_1$($H_zC_z$) relaxation. Taken together, sensitivity is reduced relative to separate data acquisition to ~70% for the $^{15}$N-resolved, to ~80% for the $^{13}$C$^{aliphatic}$-resolved, and to ~65% for the $^{13}$C$^{aromatic}$-resolved part. Requiring that the same S/N ratios are obtained in simultaneous 3D NOESY as in the separately acquired spectra, one obtains an effective acceleration of data acquisition speed by ~1.5. (Following these sensitivity considerations, the impact of simultaneous NOESY acquisition on NMR data collection speed shall be illustrated. For example, one can assume that $^{15}$N-resolved, $^{13}$C$^{aliphatic}$-resolved and $^{13}$C$^{aromatic}$-resolved NOESY are acquired in 12 hours each (yielding 36 hours total measurement time). About 30-35% sensitivity is lost due to simultaneous acquisition for $^{15}$N-resolved as well as for the $^{13}$C$^{aromatic}$ resolved part. To compensate for these losses, the measurement time needs to be doubled. As a result, data collection speed is effectively increased by a factor of 1.5 (24 hours instead of 36 hours). Notably, use of a simultaneous [$^{15}$N, $^1$H]/[$^{13}$C, $^1$H]-HSQC detection module (Sattler et al., J. Biomol. NMR 5:97-102 (1995), which is hereby incorporated by reference in its entirety) could increase the sensitivity of the $^{15}$N-resolved part.)

Figure 36:
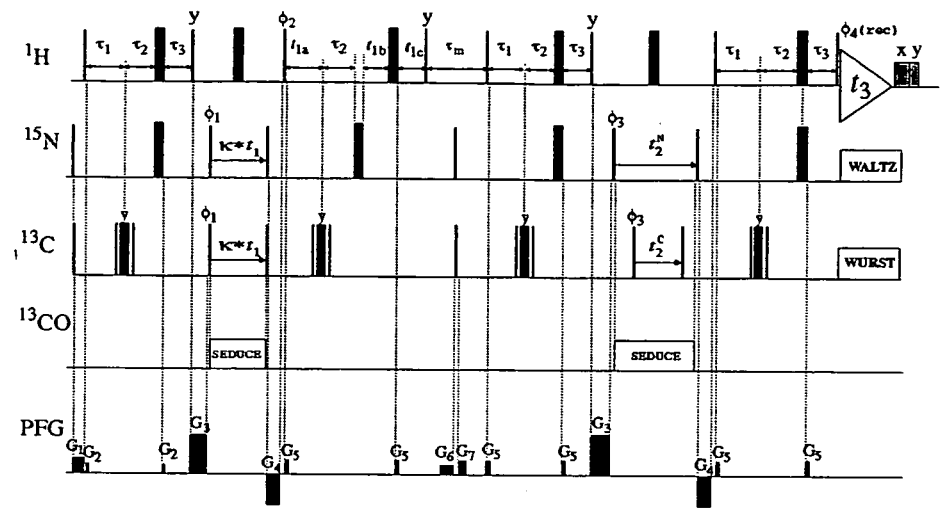
Figure 36:
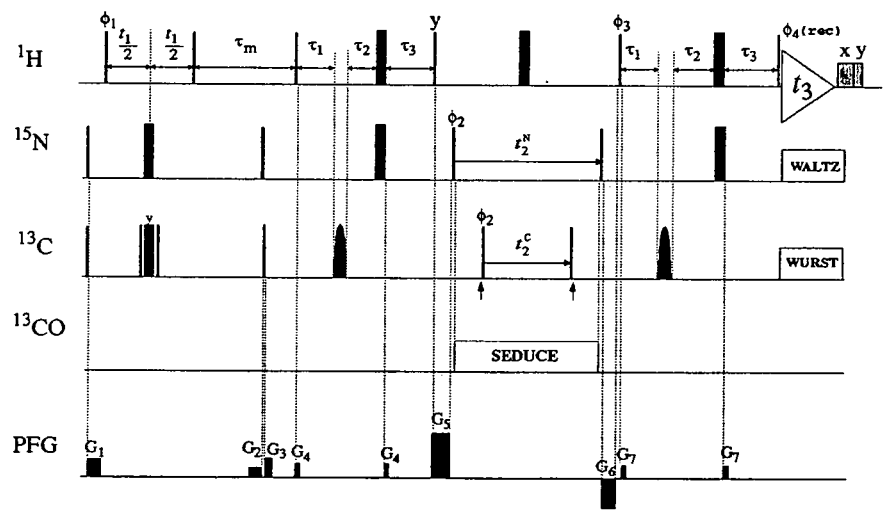

Next, the sensitivity of central peak detection in 3D [H]-NOESY-[CH$^{ali}$/CH$^{aro}$/NH] was compared with shift doublet detection in (4,3)D [HC$^{ali}$/HN]-NOESY-[CH$^{ali}$/NH]. Since the shift doublets arose from an in-phase splitting of the central peaks, the intrinsic sensitivity of detecting each peak of a shift doublet was a priori reduced to 50% when compared with central peak detection. However, the fact that only shift doublets represent viable signals allowed one to identify peaks significantly closer to the noise level (Szyperski et al., *J. Am. Chem. Soc.* 115:9307-9308 (1993), which is hereby incorporated by reference in its entirety). This compensated, at least partly, for the 2-fold loss in sensitivity. The sensitivity of shift doublet detection was further reduced due to the transverse relaxation occurring during the additional simultaneous [$^{15}$N, $^{1}$H]/[$^{13}$C, $^{1}$H]-HSQC module (FIG. 36). This loss depends on protein size and shape, which determine the correlation time(s) for the overall rotational tumbling, as well as internal mobility. For a rigid spherical protein, calculation of $^{1}$H$^{N}$, $^{15}$N, $^{1}$H$^{aliphatic}$, and $^{13}$C$^{aliphatic}$ (non-methyl) transverse relaxation rates (Cavanagh et al., *Protein NMR Spectroscopy* Academic Press: San Diego (1996), which is hereby incorporated by reference in its entirety) is feasible. This allows one to estimate, with the transfer delays defined in FIG. 36(a), the reduction of sensitivity as a function of the correlation time for isotropic reorientation (FIG. 39). For YqfB ($\tau_r$~7.7 ns), theory (Cavanagh et al., *Protein NMR Spectroscopy* Academic Press: San Diego (1996), which is hereby incorporated by reference in its entirety) predicted (FIG. 39) that relaxation would further reduce S/N ratios of shift doublet components to, respectively, ~38% and ~28% of the sensitivity of central peak detection after a splitting with $\Omega(^{15}$N) and $\Omega(^{13}$C) is encoded. Additional smaller losses can be expected to arise from (i) signal de-phasing due to the presence of passive one-bond $^{13}$C—$^{13}$C, and one- and two-bond $^{15}$N—$^{13}$C$^{\alpha}$ scalar couplings, (ii) r.f. pulse inhomogeneities, and (iii) r.f. pulse off-resonance effects. (Note that for $^{13}$C$^{aliphatic}$-resolved shift doublets, a slight gain in sensitivity relative to central peak detection in 3D [H]-NOESY-[CH$^{ali}$/CH$^{aro}$/NH] was due to the fact the $^{13}$C—$^{1}$H INEPT delay was not tuned to a compromise value; FIG. 36.) Experimentally, it was observed that the S/N of the peaks constituting the shift doublets was reduced to ~30±5% for $^{15}$N-resolved, and to ~29±6% (non-methyl) and ~37±4% (methyl) for $^{13}$C-resolved central peaks. These values were in good agreement with the theoretical estimates (FIG. 39), suggesting that these allow one to assess the role of (4,3)D [HC$^{ali}$/HN]-NOESY-[CH$^{ali}$/NH] for larger systems.

Example 21

GFT NOESY-Based Protocol—Completeness of Central Peak Versus Shift Doublet Detection The 3D [H]-NOESY-[CH$^{ali}$/CH$^{aro}$/NH] was acquired in 9.1 hours (Table 11). Considering that the sensitivity for detecting each peak of a shift doublet was only ~30% of the sensitivity for central peak detection (see Example 20; FIG. 39), ten-fold longer measurement time, i.e., about 90 hours, would be required to achieve comparable completeness of NOE detection in central peak and shift doublet subspectra. This appeared to be inappropriately long considering that through-bond GFT NMR and 3D NOESY spectra required for structure determination of YqfB were recorded in 26 hours (Table 11). Importantly, it may well suffice to detect shift doublets only for stronger NOEs in order to increase the fraction of assigned long-range NOEs to a level that an accurate initial structure can be calculated. Hence, for shift doublet data sets recorded with 30 hours (data set I) and 60 hours (data set II) of measurement time, the fraction of NOEs in 3D [H]-NOESY-[CH$^{ali}$/CH$^{aro}$/NH] was determined for which a corresponding shift doublet peak was detected. In data set I (data set II), 75% (93%) of the $^{15}$N-resolved long-range NOEs (total: 104) and 64% (95%) of the $^{13}$C$^{aliphatic}$-resolved long-range NOEs (total: 225) were detected. (Similar fractions were obtained for medium-range NOEs assigned based on chemical shifts in 3D NOESY/3D NOESY plus shift doublet data set I/3D NOESY plus shift doublet data set II: $^{15}$N-resolved NOEs (total: 114) 21%/53%/72%; $^{13}$C$^{aliphatic}$-resolved NOEs (total: 90) 14%/64%/76%. Moreover, 60%/100%/100% was obtained for long-range H$^{N}$—H$^{N}$ (total: 25) and 29%/69%/83% for long-range CH$_3$—CH$_3$ NOEs (total: 29).) Hence, the majority of long-range NOEs were detected after 30 hours measurement time, while NOE detection approached completeness (relative to 3D [H]-NOESY-[CH$^{ali}$/CH$^{aro}$/NH]) only when investing 60 or more hours of spectrometer time. Thus, it was proposed that, for proteins up to ~15-20 kDa ($\tau_r$~8-10 ns), the measurement time for shift doublet detection should be ~2-3 times longer than that for central peak detection. Considering increased losses due to spin relaxation at longer $\tau_r$ (FIG. 39), it was anticipated that 3-4 times longer measurement times would be required for larger proteins in the 20-25 kDa range ($\tau_r$~10-13 ns).

Example 22

GFT NOESY-Based Protocol—Chemical Shift-Based Unambiguous NOE Assignment

The fraction of NOEs which can be unambiguously assigned directly from chemical shift data represents a key "figure of merit" determining the robustness of an NMR structure determination protocol (Güntert, *Prog. NMR Spectroscopy* 43:105-125 (2003); Baran et al., *Chem. Reviews* 104:3451-3455 (2004); Huang et al., *Methods Enzymol.* 394: 111-141 (2005), which are hereby incorporated by reference in their entirety). Hence, it was examined to which extent the measurement of the fourth chemical shift encoded in the splitting of the shift doublets resolve assignment ambiguities encountered in 3D NOESY (FIG. 40).

Among the long-range NOEs in 3D [H]-NOESY-[CH$^{ali}$/CH$^{aro}$/NH], only 33% of the $^{15}$N-resolved and 18% of the $^{13}$C$^{aliphatic}$-resolved NOEs can be assigned without reference to an (initial) structure. When considering also the 4D information encoded in the shift doublets of data set I (data set II), these fractions increase to 74% (88%) and 71% (83%). Hence, most shift doublets can be unambiguously assigned based on chemical shifts; that is, the detection yield of shift doublets largely determines the fraction of unambiguously assigned NOEs (FIG. 40).

Example 23

GFT NOESY-Based Protocol—Additional NOEs Resolved in Shift Doublet Subspectra

Due to the lower sensitivity of shift doublet detection, one expects to register only those NOEs as shift doublets which are also present in 3D [H]-NOESY-[CH$^{ali}$/CH$^{aro}$/NH] as central peaks. However, peak overlap and cases of severe chemical shift degeneracy quite generally prevent one from completely assigning peaks in 3D [H]-NOESY-[CH$^{ali}$/CH$^{aro}$/NH], even with reference to a high-quality structure (for YqfB, 86% of all NOE peaks could be assigned). Analysis of the shift doublet subspectra of data set II yielded 22 unidentified (new) $^{15}$N-resolved and 19 $^{13}$C$^{aliphatic}$-resolved NOEs. Hence, as long as the measurement time invested for shift doublet and central peak acquisition are similar, shift doublets are primarily expected to play a key role for assigning central peak NOEs in 3D NOESY. Otherwise, except for small proteins, comparably few new distance constraints are anticipated.

Example 24

GFT NOESY-Based Protocol—QUEEN Analysis of NOE Constraint Networks

Depending on their uniqueness, upper distance limit constraints vary in their impact on structure determination and refinement. Hence, reporting the sheer number of NOEs (Table 12) provided only a semiquantitative assessment of the constraint network obtained with a given protocol. Recently, the algorithm and program QUEEN (Nabuurs et al., *J. Am. Chem. Soc.* 125:12026-12034 (2003), which is hereby incorporated by reference in its entirety) were devised to quantify information contained in experimental NMR data by information theoretical analysis in distance space. QUEEN was used to evaluate the long-range constraint networks obtained for protein YqfB when recording (4,3)D [$HC^{ali}$/HN]-NOESY-[$CH^{ali}$/NH] acquired with 3D [H]-NOESY-[$CH^{ali}$/$CH^{aro}$/NH] for central peak detection (FIG. 38). As expected, the total information, $I_{total}$, of the reference constraint list (1.577 bits/atom$^2$) was significantly higher than $I_{total}$ of the constraint list derived from 3D NOESY with sole reference to chemical shifts (1.327 bits/atom$^2$). In contrast, $I_{total}$ of the constraint lists derived with reference to (4,3)D [$HC^{ali}$/HN]-NOESY-[$CH^{ali}$/NH] shift doublet data sets I and II (1.539 and 1.547 bits/atom$^2$) were nearly the same and also quite similar to $I_{total}$ of the reference list. This showed that shift doublet data set I (30 hours measurement time) enabled one to derive the major fraction of the final $I_{total}$, predicting that an accurate initial structure can be obtained from the thus obtained initial constraint network.

Furthermore, a calculation of the distribution of unique information, $I_{uni}$, and average information, $I_{ave}$, of the constraints yielding the reference structure (1TE7) confirmed that chemical shift based NOE assignment identified constraints irrespective of their location in the [$I_{uni}$, $I_{ave}$] plot; that is, the highly informative constraints were identified with the same probability as those with a low information content (FIG. 38(a)). This feature of shift based NOE assignment was in contrast to what can be expected for the algorithm implemented in the program CYANA. Network anchoring (Herrmann et al., *J. Mol. Biol.* 319:209-227 (2002), which is hereby incorporated by reference in its entirety) favors identification of distance constraints with comparably lower information content, since the constraints with high information content are not embedded in a (dense) network which might serve for assignment. As a result, constraints identified for calculating an initial CYANA structure represented less information in the context of the final constraint network (FIG. 38(b)). This might imply that, in general, initial structures derived from (4,3)D NOESY may be more accurate than those obtained with CYANA from 3D NOESY.

Example 25

GFT NOESY-Based Protocol—Comparative NMR Structure Calculations

Comparative structure calculations were performed to explore the impact of NOEs which could be assigned directly based on chemical shift data when having shift doublet data sets I or II along with 3D [H]-NOESY-[$CH^{ali}$/$CH^{aro}$/NH] (Table 13; FIGS. 41 and 42). As usual, mean pairwise r.m.s.d. values were calculated relative to mean coordinates in order to assess the precision of the resulting bundles of conformers. Stereospecific assignments, which are mostly obtained during the last stages of structural refinement by using the GLOMSA module of DYANA (Güntert et al., *J. Mol. Biol.* 273:283-298 (1997), which is hereby incorporated by reference in its entirety), were not considered. Hence, precision was assessed relative to a YqfB structure obtained with the NOEs used for the PDB structure (1TE7) but after omission of all stereospecific assignments (column 1 in Table 12 denoted "without SSA"). Accuracy was assessed by calculating the r.m.s.d. values between the mean coordinates of the resulting bundle of conformers and the mean coordinates of the reference structure of YqfB deposited in the PDB ID 1TE7 (column 2 in Table 12 denoted "PDB"). Assuming a small number of (unavoidable) human errors for NOE assignment (see Example 15), it is certainly so that the "true" structure is somewhere "in between" the manual structure and the structures obtained either with reduced NOE constraint input or with automated methods. However, NOE assignments were carefully double-checked by visual line-shape comparison, which ensured that the remaining number of assignment errors was very small. Clearly, automated methodology relying on chemical shift data only cannot accomplish the same high reliability. Hence, for the experiment disclosed herein, it was assumed that the manual structure represented, in a good approximation, a "gold standard" for benchmarking the alternative structure determination protocols. A summary of r.m.s.d. values obtained from the comparative structure calculations is given in Table 13 and FIG. 41.

TABLE 13

R.m.s.d. Values of Comparative NMR Structure Calculations

| | r.m.s.d$^a$ [Å] | | | |
| --- | --- | --- | --- | --- |
| | Precision$^c$ | | Accuracy$^d$ | |
| Structure$^b$ | Backbone | Heavy atoms | Backbone | Heavy atoms |
| (1.) Reference (PDB ID 1TE7) (x)$^e$ | 0.65 ± 0.18 | 1.19 ± 0.25 | — | — |
| (2.) Reference ("no SSA") (+)$^f$ | 0.97 ± 0.22 | 1.58 ± 0.24 | 1.28 | 1.62 |
| (3.) 3D NOESY and shifts only (■)$^g$ | 4.02 ± 1.03 | 5.00 ± 0.96 | 3.22 | 3.70 |
| (4.) 3D NOESY and shifts + (4,3)D dataset "I" (●)$^h$ | 1.97 ± 0.44 | 2.86 ± 0.46 | 1.58 | 2.27 |
| (5.) 3D NOESY and shifts + (4,3)D dataset "II" (○)$^h$ | 1.53 ± 0.28 | 2.42 ± 0.33 | 1.35 | 1.80 |
| (6.) CYANA (1$^{st}$ Cycle) (▼)$^i$ | 2.18 ± 0.49 | 2.96 ± 0.55 | 2.81 | 3.69 |

TABLE 13-continued

R.m.s.d. Values of Comparative NMR Structure Calculations

| | r.m.s.d[a] [Å] | | | |
|---|---|---|---|---|
| | Precision[c] | | Accuracy[d] | |
| Structure[b] | Backbone | Heavy atoms | Backbone | Heavy atoms |
| (7.) CYANA starting from (4.) (▲)[j] | 0.82 ± 0.19 | 1.35 ± 0.23 | 1.57 | 2.17 |
| (8.) CYANA staring from (5.) (Δ)[j] | 0.90 ± 0.18 | 1.46 ± 0.22 | 1.58 | 2.17 |

[a]R.m.s.d. values were calculated for residues 4-101 of YqfB. For a graphical representation of the values, see FIG. 41.
[b]Symbols provided in parentheses are those identifying the corresponding bundle in FIG. 42.
[c]Precision was assessed by calculating the mean pairwise r.m.s.d. for the bundle of NMR conformers relative to their mean coordinates.
[d]Accuracy was assessed by calculating the r.m.s.d. between the mean coordinates of the bundle of NMR conformers and the reference structure.
[e]Reference structure.
[f]Reference structure calculated after omission of stereospecific assignments (see Table 12).
[g]Initial structure calculated from NOEs assigned in 3D [H]-NOESY-[CH$^{ali}$/CH$^{aro}$/NH] based on chemical shift data only.
[h]Initial structure calculated from NOEs assigned in 3D [H]-NOESY-[CH$^{ali}$/CH$^{aro}$/NH] based on chemical shift data only but with reference to shift doublet datasets I and II of (4,3)D [HC$^{ali}$/HN]-NOESY-[CH$^{ali}$/NH].
[i]Initial structure calculated with the program CYANA in the 1$^{st}$ cycle using the final 3D [H]-NOESY-[CH$^{ali}$/CH$^{aro}$/NH] peak list used for determining the reference structure (PDB ID 1TE7).
[j]Structures calculated with the program CYANA when starting with the constraint input yielding the structures indicated with footnote "h".

A. Impact on Precision of Initial Structure

For comparison of precision, r.m.s.d. values were calculated for a structure obtained with the NOE input used for determining the reference YqfB structure (1TE7; FIG. 42(*a*)), except that stereospecific assignments were omitted. This yielded r.m.s.d. values of 0.97±0.22 Å (FIG. 42(*b*)) and 1.58±0.24 Å for backbone and heavy atoms of residues 4-101, respectively (Tables 12 and 13). As expected, a structure of rather low precision was obtained when considering solely long-range NOEs which can be assigned in 3D [H]-NOESY-[CH$^{ali}$/CH$^{aro}$/NH] based on shift data; the corresponding r.m.s.d. values were 4.02±1.03 Å (FIG. 42(*c*)) and 5.00±0.96 Å, respectively. Evidently, if the structure refinement is to be completed using manual methods with the 3D NOESY data set alone, great care would be necessary to ensure proper convergence. When including also NOEs that could be assigned with reference to the shift doublets detected in data set I (or data set II), these values dropped to 1.97±0.44 Å (FIG. 42(*d*)) (1.53±0.28 Å; FIG. 42(*e*)) and 2.86±0.46 Å (2.42±0.33 Å). This showed that (i) the 4D information encoded in (4,3)D [HC$^{ali}$/HN]-NOESY-[CH$^{ali}$/NH] allowed one to generate quite precise initial structures, and (ii) the structure obtained with data set I exhibited r.m.s.d. values which were only ~1 Å above those of the reference structure (calculated after omission of stereospecific assignments; Table 12). The r.m.s.d values were consistent with the finding that ~70-75% (~80-90%) of all backbone and aliphatic long-range NOEs can be assigned as central peaks in 3D NOESY (see above) when having the information of shift doublet data set I (data set II). Furthermore, the major part of the precision gap to the reference structure was due to the fact that the shift doublet spectra did not exhibit aromatic NOEs: when including all aromatic constraints, the backbone r.m.s.d. value dropped to 1.41±0.23 Å (1.12±0.17 Å for data set II). This was close to the reference value of 0.97±0.22 Å. It was thus concluded that, in agreement with information-theoretical QUEEN analysis of the constraint networks (FIG. 38), the measurement time invested for recording shift doublet data set I (30 hours) represented the most effective approach for obtaining a precise initial fold which ensures smooth convergence of the structure refinement.

B. Impact on Accuracy of Initial Structure

The 20 best conformers representing the PDB reference structure were used to assess accuracy and exhibited mean r.m.s.d. values of 0.65±0.18 Å (backbone) and 1.19±0.25 Å (all heavy atoms) relative to the mean coordinates of residues 4-101 (Table 12). These r.m.s.d. values define, arguably somewhat arbitrarily, the "allowed conformational space" associated with the reference structure. An initial structure was considered as "accurate" if the conformational space associated with the initial structure overlapped with the allowed conformational space. This criterion was fulfilled if the r.m.s.d values calculated between the mean coordinates of initial and reference structure was smaller than the sum of the mean r.m.s.d. values to the mean coordinates of the two structure calculations. Root mean square deviation calculations showed that initial structures derived from NOEs assigned based on chemical shift data were accurate (Table 13; FIGS. 41 and 42). In fact, the initial structures were accurate enough to even have the mean coordinates of the reference structure located within their allowed conformational space.

C. Comparison with CYANA's Initial Structure

To compare the impact of (4,3)D [HC$^{ali}$/HN]-NOESY-[CH$^{ali}$/NH] data acquisition versus an approach to automatically assign NOEs in 3D NOESY, a CYANA (Herrmann et al., *J. Mol. Biol.* 319:209-227 (2002), which is hereby incorporated by reference in its entirety) calculation was performed. The first cycle of a CYANA calculation generated an initial structure by using network anchoring and constraint combination, that is, likewise without reference to three-dimensional structural knowledge (Herrmann et al., *J. Mol. Biol.* 319:209-227 (2002), which is hereby incorporated by reference in its entirety). When providing only TALOS dihedral angle constraints, and intraresidue, sequential, and medium-range $^1$H—$^1$H upper distance limit constraints as input, along with the unassigned reference 3D NOESY peak list, the resulting initial CYANA structure exhibited r.m.s.d. values of 2.18±0.49 Å (backbone) and 2.96±0.55 Å (all heavy atoms) relative to the mean coordinates (Table 13; FIGS. 41 and 42). Hence, with the final peak list as input, the algorithm implemented in CYANA for solving the NOE assignment problem resulted in a precision which was comparable to what was obtained with 4D NOESY information (Table 13). However, the corresponding accuracy after the 1$^{st}$ cycle turned out to be lower than the initial structure obtained with 4D NOESY information based on chemical shifts only (Table 13). This may have well been due to the fact that employment of network anchoring could not support the assignment of NOEs with the highest information content (FIG. 38). This is because the high information content arose from not being embedded in a (dense) NOE network (which may serve to "anchor" them). Moreover, it might be that use of a larger number of ambiguous long range constraints simply led to an overestimation of the precision of the initial structure.

D. CYANA Structures Derived from (4,3)D NOESY-Derived Initial Structures

The high accuracy of the initial folds obtained from (4,3)D [HC$^{ali}$/HN]-NOESY-[CH$^{ali}$/NH] (Table 13; FIG. 41) allows one to reliably obtain most of the remaining NOE assignments using the program CYANA. Both precision and accuracy of the obtained structures were close to the values of the manually obtained reference structure (a slightly lower accuracy compared to the manually refined structure indicated, however, that manual intervention such as visual line shape comparison, would be required for finishing the refinement). It was thus concluded that the combination of (4,3)D [HC$^{ali}$/HN]-NOESY-[CH$^{ali}$/NH] with automated structure determination protocols (Moseley et al., *Methods Enzymol.* 339:91-108 (2001); Huang et al., *J. Mol. Biol.* 327:521-536 (2003); Huang et al., *J. Am. Chem. Soc.* 127:1665-1674 (2005); Güntert et al., *J. Mol. Biol.* 273:283-298 (1997); Herrmann et al., *J. Mol. Biol.* 319:209-227 (2002); Güntert, *Methods Mol. Biol.* 278:347-372 (2004), which are hereby incorporated by reference in their entirety), possibly a parallel consensus operation of bottom-up and top-down protocols, represented a powerful approach to ensure fast and robust high throughput determination of high-quality NMR structures.

E. Refinement of YqfB Reference Structure

The reference structure (1TE7) determined with distance constraints derived from 3D [H]-NOESY-[CH$^{ali}$/CH$^{aro}$/NH] was further refined by incorporating NOEs that could be resolved in the shift doublet subspectra (data set II; FIG. 40). As expected, the comparably few new NOEs resulted in only a moderate increase in precision: only the r.m.s.d. value calculated for backbone and best-defined side chains (that is, the molecular core) was somewhat decreased (column 3 in Table 12 denoted "refined"). This finding supported the view that shift doublet detection in (4,3)D [HC$^{ali}$/HN]-NOESY-[CH$^{ali}$/NH] was primarily a valuable tool to assign the majority of the (stronger) NOEs directly based on chemical shift data only.

Example 26

GFT NOESY-Based Protocol for High-Quality Protein Structure Determination

GFT NMR enables one to "cut the Gordian knot" and combine rapid NMR data collection with robust, high-quality NMR structure determination. This is pivotal for NMR-based structural biology and genomics. The resonance assignment is facilitated by the fact that only five GFT NMR experiments are required, each providing 4D and 5D NMR spectral information at high digital resolution. (4,3)D [HC$^{ali}$/HN]-NOESY-[CH$^{ali}$/NH] acquired with 3D [H]-NOESY-[CH$^{ali}$/CH$^{aro}$/NH] for central peak detection affords the information of several 3D and 4D heteronuclear resolved NOESY spectra and enables detection of a dense networks of $^1$H-$^1$H upper distance constraints, as required for high-quality structures. The majority of NOEs detected as shift doublets can be assigned based on chemical shift data only, and assignment of the weaker NOEs, which are often not detectable as shift doublets, is greatly facilitated by having in a single 3D [H]-NOESY-[CH$^{ali}$/CH$^{aro}$/NH] spectrum with each X1-H$^1$...H$^1$—X2 NOE resolved at the chemical shift of X1 and the corresponding to the transposed peak resolved at the chemical shift of X2. Moreover, the impact of distance constraints referred to aromatic rings for structural refinement has long been documented (Wüthrich, *NMR of proteins and Nucleic Acids* Wiley: New York (1986); Skalicky et al., *J. Am. Chem. Soc.* 123:388-397 (2001), which are hereby incorporated by reference in their entirety), which emphasizes the importance of including $^{13}$C$^{aromatic}$-resolved [$^1$H, $^1$H]-NOESY in the scheme for simultaneous acquisition. For proteins comprising a large number of aromatic rings, recording of (4,3)D [HC$^{ali}$/HN]-NOESY-[CH$^{aro}$] might be advisable. ((4,3)D [HC$^{ali}$,HN]-NOESY-[CH$^{aromatic}$] can be readily implemented by eliminating the second [$^{15}$N, $^1$H$^N$]-HSQC module and tuning the second [$^{13}$C, $^1$H]-HSQC module in FIG. 36(a) for aromatic CH moieties. Except for $^1$H$^{aromatic}$—$^1$H$^{aromatic}$ NOEs, all NOEs involving aromatic protons are detected in such an experiment, and allow their assignment based on detection of shift doublets. Considering that the spectral width of $^{13}$C$^{aromatic}$ is about one-half of the spectral width of $^{13}$C$^{aliphatic}$, the minimal measurement time is ~6.5 hrs at 600 MHz (i.e., about half of the minimal measurement time of the aliphatic congener; Table 11).) The present invention demonstrates that, for proteins up to ~15-20 (~20-25) kDa, it is recommended to acquire the shift doublet subspectra with ~2-3 (~3-4) times of the measurement required for 3D [H]-NOESY-[CH$^{ali}$/CH$^{aro}$/NH] (the central peak spectra). This suffices to assign most of the stronger NOEs by detection of shift doublets, and the thus obtainable precise and accurate initial structures ensure rapid convergence of the structure refinement. For smaller proteins, it can be envisaged that (4,2)D [HC$^{ali}$/HN]-NOESY-[CH$^{ali}$/NH] or (3,2)D [H]-NOESY-[CH$^{ali}$/CH$^{aro}$/NH] are valuable tools to study protein structure and folding. In (4,2)D $^{15}$N/$^{13}$C$^{aliphatic}$ [$^1$H—$^1$H] NOESY, magnetization is first transferred from given $^1$H nucleus to its directly attached heteroatom ($^{15}$N/$^{13}$C$^{aliph}$) which is frequency labeled in conjunction with $^1$H during $\tau_1(\omega_1)$. Subsequently, magnetization is transferred through the nuclear Overhauser effect to all $^1$H spins that are located within ~5 Å in space. The resulting $^1$H magnetization is transferred again to its directly attached heteroatom for frequency labeling ($^{15}$N/$^{13}$C$^{aliph}$) along $\omega_1$, before transferring back for direct detection. The peak patterns observed in this experiment is shown in FIG. 43 and the r.f pulse scheme is shown in FIG. 44. In (3,2)D $^{15}$N/$^{13}$C$^{aliphatic}$-resolved [$^1$H-$^1$H] NOESY, after frequency labeling of a given $^1$H nucleus along $\omega_2$, magnetization is transferred through the nuclear Overhauser effect to all $^1$H spins that are located within ~5 Å in space. Subsequently, magnetization from $^1$H is transferred to its directly attached heteroatom ($^{15}$N/$^{13}$C$^{aliph}$) for frequency labeling along $\omega_1$ and back for direct detection ($\omega_1$). The peak pattern observed in this experiment is shown in FIG. 45 and the r.f pulse scheme is shown in FIG. 46. Table 14 shows the acquisition parameters for the (4,2)D [HC$^{ali}$/HN]-NOESY-[CH$^{ali}$/NH] and (3,2)D [H]-NOESY-[CH$^{ali}$/CH$^{aro}$/NH] experiments.

TABLE 14

Acquisition Parameters for GFT NMR Experiments Recorded for 15 kDa Protein ET99

| | (3,2)D $^{15}$N/$^{13}$C$^{aliphatic}$[$^1$H,$^1$H]-NOESY | (4,2)D $^{15}$N/$^{13}$C$^{aliphatic}$[$^1$H,$^1$H]-NOESY |
|---|---|---|
| $^1$H resonance frequency | 750 MHz | 750 MHz |
| No. of Points (t$_1$, t$_2$) Collected: | 256, 512 | 320, 512 |
| After LP: | 256, 512 | 320, 512 |
| After zero filling: | 512, 64, 1024 | 512, 64, 1024 |
| Window functions: | sine 70/70 | sine 70/70 |
| No. of transients: | 4 | 4 |
| Spectral width ($\omega_1$, $\omega_2$; Hz) | 16000, 8000 | 20000, 8000 |
| t$_{max}$ (ms) | 16.0, 64.0 | 16.0, 64.0 |
| Carrier Position ($\omega_1$, $\omega_2$; ppm) | 4.78/36/118.0, 4.78 | 4.78/36/119, 4.78 |
| Recycle delay(s) | 1.0 | 1.0 |
| Collection time (hrs) | 0.3 | 0.4 |

In the future, new software for efficiently symmetrizing (Szyperski et al., *J. Magn. Reson.* B108:197-203 (1995), which is hereby incorporated by reference in its entirety) (4,3)D [HC$^{ali}$/HN]-NOESY-[CH$^{ali}$/NH] subspectra about the position of the central peaks along the GFT dimension will allow one to increase the effective S/N ratio of the shift doublets. (With such software, the precision and accuracy of the initial structure obtained with data set II (60 hours measurement time; Table 13; FIGS. 41 and 42) can be expected to be obtained with data set I (30 hours measurement time).) This will further reduce the NMR measurement time required for (4,3)D NOESY and/or increase its feasibility for large proteins, and combination of (4,3)D [HC$^{ali}$/HN]-NOESY-[CH$^{ali}$/NH] with automated structure determination protocols promises to be an ideal choice for high throughput determination of proteins.

Example 27

Implementation of J-GFT (6,2)D (H$^\alpha$—C$^\alpha$—CO)—N—HN

The r.f. pulse scheme of J-GFT (6,2)D (H$^\alpha$—C$^\alpha$—CO)—N—HN (FIG. 47) was derived from previously published (5,2)D HACACONHN (Kim et al., *J. Am. Chem. Soc.* 125:1385-1393 (2003); Kim et al., *J. Biomol. NMR* 28:117-130 (2004), which are hereby incorporated by reference in their entirety). Except for $\Omega(^{15}$N), chemical shifts were refocused during constant-time delays serving for polarization transfer and evolution of couplings. In contrast to IPAP (Ottiger et al., *J. Magn. Reson.* 131:373-378 (1998), which is hereby incorporated by reference in its entirety) and other spin-state filtered experiments (Meissner et al., *J. Magn. Reson.* 128:92-97 (1997); Sørensen et al., *J. Biomol. NMR* 10:181-186 (1997); Andersson et al., *J. Biomol. NMR* 12:435-441 (1998), which are hereby incorporated by reference in their entirety), no additional delays were required to generate transfer amplitudes which were either cosine or sine modulated by the coupling evolutions.

The acquisition scheme of FIG. 47 can be readily understood when considering the r.f. pulse module depicted in FIG. 48 since this module was repeatedly incorporated for simultaneous measurement of multiple RDCs during polarization transfers. Cosine or sine-modulations were achieved during I-S polarization transfers while I-S anti-phase magnetization was refocused to in-phase transverse S magnetization (FIG. 48), which then led to observable magnetization during signal detection. With I and S representing the product operators (Sørensen et al., *Prog. NMR Spectrosc.* 16:163-192 (1983), which is hereby incorporated by reference in its entirety) of spins I and S, and $^1$J, $^1$D and $^1$K indicating scalar coupling, RDC and their sum, respectively, one obtains at $\tau = \frac{1}{2}J_{IS}$ for the "cosine modulated data set"

$$I_zS_y \text{ (at point a)} \rightarrow S_x \sin[\pi^1K_{IS}(\tau+t_1)] = S_x \cos[\pi^1K_{IS}t_1 + \phi] \text{ with } \phi = \pi/2(^1D/^1J) \text{ (at point b in FIG. 48)} \quad (20),$$

and for the "sine modulated data set"

$$I_zS_y \text{ (at point a)} \rightarrow S_x \sin(\pi^1K_{IS}t_1) \text{ (at point b in FIG. 48)} \quad (21).$$

Although being a scalar quantity, the coupling $K_{IS}$ is thus measured in a "pseudo phase-sensitive manner", that is, two subspectra are acquired in which the transfer amplitude is either cosine or sine modulated. As a result, the coupling evolution can formally be treated like a chemical shift and several couplings can be jointly sampled as was introduced for chemical shifts in the framework of GFT NMR spectroscopy (Kim et al., *J. Am. Chem. Soc.* 125:1385-1393 (2003), which is hereby incorporated by reference in its entirety). Then, a G-matrix transformation of the time domain data yields subspectra in which linear combinations of couplings (and chemical shifts) are measured and the different linear combinations are edited into different subspectra.

For (6,2)D (H$^\alpha$—C$^\alpha$—CO)—N—HN (FIG. 47), the backbone $^{15}$N shift was detected in quadrature and the multiplets of the basic spectra (Kim et al., *J. Am. Chem. Soc.* 125:1385-1393 (2003), which is hereby incorporated by reference in its entirety) encoded along with $\Omega(^{15}$N) the four mutually correlated one-bond couplings $^1K_{C\alpha H\alpha}$, $^1K_{C\alpha C'}$, $^1K_{NC'}$ and $^1K_{NH}$ (FIG. 49). Unambiguous grouping of multiplet components in cases of $^{15}$N, $^1$H$^N$-shift degeneracy can be accomplished by central peak detection, as introduced in reduced-dimensionality (RD) NMR spectroscopy (Szyperski et al., *J. Am. Chem. Soc.* 115:9307-9308 (1993); Szyperski et al., *J. Magn. Reson. Ser. B* 108:197-203 (1995); Szyperski et al., *J. Am. Chem. Soc.* 118:8146-8147 (1996); Szyperski et al., *Proc. Natl. Acad. Sci. USA* 99:8009-8014 (2002); Brutscher et al., *J. Magn. Reson. Ser. B* 105:77-82 (1994); Szyperski et al., *J. Magn. Reson. Ser. B* 105:188-191 (1994); Szyperski et al., *J. Biomol. NMR* 11:387-405 (1998), which are hereby incorporated by reference in their entirety). The choice of a particular scheme for central peak detection is guided by experimental sensitivity and one may also consider that the precision of the measurements depends on the degree of over-determination (Kim et al., *J. Am. Chem. Soc.* 125:1385-1393 (2003), which is hereby incorporated by reference in its entirety). For the implementation of (6,2)D (H$^\alpha$—C$^\alpha$—CO)—N—HN, the following was encoded: (i) $^{13}$C$^\alpha$—$^{13}$C', $^{15}$N—$^{13}$C', $^{15}$N—$^1$H$^N$ couplings and $^{15}$N shifts in 1$^{st}$ order central peak spectra, (ii) $^{15}$N—$^{13}$C', $^{15}$N—$^1$H$^N$ couplings and $^{15}$N shifts in 2$^{nd}$ order central peak spectra, (iii) $^{15}$N—$^1$H$^N$ couplings and $^{15}$N shifts in 3$^{rd}$ order central peak spectra, and (iv) $^{15}$N shifts in 4$^{th}$ order central peak spectra. Hence, a total of 31 2D planes constituted the (6,2)D (H$^\alpha$—C$^\alpha$—CO)—N—HN experiment (resulting in a minimal required measurement time of 31 times 1.5 min=47 min), and $^{15}$N—$^1$H$^N$ (~92 Hz), $^{15}$N—$^{13}$C' (~15 Hz), $^{13}$C$^\alpha$—$^{13}$C'(~55 Hz), and $^{13}$C$^\alpha$—$^1$H$^\alpha$ (~135 Hz) couplings were obtained from a least squares fit to linear combinations of couplings detected in, respectively, 30, 28, 24, and 16 subspectra. Such a peak pattern is illustrated in FIG. 50(a). This experiment can also be used to measure the residual dipolar complings (RDC) for proteins dissolved in liquid crystalline media as shown in FIG. 50(b). Table 15 shows the acquisition parameters for the (6,2)D (H$^\alpha$—C$^\alpha$—CO)—N—HN experiment.

TABLE 15

Acquisition Parameters for GFT NMR Experiments Recorded for 8.0 kDa Protein Z-domain

| | RDCs (isotropic state) | RDCs (partially aligned state) |
|---|---|---|
| $^1$H resonance frequency | 750 MHz | 750 MHz |
| No. of Points ($t_1$, $t_2$) Collected: | 50, 512 | 50, 512 |
| After LP: | 50, 512 | 50, 512 |
| After zero filling: | 512, 1024 | 512, 1024 |
| Window functions: | sine 70/70/70 | sine 70/70/70 |
| No. of transients: | 64 | 128 |
| Spectral width ($\omega_1$, $\omega_2$, $\omega_3$; Hz) | 2000, 8000 | 2000, 8000 |
| $t_{max}$ (ms) | 24.5, 64.0 | 24.5, 64.0 |
| Carrier Position ($\omega_1$, $\omega_2$; ppm) | 118.9, 4.78 | 118.9, 4.78 |
| Recycle delay(s) | 1.0 | 1.0 |
| Collection time (hrs) | 24.0 | 48.0 |

Importantly, the constant-time evolution (Cavanagh et al., *Protein NMR Spectroscopy* Academic Press: San Diego, Calif. (1996), which is hereby incorporated by reference in its entirety) of couplings (FIG. 47) prevents line broadening when measuring multiple RDCs simultaneously, as was discussed for simultaneous measurement of several chemical shifts (Kim et al., *J. Am. Chem. Soc.* 125:1385-1393 (2003), which is hereby incorporated by reference in its entirety). Furthermore, cancellation artifacts due to differential relaxation are avoided. To minimize line broadening due to passive $^1$H—$^1$H RDCs, $^1K_{C\alpha_H\alpha}$-evolution is preferably accomplished while transverse $^{13}C^\alpha$ magnetization is present for $^{13}C^\alpha$—$^{13}C'$ INEPT, and not at the start of the experiment when transverse $^1H^\alpha$ magnetization is present. Since the corresponding INEPT delay is set to 8.8 ms, $^1K_{C\alpha_H\alpha}$-evolution has to be scaled down by a factor ⅓ in order to achieve a maximal evolution time of ~25 ms for $\Omega(^{15}N)$ and the other couplings (notably, $^1K_{C\alpha_C'}$-evolution is accomplished during the long $^{13}C'$—$^{15}N$ transfer step of ~30 ms).

Example 28

J-GFT (6,2)D (H$^\alpha$—C$^\alpha$—CO)—N—HN NMR Data Acquisition and Processing RDCs were extracted from (6,2)D (H$^\alpha$—C$^\alpha$—CO)—N—HN experiments acquired at 25° C. for (i) a ~1 mM $^{13}$C/$^{15}$N doubly labeled solution of the protein Z-domain (Zheng et al., *Protein Sci.* 13:549-554 (2004), which is hereby incorporated by reference in its entirety) ($M_r$~8 kDa), and (ii) a ~0.5 mM solution aligned with Pf1 phages (Hansen et al., *Nat. Struct. Biol.* 5:1065-1074 (1998), which is hereby incorporated by reference in its entirety), characterized by a 25 Hz splitting of the $^2$H$_2$O line. Both experiments were performed at once each on Varian INOVA 600 and 750 spectrometers equipped, respectively, with cryogenic and conventional triple resonance probes. To ensure identical r.f. pulse duty cycle, central peak spectra (Kim et al., *J. Am. Chem. Soc.* 125:1385-1393 (2003), which is hereby incorporated by reference in its entirety) were acquired with the same pulse scheme by successively omitting coupling evolutions (FIG. 48). Spectra on the 750 MHz (600 MHz) spectrometer were acquired with 50 complex points and 32 (16) transients per free induction decay (FID) resulting in a total acquisition time of ~24 (12) hours for the full set of GFT experiments (i.e., basic as well as central peak spectra). No linear prediction was employed and the time domain signal was extended in the GFT dimension to 4096 complex points by zero-filling prior to Fourier transformation (FT).

Example 29

J-GFT (6,2)D (H$^\alpha$—C$^\alpha$—CO)—N—HN: Measurement of One-Bond RDCs

Data analysis of the experimentally observed peak pattern for the Z-domain sample yielded two sets ("600 MHz" and "750 MHz" data sets) of 44 $^{15}$N—$^1$H$^N$, $^{15}$N—$^{13}$C', $^{13}$C$^\alpha$—$^{13}$C' and $^{13}$C$^\alpha$—$^1$H$^\alpha$ accurately measurable RDCs out of the 50 observable peaks (corresponding to a yield of ~88%). These RDCs were further analyzed for accuracy and precision as described in the following. Accuracy of RDC measurement was confirmed by comparison of the "750 MHz" data sets (corrected for the phase errors resulting from J-mismatch) with values obtained from conventional 2D IPAP (Ottiger et al., *J. Magn. Reson.* 131:373-378 (1998), which is hereby incorporated by reference in its entirety) or $\omega_1$-coupled 2D spectra recorded at the same field strength. A root mean square deviation (rmsd) (and correlation coefficient) of 2.0 Hz (0.96) and 0.8 Hz (0.85) was obtained, respectively, for $^1J_{NH}$ and $^1J_{NC'}$ couplings. Notably, since the couplings were extracted from the full set comprising both basic and central peak GFT spectra encoding all the four one-bond dipolar couplings, such accuracy was equally expected also for $^1J_{C\alpha C'}$ and $^1J_{C\alpha H\alpha}$ couplings.

In sum, J-GFT (6,2)D (H$^\alpha$—C$^\alpha$—CO)—N—HN promises to be a valuable new experiment for measurement of mutually correlated $^{15}$N—$^1$H$^N$, $^{15}$N—$^{13}$C', $^{13}$C$^\alpha$—$^{13}$C' and $^{13}$C$^\alpha$—$^1$H$^\alpha$ couplings in proteins. Measurement of correlated RDCs can be combined with chemical shift detected multidimensional NMR experiments for aid in resonance assignments (Tian et al., *J. Am. Chem. Soc.* 123:11791-11796 (2001); Zweckstetter et al., *J. Am. Chem. Soc.* 123:9490-9491 (2001), which are hereby incorporated by reference in their entirety). For protein with known 3D structure, (6,2)D (H$^\alpha$—C$^\alpha$—CO)—N—HN can be used for measurement of mutually correlated RDCs for backbone assignments without the need for sequential connectivity information (Jung et al., *J. Biomol. NMR* 30:25-35 (2004), which is hereby incorporated by reference in its entirety). While the present scheme of the J-GFT experiment is based on an "out-and-stay" type of experiment (Cavanagh et al., *Protein NMR Spectroscopy* Academic Press: San Diego, Calif. (1996), which is hereby incorporated by reference in its entirety), analogues "out-and-back" HN-detected J-GFT experiments can be easily devised for application to larger and/or deuterated proteins. Further, since only evolution due to one-bond scalar/dipolar coupling takes place during the $^1$H$^\alpha$—$^{13}$C$^\alpha$, $^{13}$C$^\alpha$—$^{13}$C' and $^{13}$C'—$^{15}$N INEPT transfers, the existing delays in this time period can be additionally used for chemical shift evolution of the respective spins to gain dispersion, either in a separate indirect dimension or/and jointly with $^{15}$N chemical shift and one-bond couplings in the GFT dimension. This provides new avenues to study proteins with high chemical shift degeneracy.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A method of conducting a (5,3) dimensional (D) [HN{N, CO}{$C^{\alpha\beta}C^{\alpha}$}] G-matrix Fourier transformation (GFT) nuclear magnetic resonance (NMR) experiment, said method comprising:

providing a sample, wherein said sample is a protein molecule having two consecutive amino acid residues, i−1 and i, and the chemical shift values for the following nuclei are measured: (1) α- and β-carbons of amino acid residues i and i−1, $^{13}C^{\alpha/\beta}_{i/i-1}$; (2) a polypeptide backbone amide nitrogen of amino acid residue i, $^{15}N_i$; (3) a polypeptide backbone carbonyl carbon of amino acid residue i−1, $^{13}C'_{i-1}$; and (4) a polypeptide backbone amide proton of amino acid residue i, $^{1}H^{N}_i$;

applying radiofrequency pulses for a first 5D FT NMR experiment to the sample; using a spectrometer;

selecting a first set of 2 indirect chemical shift evolution periods of the 5D FT NMR experiment, $^{13}C^{\alpha/\beta}_{i/i-1}$ and $^{13}C^{\alpha}_{i/i-1}$;

jointly sampling the first set of 2 indirect chemical shift evolution periods in a first indirect time domain dimension, $t_1(^{13}C^{\alpha/\beta}_{i/i-1}, ^{13}C^{\alpha}_{i/i-1})$, whereby chemical shift evolution periods which provide sequential connectivities and spectral resolution are subjected to the joint sampling in the first indirect time dimension;

selecting a second set of 2 indirect chemical shift evolution periods of the 5D FT NMR experiment, $^{15}N_i$ and $^{13}C'_{i-1}$;

jointly sampling the second set of 2 indirect chemical shift evolution periods in a second indirect time domain dimension, $t_2(^{15}N_i, ^{13}C'_{i-1})$, whereby chemical shift evolution periods which serve to provide spectral resolution are subjected to separate joint sampling in the second indirect time dimension;

independently cosine and sine modulating NMR signals detected in a direct dimension to generate 3D basic NMR spectra comprising frequency domain signals having a chemical shift multiplet with 4 components resulting from each of 2 chemical shift doublet components in a first frequency domain dimension, $\omega_1(^{13}C^{\alpha/\beta}, ^{13}C^{\alpha})$, giving rise to 2 chemical shift doublet components in a second frequency domain dimension, $\omega_2(^{15}N, ^{13}C')$, thereby enabling phase-sensitive sampling of all 4 indirect chemical shift evolution periods; and transforming the 3D basic NMR spectra into 3D phase-sensitively edited basic NMR spectra, wherein the 4 chemical shift multiplet components of the 3D basic NMR spectra are edited to yield 3D phase-sensitively edited basic NMR spectra having individual chemical shift multiplet components.

2. The method according to claim 1, wherein said transforming is carried out by applying a G-matrix defined as $$\hat{G}(1) = \begin{bmatrix} 1 & i \\ 1 & -i \end{bmatrix} \otimes [1 i],$$

wherein $i=\sqrt{-1}$, along the first and second indirect time domain dimensions under conditions effective to edit the chemical shift multiplet components in the time domain.

3. The method according to claim 1, wherein said transforming is carried out by applying a F-matrix defined as $$\hat{F}(1) = \begin{bmatrix} 1 & 1 \\ 1 & -1 \end{bmatrix}$$

along the first and second frequency domain dimensions under conditions effective to edit the chemical shift multiplet components in the frequency domain.

4. The method according to claim 1, wherein said applying radiofrequency pulses comprises applying radiofrequency pulses for a 5D FT NMR experiment according to the scheme shown in FIG. 5.

5. The method according to claim 1 further comprising: conducting a (5,3) dimensional (D) [HN{NCO}{$C^{\alpha\beta}C^{\alpha}$}] G-matrix Fourier transformation (GFT) nuclear magnetic resonance (NMR) experiment on the sample, said method comprising:

applying radiofrequency pulses for a second 5D FT NMR experiment to the sample using a spectrometer, wherein the chemical shift values for the following nuclei are measured: (1) α- and β-carbons of amino acid residue i−1, $^{13}C^{\alpha/\beta}_{i-1}$; (2) a polypeptide backbone amide nitrogen of amino acid residue i, $^{15}N_i$; (3) a polypeptide backbone carbonyl carbon of amino acid residue i−1, $^{13}C'_{i-1}$; and (4) a polypeptide backbone amide proton of amino acid residue i, $^{1}H^{N}_i$;

selecting a third set of 2 indirect chemical shift evolution periods of the 5D FT NMR experiment, $^{13}C^{\alpha/\beta}_{i-1}$ and $^{13}C^{\alpha}_{i-1}$;

jointly sampling the third set of 2 indirect chemical shift evolution periods in a first indirect time domain dimension, $t_1(^{13}C^{\alpha/\beta}_{i-1}, ^{13}C^{\alpha}_{i-1})$;

selecting a fourth set of 2 indirect chemical shift evolution periods of the 5D FT NMR experiment, $^{15}N_i$ and $^{13}C'_{i-1}$;

jointly sampling the fourth set of 2 indirect chemical shift evolution periods in a second indirect time domain dimension, $t_2(^{15}N_i, ^{13}C'_{i-1})$, independently cosine and sine modulating NMR signals detected in a direct dimension to generate 3D basic NMR spectra comprising frequency domain signals having a chemical shift multiplet with 4 components resulting from each of 2 chemical shift doublet components in a first frequency domain dimension, $\omega_1({}^{13}C^{\alpha/\beta}, {}^{13}C^{\alpha})$, giving rise to 2 chemical shift doublet components in a second frequency domain dimension, $\omega_2({}^{15}N, {}^{13}C')$, thereby enabling phase-sensitive sampling of all 4 indirect chemical shift evolution periods; and transforming the 3D basic NMR spectra into 3D phase-sensitively edited basic NMR spectra, wherein the 4 chemical shift multiplet components of the 3D basic NMR spectra are edited to yield 3D phase-sensitively edited basic NMR spectra having individual chemical shift multiplet components.

6. The method according to claim 5, wherein said transforming in the (5,3) dimensional (D) [HN{NCO}{$C^{\alpha\beta}C^{\alpha}$}] GFT NMR experiment is carried out by applying a G-matrix defined as $$\hat{G}(1) = \begin{bmatrix} 1 & i \\ 1 & -i \end{bmatrix} \otimes [1\,i],$$

wherein $i=\sqrt{-1}$, along the first and second indirect time domain dimensions under conditions effective to edit the chemical shift multiplet components in the time domain.

7. The method according to claim 5, wherein said transforming in the (5,3) dimensional (D) [HN{NCO}{$C^{\alpha\beta}C^{\alpha}$}] GFT NMR experiment is carried out by applying a F-matrix defined as $$\hat{F}(1) = \begin{bmatrix} 1 & 1 \\ 1 & -1 \end{bmatrix}$$

along the first and second frequency domain dimensions under conditions effective to edit the chemical shift multiplet components in the frequency domain.

8. The method according to claim 5, wherein said applying radiofrequency pulses in the (5,3) dimensional (D) [HN{NCO}{$C^{\alpha\beta}C^{\alpha}$}] GFT NMR experiment comprises applying radiofrequency pulses for a 5D FT NMR experiment according to the scheme shown in FIG. 6.

* * * * *

UNITED STATES PATENT AND TRADEMARK OFFICE
CERTIFICATE OF CORRECTION

| | | |
|---|---|---|
| PATENT NO. | : 7,920,972 B2 | Page 1 of 1 |
| APPLICATION NO. | : 11/253262 | |
| DATED | : April 5, 2011 | |
| INVENTOR(S) | : Thomas A. Szyperski et al. | |

It is certified that error appears in the above-identified patent and that said Letters Patent is hereby corrected as shown below:

Column 107, line 34, delete the first instance of ";".

Signed and Sealed this
Second Day of August, 2011

David J. Kappos
*Director of the United States Patent and Trademark Office*